US012344893B2

(12) United States Patent
Storch et al.

(10) Patent No.: US 12,344,893 B2
(45) Date of Patent: Jul. 1, 2025

(54) NASAL GENES USED TO IDENTIFY, CHARACTERIZE, AND DIAGNOSE VIRAL RESPIRATORY INFECTIONS

(71) Applicant: Washington University, St. Louis, MO (US)

(72) Inventors: Gregory Storch, St. Louis, MO (US); Jinsheng Yu, St. Louis, MO (US); Thomas J. Mariani, St. louis, MO (US)

(73) Assignees: Washington University, St. Louis, MO (US); University of Rochester, Rochester, NY (US)

( * ) Notice: Subject to any disclaimer, the term of this patent is extended or adjusted under 35 U.S.C. 154(b) by 1006 days.

(21) Appl. No.: 16/972,440

(22) PCT Filed: Jun. 5, 2019

(86) PCT No.: PCT/US2019/035673
§ 371 (c)(1),
(2) Date: Dec. 4, 2020

(87) PCT Pub. No.: WO2019/236768
PCT Pub. Date: Dec. 12, 2019

(65) Prior Publication Data
US 2021/0230694 A1 Jul. 29, 2021

Related U.S. Application Data

(60) Provisional application No. 62/812,026, filed on Feb. 28, 2019, provisional application No. 62/680,800, filed on Jun. 5, 2018.

(51) Int. Cl.
*C12Q 1/6883* (2018.01)

(52) U.S. Cl.
CPC ..... *C12Q 1/6883* (2013.01); *C12Q 2600/158* (2013.01)

(58) Field of Classification Search
CPC .................. C12Q 1/68; C07H 21/00
See application file for complete search history.

(56) References Cited

U.S. PATENT DOCUMENTS

| 11,286,529 B2* | 3/2022 | Storch ............. G01N 33/56983 |
| 2012/0114661 A1* | 5/2012 | Ginsburg ............ C12Q 1/6883 514/459 |
| 2017/0030909 A1 | 2/2017 | Oved et al. |
| 2017/0327874 A1 | 11/2017 | Falsey et al. |
| 2018/0245154 A1* | 8/2018 | Tsalik .................... A61K 39/00 |

FOREIGN PATENT DOCUMENTS

| WO | 2014008545 A1 | 1/2014 |
| WO | 2017143152 A1 | 8/2017 |

OTHER PUBLICATIONS

International Preliminary Report on Patentability for International Application No. PCT/US2019/035673, mailed Dec. 17, 2020, 11 Pages.
International Search Report and Written Opinion for International Application No. PCT/US2019/035673, mailed Oct. 29, 2019, 14 Pages.
Non-Final Office Action for U.S. Appl. No. 16/972,440, mailed on Apr. 8, 2024, 8 pages.
Yu et al., "Host Gene Expression in Nose and Blood for the Diagnosis of Viral Respiratory Infection", J Infect Dis, (Apr. 1, 2019), vol. 219, pp. 1151-1161.

* cited by examiner

*Primary Examiner* — Ethan C Whisenant
(74) *Attorney, Agent, or Firm* — Polsinelli PC

(57) ABSTRACT

The present disclosure provides molecular methods to improve the rapid diagnosis of respiratory infections. In general, the present disclosure provides method of detecting host gene signatures which aid in determining the etiology of a respiratory infection and thereby improve the treatment.

24 Claims, 187 Drawing Sheets
(187 of 187 Drawing Sheet(s) Filed in Color)

Number of Differentially Expressed Genes within the 28,476 Genes

| Sample Type | Comparison | Differentially Expressed Genes at p<0.05 & FC abs >=1.5 | | | | | |
|---|---|---|---|---|---|---|---|
| | | Before DSA | | | After DSA | | |
| | | Up | Down | Total | Up | Down | Total |
| Nasal | RSV vs. Ctrl | 815 | 3989 | 4804 | 1546 | 2780 | 4326 |
| Nasal | nRSV vs. Ctrl | 700 | 2108 | 2808 | 904 | 1788 | 2692 |
| Nasal | asRV vs. Ctrl | 107 | 1248 | 1355 | 195 | 907 | 1102 |
| Nasal | RSV vs. Ctrl | 67 | 501 | 568 | 130 | 341 | 471 |
| Nasal | nRSV vs. asRV | 304 | 343 | 647 | 269 | 443 | 712 |
| Nasal | RSV+sPV vs. Ctrl | 739 | 2882 | 3621 | 1016 | 2151 | 3167 |
| Nasal | RSV+sPV vs. asRV | 334 | 474 | 808 | 344 | 573 | 917 |

| index | Symbol | symp_ctrl | symp_vs_asymp | Up_total | nCom 0.5 | FCTB W:Dm C | FCTB W:Dav C | A:TBW Avg | B:TBW Avg | C:TBW Avg | D:TBW Avg | A:Linear Avg | B:Linear Avg | C:Linear Avg | D:Linear Avg |
|---|---|---|---|---|---|---|---|---|---|---|---|---|---|---|---|
| 1 | ISG15 | | | 2 | 3 | 10.8 | 8.3 | 661.7 | 187.4 | 113.0 | 1217.7 | 640.3 | 203.3 | 125.7 | 1236.1 |
| 2 | FCER1G | 1 | 1 | 2 | 6 | 6.1 | 6.3 | 922.9 | 418.8 | 145.0 | 891.4 | 1535.8 | 448.0 | 213.0 | 2159.0 |
| 3 | S100A12 | 1 | 1 | 2 | 2 | 9.8 | 11.4 | 572.1 | 136.2 | 44.0 | 433.5 | 1016.5 | 174.3 | 64.2 | 1164.9 |
| 4 | SELL | 1 | 1 | 2 | 12 | 9.4 | 8.0 | 236.8 | 78.2 | 33.1 | 310.8 | 383.3 | 100.2 | 58.9 | 490.2 |
| 5 | TNFAIP6 | 1 | 1 | 2 | 5 | 18.6 | 14.1 | 238.9 | 58.1 | 25.1 | 467.9 | 606.0 | 83.5 | 54.2 | 816.4 |
| 6 | IFIT1 | 1 | 1 | 2 | 3 | 14.0 | 9.0 | 116.2 | 25.6 | 29.4 | 413.0 | 153.6 | 37.8 | 32.3 | 599.7 |
| 7 | C3AR1 | 1 | 1 | 2 | 2 | 7.9 | 6.9 | 82.1 | 26.2 | 14.0 | 111.4 | 196.3 | 30.4 | 19.1 | 199.7 |
| 8 | CD163 | 1 | 1 | 2 | 0 | 4.9 | 4.3 | 334.0 | 157.6 | 89.3 | 439.8 | 344.1 | 138.3 | 98.6 | 500.7 |
| 9 | FCGR1A | 1 | | 1 | 3 | 6.2 | 5.9 | 88.0 | 34.1 | 15.8 | 98.4 | 114.4 | 41.1 | 24.0 | 191.0 |
| 10 | IFI6 | 1 | | 1 | 0 | 5.9 | 4.6 | 501.5 | 235.6 | 150.1 | 885.3 | 529.7 | 254.9 | 164.6 | 836.5 |
| 11 | FCGR3B | 1 | | 1 | 5 | 12.0 | 9.8 | 359.5 | 182.3 | 46.2 | 556.4 | 512.0 | 243.7 | 93.6 | 930.7 |
| 12 | CCRL2 | 1 | | 1 | 3 | 4.9 | 3.9 | 203.7 | 65.6 | 68.8 | 335.5 | 441.7 | 107.4 | 85.1 | 590.9 |
| 13 | PADI2 | 1 | | 1 | 5 | 15.5 | 14.5 | 477.7 | 276.3 | 35.5 | 546.7 | 893.7 | 324.6 | 80.3 | 1104.9 |
| 14 | IFITM2 | 1 | | 1 | 4 | 3.3 | 3.1 | 537.5 | 308.7 | 187.4 | 617.4 | 961.0 | 383.3 | 191.8 | 1528.5 |
| 15 | IFITM1 | 1 | | 1 | 0 | 4.5 | 3.8 | 2048.0 | 893.4 | 613.1 | 2646.7 | 1785.8 | 959.9 | 663.1 | 2738.3 |
| 16 | IDI1 | 1 | | 1 | 3 | 4.1 | 4.1 | 120.3 | 65.3 | 28.8 | 117.8 | 196.9 | 60.1 | 47.6 | 187.7 |
| 17 | TNFSF13B | 1 | | 1 | 7 | 5.2 | 5.2 | 116.2 | 66.7 | 27.7 | 173.6 | 170.1 | 68.4 | 32.8 | 285.5 |
| 18 | AQP9 | 1 | | 1 | 9 | 6.3 | 6.3 | 421.7 | 166.6 | 37.3 | 488.0 | 792.8 | 200.7 | 104.9 | 921.8 |
| 19 | BCL2A1 | 1 | | 1 | 10 | 13.8 | 12.3 | 734.1 | 315.2 | 63.6 | 632.8 | 1148.5 | 335.5 | 158.9 | 1347.8 |
| 20 | FFAR2 | 1 | | 1 | 7 | 10.3 | 10.3 | 207.9 | 94.4 | 26.2 | 306.6 | 421.8 | 104.5 | 39.0 | 611.3 |
| 21 | PPR1 | 1 | | 1 | 5 | 11.7 | 9.8 | 226.8 | 112.2 | 28.4 | 144.0 | 406.9 | 129.4 | 50.2 | 526.6 |
| 22 | RSAD2 | | 1 | 1 | 1 | 5.1 | 6.3 | 104.7 | 45.3 | 42.7 | 243.9 | 147.1 | 47.8 | 46.7 | 300.8 |
| 23 | DDX60L | | 1 | 1 | 1 | 3.6 | 2.8 | 99.0 | 50.2 | 49.9 | 177.3 | 182.3 | 54.6 | 43.5 | 245.0 |
| 24 | IFIT3 | | | 1 | 4 | 6.5 | 4.9 | 843.4 | 347.3 | 265.0 | 1734.1 | 1005.9 | 354.3 | 322.9 | 1893.1 |

| Index | Symbol | symp_ctrl | symp_vs_asymp | Up | Total | ncont.3 | A:CV% | B:CV% | C:CV% | D:CV% | A: nDetected_of_3samples | B: nDetected_of_3samples | C: nDetected_of_6samples | D: nDetected_of_6samples | nDetected_of_26 | Diagnostic signal strength |
|---|---|---|---|---|---|---|---|---|---|---|---|---|---|---|---|---|
| 1 | ISG15 | | | | 2 | 3 | 48.7 | 33.2 | 40.3 | 55.6 | 9 | 5 | 6 | 0 | 26 | |
| 2 | FCER1G | 1 | 1 | | 2 | 6 | 107.3 | 45.2 | 87.1 | 94.2 | 9 | 5 | 6 | 0 | 26 | x |
| 3 | SIGLEC12 | 1 | 1 | | 2 | 3 | 133.7 | 78.5 | 88.9 | 145.1 | 9 | 5 | 6 | 0 | 26 | |
| 4 | SELL | 1 | 1 | | 2 | 12 | 118.7 | 59.8 | 105.6 | 92.7 | 9 | 5 | 6 | 0 | 20 | x |
| 5 | TNFAIP6 | 1 | 1 | | 2 | 5 | 150.0 | 39.9 | 126.3 | 102.0 | 9 | 5 | 4 | 0 | 24 | |
| 6 | IFIT1 | 1 | 1 | | 2 | 2 | 64.7 | 54.2 | 61.5 | 101.2 | 9 | 5 | 6 | 0 | 25 | |
| 7 | C3AR1 | 1 | 1 | | 2 | 3 | 175.6 | 55.7 | 71.0 | 111.6 | 9 | 5 | 6 | 0 | 23 | x |
| 8 | CD163 | 1 | 1 | | 2 | 0 | 38.8 | 20.3 | 45.4 | 55.1 | 9 | 5 | 6 | 0 | 26 | x |
| 9 | FCGR1A | 1 | | 3 | | 3 | 75.8 | 36.0 | 95.9 | 118.4 | 9 | 5 | 6 | 0 | 24 | |
| 10 | IFI6 | 1 | | 3 | | 0 | 62.5 | 38.3 | 45.0 | 46.1 | 9 | 5 | 6 | 0 | 26 | |
| 11 | FCGR1B | 1 | | 3 | | 5 | 95.9 | 84.3 | 124.7 | 99.6 | 9 | 5 | 6 | 0 | 26 | x |
| 12 | CCL2 | 1 | | 3 | | 3 | 139.7 | 46.3 | 54.1 | 93.9 | 9 | 5 | 6 | 0 | 26 | x |
| 13 | PROK2 | 1 | | 3 | | 5 | 118.9 | 58.9 | 126.8 | 109.8 | 9 | 5 | 6 | 0 | 26 | |
| 14 | IFITM3 | 1 | | 3 | | 5 | 95.2 | 61.6 | 39.5 | 94.2 | 9 | 5 | 6 | 0 | 26 | |
| 15 | IFITM1 | 1 | | 3 | | 1 | 33.6 | 36.6 | 46.1 | 22.5 | 9 | 5 | 6 | 0 | 26 | |
| 16 | CLU | 1 | | 3 | | 0 | 116.5 | 38.7 | 98.1 | 88.5 | 9 | 5 | 6 | 0 | 26 | |
| 17 | TNFSF13B | 1 | | 3 | | 3 | 87.7 | 35.1 | 57.1 | 95.4 | 9 | 5 | 6 | 0 | 26 | x |
| 18 | AQP9 | 1 | | 3 | | 7 | 116.0 | 61.1 | 154.8 | 103.9 | 9 | 5 | 6 | 0 | 25 | |
| 19 | BCL6A1 | 1 | | 3 | | 9 | 100.9 | 53.8 | 149.2 | 101.8 | 9 | 5 | 6 | 0 | 28 | |
| 20 | FAR2 | 1 | | 3 | | 10 | 134.8 | 51.1 | 98.3 | 115.0 | 9 | 5 | 4 | 0 | 24 | x |
| 21 | FPR1 | 1 | | 3 | | 7 | 122.6 | 60.3 | 110.9 | 118.6 | 9 | 5 | 6 | 0 | 23 | |
| 22 | RSAD2 | 1 | | 3 | | 3 | 66.4 | 20.4 | 33.2 | 71.6 | 9 | 5 | 6 | 0 | 28 | x |
| 23 | DDX60L | 1 | | 3 | | 1 | 84.6 | 49.6 | 37.7 | 71.0 | 9 | 5 | 6 | 0 | 26 | |
| 24 | IFIT5 | 1 | | 3 | | 4 | 58.0 | 25.0 | 61.7 | 51.5 | 9 | 5 | 6 | 0 | 26 | |

| Index | Symbol | symp_ctrl | symp_vs_asymp | Down Total | ncom.s | Pred | Actual | Both | A:TBW Avg | B:TBW Avg | C:TBW Avg | D:TBW Avg | A: Linear Avg | B: Linear Avg |
|---|---|---|---|---|---|---|---|---|---|---|---|---|---|---|
| 1 | SPAG17 | 1 | 1 | 2 | 14 | | | | 9.8 | 36.5 | | 5.5 | 13.4 | 43.3 |
| 2 | LRRC74B | 1 | 1 | 2 | 13 | | | | 47.8 | 132.5 | | 70.5 | 57.8 | 213.0 |
| 3 | PPO | 1 | | | 17 | | | | 64.4 | 247.3 | | 46.5 | 102.7 | 269.8 |
| 4 | C5orf26 | 1 | | | 6 | | | | 19.7 | 35.8 | | 29.4 | 23.8 | 36.1 |
| 5 | DNAI3 | 1 | | | 15 | | | | 27.5 | 76.6 | | 30.5 | 36.6 | 85.7 |
| 6 | VWA3B | 1 | | | 14 | | | | 23.4 | 46.2 | | 18.1 | 27.1 | 70.4 |
| 7 | KIAA2012 | 1 | | | 15 | | | | 19.7 | 31.3 | | 17.1 | 22.2 | 70.9 |
| 8 | C6orf58 | 1 | | | 8 | | | | 8.3 | 14.1 | | 9.4 | 10.7 | 13.6 |
| 9 | TBC1D9 | 1 | | | 3 | | | | 82.1 | 134.4 | | 66.7 | 93.5 | 134.7 |
| 10 | HHLA2 | 1 | | | 6 | | | | 8.5 | 40.8 | | 6.9 | 18.1 | 39.2 |
| 11 | ANKUB1 | 1 | | | 14 | | | | 35.3 | 106.2 | | 26.7 | 52.3 | 124.8 |
| 12 | ECT2L | 1 | | | 9 | | | | 14.8 | 23.6 | | 14.0 | 14.5 | 28.5 |
| 13 | LRRC6 | 1 | | | 15 | | | | 20.3 | 37.5 | | 16.4 | 24.8 | 43.8 |
| 14 | MORN5 | 1 | | | 5 | | | | 38.3 | 74.5 | | 22.9 | 38.0 | 84.3 |
| 15 | AGBL2 | 1 | | | 14 | | | | 15.3 | 41.1 | | 11.8 | 19.2 | 49.9 |
| 16 | CCDC65 | 1 | | | 7 | | | | 5.9 | 19.2 | | 4.9 | 9.2 | 21.9 |
| 17 | MATN3 | 1 | | | 14 | | | | 12.0 | 26.4 | | 11.2 | 13.9 | 29.7 |
| 18 | DNAL1 | 1 | | | 2 | | | | 7.5 | 10.0 | | 8.8 | 9.4 | 13.5 |
| 19 | ANKFN1 | 1 | | | 6 | | | | 5.1 | 6.5 | | 4.6 | 5.2 | 11.0 |
| 20 | WDR65 | | | | 15 | | | | 54.9 | 145.0 | | 37.5 | 61.8 | 134.1 |
| 21 | EFHB | | 1 | 1 | 5 | | | | 26.9 | 85.6 | | 22.6 | 33.1 | 120.6 |
| 22 | C7orf31 | | 1 | 1 | 5 | | | | 21.0 | 59.7 | | 20.5 | 26.8 | 67.5 |
| 23 | FABP6 | | | | 14 | | | | 56.9 | 168.9 | | 51.6 | 63.4 | 210.4 |

FIG. 15 (Cont.)

| TC_ID | Symbol | nCorr0.85 | nCorr0.90 | Clusters | | | | | | | |
|---|---|---|---|---|---|---|---|---|---|---|---|
| TC0100015656.hg.1 | S100A12 | 15 | 9 | C1 | 15var_5knn | 11.01 | 0.0117 | 11.10 | 0.0178 | 11.048 | 0.003 |
| TC1200009692.hg.1 | OLR1 | 6 | 6 | C1 | | 3.40 | 0.0485 | 4.08 | 0.0251 | 3.654 | 0.011 |
| TC1200012749.hg.1 | CD163 | 8 | 6 | C2 | 15var_5knn | 3.55 | 0.0002 | 4.83 | 0.0001 | 4.020 | 0.000 |
| TC1300010030.hg.1 | TNFSF13B | 46 | 14 | C2 | 15var_5knn | 4.43 | 0.0055 | 6.98 | 0.0008 | 5.333 | 0.000 |
| TC0100010341.hg.1 | FCER1G | 53 | 16 | C2 | 15var_5knn | 6.48 | 0.0013 | 9.15 | 0.0005 | 7.441 | 0.000 |
| TC1200007807.hg.1 | C3AR1 | 31 | 7 | C2 | 15var_5knn | 5.59 | 0.0158 | 8.53 | 0.0044 | 6.621 | 0.002 |
| TC0300007253.hg.1 | CCR2 | 26 | 9 | C3 | | 3.55 | 0.0500 | 4.95 | 0.0143 | 4.056 | 0.009 |
| TC0200009862.hg.1 | TNFAIP6 | 59 | 7 | C3 | 15var_5knn | 8.72 | 0.0216 | 16.83 | 0.0043 | 11.341 | 0.003 |
| TC0100016359.hg.1 | SELL | 52 | 33 | C3 | 15var_5knn | 5.48 | 0.0101 | 7.90 | 0.0034 | 6.344 | 0.001 |
| TC1500007355.hg.1 | AQP9 | 46 | 28 | C3 | 15var_5knn | 9.96 | 0.0158 | 12.34 | 0.0125 | 10.849 | 0.003 |
| TC0800007355.hg.1 | PROK2 | 57 | 28 | C3 | 15var_5knn | 9.88 | 0.0131 | 12.72 | 0.0066 | 10.982 | 0.002 |
| TC1500011517.hg.1 | BCL2A1 | 47 | 28 | C3 | 15var_5knn | 9.10 | 0.0056 | 10.27 | 0.0067 | 9.547 | 0.001 |
| TC1900007859.hg.1 | FFAR2 | 47 | 29 | C4 | 15var_5knn | 8.07 | 0.0221 | 11.86 | 0.0052 | 9.416 | 0.002 |
| TC0800011271.hg.1 | FPR1 | 42 | 27 | C4 | | 6.69 | 0.0352 | 8.30 | 0.0030 | 7.291 | 0.008 |
| TC1100016183.hg.1 | FCGR3B | 41 | 31 | C4 | 15var_5knn | 6.01 | 0.0394 | 10.29 | 0.0090 | 7.455 | 0.006 |
| TC0100016348.hg.1 | IFITM2 | 48 | 15 | C4 | 15var_5knn | 3.95 | 0.0157 | 6.03 | 0.0028 | 4.682 | 0.002 |
| TC1000009866.hg.1 | FCGR1A | 58 | 21 | C5 | | 4.67 | 0.0333 | 6.35 | 0.0134 | 5.279 | 0.006 |
| TC1000008400.hg.1 | IFIT1 | 5 | 2 | C5 | 15var_5knn | 4.77 | 0.0196 | 13.85 | 0.0003 | 7.310 | 0.006 |
| TC0100006483.hg.1 | ISG15 | 10 | 6 | C5 | 15var_5knn | 4.73 | 0.0003 | 8.85 | 0.0000 | 6.073 | 0.000 |
| TC0100013443.hg.1 | IFI6 | 6 | 8 | C5 | | 2.84 | 0.0362 | 4.90 | 0.0220 | 3.534 | 0.004 |
| TC1100012949.hg.1 | IFITM1 | 8 | 3 | C5 | 15var_5knn | 2.79 | 0.0086 | 4.46 | 0.0001 | 3.369 | 0.000 |

FIG. 16A

| TC_ID | Symbol | nCom0.85 | nCom0.9 | cluster | | FC.AvsC | FDR.AvsC | FC.DvsC | FDR.DvsC | BvsC | P.BvsC | DAvsB | P.DAvsB |
|---|---|---|---|---|---|---|---|---|---|---|---|---|---|
| TC1300009807.hg.1 | C3AR1 | 8 | 3 | C1 | | 5.592 | 0.016 | 8.329 | 0.004 | 1.650 | 0.323 | 4.013 | 0.003 |
| TC0200009662.hg.1 | TNFAIP6 | 12 | 2 | C1 | var10_knn5 | 8.716 | 0.022 | 16.832 | 0.004 | 2.002 | 0.296 | 5.665 | 0.004 |
| TC0100016359.hg.1 | SELL | 13 | 10 | C1 | | 5.480 | 0.010 | 7.902 | 0.003 | 2.035 | 0.138 | 3.117 | 0.006 |
| TC0100015856.hg.1 | S100A12 | 6 | 1 | C1 | | 11.013 | 0.012 | 11.102 | 0.018 | 2.951 | 0.117 | 3.744 | 0.026 |
| TC0100010341.hg.1 | FCER1G | 12 | 4 | C1 | | 6.484 | 0.001 | 9.148 | 0.001 | 2.444 | 0.042 | 3.045 | 0.004 |
| TC1000008400.hg.1 | IFIT1 | 4 | 2 | C2 | var10_knn5 | 4.773 | 0.020 | 13.834 | 0.000 | 1.287 | 0.591 | 5.679 | 0.000 |
| TC1000006483.hg.1 | ISG15 | 7 | 5 | C2 | var10_knn5 | 4.732 | 0.000 | 8.849 | 0.000 | 1.623 | 0.118 | 3.746 | 0.000 |
| TC0200016402.hg.1 | RSAD2 | 8 | 4 | C2 | var10_knn5 | 2.817 | 0.032 | 5.241 | 0.001 | 1.053 | 0.877 | 3.429 | 0.000 |
| TC0400012390.hg.1 | DDX60L | 7 | 2 | C3 | | 2.971 | 0.033 | 4.640 | 0.004 | 1.081 | 0.825 | 3.286 | 0.000 |
| TC1200012749.hg.1 | CD163 | 5 | 0 | C3 | var10_knn5 | 3.545 | 0.000 | 4.853 | 0.000 | 1.494 | 0.007 | 2.690 | 0.000 |
| TC1000008397.hg.1 | IFIT3 | 7 | 4 | C4 | var10_knn5 | 3.072 | 0.009 | 5.958 | 0.000 | 1.237 | 0.488 | 3.237 | 0.000 |

FIG. 16B

| TC_ID | Symbol | nCorr.85 | nCorr.90 | Cluster | mod | FL.Aux | FDR.Aux | FL.Disc | FDR.Disc | FL.Abs | FDR.Abs |
|---|---|---|---|---|---|---|---|---|---|---|---|
| TC0300010015.hg.1 | WFDC6 | 39 | 2 | C1 | | -4.57 | 0.0001 | -6.99 | 0.0000 | -5.41 | 0.00001 |
| TC0900008653.hg.1 | MORN5 | 110 | 73 | C1 | | -5.83 | 0.0000 | -7.65 | 0.0000 | -6.50 | 0.00000 |
| TC0200016717.hg.1 | TBC1D8 | 56 | 6 | C2 | | -3.74 | 0.0000 | -4.58 | 0.0000 | -4.06 | 0.00000 |
| TC1200007536.hg.1 | CCDC65 | 74 | 21 | C2 | | -6.96 | 0.0001 | -8.26 | 0.0001 | -7.46 | 0.00000 |
| TC1100010760.hg.1 | AGBL2 | 120 | 76 | C3 | var10_knn5 | -11.68 | 0.0000 | -13.44 | 0.0000 | -12.36 | 0.00000 |
| TC2200010474.hg.1 | KIAA2012 | 103 | 73 | C3 | var10_knn5 | -9.40 | 0.0000 | -9.49 | 0.0001 | -9.44 | 0.00001 |
| TC1400007653.hg.1 | DNAL1 | 22 | 2 | C3 | | -3.85 | 0.0001 | -3.92 | 0.0002 | -3.88 | 0.00001 |
| TC0200016571.hg.1 | OSBPL6 | 9 | 0 | C4 | | -4.00 | 0.0000 | -4.20 | 0.0001 | -4.08 | 0.00001 |
| TC1700008223.hg.1 | DNAH6 | 118 | 98 | C4 | | -10.37 | 0.0000 | -10.29 | 0.0001 | -10.34 | 0.00000 |
| TC1700006173.hg.1 | ANKFN1 | 81 | 17 | C5 | | -6.11 | 0.0000 | -6.32 | 0.0000 | -6.20 | 0.00000 |
| TC0100016173.hg.1 | CFAP126 | 0 | 0 | C5 | | -3.87 | 0.0000 | -2.93 | 0.0003 | -3.46 | 0.00000 |
| TC0600009623.hg.1 | ECT2L | 7 | 0 | C6 | var10_knn5 | -6.81 | 0.0000 | -6.79 | 0.0000 | -6.80 | 0.00000 |
| TC0300011861.hg.1 | LRRC6 | 55 | 9 | C6 | | -5.42 | 0.0001 | -6.46 | 0.0001 | -5.81 | 0.00000 |
| TC0100015436.hg.1 | SPAG17 | 116 | 85 | C7 | var10_knn5 | -11.34 | 0.0000 | -15.36 | 0.0001 | -12.80 | 0.00001 |
| TC0300014062.hg.1 | ANKUB1 | 110 | 69 | C7 | var10_knn5 | -12.26 | 0.0001 | -15.50 | 0.0001 | -13.46 | 0.00001 |
| TC0800008284.hg.1 | HHLA2 | 95 | 47 | C7 | | -11.08 | 0.0001 | -15.49 | 0.0001 | -12.67 | 0.00001 |
| TC0100009408.hg.1 | PIFO | 118 | 94 | C7 | | -11.00 | 0.0000 | -13.27 | 0.0000 | -11.86 | 0.00001 |
| TC0300012778.hg.1 | LMNTD1 | 115 | 85 | C7 | var10_knn5 | -7.92 | 0.0000 | -8.72 | 0.0001 | -8.23 | 0.00000 |
| TC0200008563.hg.1 | VWA3B | 116 | 82 | C7 | | -8.79 | 0.0000 | -11.30 | 0.0000 | -9.72 | 0.00000 |
| TC2200006688.hg.1 | LRRC74B | 103 | 68 | C7 | var10_knn5 | -12.22 | 0.0000 | -11.42 | 0.0001 | -11.69 | 0.00000 |

FIG. 16C

| TC_ID | GeneId | nCorr0.85 | nCorr0.9 | Cluster | | FC AxnC | FDR AxnC | FC DxnC | FDR DxnC | BxC | p.BxC | DAxB | p.DAxB |
|---|---|---|---|---|---|---|---|---|---|---|---|---|---|
| TC22000366668.hg.1 | LRRC74B | 124 | 92 | C3 | | -12.220 | 0.000 | -11.418 | 0.000 | -3.208 | 0.005 | 3.707 | 0.000 |
| TC0400007225.hg.1 | DTHD1 | 128 | 113 | C4 | var5_knn5 | -8.046 | 0.000 | -7.998 | 0.000 | -2.833 | 0.010 | 3.049 | 0.001 |
| TC0100015436.hg.1 | SPAG17 | 128 | 114 | C4 | var5_knn5 | -11.336 | 0.000 | -15.359 | 0.000 | -3.155 | 0.006 | 4.057 | 0.000 |
| TC0500009274.hg.1 | FABP6 | 126 | 105 | C5 | var5_knn5 | -7.439 | 0.000 | -7.827 | 0.000 | -2.458 | 0.007 | 3.088 | 0.000 |
| TC0300013950.hg.1 | EPHB | 130 | 119 | C7 | var5_knn5 | -10.272 | 0.000 | -10.603 | 0.000 | -2.893 | 0.011 | 3.398 | 0.000 |

| Index | Gene Symbol | Avg Pvalue | Stdev Pvalue | Incoming 85 | Incoming 90 | Clusters | A: TBW Avg | B: TBW Avg | C: TBW Avg | D: TBW Avg | A: Linear Avg | B: Linear Avg | C: Linear Avg |
|---|---|---|---|---|---|---|---|---|---|---|---|---|---|
| 1 | TIMP1 | 2.357 | 0.003 | 4 | 0 | CJ | 357.1 | 280.1 | 137.2 | 303.2 | 383.9 | 252.8 | 148.2 |
| 2 | APOBEC3A | 3.987 | 0.002 | 38 | 13 | CJ | 288.0 | 128.9 | 79.3 | 224.0 | 421.9 | 143.3 | 91.9 |
| 3 | LILRA1 | 2.080 | 0.004 | 22 | 3 | CJ | 54.2 | 40.2 | 23.8 | 54.2 | 59.1 | 40.5 | 27.2 |
| 4 | LILRB2 | 2.695 | 0.005 | 37 | 9 | CJ | 167.7 | 113.4 | 62.2 | 146.0 | 283.3 | 126.8 | 65.2 |
| 5 | S100A12 | 11.048 | 0.003 | 35 | 3 | CJ | 572.1 | 136.2 | 44.0 | 433.5 | 1016.5 | 174.3 | 64.2 |
| 6 | SLC7A5 | 2.779 | 0.008 | 31 | 0 | CJ | 52.0 | 53.1 | 22.6 | 65.3 | 80.7 | 49.1 | 30.1 |
| 7 | OLR1 | 3.654 | 0.011 | 6 | 4 | CJ | 120.3 | 65.3 | 28.8 | 117.8 | 196.9 | 60.1 | 47.6 |
| 8 | GPR183 | 3.080 | 0.004 | 10 | 0 | CJ | 74.5 | 45.3 | 23.9 | 64.4 | 108.8 | 47.6 | 31.6 |
| 9 | LILRB1 | 2.161 | 0.002 | 15 | 3 | CJ | 75.1 | 45.9 | 37.8 | 66.3 | 81.0 | 51.9 | 36.7 |
| 10 | MYO1G | 2.323 | 0.003 | 7 | 0 | CJ | 86.2 | 50.6 | 33.1 | 69.6 | 90.6 | 55.0 | 35.8 |
| 11 | DOK2 | 2.365 | 0.003 | 36 | 5 | CJ | 161.0 | 135.3 | 80.4 | 157.6 | 216.7 | 147.9 | 84.2 |
| 12 | EMP3 | 3.100 | 0.001 | 4 | 3 | CJ | 439.8 | 238.9 | 142.0 | 362.0 | 540.5 | 234.4 | 178.6 |
| 13 | CYBB | 2.787 | 0.009 | 13 | 2 | CJ | 243.9 | 121.9 | 85.9 | 224.4 | 273.3 | 112.6 | 98.2 |
| 14 | SP140 | 2.384 | 0.006 | 18 | 0 | CJ | 129.8 | 71.0 | 61.8 | 128.0 | 166.2 | 72.8 | 65.0 |
| 15 | MLXL | 2.315 | 0.004 | 19 | 7 | CJ | 41.4 | 27.3 | 20.5 | 42.5 | 60.9 | 29.6 | 22.7 |
| 16 | DDX60L | 3.531 | 0.004 | 13 | 14 | CJ | 99.0 | 50.2 | 49.9 | 177.3 | 182.3 | 54.6 | 48.5 |
| 17 | FPR3 | 2.495 | 0.003 | 4 | 28 | CJ | 101.8 | 44.9 | 36.5 | 77.7 | 106.9 | 50.8 | 45.9 |
| 18 | MILR1 | 2.452 | 0.000 | 11 | 0 | CJ | 37.0 | 26.2 | 17.1 | 50.2 | 40.9 | 25.1 | 19.3 |
| 19 | CD163 | 4.020 | 0.001 | 6 | 7 | CJ | 324.0 | 157.6 | 89.3 | 439.6 | 344.1 | 138.3 | 98.6 |
| 20 | CXorf21 | 3.661 | 0.000 | 20 | 0 | CJ | 58.9 | 46.9 | 20.4 | 81.6 | 91.8 | 47.1 | 24.4 |
| 21 | TNFSF13B | 5.115 | 0.000 | 46 | 14 | CJ | 116.2 | 66.7 | 27.7 | 173.8 | 170.1 | 68.4 | 32.8 |
| 22 | CCR1 | 5.387 | 0.002 | 49 | 0 | CJ | 184.3 | 105.4 | 43.7 | 168.9 | 287.0 | 116.0 | 55.8 |
| 23 | LGALS1 | 2.256 | 0.004 | 10 | 2 | CJ | 247.3 | 155.4 | 103.4 | 222.9 | 279.5 | 184.4 | 121.6 |
| 24 | SLC15A3 | 2.458 | 0.003 | 22 | 8 | CJ | 172.4 | 97.0 | 80.4 | 176.1 | 219.9 | 103.2 | 82.3 |
| 25 | RELB | 2.358 | 0.003 | 10 | 2 | CJ | 155.4 | 122.8 | 71.0 | 178.5 | 212.2 | 122.1 | 83.8 |
| 26 | FLNA | 2.246 | 0.004 | 43 | 8 | CJ | 135.3 | 98.3 | 67.2 | 182.3 | 182.0 | 97.4 | 77.2 |
| 27 | FCER1G | 7.441 | 0.000 | 53 | 18 | CJ | 922.9 | 418.8 | 145.0 | 891.4 | 1555.8 | 448.0 | 213.0 |

FIG. 17 (Cont.)

| input | Gene Symbol | nlmean.all | rpm.mean.all | nconds.85 | nconds.90 | clusters | D: Linear Avg | A.CV% | B.CV% | C.CV% | D.CV% | A: nDetected_of_9samples | B: nDetected_of_5samples | C: nDetected_of_6samples | D: nDetected_of_6samples | Np nDetected_of_26 |
|---|---|---|---|---|---|---|---|---|---|---|---|---|---|---|---|---|
| 1 | TIMP1 | 2,357 | 0.003 | 2 | 6 | C1 | 335.7 | 41.2 | 35.4 | 34.9 | 49.9 | 9 | 5 | 6 | 6 | 26 |
| 2 | APOBEC3A | 3,987 | 0.002 | 38 | 13 | C1 | 480.0 | 101.6 | 47.4 | 46.6 | 70.9 | 9 | 5 | 6 | 6 | 26 |
| 3 | LILRA1 | 2,080 | 0.004 | 22 | 3 | C1 | 60.5 | 43.4 | 15.1 | 29.4 | 41.3 | 9 | 5 | 6 | 6 | 26 |
| 4 | LILRB2 | 2,695 | 0.005 | 37 | 9 | C1 | 185.4 | 63.3 | 39.2 | 35.7 | 53.8 | 9 | 5 | 6 | 6 | 26 |
| 5 | S100A12 | 11,048 | 0.003 | 35 | 9 | C1 | 1164.9 | 133.7 | 78.5 | 88.9 | 145.1 | 9 | 5 | 6 | 6 | 26 |
| 6 | SLC7A5 | 2,779 | 0.008 | 31 | 3 | C1 | 83.8 | 74.3 | 44.4 | 70.3 | 63.7 | 9 | 5 | 6 | 6 | 26 |
| 7 | OLR1 | 3,654 | 0.031 | 6 | 1 | C1 | 107.7 | 116.5 | 38.7 | 98.1 | 88.5 | 9 | 5 | 6 | 6 | 26 |
| 8 | GPR183 | 3,086 | 0.004 | 10 | 0 | C1 | 92.6 | 80.9 | 42.8 | 68.0 | 75.8 | 9 | 5 | 6 | 6 | 26 |
| 9 | LILRB1 | 2,161 | 0.002 | 15 | 4 | C1 | 84.3 | 38.0 | 27.0 | 27.8 | 48.5 | 9 | 5 | 6 | 6 | 26 |
| 10 | MYO1G | 2,323 | 0.003 | 7 | 0 | C1 | 75.8 | 45.3 | 29.9 | 39.5 | 38.7 | 9 | 5 | 6 | 6 | 26 |
| 11 | DOK2 | 2,365 | 0.003 | 8 | 0 | C2 | 186.6 | 52.6 | 33.7 | 36.1 | 59.4 | 9 | 5 | 6 | 6 | 26 |
| 12 | EMP3 | 3,100 | 0.001 | 4 | 3 | C1 | 516.3 | 65.8 | 37.4 | 64.5 | 48.5 | 9 | 5 | 6 | 6 | 26 |
| 13 | CYBB | 2,787 | 0.009 | 18 | 1 | C1 | 297.4 | 53.9 | 32.9 | 55.0 | 75.6 | 9 | 5 | 6 | 6 | 26 |
| 14 | SP140 | 2,384 | 0.006 | 19 | 0 | C1 | 170.6 | 68.6 | 9.9 | 38.4 | 64.8 | 9 | 5 | 6 | 6 | 26 |
| 15 | MLKL | 2,315 | 0.004 | 11 | 2 | C2 | 48.9 | 51.8 | 36.7 | 32.7 | 48.6 | 9 | 5 | 6 | 6 | 26 |
| 16 | DDX60L | 3,551 | 0.004 | 1 | 0 | C1 | 243.0 | 84.6 | 48.8 | 37.7 | 71.0 | 9 | 5 | 6 | 6 | 26 |
| 17 | FPR3 | 2,495 | 0.009 | 11 | 2 | C1 | 121.0 | 32.9 | 52.1 | 57.0 | 64.9 | 9 | 5 | 6 | 6 | 26 |
| 18 | MILR1 | 2,452 | 0.003 | 8 | 0 | C2 | 66.8 | 45.9 | 28.9 | 36.9 | 64.7 | 9 | 5 | 6 | 6 | 26 |
| 19 | CD163 | 4,020 | 0.008 | 30 | 7 | C2 | 500.7 | 38.8 | 20.9 | 45.4 | 55.1 | 9 | 5 | 6 | 6 | 26 |
| 20 | CXorf21 | 3,663 | 0.001 | 46 | 14 | C2 | 125.6 | 23.4 | 23.4 | 44.6 | 84.4 | 9 | 5 | 6 | 6 | 26 |
| 21 | TNFSF13B | 5,315 | 0.002 | 49 | 20 | C2 | 283.5 | 87.7 | 35.1 | 57.1 | 95.4 | 9 | 5 | 6 | 6 | 26 |
| 22 | CCR1 | 5,387 | 0.004 | 10 | 0 | C2 | 462.7 | 103.5 | 35.0 | 78.6 | 99.2 | 9 | 5 | 6 | 6 | 26 |
| 23 | LGALS1 | 2,256 | 0.002 | 22 | 3 | C2 | 316.4 | 47.6 | 21.5 | 37.0 | 71.2 | 9 | 5 | 6 | 6 | 26 |
| 24 | SLC15A3 | 2,458 | 0.002 | 10 | 2 | C2 | 242.4 | 68.1 | 22.5 | 22.1 | 63.6 | 9 | 5 | 6 | 6 | 26 |
| 25 | RELB | 2,359 | 0.005 | 41 | 8 | C2 | 225.9 | 72.3 | 17.3 | 33.1 | 53.4 | 9 | 5 | 6 | 6 | 26 |
| 26 | FLNA | 2,248 | 0.004 | 4 | 1 | C2 | 192.4 | 67.1 | 14.2 | 35.2 | 35.7 | 9 | 5 | 6 | 6 | 26 |
| 27 | FCER1G | 7,441 | 0.000 | 53 | 16 | C2 | 2159.0 | 107.3 | 45.2 | 87.1 | 94.2 | 9 | 5 | 6 | 6 | 26 |

| Index | Gene Symbol | FC AVG | PDR AVG | norm>0 85 | norm>0 90 | Clusters | A:TBW Avg | B:TBW Avg | C:TBW Avg | D:TBW Avg | A: Linear Avg | B: Linear Avg | C: Linear Avg |
|---|---|---|---|---|---|---|---|---|---|---|---|---|---|
| 28 | LY96 | 4.172 | 0.016 | 19 | 4 | C2 | 80.4 | 45.8 | 26.7 | 98.4 | 178.8 | 42.8 | 27.0 |
| 29 | SLAMF7 | 3.475 | 0.005 | 21 | 5 | C2 | 136.2 | 72.0 | 46.2 | 125.8 | 227.1 | 83.3 | 51.6 |
| 30 | C3AR1 | 6.621 | 0.002 | 31 | 7 | C3 | 62.1 | 26.2 | 14.0 | 111.4 | 196.6 | 30.4 | 19.1 |
| 31 | CCR2 | 4.056 | 0.009 | 26 | 3 | C3 | 203.7 | 85.6 | 68.6 | 335.5 | 441.7 | 107.4 | 85.1 |
| 32 | TNFAIP6 | 11.241 | 0.003 | 39 | 7 | C3 | 238.9 | 58.1 | 25.1 | 467.9 | 606.0 | 61.5 | 54.2 |
| 33 | SELL | 6.344 | 0.001 | 52 | 38 | C3 | 216.8 | 78.2 | 33.1 | 310.8 | 385.3 | 100.2 | 58.9 |
| 34 | LILRB3 | 4.139 | 0.009 | 31 | 16 | C3 | 86.2 | 42.2 | 21.4 | 74.5 | 113.5 | 47.5 | 24.4 |
| 35 | SIGLEC14 | 3.157 | 0.007 | 48 | 26 | C3 | 81.6 | 35.3 | 24.9 | 78.0 | 109.1 | 41.1 | 27.0 |
| 36 | DYSF | 5.771 | 0.009 | 34 | 10 | C3 | 121.9 | 40.8 | 18.9 | 121.1 | 204.2 | 50.7 | 24.1 |
| 37 | LAT2 | 2.261 | 0.008 | 42 | 30 | C3 | 72.3 | 57.7 | 35.5 | 57.7 | 65.5 | 60.1 | 36.3 |
| 38 | CREB5 | 3.878 | 0.004 | 46 | 28 | C3 | 93.1 | 55.7 | 24.9 | 99.7 | 138.1 | 63.7 | 33.1 |
| 39 | MNDA | 6.324 | 0.005 | 51 | 28 | C3 | 97.4 | 34.1 | 9.8 | 51.6 | 143.3 | 45.6 | 24.1 |
| 40 | SAMSN1 | 6.188 | 0.006 | 42 | 23 | C3 | 168.9 | 68.1 | 23.8 | 83.6 | 304.9 | 75.7 | 40.7 |
| 41 | PLEK | 6.794 | 0.006 | 49 | 38 | C3 | 250.7 | 126.2 | 30.5 | 149.1 | 546.9 | 142.3 | 68.2 |
| 42 | CD53 | 4.824 | 0.003 | 51 | 32 | C3 | 653.6 | 321.8 | 155.4 | 471.1 | 1037.8 | 348.1 | 191.2 |
| 43 | FCGR3A | 4.342 | 0.003 | 42 | 32 | C3 | 324.0 | 179.8 | 73.5 | 284.0 | 442.1 | 210.2 | 107.8 |
| 44 | CSF2RB | 3.063 | 0.004 | 49 | 27 | C3 | 159.8 | 110.7 | 56.1 | 115.4 | 252.3 | 117.0 | 66.9 |
| 45 | LINC01272 | 3.474 | 0.024 | 37 | 27 | C3 | 230.7 | 163.1 | 72.0 | 160.9 | 418.2 | 171.9 | 89.0 |
| 46 | PROK2 | 10.922 | 0.002 | 48 | 30 | C3 | 477.7 | 276.3 | 35.5 | 548.7 | 891.7 | 324.6 | 80.3 |
| 47 | SRGN | 5.258 | 0.024 | 46 | 28 | C3 | 404.5 | 190.0 | 77.2 | 310.8 | 748.2 | 230.1 | 130.0 |
| 48 | AQP9 | 10.369 | 0.003 | 47 | 29 | C3 | 421.7 | 166.6 | 37.3 | 458.0 | 792.8 | 203.7 | 104.9 |
| 49 | BCL2A1 | 9.547 | 0.001 | 48 | 27 | C3 | 734.1 | 315.2 | 63.6 | 652.8 | 1148.6 | 333.5 | 158.9 |
| 50 | FFAR2 | 3.416 | 0.002 | 40 | 3 | C3 | 207.9 | 94.4 | 26.2 | 386.6 | 421.8 | 104.5 | 39.0 |
| 51 | FPR1 | 7.291 | 0.008 | 37 | 5 | C3 | 216.8 | 112.2 | 28.4 | 144.0 | 406.9 | 129.4 | 50.2 |
| 52 | CSRNP1 | 2.686 | 0.032 | 15 | 10 | C3 | 83.3 | 52.0 | 36.3 | 117.0 | 139.7 | 62.5 | 41.9 |
| 53 | IER3 | 2.129 | 0.005 | 25 | 5 | C3 | 306.6 | 206.5 | 156.5 | 352.1 | 354.6 | 235.8 | 164.4 |
| 54 | PLAUR | 5.510 | 0.007 | 28 | 10 | C3 | 1176.3 | 515.6 | 205.1 | 1243.3 | 1860.4 | 665.3 | 459.8 |

FIG. 17 (Cont.)

| Gene Symbol | nV/D IQR | nV/D cv | nCtrl 85 | nCtrl 90 | S/N ratio | D: Linear Avg | A: CV% | B: CV% | C: CV% | D: CV% | A: nDetected d_of_5samples | B: nDetected d_of_6samples | C: nDetected d_of_6samples | D: nDetected d_of_6samples | nDetected NP d_of_26 |
|---|---|---|---|---|---|---|---|---|---|---|---|---|---|---|---|
| 28 LY96 | 0.010 | 4.172 | 13 | 4 | 0 | 224.4 | 125.2 | 23.5 | 30.3 | 126.0 | 9 | 5 | 6 | 6 | 26 |
| 29 SLAMF7 | 0.005 | 3.479 | 18 | 5 | 0 | 255.5 | 114.7 | 37.4 | 40.9 | 104.5 | 9 | 5 | 6 | 6 | 26 |
| 30 C3AR1 | 0.002 | 6.621 | 21 | 7 | 0 | 189.7 | 175.6 | 55.7 | 72.0 | 111.6 | 9 | 5 | 4 | 6 | 23 |
| 31 CCR2 | 0.009 | 4.056 | 30 | 13 | 0 | 590.9 | 133.7 | 46.3 | 54.1 | 99.9 | 9 | 5 | 6 | 6 | 26 |
| 32 TNFAIP6 | 0.003 | 11.341 | 26 | 7 | 0 | 816.4 | 150.0 | 36.9 | 126.3 | 102.0 | 9 | 5 | 4 | 6 | 24 |
| 33 SELL | 0.001 | 6.344 | 52 | 33 | 0 | 480.2 | 118.7 | 59.8 | 105.6 | 92.7 | 9 | 5 | 6 | 6 | 26 |
| 34 LURB3 | 0.009 | 4.159 | 39 | 18 | 0 | 194.3 | 75.9 | 36.8 | 47.3 | 120.1 | 9 | 5 | 6 | 6 | 26 |
| 35 SIGLEC14 | 0.007 | 3.157 | 31 | 16 | 0 | 113.6 | 76.0 | 32.7 | 26.1 | 98.9 | 9 | 5 | 6 | 6 | 26 |
| 36 DYSF | 0.005 | 5.771 | 38 | 18 | 0 | 282.8 | 113.8 | 67.9 | 51.4 | 121.9 | 9 | 5 | 6 | 6 | 26 |
| 37 LAT2 | 0.008 | 2.261 | 34 | 18 | 0 | 93.1 | 55.0 | 16.9 | 32.2 | 59.5 | 9 | 5 | 6 | 6 | 26 |
| 38 CREB5 | 0.008 | 3.878 | 40 | 23 | 0 | 190.3 | 81.8 | 45.5 | 70.9 | 96.9 | 9 | 5 | 6 | 6 | 26 |
| 39 MNDA | 0.004 | 6.324 | 48 | 26 | 0 | 145.9 | 94.2 | 70.0 | 142.2 | 103.7 | 9 | 5 | 3 | 6 | 23 |
| 40 SAA2SN1 | 0.006 | 6.158 | 34 | 19 | 0 | 286.4 | 123.1 | 56.9 | 108.3 | 109.0 | 9 | 5 | 6 | 6 | 26 |
| 41 PLEK | 0.003 | 6.784 | 42 | 22 | 0 | 523.6 | 149.0 | 60.1 | 133.1 | 113.4 | 9 | 5 | 6 | 6 | 26 |
| 42 CD53 | 0.005 | 4.824 | 49 | 33 | 0 | 1201.3 | 105.1 | 42.0 | 66.1 | 95.0 | 9 | 5 | 6 | 6 | 26 |
| 43 FCGR2A | 0.014 | 4.342 | 51 | 38 | 0 | 680.7 | 84.4 | 54.8 | 88.2 | 98.0 | 9 | 5 | 6 | 6 | 26 |
| 44 CSF2RB | 0.014 | 3.063 | 48 | 27 | 0 | 258.0 | 99.1 | 27.7 | 53.4 | 88.2 | 9 | 5 | 6 | 6 | 26 |
| 45 LINC01272 | 0.002 | 1.474 | 42 | 27 | 0 | 495.6 | 113.0 | 37.9 | 50.4 | 98.2 | 9 | 5 | 6 | 6 | 26 |
| 46 PROK2 | 0.003 | 10.853 | 37 | 20 | 0 | 1104.9 | 118.9 | 58.9 | 136.6 | 109.6 | 9 | 5 | 6 | 6 | 26 |
| 47 SRGN | 0.001 | 5.238 | 49 | 36 | 0 | 666.0 | 111.3 | 68.3 | 129.3 | 100.5 | 9 | 5 | 5 | 6 | 25 |
| 48 AQP9 | 0.003 | 10.649 | 46 | 28 | 0 | 921.8 | 116.0 | 61.1 | 154.8 | 103.0 | 9 | 5 | 6 | 6 | 26 |
| 49 BCL2A1 | 0.001 | 9.547 | 47 | 28 | 0 | 1347.8 | 134.8 | 53.8 | 149.2 | 103.8 | 9 | 5 | 6 | 6 | 26 |
| 50 FFAR2 | 0.002 | 9.416 | 42 | 27 | 0 | 611.3 | 100.9 | 51.1 | 98.5 | 101.8 | 9 | 5 | 4 | 5 | 25 |
| 51 FPR1 | 0.008 | 7.291 | 37 | 9 | 0 | 556.6 | 122.6 | 60.9 | 110.9 | 115.0 | 9 | 5 | 6 | 6 | 26 |
| 52 CSRNP1 | 0.012 | 2.686 | 16 | 5 | 0 | 137.6 | 107.4 | 46.3 | 33.2 | 119.6 | 9 | 5 | 4 | 6 | 24 |
| 53 IER2 | 0.005 | 2.129 | 25 | 3 | 0 | 376.2 | 51.2 | 35.6 | 33.6 | 62.4 | 9 | 5 | 5 | 6 | 25 |
| 54 PLAUR | 0.007 | 5.536 | 18 | 10 | 0 | 1919.6 | 104.7 | 84.0 | 150.3 | 98.9 | 9 | 5 | 6 | 6 | 26 |

| Index | Gene Symbol | H.pval | low.pval | incomo85 | incomo90 | Clusters | A:TBW Avg | B:TBW Avg | C:TBW Avg | D:TBW Avg | A:Linear Avg | B:Linear Avg | C:Linear Avg |
|---|---|---|---|---|---|---|---|---|---|---|---|---|---|
| 55 | FCGR3B | 7.455 | 0.006 | 44 | 21 | C4 | 359.5 | 162.3 | 46.2 | 356.4 | 512.0 | 243.7 | 93.6 |
| 56 | FCGR3A | 6.393 | 0.005 | 44 | 24 | C4 | 179.8 | 88.0 | 25.8 | 257.8 | 227.4 | 108.7 | 47.5 |
| 57 | ARHGAP25 | 2.626 | 0.008 | 39 | 11 | C4 | 48.5 | 23.4 | 18.0 | 41.6 | 59.1 | 24.0 | 21.1 |
| 58 | EVI2A | 3.673 | 0.003 | 49 | 21 | C4 | 29.9 | 16.2 | 8.8 | 32.4 | 40.0 | 17.2 | 10.3 |
| 59 | IFITM2 | 4.682 | 0.002 | 46 | 15 | C4 | 537.5 | 308.7 | 187.4 | 617.4 | 961.0 | 383.3 | 191.8 |
| 60 | CD48 | 4.024 | 0.007 | 39 | 19 | C4 | 104.7 | 58.9 | 32.9 | 97.0 | 201.2 | 59.6 | 38.5 |
| 61 | RAC2 | 3.112 | 0.009 | 43 | 23 | C4 | 195.4 | 128.9 | 81.0 | 158.7 | 287.3 | 152.1 | 83.7 |
| 62 | WAS | 3.283 | 0.013 | 38 | 27 | C4 | 170.1 | 78.8 | 60.1 | 112.2 | 260.2 | 119.8 | 69.5 |
| 63 | COTL1 | 2.449 | 0.008 | 49 | 38 | C4 | 150.1 | 121.9 | 73.0 | 163.1 | 207.5 | 123.9 | 80.1 |
| 64 | FCGR1A | 5.279 | 0.006 | 53 | 21 | C4 | 58.0 | 34.1 | 15.8 | 98.4 | 134.4 | 41.1 | 24.0 |
| 65 | AIF1 | 4.199 | 0.006 | 37 | 11 | C4 | 354.8 | 200.9 | 78.2 | 284.0 | 537.5 | 214.9 | 107.2 |
| 66 | GMFG | 4.652 | 0.008 | 46 | 27 | C4 | 734.2 | 369.6 | 151.2 | 522.8 | 980.3 | 404.9 | 210.9 |
| 67 | PTPRC | 4.173 | 0.009 | 41 | 24 | C4 | 1060.1 | 596.3 | 266.9 | 849.2 | 1514.8 | 623.7 | 377.2 |
| 68 | CORO1A | 2.937 | 0.009 | 56 | 28 | C4 | 217.4 | 177.3 | 103.3 | 215.3 | 366.1 | 171.9 | 117.4 |
| 69 | MX2 | 2.868 | 0.002 | 10 | 2 | C3 | 166.6 | 93.7 | 70.5 | 296.1 | 211.3 | 89.8 | 81.1 |
| 70 | IFIT1 | 7.310 | 0.002 | 3 | 0 | C3 | 116.2 | 25.6 | 29.4 | 413.0 | 159.6 | 37.8 | 32.3 |
| 71 | ISG15 | 6.079 | 0.001 | 10 | 6 | C3 | 661.7 | 187.4 | 113.0 | 1217.7 | 640.3 | 280.3 | 125.7 |
| 72 | IFIT2 | 5.026 | 0.002 | 11 | 6 | C3 | 229.1 | 110.7 | 63.6 | 582.2 | 281.6 | 91.9 | 75.5 |
| 73 | IFIT3 | 4.004 | 0.001 | 10 | 6 | C3 | 843.4 | 347.3 | 205.0 | 1734.1 | 1005.8 | 354.3 | 322.3 |
| 74 | RSAD2 | 3.611 | 0.003 | 8 | 5 | C3 | 104.7 | 45.3 | 43.7 | 243.9 | 147.1 | 47.8 | 46.7 |
| 75 | OASL | 2.668 | 0.004 | 6 | 4 | C3 | 151.2 | 75.6 | 74.5 | 319.6 | 162.5 | 79.1 | 75.2 |
| 76 | IFI6 | 3.334 | 0.004 | 10 | 5 | C3 | 501.5 | 235.6 | 150.1 | 885.3 | 539.7 | 254.9 | 164.6 |
| 77 | IFITM3 | 3.380 | 0.008 | 8 | 2 | C3 | 1807.8 | 873.1 | 626.0 | 2402.0 | 1794.0 | 977.1 | 671.2 |
| 78 | IFITM1 | 3.369 | 0.000 | 8 | 2 | C3 | 2049.0 | 803.4 | 613.1 | 2646.7 | 1783.8 | 959.9 | 803.1 |
| 79 | ISG20 | 2.203 | 0.001 | 2 | 0 | C5 | 541.2 | 284.1 | 259.6 | 530.1 | 534.0 | 284.3 | 246.8 |

FIG. 17 (Cont.)

| Index | Gene Symbol | AVG_Ct | AVG_Ct SD | nconc 85 | nconc 90 | Cluster | D: Linear Avg | A: Ct% | B: Ct% | C: Ct% | D: Ct% | A: nDetected of_9 samples | B: nDetected of_5 samples | C: nDetected of_6 samples | D: nDetected of_6 samples | NP nDetected of_26 |
|---|---|---|---|---|---|---|---|---|---|---|---|---|---|---|---|---|
| 55 | FCGR3B | 7.455 | 0.006 | 40 | 22 | C4 | 930.7 | 95.9 | 84.3 | 124.7 | 99.6 | 9 | 5 | 6 | 6 | 26 |
| 56 | FCGR2A | 6.385 | 0.005 | 41 | 24 | C4 | 504.9 | 77.1 | 67.6 | 109.5 | 113.5 | 9 | 5 | 5 | 6 | 25 |
| 57 | ARHGAP25 | 2.866 | 0.028 | 33 | 11 | C4 | 54.4 | 64.9 | 31.0 | 54.5 | 61.5 | 9 | 5 | 4 | 6 | 24 |
| 58 | EVI2A | 3.673 | 0.003 | 46 | 21 | C4 | 44.4 | 70.7 | 41.5 | 59.4 | 78.4 | 8 | 3 | 1 | 6 | 18 |
| 59 | IFITM2 | 4.682 | 0.002 | 46 | 15 | C4 | 1538.5 | 95.2 | 61.6 | 38.5 | 54.2 | 9 | 5 | 6 | 6 | 26 |
| 60 | CD48 | 4.024 | 0.007 | 33 | 20 | C4 | 230.4 | 143.6 | 31.8 | 56.0 | 104.8 | 9 | 5 | 6 | 6 | 26 |
| 61 | RAC2 | 3.112 | 0.009 | 43 | 23 | C4 | 393.5 | 98.9 | 31.8 | 40.5 | 97.7 | 9 | 5 | 6 | 6 | 26 |
| 62 | WAS | 3.283 | 0.013 | 38 | 27 | C4 | 252.6 | 82.9 | 47.0 | 54.8 | 98.7 | 9 | 5 | 6 | 6 | 26 |
| 63 | COTL1 | 2.443 | 0.008 | 40 | 28 | C4 | 212.0 | 67.0 | 22.6 | 45.4 | 58.3 | 9 | 5 | 6 | 6 | 26 |
| 64 | FCGR1A | 5.179 | 0.006 | 53 | 21 | C4 | 191.0 | 75.8 | 56.0 | 59.5 | 113.4 | 9 | 5 | 6 | 4 | 24 |
| 65 | AIF1 | 4.199 | 0.006 | 37 | 11 | C4 | 450.1 | 92.1 | 47.1 | 43.4 | 98.0 | 9 | 5 | 6 | 6 | 26 |
| 66 | GMFG | 4.652 | 0.008 | 46 | 27 | C4 | 1154.8 | 93.2 | 42.5 | 73.9 | 101.8 | 9 | 5 | 6 | 6 | 26 |
| 67 | PTPRC | 4.173 | 0.009 | 41 | 24 | C4 | 1493.5 | 90.8 | 38.4 | 87.2 | 83.8 | 9 | 5 | 6 | 6 | 26 |
| 68 | CORO1A | 2.937 | 0.009 | 50 | 30 | C5 | 381.2 | 65.0 | 29.4 | 82.8 | 81.3 | 9 | 5 | 6 | 6 | 26 |
| 69 | MX2 | 2.868 | 0.008 | 18 | 2 | C5 | 284.8 | 50.7 | 24.8 | 54.3 | 42.5 | 9 | 5 | 6 | 6 | 25 |
| 70 | IFIT1 | 7.310 | 0.002 | 5 | 2 | C5 | 599.7 | 64.7 | 54.2 | 42.3 | 101.2 | 9 | 5 | 6 | 6 | 26 |
| 71 | ISG15 | 6.079 | 0.008 | 10 | 6 | C5 | 1236.1 | 48.7 | 33.1 | 61.5 | 55.6 | 9 | 5 | 6 | 6 | 26 |
| 72 | IFIT2 | 5.026 | 0.002 | 24 | 6 | C5 | 739.1 | 66.9 | 29.4 | 40.3 | 69.8 | 9 | 5 | 6 | 6 | 26 |
| 73 | IFIT3 | 4.034 | 0.001 | 11 | 6 | C5 | 1893.1 | 58.0 | 25.0 | 62.3 | 51.5 | 9 | 5 | 6 | 6 | 26 |
| 74 | RSAD2 | 3.611 | 0.003 | 10 | 2 | C5 | 300.8 | 86.4 | 30.4 | 61.7 | 71.6 | 9 | 5 | 6 | 6 | 26 |
| 75 | OASL | 2.668 | 0.004 | 8 | 6 | C5 | 361.0 | 44.6 | 22.2 | 39.3 | 57.9 | 9 | 5 | 6 | 6 | 25 |
| 76 | IFI6 | 3.534 | 0.008 | 10 | 4 | C5 | 836.5 | 62.5 | 38.5 | 45.0 | 46.1 | 9 | 5 | 6 | 6 | 26 |
| 77 | IFITM3 | 3.380 | 0.009 | 8 | 0 | C5 | 2624.0 | 35.1 | 41.2 | 51.1 | 23.8 | 9 | 5 | 6 | 6 | 26 |
| 78 | IFITM1 | 3.169 | 0.008 | 2 | 2 | C5 | 2736.3 | 33.8 | 36.6 | 46.1 | 22.5 | 9 | 5 | 6 | 6 | 26 |
| 79 | ISG20 | 2.202 | 0.001 | 3 | 0 | C5 | 598.5 | 30.3 | 13.8 | 27.9 | 41.6 | 9 | 5 | 6 | 6 | 26 |

| Index | Symbol | FC DAWG | pv DAWG | ncomo 85 | ncomo 90 | clusters | A.CV% | B.CV% | C.CV% | D.CV% | A: nDetecte d_of_9sa mples | B: nDetecte d_of_5sa mples | C: nDetecte d_of_6sa mples | D: nDetecte d_of_6sa mples | Np. nDetecte d_of_26 |
|---|---|---|---|---|---|---|---|---|---|---|---|---|---|---|---|
| 29 | C1orf158 | -7.07 | 0.00001 | 75 | 80 | C3 | 44.0 | 69.8 | 61.9 | 53.2 | 5 | 5 | 6 | 5 | 21 |
| 99 | CFAP57 | -12.27 | 0.00001 | 110 | 79 | C7 | 89.1 | 77.1 | 67.8 | 79.0 | 4 | 5 | 6 | 3 | 18 |
| 15 | PALMD | -5.36 | 0.00000 | 68 | 8 | C0 | 50.9 | 57.2 | 54.9 | 52.9 | 9 | 5 | 6 | 6 | 26 |
| 116 | PIFO | -11.86 | 0.00001 | 118 | 94 | C2 | 97.3 | 59.5 | 52.6 | 93.1 | 9 | 5 | 6 | 6 | 26 |
| 97 | PPOX | -3.10 | 0.00001 | 102 | 49 | C1 | 38.5 | 33.1 | 38.9 | 22.7 | 9 | 5 | 6 | 6 | 28 |
| 26 | FMO3 | -6.50 | 0.00001 | 71 | 11 | C4 | 49.1 | 44.6 | 44.2 | 46.7 | 5 | 5 | 6 | 6 | 26 |
| 19 | SPATA17 | -3.34 | 0.00001 | 104 | 59 | C1 | 41.2 | 27.1 | 33.1 | 27.3 | 8 | 5 | 6 | 2 | 18 |
| 25 | STPG1 | -4.18 | 0.00000 | 60 | 8 | C0 | 29.9 | 32.6 | 27.2 | 42.7 | 9 | 5 | 6 | 6 | 26 |
| 73 | BEST4 | -4.18 | 0.00001 | 10 | 0 | C0 | 29.0 | 34.3 | 64.8 | 44.1 | 3 | 5 | 6 | 6 | 24 |
| 65 | CCDC17 | -3.39 | 0.00001 | 83 | 33 | C4 | 32.0 | 28.4 | 50.2 | 21.8 | 3 | 5 | 6 | 6 | 26 |
| 69 | C1orf87 | -5.16 | 0.00001 | 67 | 13 | C0 | 42.7 | 50.9 | 73.8 | 46.5 | 9 | 5 | 6 | 3 | 28 |
| 36 | WDR78 | -8.22 | 0.00001 | 93 | 56 | C7 | 78.2 | 51.8 | 55.8 | 62.4 | 3 | 5 | 6 | 1 | 17 |
| 108 | SPAG17 | -12.80 | 0.00001 | 118 | 85 | C2 | 81.0 | 68.3 | 63.9 | 93.9 | 3 | 5 | 6 | 0 | 15 |
| 77 | CFAP126 | -3.46 | 0.00000 | 0 | 0 | C1 | 39.8 | 14.7 | 36.9 | 33.1 | 2 | 5 | 4 | 1 | 26 |
| 41 | APOBEC4 | -4.95 | 0.00001 | 69 | 29 | C3 | 63.4 | 70.3 | 41.8 | 47.3 | 3 | 5 | 4 | 1 | 13 |
| 12 | CCDC30 | -5.42 | 0.00000 | 44 | 5 | C3 | 55.1 | 51.8 | 65.5 | 42.5 | 5 | 4 | 4 | 1 | 14 |
| 98 | CFAP45 | 5.36 | 0.00001 | 105 | 71 | C7 | 57.0 | 51.2 | 48.9 | 50.9 | 5 | 5 | 5 | 4 | 25 |
| 2 | ORC1 | -5.34 | 0.00001 | 99 | 55 | C1 | 60.2 | 47.1 | 33.3 | 36.1 | 9 | 5 | 5 | 4 | 19 |
| 82 | FAM179A | -3.65 | 0.00000 | 9 | 1 | C6 | 27.6 | 34.0 | 55.5 | 26.6 | 9 | 5 | 5 | 5 | 28 |
| 53 | DNAH6 | -10.34 | 0.00001 | 118 | 98 | C4 | 78.1 | 45.5 | 47.6 | 68.6 | 7 | 3 | 5 | 2 | 23 |
| 127 | VWA3B | -9.72 | 0.00001 | 116 | 82 | C7 | 59.3 | 70.3 | 36.6 | 49.6 | 9 | 5 | 5 | 5 | 22 |
| 113 | CFAP221 | -8.85 | 0.00001 | 117 | 89 | C7 | 80.4 | 59.0 | 71.8 | 68.7 | 6 | 5 | 5 | 0 | 16 |
| 33 | KIAA2012 | 9.44 | 0.00000 | 103 | 78 | C1 | 52.1 | 100.5 | 60.2 | 58.7 | 3 | 5 | 5 | 5 | 22 |
| 18 | IGFBP2 | -3.67 | 0.00001 | 77 | 12 | C6 | 34.5 | 40.8 | 42.1 | 27.6 | 9 | 5 | 5 | 6 | 26 |
| 134 | IFT172 | 5.63 | 0.00001 | 117 | 82 | C7 | 57.2 | 47.1 | 45.9 | 59.3 | 9 | 5 | 5 | 6 | 28 |
| 131 | TSGA10 | -6.53 | 0.00001 | 101 | 59 | C7 | 80.9 | 49.3 | 44.7 | 62.5 | 5 | 5 | 5 | 3 | 19 |

| Index | Symbol | PC DAWG | NORM DAWG | ncorm 85 | ncorm 90 | Clusters | FAM179A | LRRC6 | BTG4 | STK33 | STX2 | RSPH14 | DNAI1 | DNAH3 | CFAP45 | SPAG6 |
|---|---|---|---|---|---|---|---|---|---|---|---|---|---|---|---|---|
| 71 | ALS2CR12 | -4.24 | 0.00000 | 5 | 86 | C3 | 0.692 | 0.708 | 0.734 | 0.781 | 0.708 | 0.695 | 0.812 | 0.761 | 0.745 | 0.800 |
| 60 | MDH1B | -4.98 | 0.00000 | 106 | 84 | C4 | 0.769 | 0.854 | 0.809 | 0.874 | 0.857 | 0.863 | | | | |
| 54 | CFAP65 | -4.21 | 0.00001 | 113 | 84 | C4 | 0.862 | 0.868 | 0.833 | 0.865 | 0.807 | 0.828 | | | 0.843 | |
| 43 | OSBPL6 | -4.08 | 0.00001 | 9 | 6 | C2 | 0.773 | 0.786 | 0.809 | 0.813 | 0.703 | 0.771 | 0.812 | 0.793 | 0.752 | 0.869 |
| 19 | TBCID8 | -4.06 | 0.00000 | 56 | 75 | C3 | 0.638 | 0.726 | 0.694 | 0.767 | 0.737 | 0.722 | 0.852 | 0.863 | 0.813 | |
| 126 | MAP3K19 | -7.11 | 0.00000 | 108 | 77 | C7 | 0.798 | 0.840 | 0.789 | 0.830 | 0.849 | 0.879 | | | 0.877 | |
| 133 | DLEC1 | -6.93 | 0.00000 | 107 | 47 | C2 | 0.847 | 0.854 | 0.848 | 0.825 | 0.834 | 0.868 | 0.860 | 0.854 | 0.819 | |
| 115 | HMJA2 | -12.67 | 0.00000 | 95 | 38 | C5 | 0.733 | 0.833 | 0.814 | 0.833 | 0.724 | 0.822 | 0.818 | 0.815 | 0.771 | 0.827 |
| 18 | MAATS1 | -6.43 | 0.00000 | 82 | 9 | C3 | 0.734 | 0.753 | 0.718 | 0.850 | 0.800 | 0.684 | | | | |
| 72 | MLF1 | -4.78 | 0.00000 | 29 | 91 | C7 | 0.664 | 0.773 | 0.759 | 0.797 | 0.813 | 0.683 | | | 0.882 | |
| 92 | NEK10 | -12.87 | 0.00000 | 117 | 48 | C3 | 0.795 | 0.845 | 0.808 | 0.865 | 0.826 | 0.831 | | | | 0.821 |
| 68 | ASB14 | -6.88 | 0.00000 | 88 | 82 | C4 | 0.732 | 0.793 | 0.805 | 0.882 | 0.817 | 0.843 | 0.769 | 0.809 | 0.767 | 0.836 |
| 56 | DNAH12 | -9.11 | 0.00000 | 111 | 1 | C7 | 0.847 | 0.897 | 0.826 | 0.849 | 0.795 | 0.870 | 0.844 | 0.846 | 0.791 | |
| 74 | KIAA1257 | -3.88 | 0.00000 | 9 | 43 | C3 | 0.575 | 0.827 | 0.802 | 0.788 | 0.692 | 0.764 | | | | |
| 44 | NME9 | -3.75 | 0.00000 | 18 | 82 | C4 | 0.770 | 0.871 | 0.847 | 0.729 | 0.665 | 0.821 | | | 0.869 | |
| 103 | LRRC34 | -9.10 | 0.00000 | 115 | 87 | C7 | 0.820 | 0.885 | 0.817 | 0.850 | 0.868 | 0.875 | 0.851 | 0.871 | 0.856 | |
| 108 | CFH8 | -10.40 | 0.00000 | 117 | 90 | C7 | 0.799 | 0.848 | 0.760 | 0.880 | 0.877 | 0.854 | | | | |
| 110 | ANKUB1 | -13.46 | 0.00000 | 110 | 86 | C7 | 0.765 | 0.827 | 0.710 | 0.863 | 0.871 | 0.805 | | | | |
| 17 | PLCH1 | -2.81 | 0.00000 | 89 | 55 | C7 | 0.787 | 0.764 | 0.820 | 0.801 | 0.779 | 0.707 | 0.767 | 0.792 | 0.743 | 0.796 |
| 95 | CC2D2A | -4.12 | 0.00000 | 116 | 84 | C7 | 0.774 | 0.851 | 0.804 | 0.837 | 0.799 | 0.839 | 0.844 | 0.809 | 0.751 | 0.808 |
| 93 | DTHD1 | -8.03 | 0.00001 | 117 | 85 | C7 | 0.792 | 0.835 | 0.835 | 0.867 | 0.847 | 0.833 | 0.870 | 0.888 | 0.876 | 0.861 |
| 78 | C4orf47 | -3.07 | 0.00000 | 4 | 83 | C3 | 0.732 | 0.868 | 0.817 | 0.810 | 0.756 | 0.742 | 0.830 | 0.823 | 0.789 | |
| 102 | C4orf22 | 8.26 | 0.00000 | 115 | 88 | C7 | 0.814 | 0.852 | 0.751 | 0.863 | 0.830 | 0.819 | | | | 0.899 |
| 14 | ROPN1L | -8.03 | 0.00000 | 82 | 11 | C1 | 0.694 | 0.841 | 0.821 | 0.783 | 0.827 | 0.822 | 0.851 | 0.871 | 0.849 | |
| 69 | SPEF2 | -4.07 | 0.00000 | 37 | 17 | C3 | 0.675 | 0.745 | 0.802 | 0.805 | 0.654 | 0.773 | | | | |
| 108 | FABP6 | -7.59 | 0.00000 | 109 | 86 | C3 | 0.823 | 0.859 | 0.762 | 0.821 | 0.851 | 0.853 | | | | |
| 5 | DNAH5 | -6.58 | 0.00001 | 97 | 46 | C1 | 0.788 | 0.819 | 0.752 | 0.778 | 0.841 | 0.830 | | | | |

| Index | Symbol | FC.DAvsC | FDR.DAvsC | ncono.85 | ncono.90 | clusters | A.C[%] | B.C[%] | C.C[%] | D.C[%] | A: nDetecte d_of_9sa mples | B: nDetecte d_of_5sa mples | C: nDetecte d_of_6sa mples | D: nDetecte d_of_6sa mples | NP: nDetecte d_of_26 |
|---|---|---|---|---|---|---|---|---|---|---|---|---|---|---|---|
| 43 | OSBPL6 | -4.08 | 0.00001 | 9 | 0 | C4 | 66.1 | 47.4 | 35.4 | 29.1 | 1 | 3 | 3 | 0 | 12 |
| 19 | TBC1D8 | -4.06 | 0.00000 | 96 | 6 | C2 | 44.5 | 27.9 | 56.7 | 24.5 | 9 | 5 | 5 | 0 | 26 |
| 126 | MAP3K19 | -7.11 | 0.00000 | 108 | 70 | C7 | 70.4 | 54.8 | 54.7 | 71.5 | 8 | 5 | 3 | 0 | 22 |
| 133 | DLEC1 | -6.93 | 0.00001 | 107 | 77 | C7 | 69.9 | 38.6 | 29.5 | 68.9 | 9 | 5 | 5 | 0 | 25 |
| 115 | HHLA2 | -12.67 | 0.00001 | 96 | 47 | C7 | 145.8 | 46.7 | 79.9 | 61.3 | 3 | 5 | 1 | 0 | 15 |
| 16 | MAATS1 | -6.43 | 0.00000 | 82 | 8 | C2 | 31.0 | 29.0 | 71.9 | 56.9 | 0 | 0 | 0 | 0 | 0 |
| 72 | MLF1 | -4.78 | 0.00000 | 26 | 30 | C5 | 34.6 | 34.5 | 42.8 | 29.0 | 3 | 5 | 5 | 0 | 13 |
| 92 | NEK10 | -12.87 | 0.00001 | 117 | 91 | C7 | 85.3 | 51.3 | 65.9 | 85.3 | 6 | 5 | 5 | 0 | 22 |
| 66 | ASB14 | -6.68 | 0.00000 | 88 | 45 | C4 | 71.6 | 49.0 | 42.6 | 33.6 | 3 | 5 | 2 | 0 | 16 |
| 56 | DNAH12 | -9.11 | 0.00001 | 131 | 82 | C4 | 31.7 | 67.3 | 60.1 | 66.4 | 9 | 5 | 6 | 0 | 28 |
| 74 | KIAA1257 | -3.88 | 0.00000 | 9 | 1 | C3 | 32.4 | 36.6 | 43.5 | 40.9 | 9 | 5 | 5 | 0 | 26 |
| 44 | NME9 | -3.75 | 0.00000 | 18 | 3 | C4 | 86.4 | 39.1 | 47.3 | 27.4 | 4 | 5 | 5 | 0 | 28 |
| 105 | LRRC34 | -9.10 | 0.00001 | 115 | 87 | CD | 60.5 | 68.5 | 53.3 | 96.9 | 7 | 5 | 5 | 0 | 20 |
| 108 | EFHB | -10.40 | 0.00001 | 117 | 90 | C4 | 94.5 | 79.1 | 71.7 | 93.5 | 6 | 5 | 6 | 0 | 23 |
| 110 | ANKUB1 | -13.46 | 0.00001 | 110 | 88 | C7 | 32.3 | 58.3 | 47.4 | 92.8 | 9 | 5 | 6 | 0 | 23 |
| 17 | RLCH1 | -2.91 | 0.00000 | 89 | 32 | C2 | 48.2 | 17.3 | 28.3 | 43.9 | 5 | 5 | 5 | 0 | 26 |
| 95 | CC20ZA | -4.12 | 0.00001 | 116 | 84 | C4 | 69.3 | 37.5 | 47.8 | 34.2 | 5 | 5 | 5 | 0 | 21 |
| 93 | OTHD1 | -8.03 | 0.00000 | 117 | 85 | CD | 27.5 | 38.6 | 72.8 | 61.4 | 6 | 5 | 5 | 0 | 26 |
| 78 | C4orf47 | -3.07 | 0.00001 | 4 | 0 | C5 | 75.2 | 17.1 | 51.6 | 22.4 | 9 | 5 | 5 | 0 | 21 |
| 102 | C4orf22 | -8.26 | 0.00001 | 115 | 88 | C5 | 66.9 | 59.6 | 55.2 | 71.2 | 5 | 5 | 5 | 0 | 26 |
| 14 | ROPN1L | -6.03 | 0.00000 | 82 | 17 | C3 | 23.9 | 65.7 | 47.9 | 39.4 | 9 | 5 | 5 | 0 | 21 |
| 69 | SPEF2 | -4.07 | 0.00001 | 37 | 0 | C5 | 47.3 | 43.1 | 80.2 | 21.2 | 9 | 5 | 5 | 0 | 26 |
| 106 | FABP6 | -7.39 | 0.00001 | 109 | 88 | CD | 78.6 | 76.5 | 61.8 | 47.8 | 9 | 5 | 5 | 0 | 26 |
| 5 | DNAH5 | -6.58 | 0.00001 | 97 | 49 | C1 | 78.6 | 66.1 | 55.3 | 63.5 | 8 | 5 | 5 | 0 | 24 |

| index | GeneId | bvsC | pvalueBvsC | BvsB | pvalueBvsB | ncomB5 | ncomB3 | cluster | A.CV% | B.CV% | C.CV% | D.CV% | A: nDetecte d_of_9sa mples | B: nDetecte d_of_6sa mples | C: nDetecte d_of_6sa mples | D: nDetecte d_of_6sa mples | nDetecte d_of_26 |
|---|---|---|---|---|---|---|---|---|---|---|---|---|---|---|---|---|---|
| 1 | DNAI1 | -2.436 | 0.010 | -2.758 | 0.001 | 63 | 60 | C1 | 73.2 | 39.8 | 42.7 | 52.9 | 9 | 5 | 6 | 6 | 26 |
| 2 | DNAH6 | -3.841 | 0.001 | -2.788 | 0.003 | 66 | 60 | C1 | 76.1 | 45.5 | 47.6 | 60.2 | 7 | 5 | 6 | 5 | 23 |
| 3 | SPAG6 | -2.748 | 0.008 | -2.689 | 0.002 | 66 | 62 | C1 | 70.8 | 45.7 | 59.5 | 60.3 | 8 | 5 | 6 | 5 | 24 |
| 4 | NEK10 | -3.180 | 0.006 | -2.792 | 0.001 | 68 | 62 | C1 | 85.3 | 51.3 | 65.9 | 83.3 | 6 | 5 | 6 | 5 | 22 |
| 5 | DTHD1 | -2.633 | 0.010 | -1.887 | 0.001 | 65 | 62 | C1 | 69.3 | 38.6 | 72.8 | 61.4 | 5 | 5 | 6 | 5 | 21 |
| 6 | DNAH3 | -3.136 | 0.001 | -3.049 | 0.001 | 66 | 58 | C1 | 68.4 | 58.5 | 64.9 | 46.4 | 9 | 5 | 6 | 6 | 26 |
| 7 | CFAP43 | -2.409 | 0.004 | -2.585 | 0.004 | 65 | 58 | C1 | 57.0 | 51.2 | 49.9 | 50.9 | 4 | 5 | 6 | 2 | 23 |
| 8 | CFAP47 | -3.623 | 0.008 | -2.220 | 0.004 | 66 | 59 | C1 | 63.0 | 81.3 | 58.3 | 45.2 | 3 | 5 | 6 | 6 | 17 |
| 9 | DNAJB13 | -2.793 | 0.002 | -3.662 | 0.006 | 65 | 53 | C1 | 57.1 | 58.4 | 46.9 | 60.4 | 9 | 5 | 6 | 6 | 26 |
| 10 | LMNTD1 | -3.662 | 0.009 | -2.289 | 0.001 | 64 | 59 | C1 | 55.3 | 51.4 | 63.8 | 60.3 | 5 | 5 | 6 | 3 | 18 |
| 11 | LRRC48 | -3.208 | 0.005 | -3.707 | 0.008 | 60 | 50 | C1 | 69.5 | 86.2 | 77.5 | 50.5 | 4 | 5 | 6 | 5 | 26 |
| 12 | CFAP157 | -3.059 | 0.002 | -3.277 | 0.005 | 63 | 58 | C2 | 65.2 | 42.3 | 60.2 | 43.3 | 2 | 4 | 6 | 1 | 13 |
| 13 | AGBL2 | -4.076 | 0.004 | -3.012 | 0.001 | 65 | 49 | C2 | 63.8 | 53.5 | 74.7 | 72.9 | 4 | 5 | 6 | 3 | 15 |
| 14 | KIAA2012 | -3.656 | 0.018 | -2.302 | 0.001 | 67 | 48 | C2 | 52.1 | 100.5 | 60.2 | 58.7 | 3 | 5 | 6 | 6 | 17 |
| 15 | FBXO15 | -3.251 | 0.001 | -2.467 | 0.001 | 63 | 39 | C2 | 56.5 | 82.2 | 52.7 | 76.3 | 9 | 5 | 6 | 6 | 26 |
| 16 | APOBEC4 | -2.239 | 0.001 | -2.116 | 0.001 | 61 | 57 | C3 | 60.4 | 70.3 | 41.8 | 47.3 | 4 | 4 | 6 | 4 | 26 |
| 17 | TEX26 | -2.346 | 0.008 | -3.004 | 0.001 | 63 | 42 | C3 | 62.8 | 71.0 | 57.0 | 38.5 | 2 | 2 | 6 | 4 | 21 |
| 18 | WDR78 | -3.567 | 0.001 | -2.806 | 0.008 | 63 | 46 | C3 | 79.2 | 51.8 | 55.8 | 62.4 | 9 | 4 | 6 | 5 | 26 |
| 19 | DCDC5 | -2.751 | 0.003 | -2.488 | 0.002 | 66 | 65 | C3 | 41.0 | 46.7 | 65.7 | 46.6 | 6 | 3 | 6 | 6 | 26 |
| 20 | NEK5 | -1.905 | 0.003 | -2.117 | 0.001 | 59 | 37 | C3 | 32.1 | 41.9 | 58.1 | 40.1 | 7 | 6 | 6 | 4 | 24 |
| 21 | AGDB | -3.381 | 0.001 | -2.103 | 0.002 | 55 | 22 | C4 | 53.5 | 72.0 | 54.3 | 72.2 | 6 | 9 | 6 | 5 | 22 |
| 22 | CCDC81 | -3.299 | 0.008 | -3.076 | 0.003 | 66 | 60 | C4 | 62.7 | 76.5 | 39.6 | 53.6 | 9 | 5 | 6 | 4 | 28 |
| 23 | CASC1 | -3.074 | 0.001 | -2.476 | 0.001 | 58 | 55 | C4 | 67.8 | 49.8 | 48.8 | 49.4 | 9 | 5 | 6 | 5 | 21 |
| 24 | DNAH12 | -3.998 | 0.001 | -3.278 | 0.013 | 64 | 55 | C4 | 71.1 | 62.3 | 60.1 | 66.4 | 8 | 5 | 6 | 5 | 26 |
| 25 | DNAH10 | -2.886 | 0.008 | -3.171 | 0.003 | 65 | 58 | C4 | 55.8 | 41.5 | 39.5 | 29.8 | 8 | 5 | 6 | 6 | 23 |

| index | Gene id | Bvsc | pvalue.Bvsc | DAvsB | pvalue.DAvsB | ncorr.85 | ncorr.9 | cluster | FC:TBW DAvsC | A:TBW Avg | B:TBW Avg | C:TBW Avg | D:TBW Avg | A:Linear Avg | B:Linear Avg | C:Linear Avg | D:Linear Avg |
|---|---|---|---|---|---|---|---|---|---|---|---|---|---|---|---|---|---|
| 51 | LRRC34 | -2.653 | 0.017 | -3.433 | 0.001 | 66 | 61 | C6 | -10.832 | 16.3 | 63.8 | 165.6 | 14.4 | 29.4 | 83.0 | 203.2 | 24.0 |
| 52 | TSPAN19 | -2.975 | 0.001 | -2.464 | 0.002 | 66 | 56 | C6 | -6.467 | 8.5 | 19.8 | 54.6 | 8.3 | 9.3 | 27.1 | 88.1 | 10.8 |
| 53 | CCDC65 | -2.924 | 0.002 | -2.550 | 0.001 | 48 | 11 | C6 | -8.361 | 5.9 | 19.2 | 44.6 | 4.9 | 9.2 | 21.9 | 64.3 | 7.7 |
| 54 | HHLA2 | -3.488 | 0.002 | -3.652 | 0.003 | 57 | 34 | C6 | -15.182 | 8.5 | 40.8 | 115.2 | 6.9 | 18.1 | 39.2 | 158.8 | 8.8 |
| 55 | DNAH5 | -2.780 | 0.006 | -2.386 | 0.005 | 65 | 49 | C6 | -7.043 | 24.4 | 49.9 | 151.2 | 18.5 | 32.0 | 65.9 | 180.4 | 23.8 |
| 56 | MORN3 | -2.576 | 0.003 | -2.524 | 0.003 | 65 | 53 | C6 | -6.076 | 38.3 | 74.5 | 186.1 | 22.9 | 38.0 | 84.3 | 218.2 | 27.7 |
| 57 | CCDC146 | -2.715 | 0.002 | -2.128 | 0.001 | 64 | 38 | C6 | -5.401 | 63.8 | 122.8 | 303.7 | 48.5 | 76.7 | 140.3 | 399.5 | 68.8 |
| 58 | MAP3K19 | -2.681 | 0.001 | -2.651 | 0.003 | 60 | 34 | C6 | -8.018 | 16.1 | 44.3 | 114.6 | 12.5 | 22.6 | 50.8 | 136.2 | 17.3 |
| 59 | VWA3B | -3.447 | 0.003 | -2.809 | 0.001 | 59 | 59 | C6 | -9.339 | 23.4 | 46.2 | 208.5 | 18.1 | 27.1 | 70.4 | 218.3 | 20.4 |
| 60 | LRRC43 | -2.317 | 0.003 | -2.500 | 0.003 | 65 | 58 | C6 | -4.818 | 72.5 | 188.7 | 415.9 | 72.5 | 97.6 | 203.3 | 454.6 | 83.7 |
| 61 | TSGA10 | -2.606 | 0.002 | -2.388 | 0.003 | 66 | 42 | C6 | -6.189 | 14.0 | 38.1 | 98.4 | 14.8 | 20.2 | 43.5 | 110.4 | 17.8 |
| 62 | C11orf88 | -2.546 | 0.005 | -2.115 | 0.002 | 63 | 58 | C6 | -4.616 | 18.5 | 41.6 | 112.2 | 17.8 | 22.5 | 44.3 | 114.1 | 21.7 |
| 63 | DLEC1 | -2.370 | 0.010 | -2.923 | 0.001 | 65 | 57 | C6 | -4.658 | 26.5 | 92.8 | 210.8 | 37.3 | 38.4 | 99.8 | 231.5 | 40.9 |
| 64 | IFT172 | -2.307 | 0.007 | -2.442 | 0.007 | 66 | 60 | C6 | -5.598 | 88.6 | 212.3 | 464.6 | 77.7 | 105.0 | 230.9 | 526.0 | 90.0 |
| 65 | EFHC1 | -3.039 | 0.003 | -2.988 | 0.004 | 66 | 62 | C6 | -8.631 | 25.5 | 88.6 | 240.5 | 30.3 | 38.5 | 98.2 | 297.0 | 35.3 |
| 66 | CFAP54 | -3.134 | 0.003 | -2.762 | 0.003 | 66 | 58 | C6 | -9.680 | 12.0 | 39.1 | 117.0 | 12.1 | 18.1 | 46.0 | 145.3 | 19.2 |
| 67 | CETN2 | -3.154 | 0.008 | -2.333 | 0.001 | 66 | 59 | C6 | -4.763 | 209.4 | 508.5 | 1067.5 | 238.9 | 252.1 | 543.8 | 1112.9 | 267.6 |

| index | geneId | bAvgC | pvalueBvgC | bAvgB | pvalueBvgB | ncorro.as | ncorro.g | cluster | A.CV% | B.CV% | C.CV% | D.CV% | A. nDetecte d_of_9sa mples | B. nDetecte d_of_5sa mples | C. nDetecte d_of_6sa mples | D. nDetecte d_of_26 mples |
|---|---|---|---|---|---|---|---|---|---|---|---|---|---|---|---|---|
| 51 | LRRC34 | -2.651 | 0.017 | -3.403 | 0.001 | 66 | 63 | C8 | 86.4 | 68.3 | 53.3 | 56.9 | 4 | 5 | 6 | 20 |
| 52 | TSPAN19 | -2.975 | 0.001 | -2.464 | 0.002 | 66 | 58 | C7 | 41.3 | 71.7 | 102.1 | 56.1 | 2 | 4 | 6 | 13 |
| 53 | CCDC65 | -2.924 | 0.002 | -3.550 | 0.002 | 48 | 11 | C7 | 71.4 | 56.1 | 74.4 | 70.4 | 2 | 4 | 6 | 13 |
| 54 | HHLA2 | -3.488 | 0.006 | -3.692 | 0.001 | 57 | 34 | C7 | 145.8 | 46.7 | 79.9 | 61.3 | 3 | 5 | 6 | 15 |
| 55 | DNAH5 | -2.760 | 0.003 | -3.986 | 0.003 | 60 | 39 | C7 | 78.6 | 66.1 | 55.3 | 63.5 | 8 | 5 | 6 | 24 |
| 56 | MORN5 | -2.576 | 0.002 | -2.534 | 0.003 | 65 | 53 | C7 | 46.9 | 49.1 | 49.7 | 45.4 | 9 | 5 | 6 | 26 |
| 57 | CCDC146 | -2.715 | 0.001 | -3.124 | 0.003 | 62 | 38 | C7 | 57.7 | 31.3 | 46.1 | 63.9 | 9 | 5 | 6 | 26 |
| 58 | MAP3K19 | -2.681 | 0.003 | -2.651 | 0.001 | 65 | 54 | C7 | 70.4 | 54.8 | 54.7 | 71.5 | 8 | 5 | 6 | 22 |
| 59 | VWA3B | -3.447 | 0.000 | -2.819 | 0.000 | 66 | 58 | C8 | 59.3 | 70.3 | 38.6 | 49.6 | 9 | 5 | 6 | 22 |
| 60 | LRRC49 | -2.317 | 0.005 | -2.184 | 0.001 | 65 | 58 | C7 | 66.6 | 45.5 | 34.8 | 51.5 | 5 | 5 | 6 | 26 |
| 61 | TSGA10 | -2.606 | 0.006 | -2.504 | 0.002 | 66 | 47 | C8 | 80.8 | 49.3 | 44.7 | 62.5 | 6 | 5 | 6 | 19 |
| 62 | C11orf88 | -2.540 | 0.002 | -2.113 | 0.003 | 65 | 58 | C8 | 57.0 | 42.2 | 43.9 | 56.1 | 5 | 5 | 6 | 22 |
| 63 | DLEC1 | -2.370 | 0.010 | -2.923 | 0.000 | 65 | 57 | C8 | 69.9 | 38.6 | 29.5 | 68.9 | 6 | 5 | 6 | 25 |
| 64 | IFT172 | -2.307 | 0.007 | -2.442 | 0.001 | 66 | 60 | C8 | 57.2 | 47.1 | 45.9 | 59.3 | 5 | 5 | 6 | 26 |
| 65 | EFHC1 | -3.039 | 0.004 | -2.988 | 0.002 | 66 | 62 | C8 | 87.3 | 51.6 | 53.0 | 69.4 | 8 | 5 | 6 | 24 |
| 66 | CFAP54 | -3.124 | 0.003 | -2.762 | 0.002 | 66 | 58 | C8 | 72.7 | 53.7 | 57.8 | 85.0 | 3 | 5 | 6 | 19 |
| 67 | CSTN2 | -2.154 | 0.008 | -3.233 | 0.001 | 66 | 59 | C8 | 62.1 | 44.1 | 25.6 | 51.1 | 9 | 5 | 6 | 26 |

…

NASAL GENES USED TO IDENTIFY, CHARACTERIZE, AND DIAGNOSE VIRAL RESPIRATORY INFECTIONS

CROSS REFERENCE TO RELATED APPLICATIONS

This application claims the benefit of International Patent Application number PCT/US2019/035673, filed Jun. 5, 2019, which claims the benefit of U.S. Provisional Application No. 62/812,026, filed Feb. 28, 2019 and the benefit of U.S. Provisional Application No. 62/680,800, filed Jun. 5, 2018, the disclosures of which are herein incorporated by reference in their entirety.

GOVERNMENTAL RIGHTS

This invention was made with government support under HHSN272201200005C awarded by the National Institutes of Health. The government has certain rights in the invention.

FIELD OF THE TECHNOLOGY

This present disclosure provides for rapid molecular testing performed on host samples that allow for detection of viral and other respiratory infections. This approach overcomes many of the limitations of current methods allowing the determination of the etiology of respiratory symptoms which aids in making treatment decisions.

BACKGROUND

Acute respiratory illnesses are extremely common, accounting for more than 500 million outpatient illnesses and 3.6 million hospitalizations per year in the U.S. and impose massive economic burden on health services. Respiratory tract infections, or acute respiratory infections (ARI) caused 3.2 million deaths around the world and 164 million disability-adjusted life years lost in 2011, more than any other cause. The diagnosis of upper respiratory infection is typically made based on review of symptoms, physical examination, and occasionally, laboratory tests. Although viral infections cause a majority of ARI it remains a significant challenge to diagnose a viral infection as the diagnosis is often one of exclusion, since current tests to rule in viral infection are often prohibitive in cost and time. The ability to rapidly diagnose the etiology of ARIs is an urgent global problem with far-reaching consequences at multiple levels: optimizing treatment for individual patients; epidemiological surveillance to identify and track outbreaks; and guiding appropriate use of antimicrobials to stem the rising tide of antimicrobial resistance. It has been well established that early and appropriate antimicrobial therapy improves outcomes in patients with serious bacterial infection. This in part drives the over-utilization of antimicrobial therapies. This leads to the caused by viruses. A further limitation of diagnostics that use the paradigm of testing for specific viruses or bacteria is that even though a pathogenic microbe may be detected, this is not proof that the patient's symptoms are due to the detected pathogen. A microorganism may be present as part of the individual's normal flora, known as colonization, or it may be detected due to contamination of the tested sample (e.g., a nasal swab or wash).

Therefore, a need in the art exists for a practical and reliable test to guide physicians and patients in the decision-making process during suspected respiratory infection.

BRIEF DESCRIPTION OF THE FIGURES

The application file contains at least one drawing executed in color. Copies of this patent application publication with color drawing(s) will be provided by the Office upon request and payment of the necessary fee.

(FIG. 1A) Principal component analysis shows that microarray chips from blood and nasal RNAs are separated with greater variability across samples in nasal compared to blood samples. The analysis used quantile-normalized log 2 signal data for all genes. (FIG. 1B) RNA integrity numbers (RINs) are higher for blood than for nasal RNAs. (FIG. 1C) Chip signal-to-noise ratio is correlated with RIN for nasal but not for blood RNAs. (FIG. 1D) The percent of detectable genes from blood and nasal RNAs are generally comparable, substantial, and independent of the RIN. Detectable genes were from among the 28,476 well annotated transcript clusters (27,823 genes) with an Entrez gene ID that had signal greater than the mean+1 standard deviation of the chip negative control probes.

(FIG. 4A) Expression profiles of 157 marker genes in the nasal samples. (FIG. 4B) The DSA (digital sorting algorithm)-estimated proportion of signal contributed by epithelial and hematopoietic cells for each of the 26 nasal samples. The numbers in the vertical bar on the right are the mean nasal/blood signal proportions for each of the four subject groups.

(FIG. 5A) RSV, (FIG. 5B) Symptomatic nRSV, (FIG. 5C) Asymptomatic RV, (FIG. 5D) RSV and nRSV combined. Comparisons are shown for matched blood and nasal data sets. These genes were among the fine-filtered 19,837 protein-coding transcript clusters (19,655 genes). In the heat map, each row represents a transcript cluster and each column is an individual study subject. The values used in the heat map were z-score normalized signals from log 2 intensity data. Within the Venn diagram, the digits in parenthesis show the number of up- and down-regulated genes, displayed before and after the slash respectively.

In FIG. 6A, a total of 36 biological process terms were selected for display that included the most highly enriched terms in either or both blood and nasal samples. These terms were arranged in nine functional groups. The percent of genes enriched is represented by the horizontal bars, and adjusted P values <0.05 are shown by colored circles. In FIG. 6B, a total of 44 biological process terms were selected for display that included the most highly enriched terms in either or both blood and nasal samples. These terms were arranged in 17 functional groups including 10 specific for nasal genes. The percent of genes enriched is represented by the horizontal bars, and adjusted P values <0.05 are shown by colored circles.

(FIG. 8A) The signal correlation between qRT-PCR and microarray was analyzed for each gene using the Spearman correlation test, and (FIG. 8B) Concordance between signal fold-change measured by qRT-PCR and microarray regression r value is shown in each plot. Each gene is represented by a dot. Each gene was analyzed separately for each of 5 between-group comparisons, which are indicated with different colors.

FIG. 10A, FIG. 10B, and FIG. 10C depict comparison between pre- and post DSA-adjusted data sets of the number of differentially expressed genes and expression profiles of the union of 4928 genes from 3 between-group comparisons of nRSV, asRV, and RSV each versus negative control subjects. (FIG. 10A) Number of differentially expressed genes before and after DSA adjustment (counted within the 28476 TCs); (FIG. 10B and FIG. 10C) Expression profiles of the 4928 genes before and after DSA adjustment. DSA: "digital sorting algorithm" for cell type-specific signal intensity adjustment on large-scale genomics data (28).

(FIG. 11A) Venn diagrams showing the total number (union) of genes with increased or decreased signal intensity from each of the three comparisons, the number of those genes from each comparison, the number of those genes that overlapped between blood and nasal samples, and the number of those genes unique for blood or nasal samples. The numbers in parentheses within the Venn ovals are for genes with increased/decreased mean signal intensity. (FIG. 11B) Heat maps displaying the total number of genes with increased or decreased mean signal intensity from the three comparisons using gene-wise z-score-normalized signal values for the four groups of study subjects. (FIG. 11C) Heat maps displaying the same genes shown in panel B using categorized log 2 fold-change values. Each heat map represents a comparison between two groups. Blood and nasal gene comparisons are shown separately. Genes with no significant difference in the comparison were assigned a value of 1 (log 2=0) (gray color).

FIG. 14 shows an exemplary gene signature which includes 24 genes that are increased during symptomatic and symptomatic versus asymptomatic viral infections.

Figure 15:
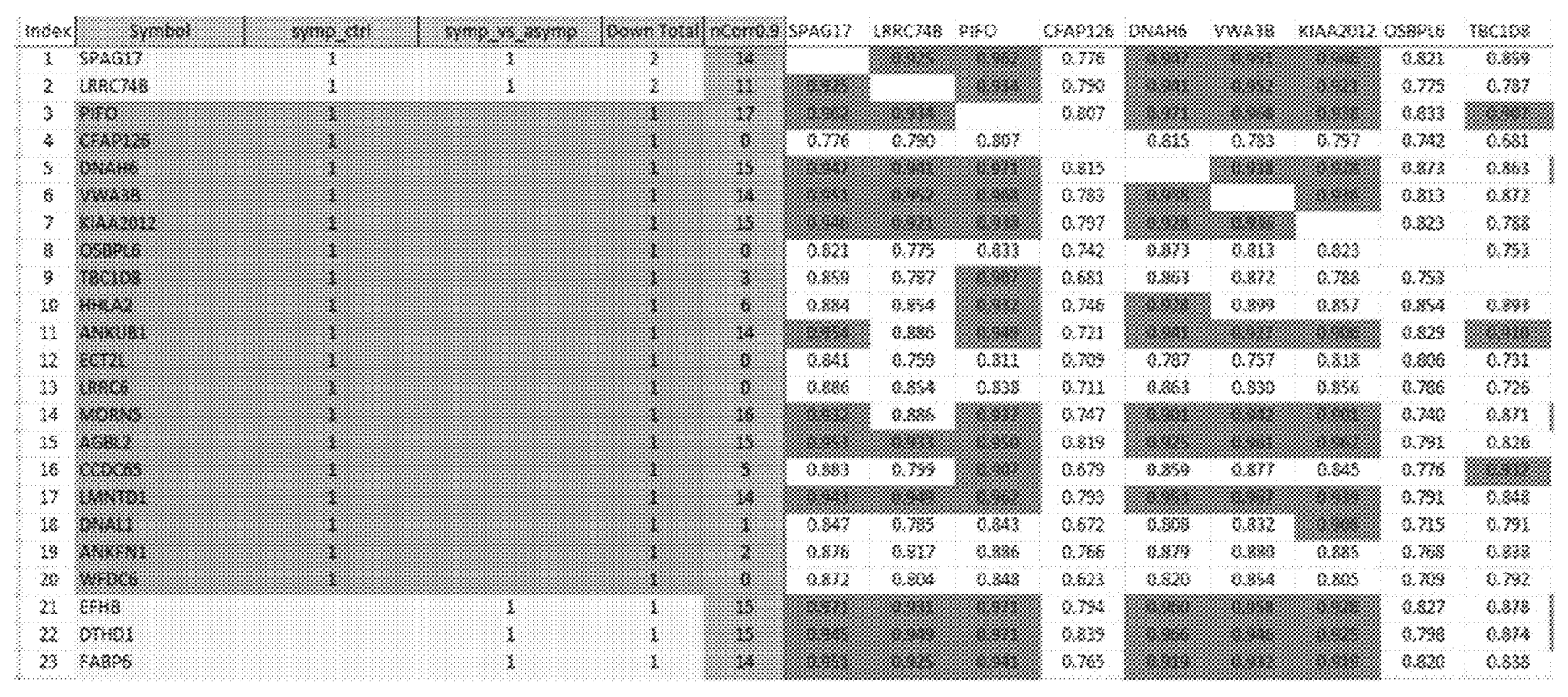
Figure 15:
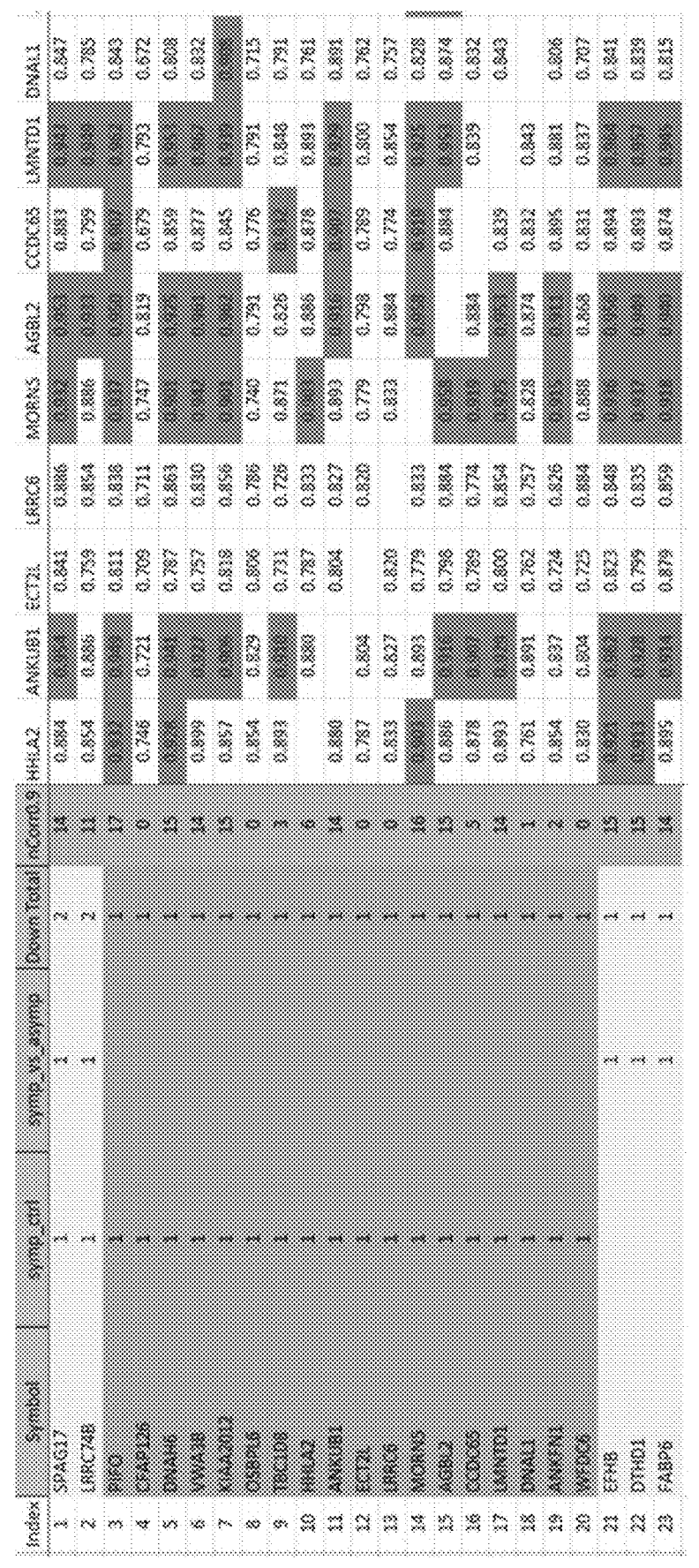
Figure 15:
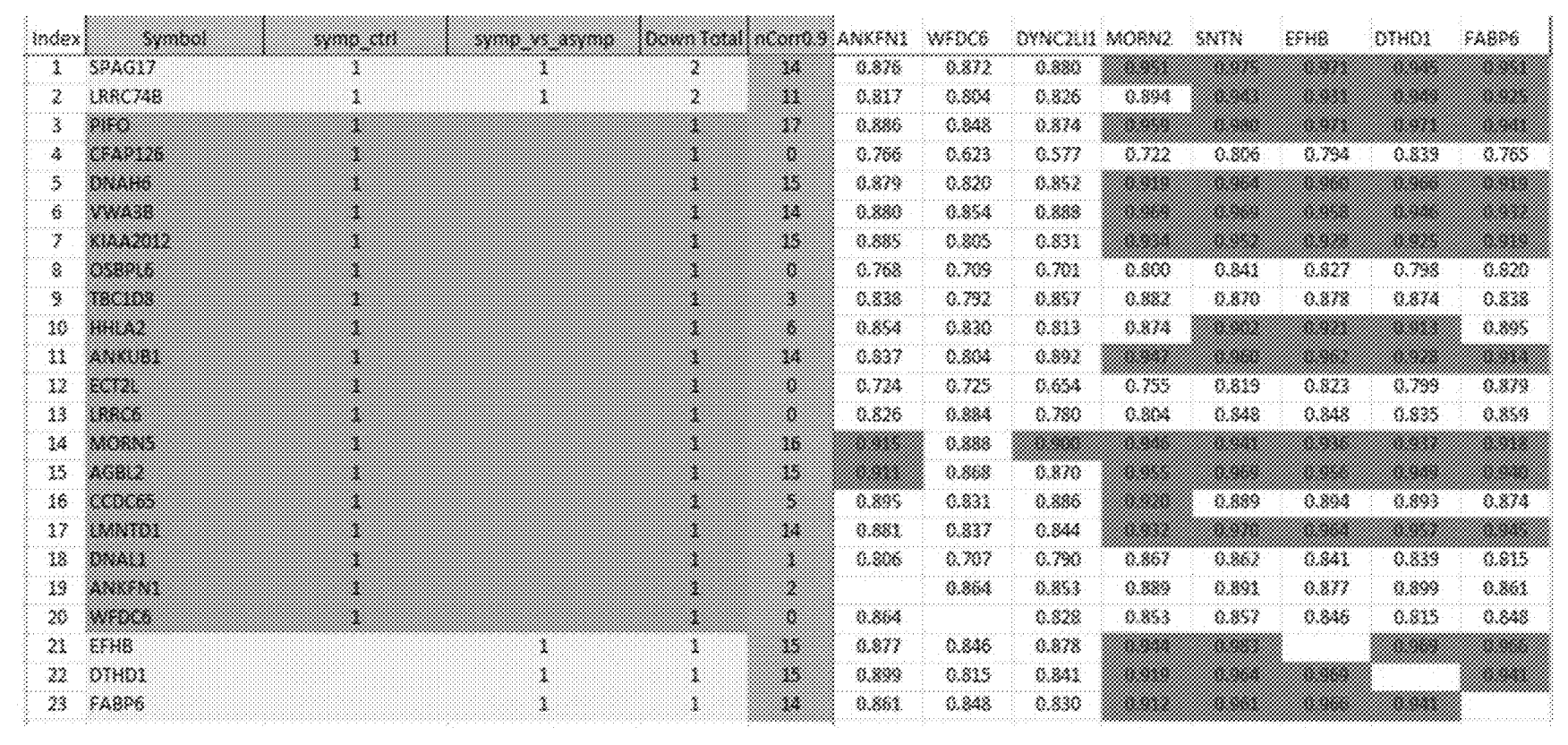
Figure 15:
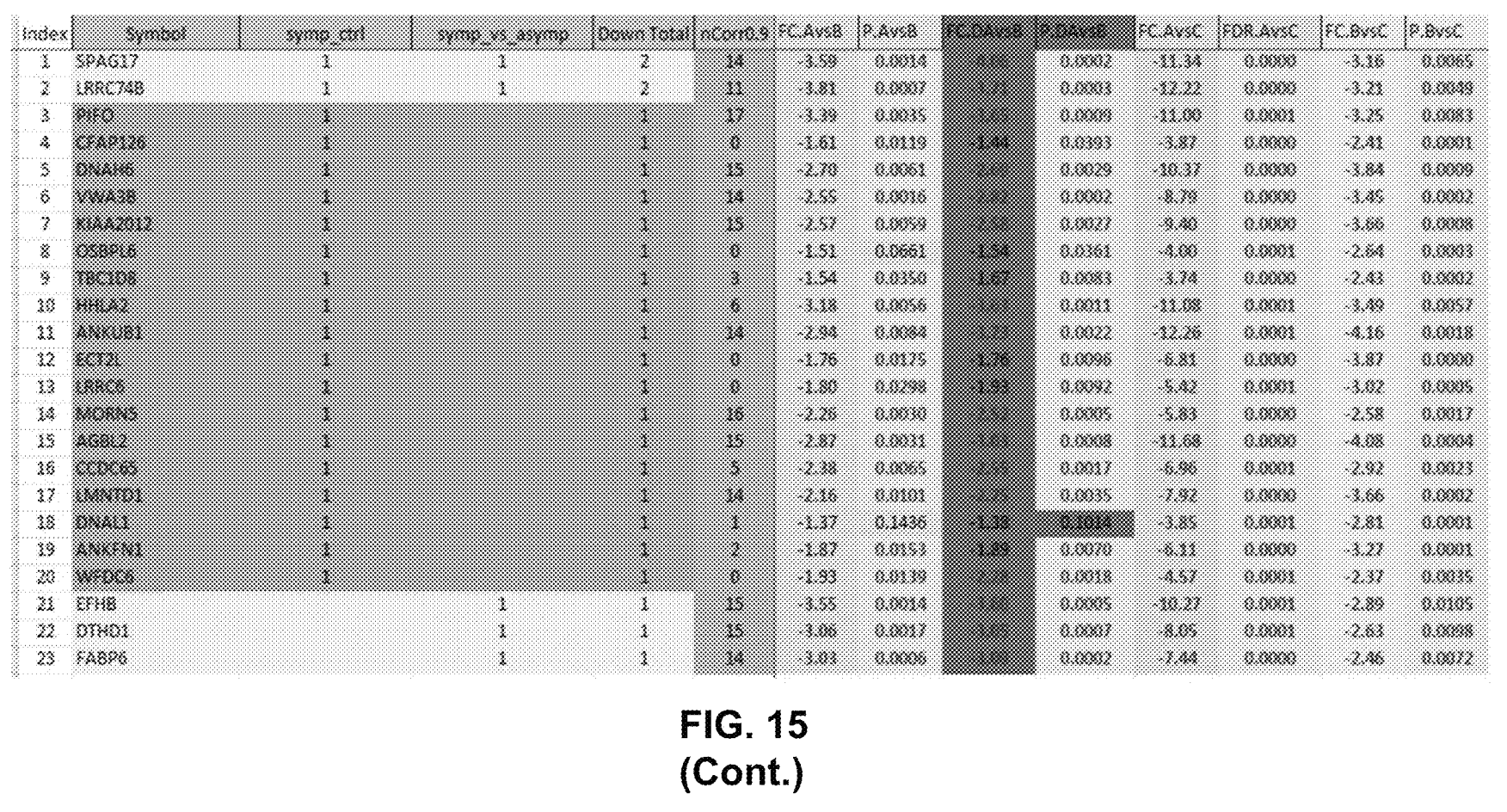
Figure 15:
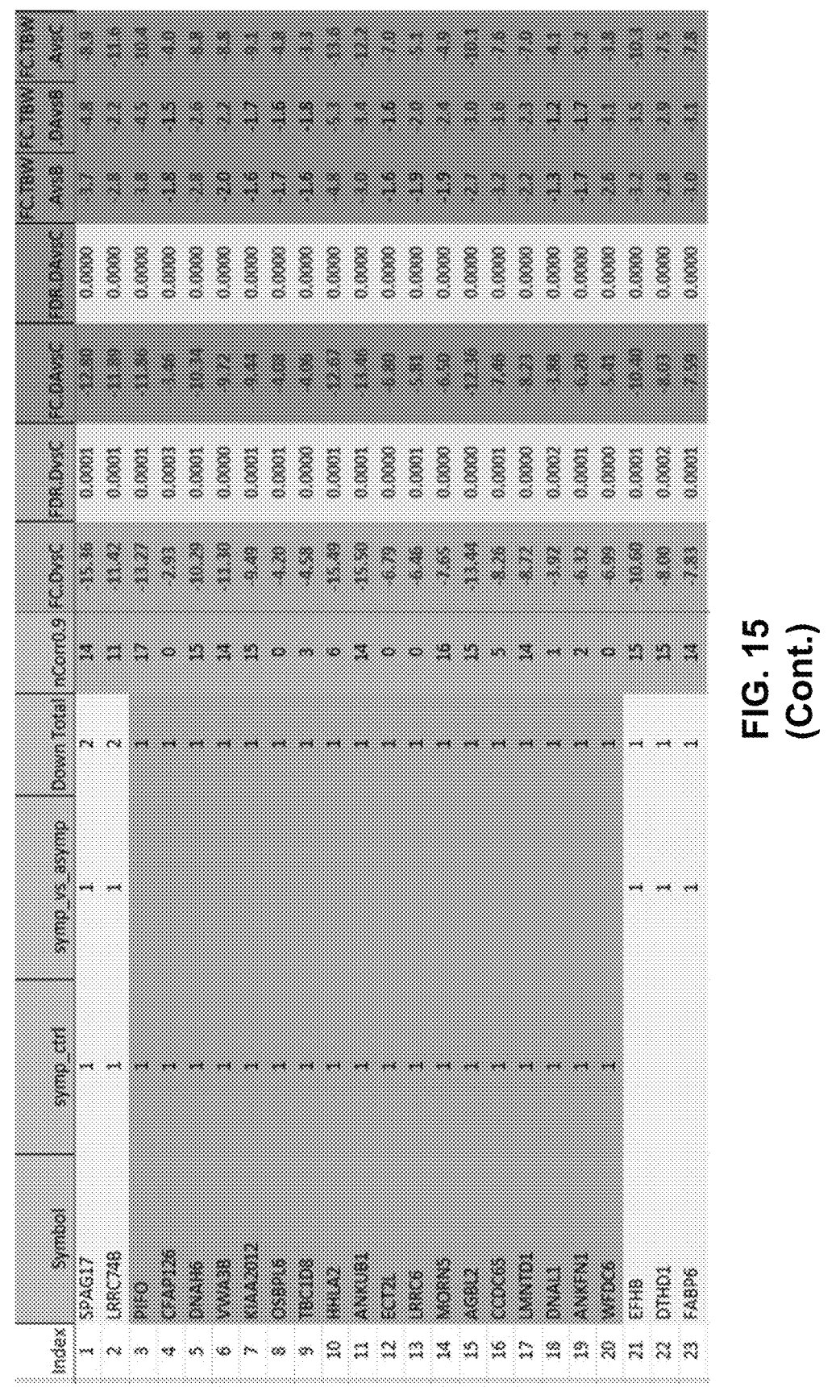
Figure 15:
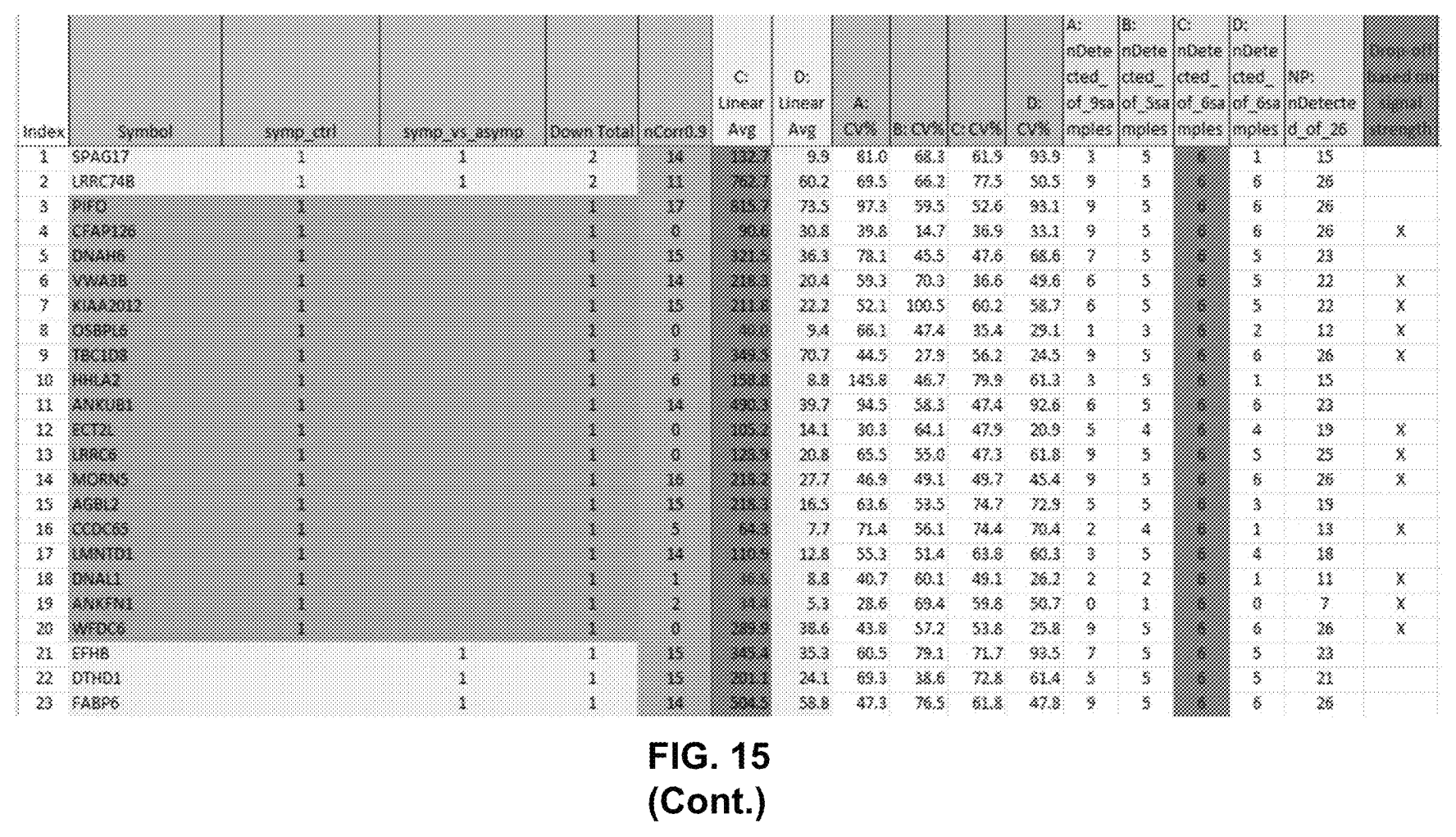

FIG. 15 shows four exemplary gene signatures including select genes.

FIG. 16 shows an exemplary gene signature which includes 23 genes that are decreased during symptomatic and symptomatic versus asymptomatic viral infections.

Figure 17:
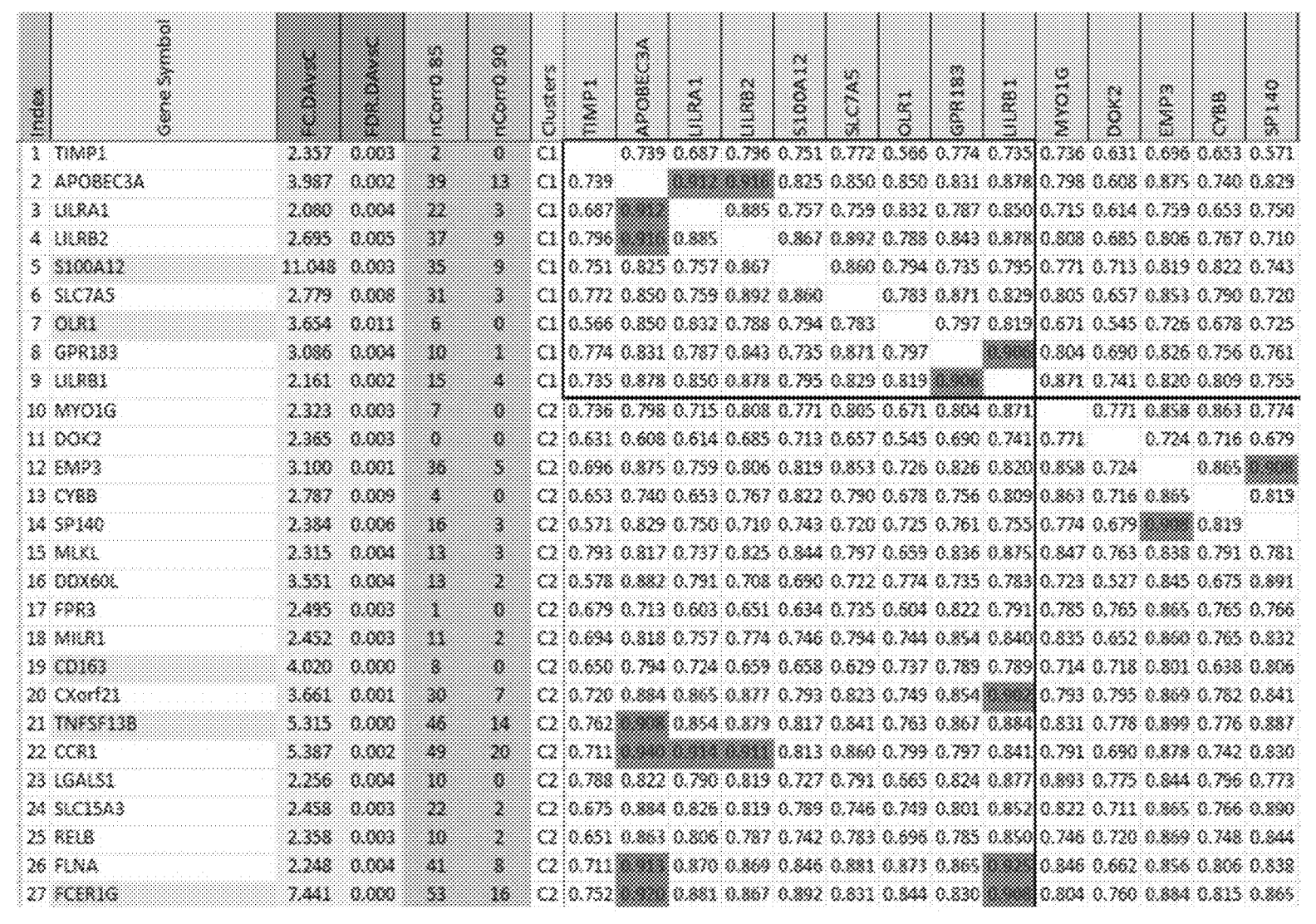
Figure 17:
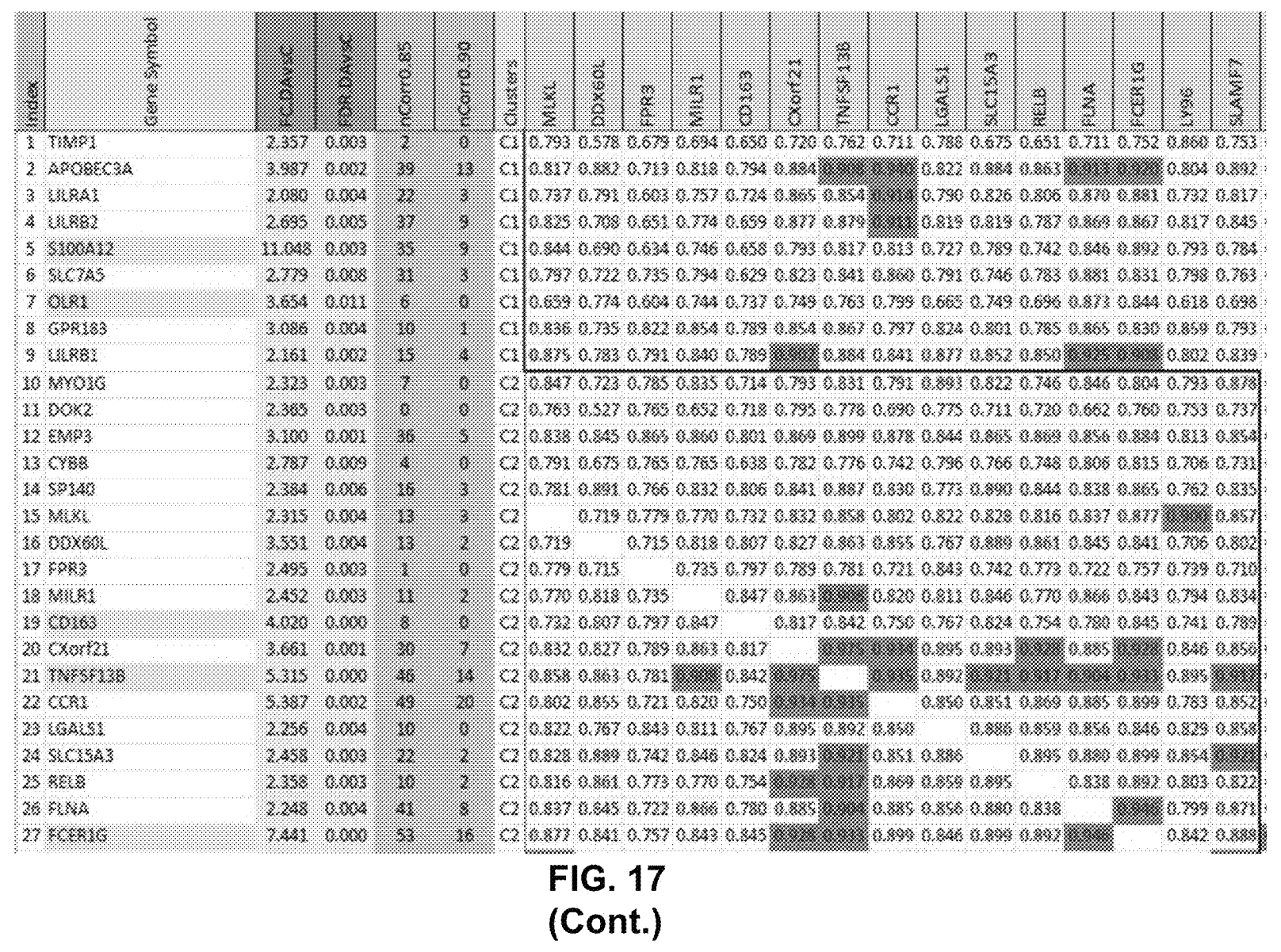
Figure 17:
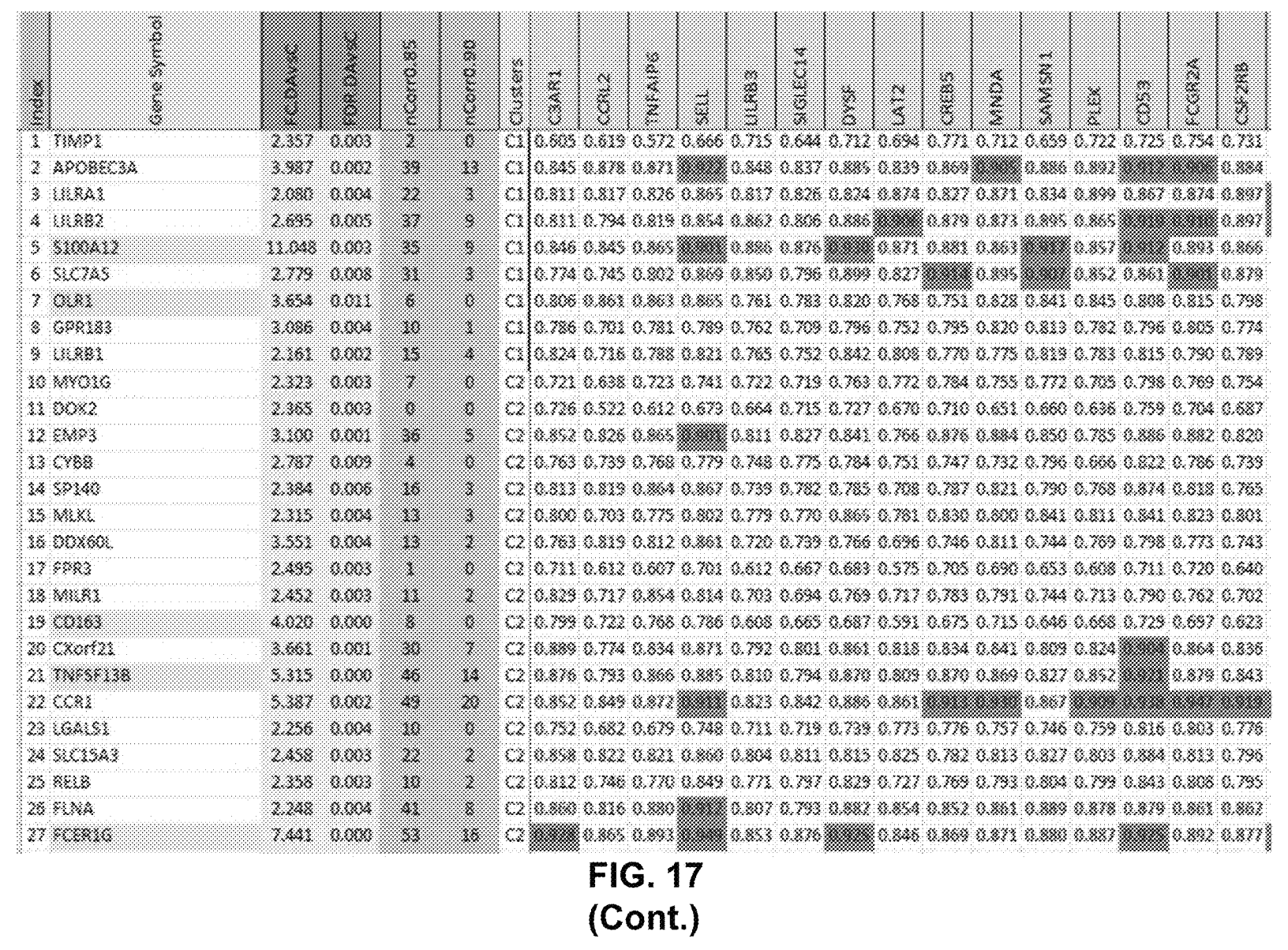
Figure 17:
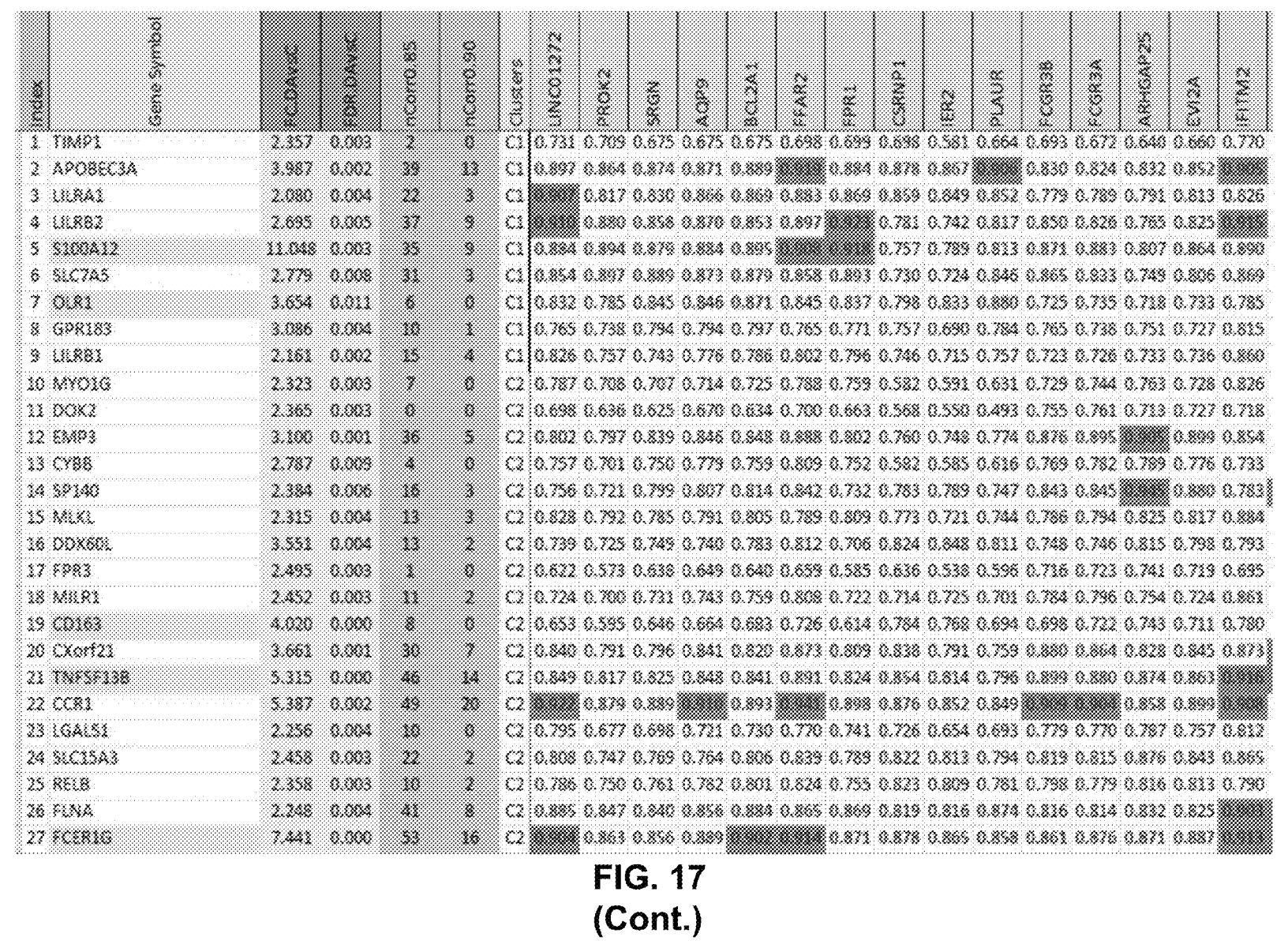
Figure 17:
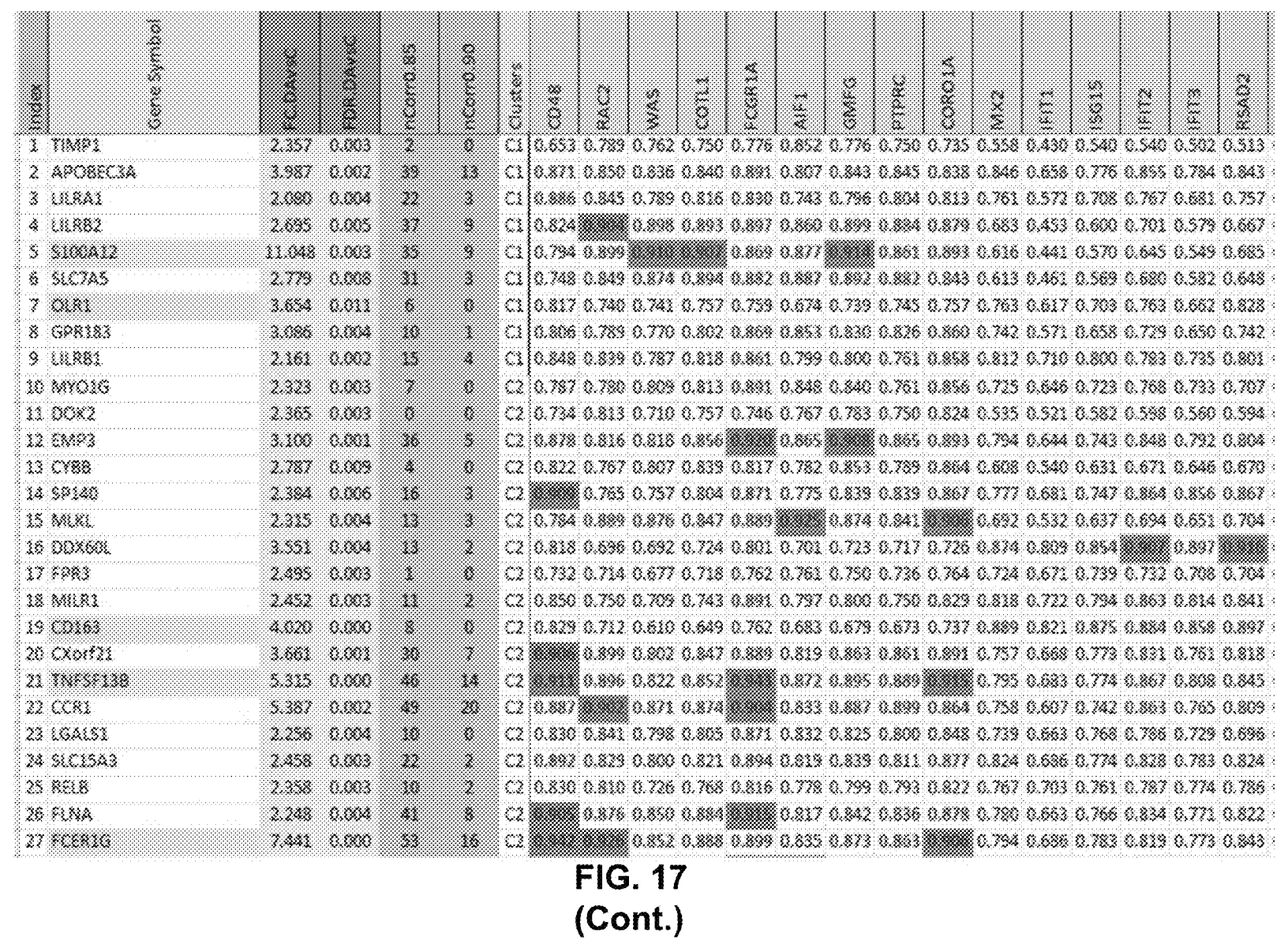
Figure 17:
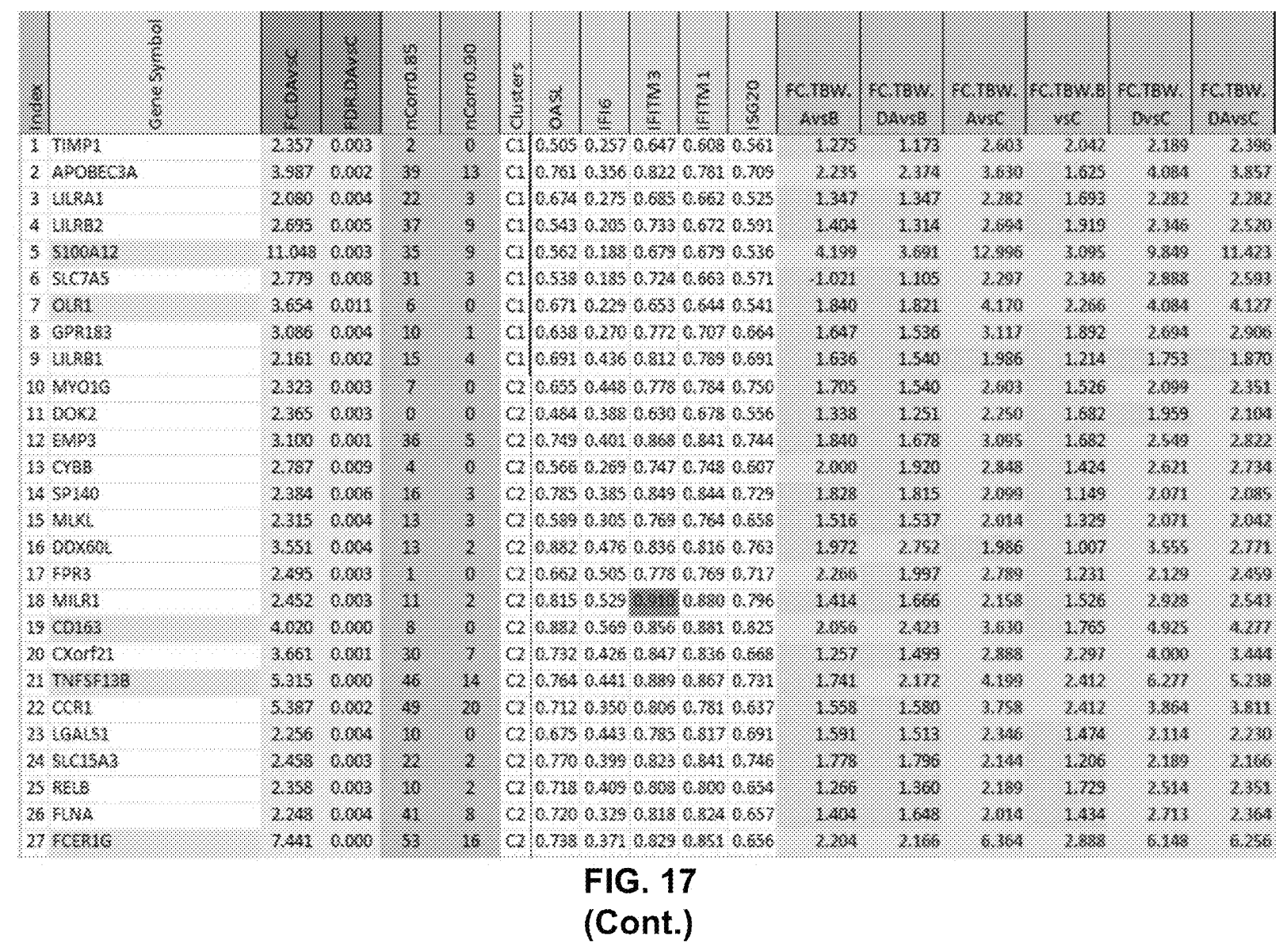
Figure 17:
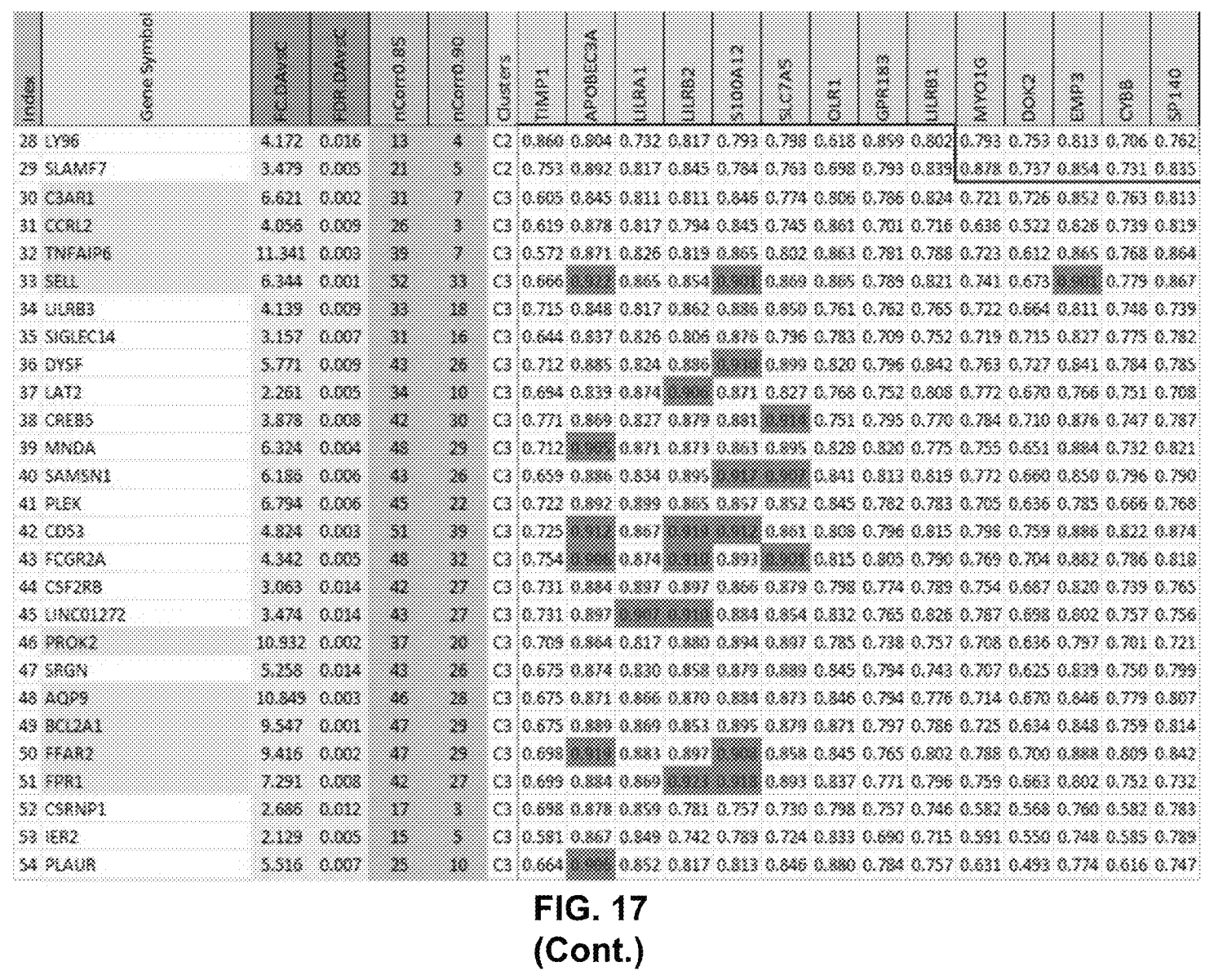
Figure 17:
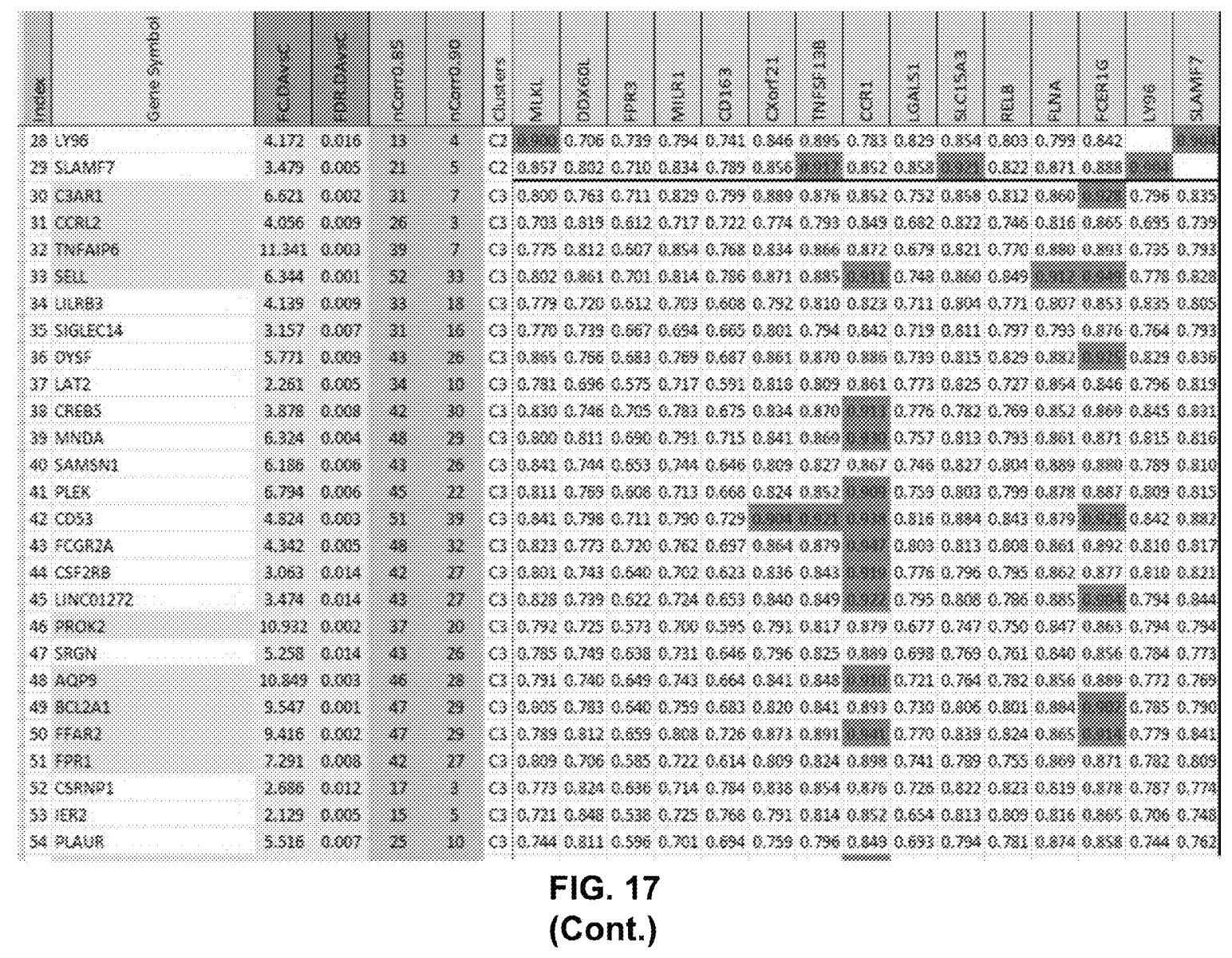
Figure 17:
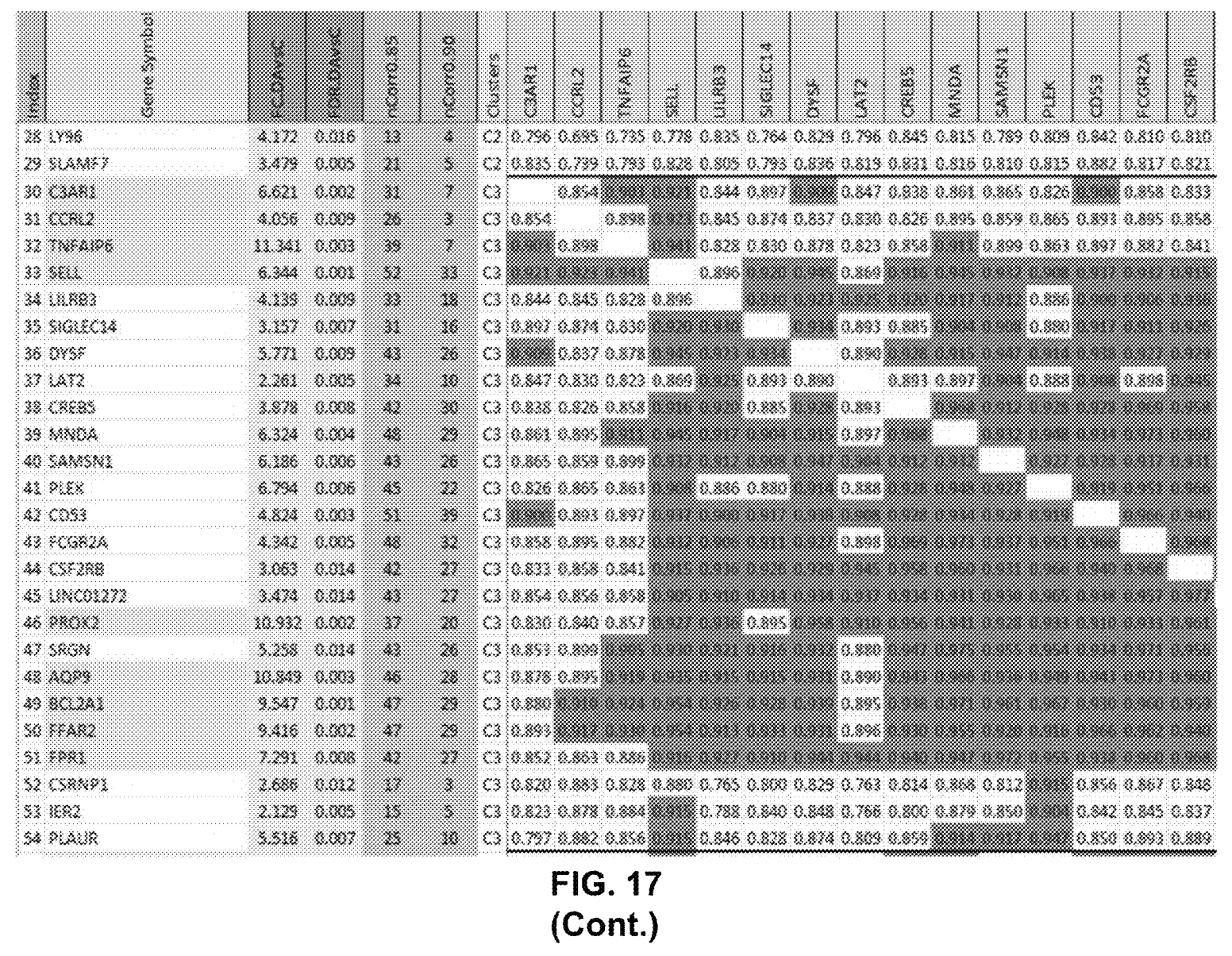
Figure 17:
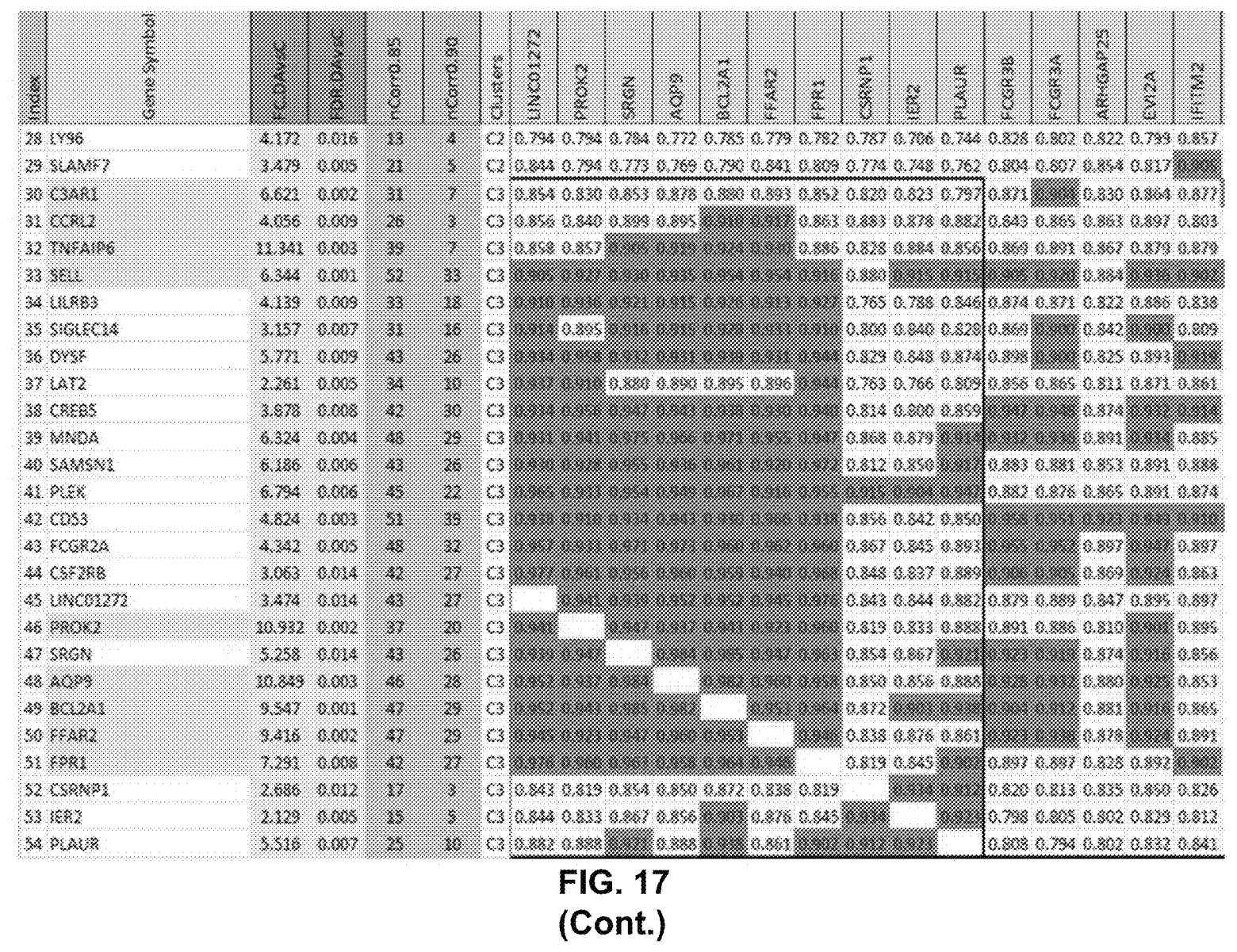
Figure 17:
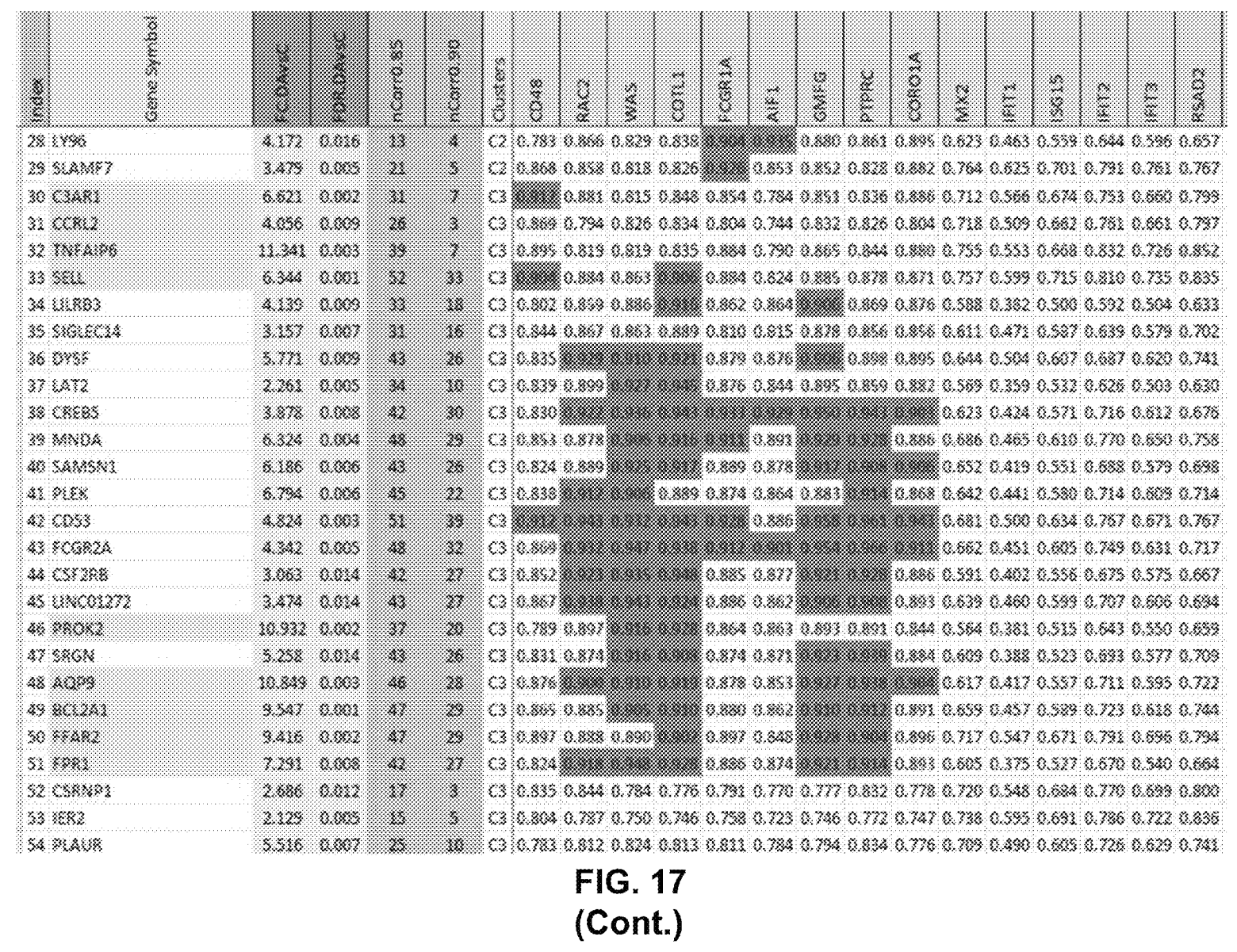
Figure 17:
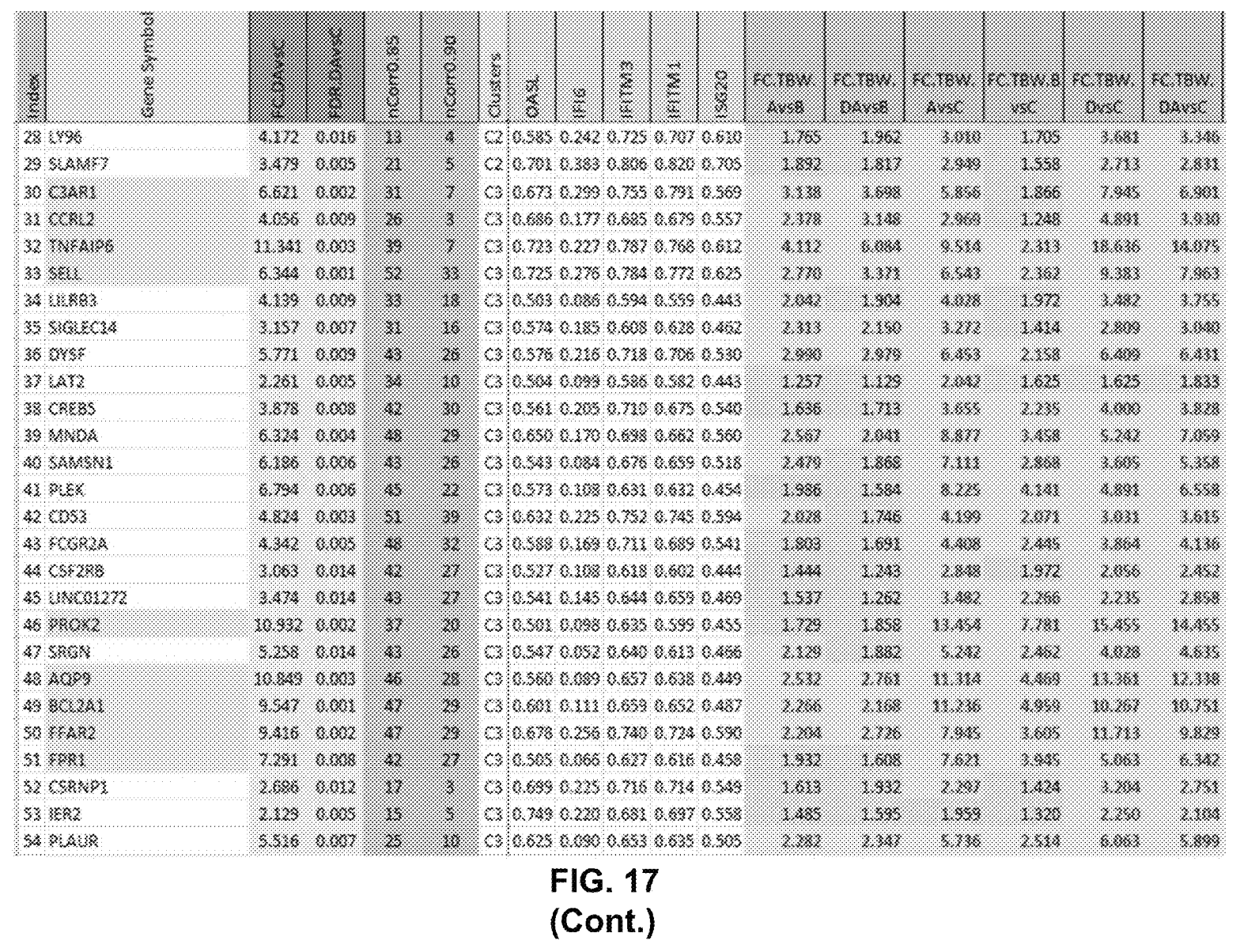
Figure 17:
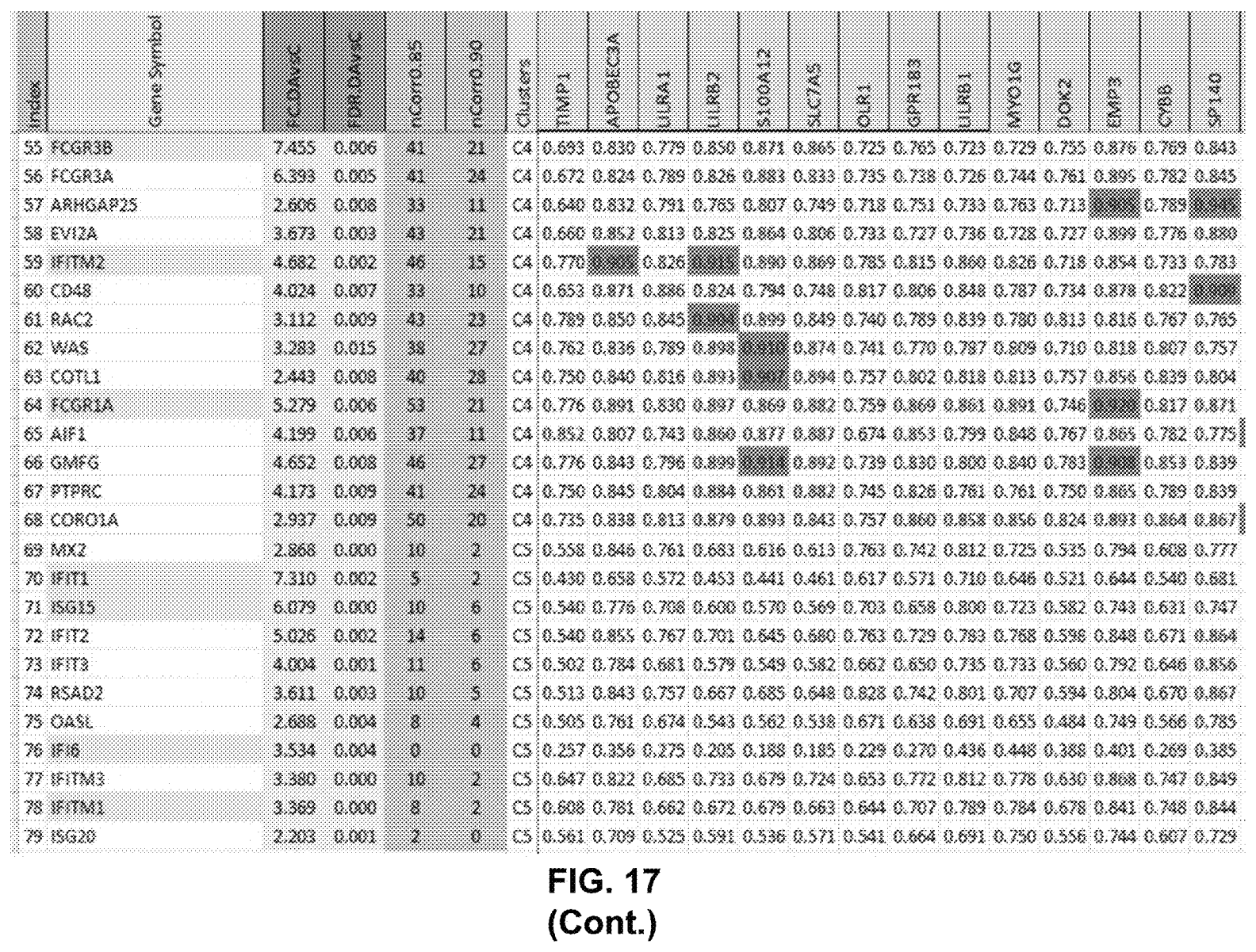
Figure 17:
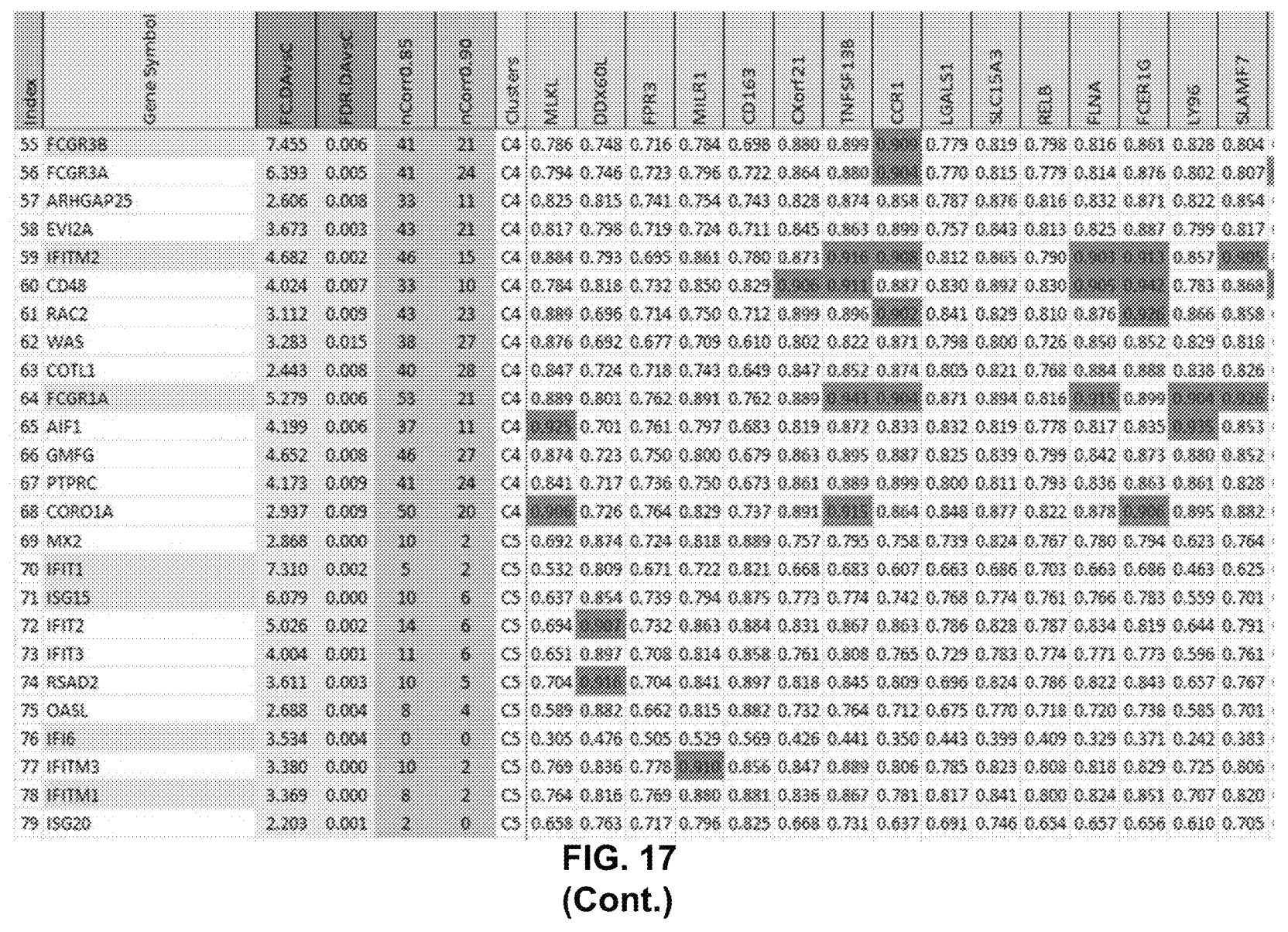
Figure 17:
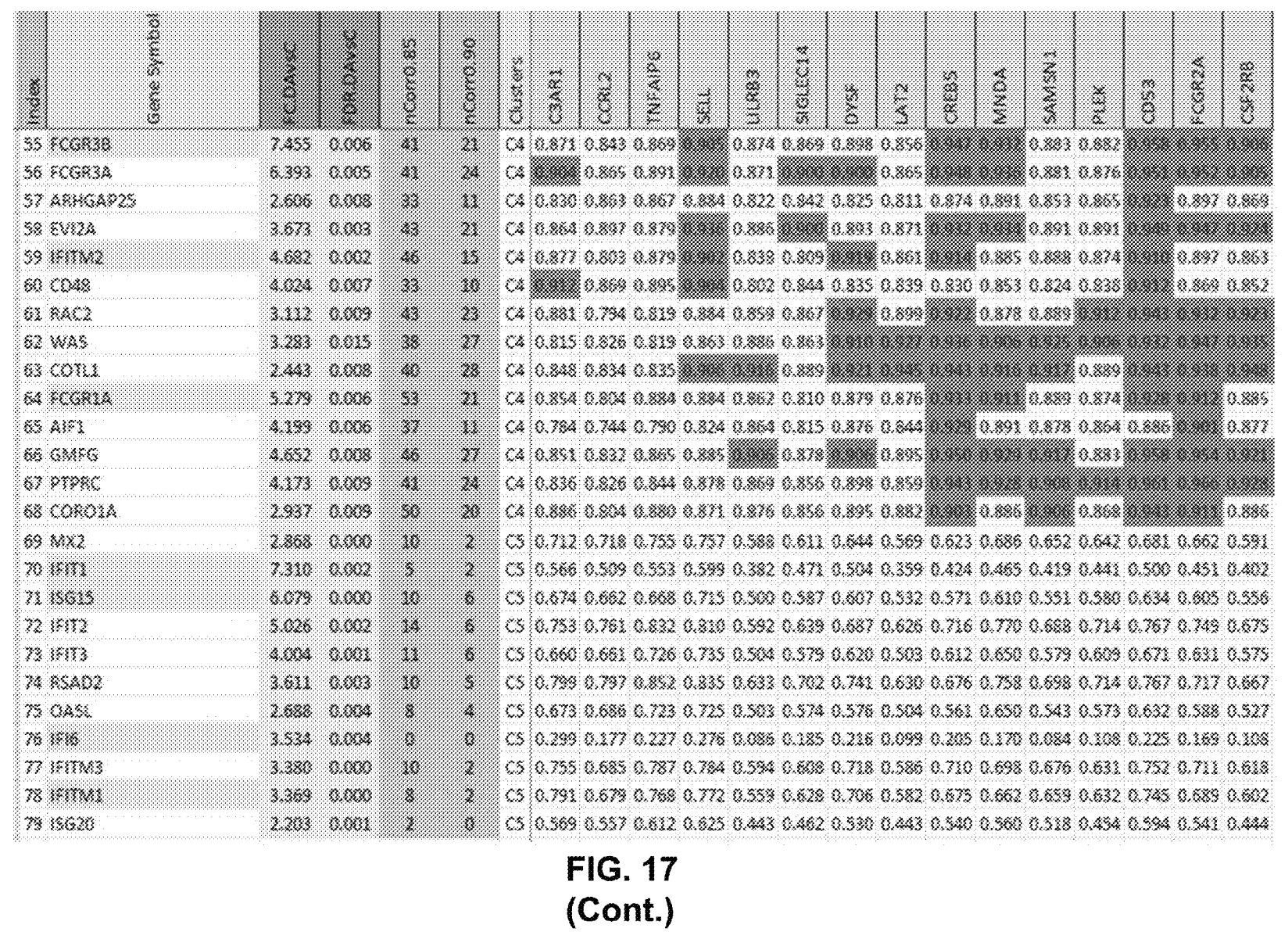
Figure 17:
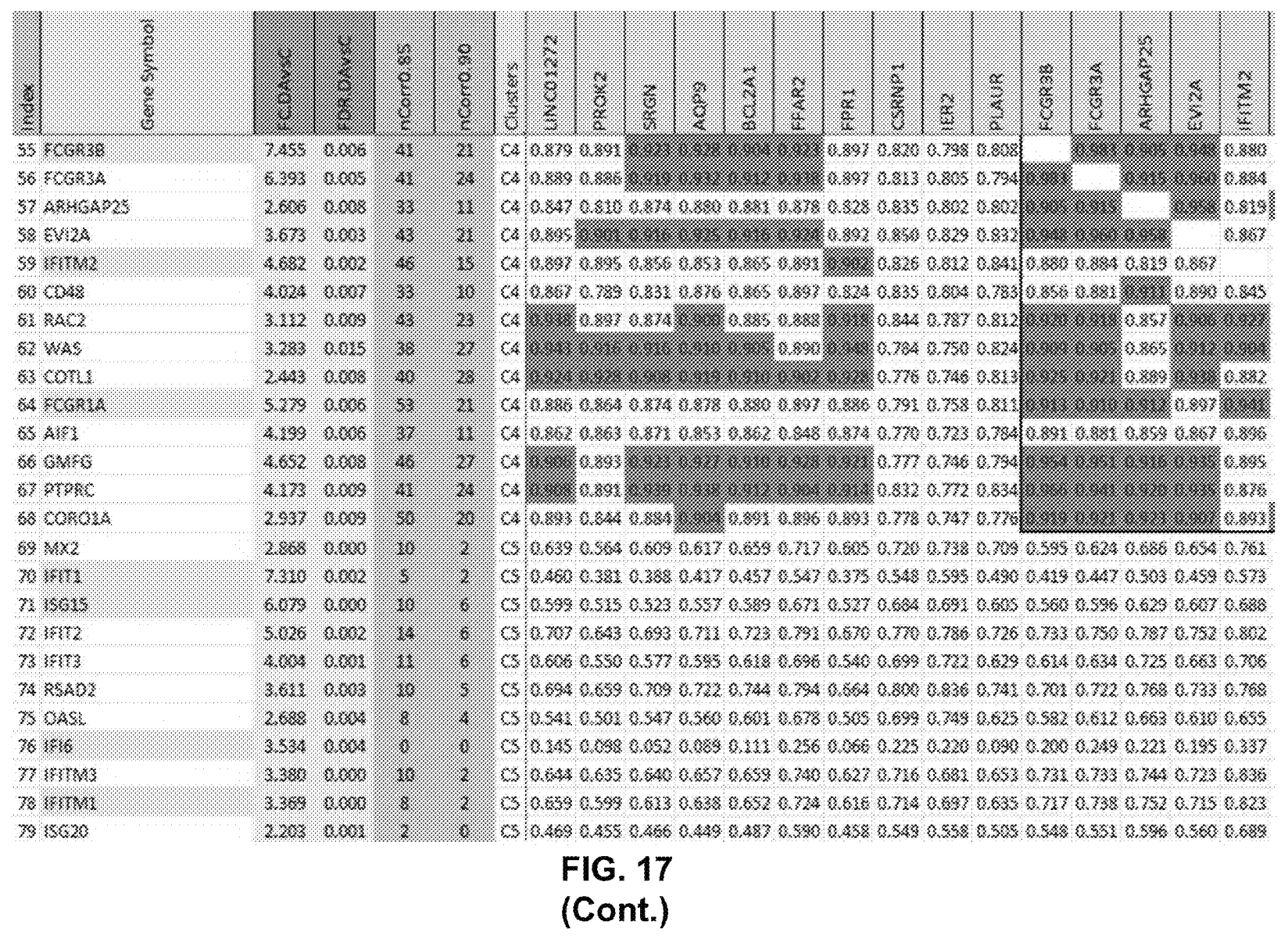
Figure 17:
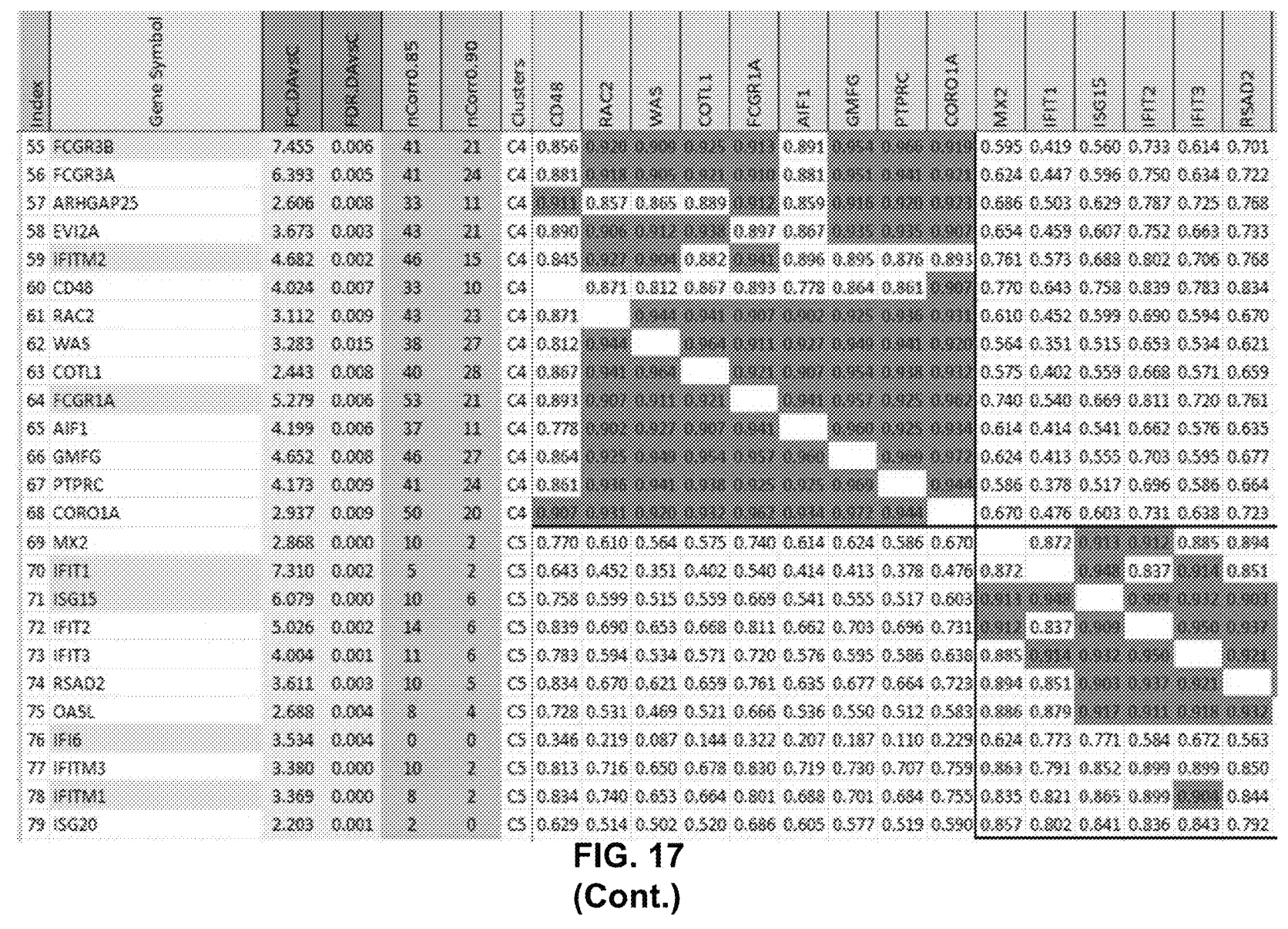
Figure 17:
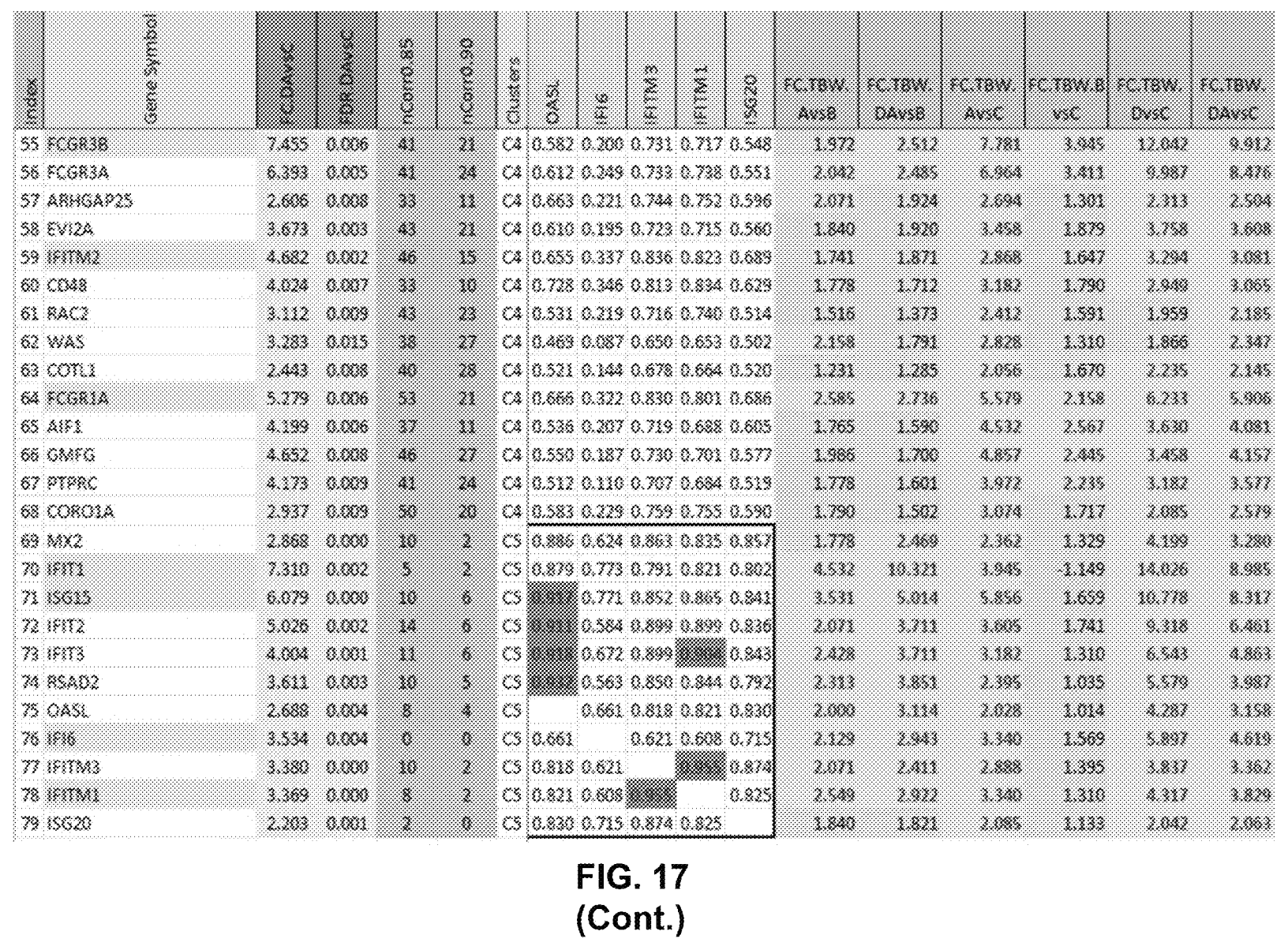

FIG. 17 shows an exemplary gene signature which includes 79 genes with increased expression in symptomatic viral infections.

Figure 18:
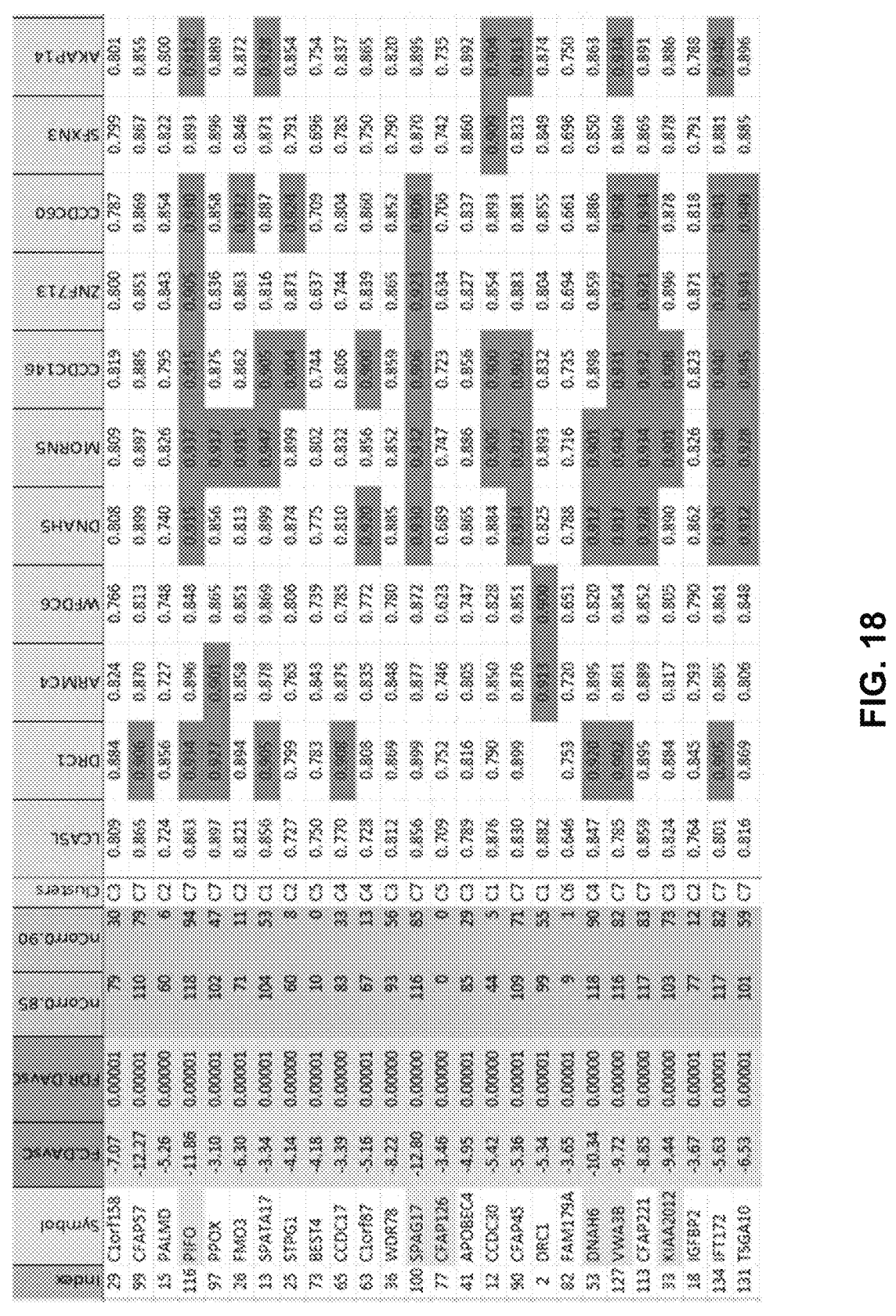
Figure 18:
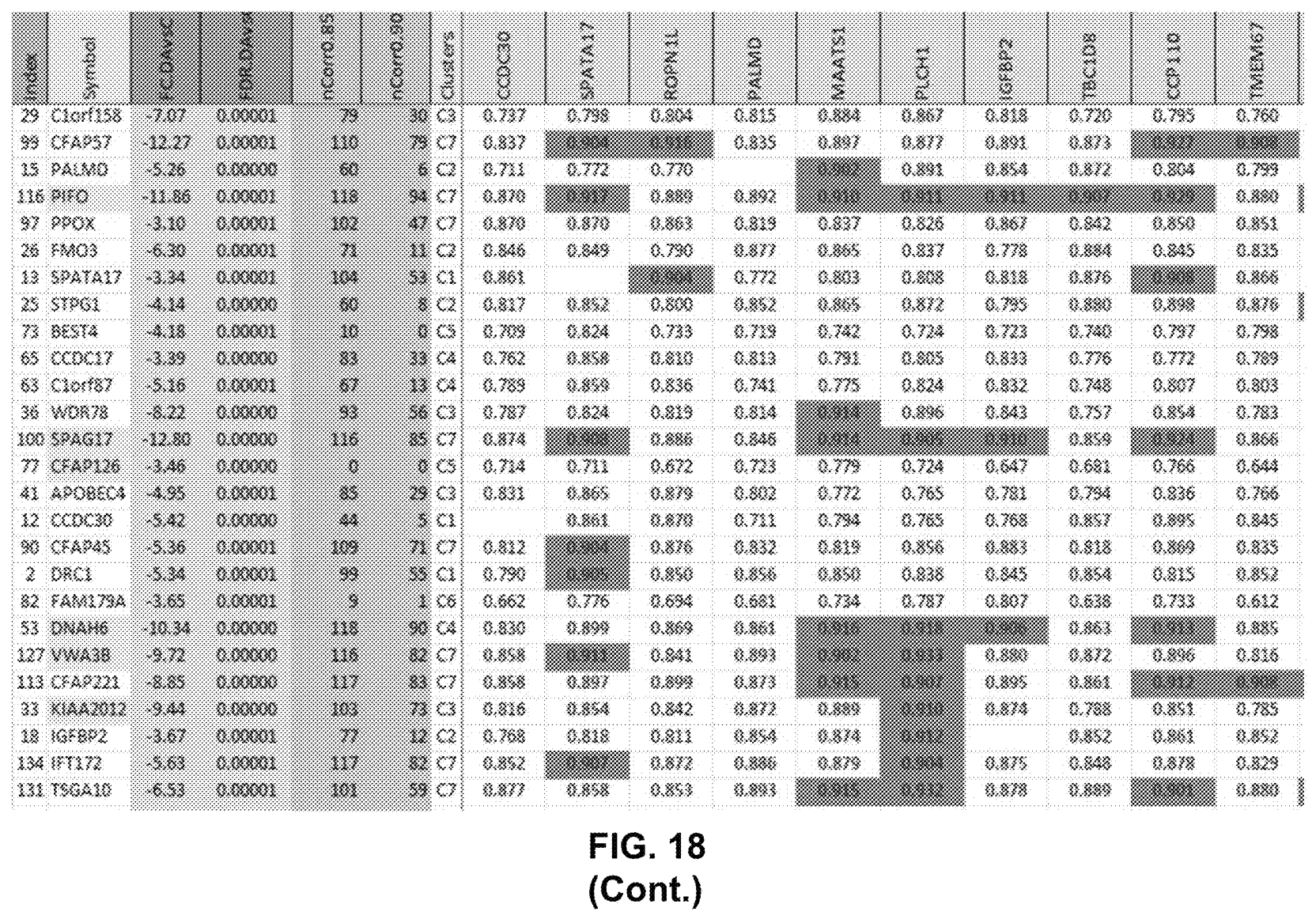
Figure 18:
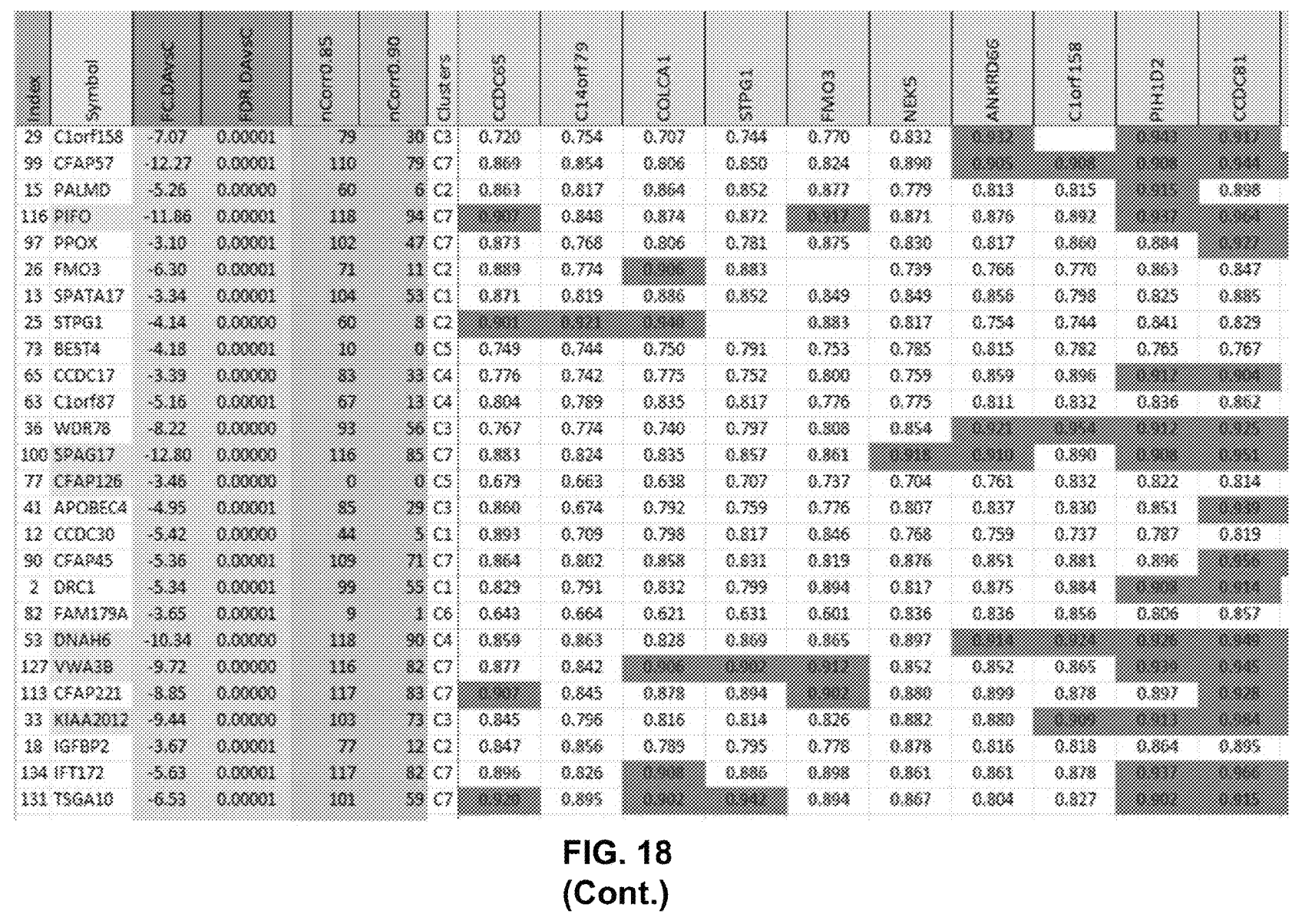
Figure 18:
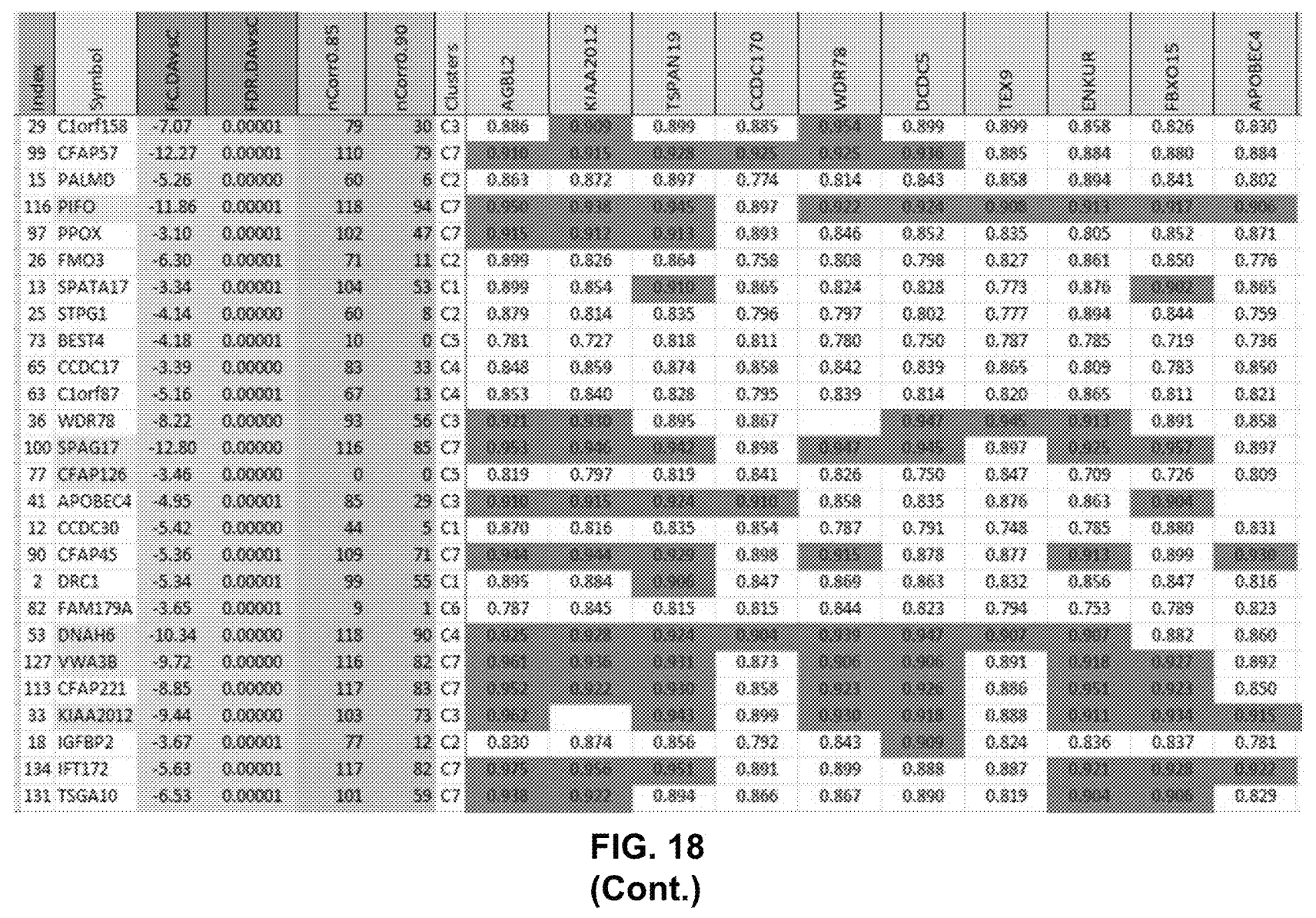
Figure 18:
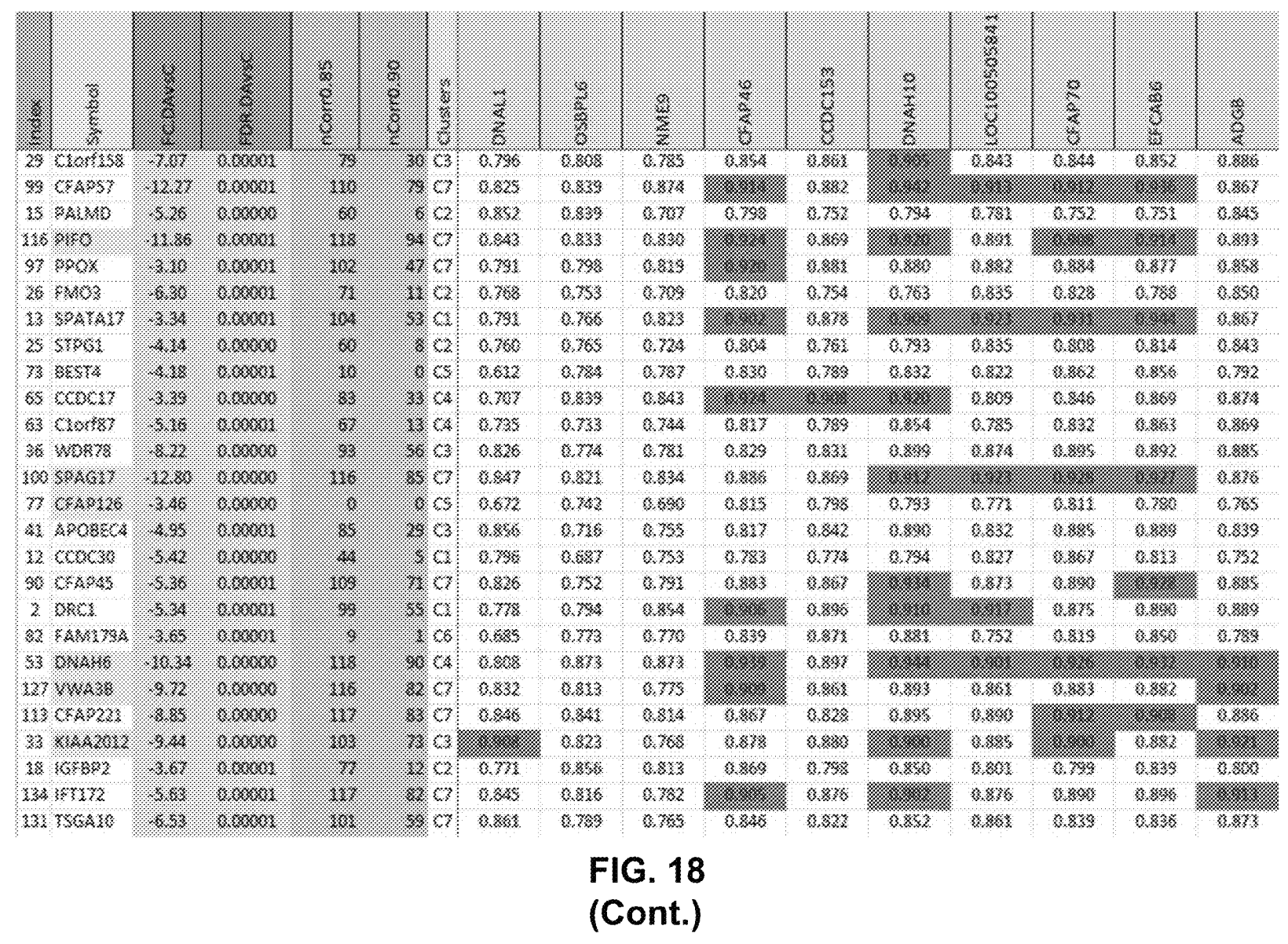
Figure 18:
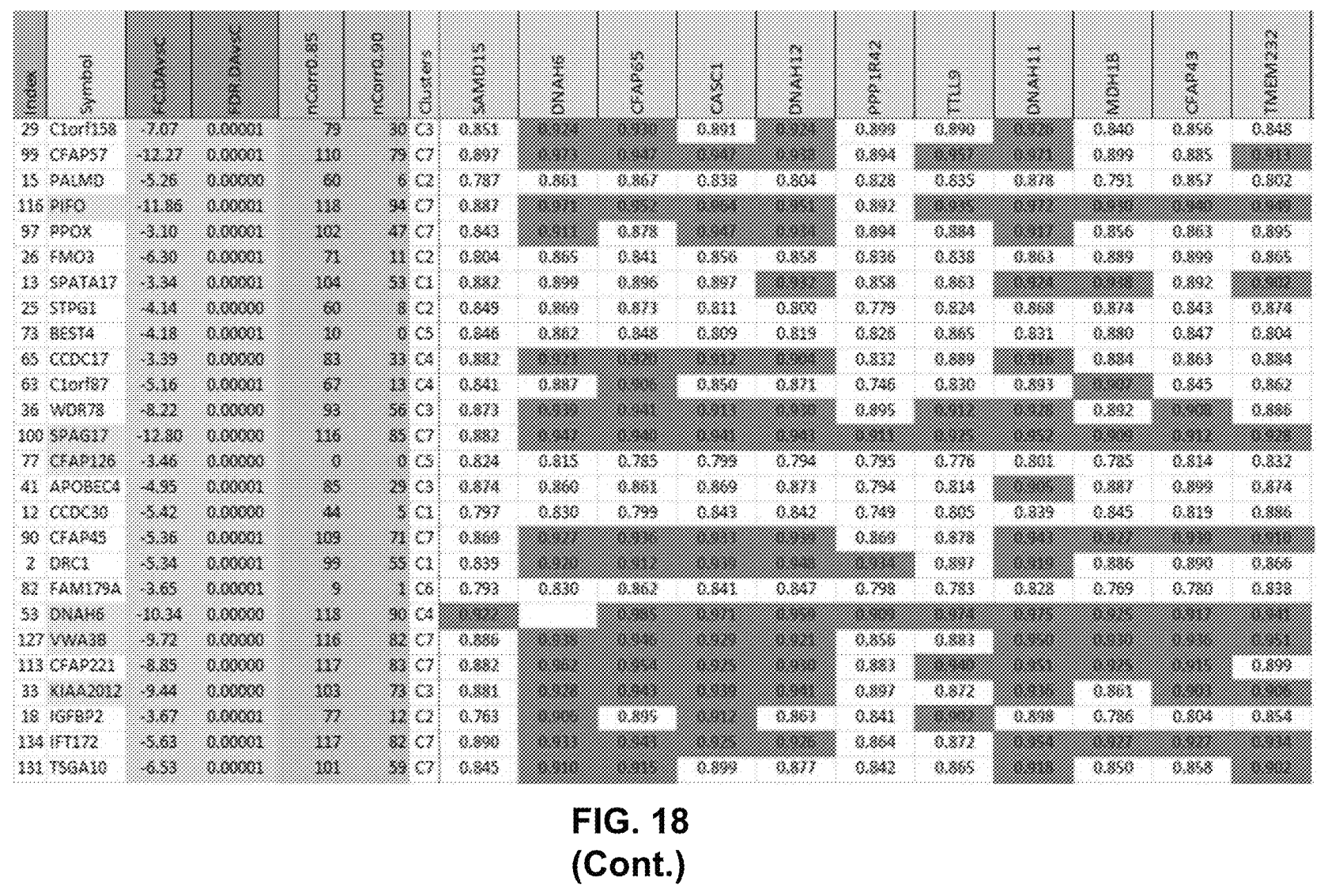
Figure 18:
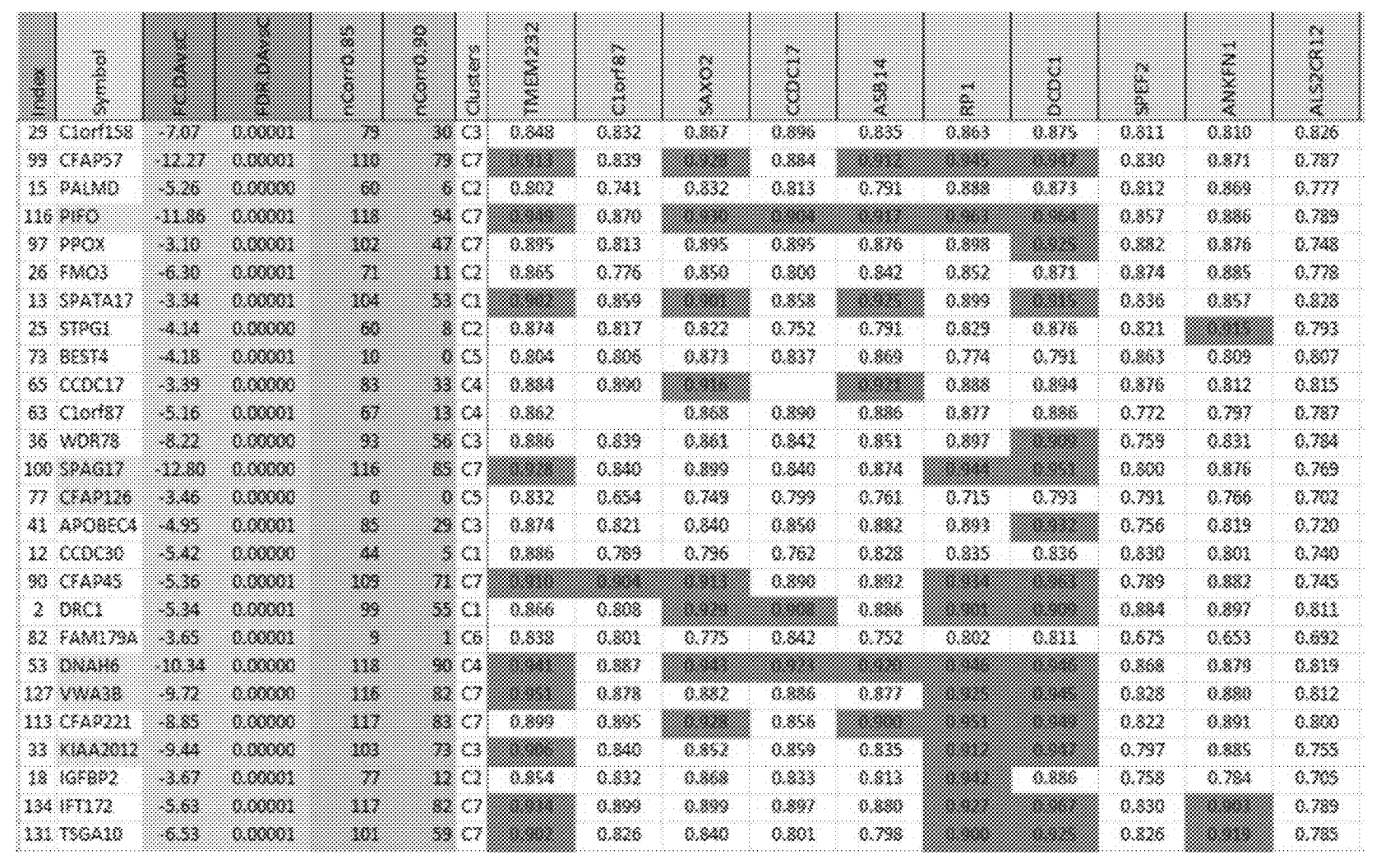
Figure 18:
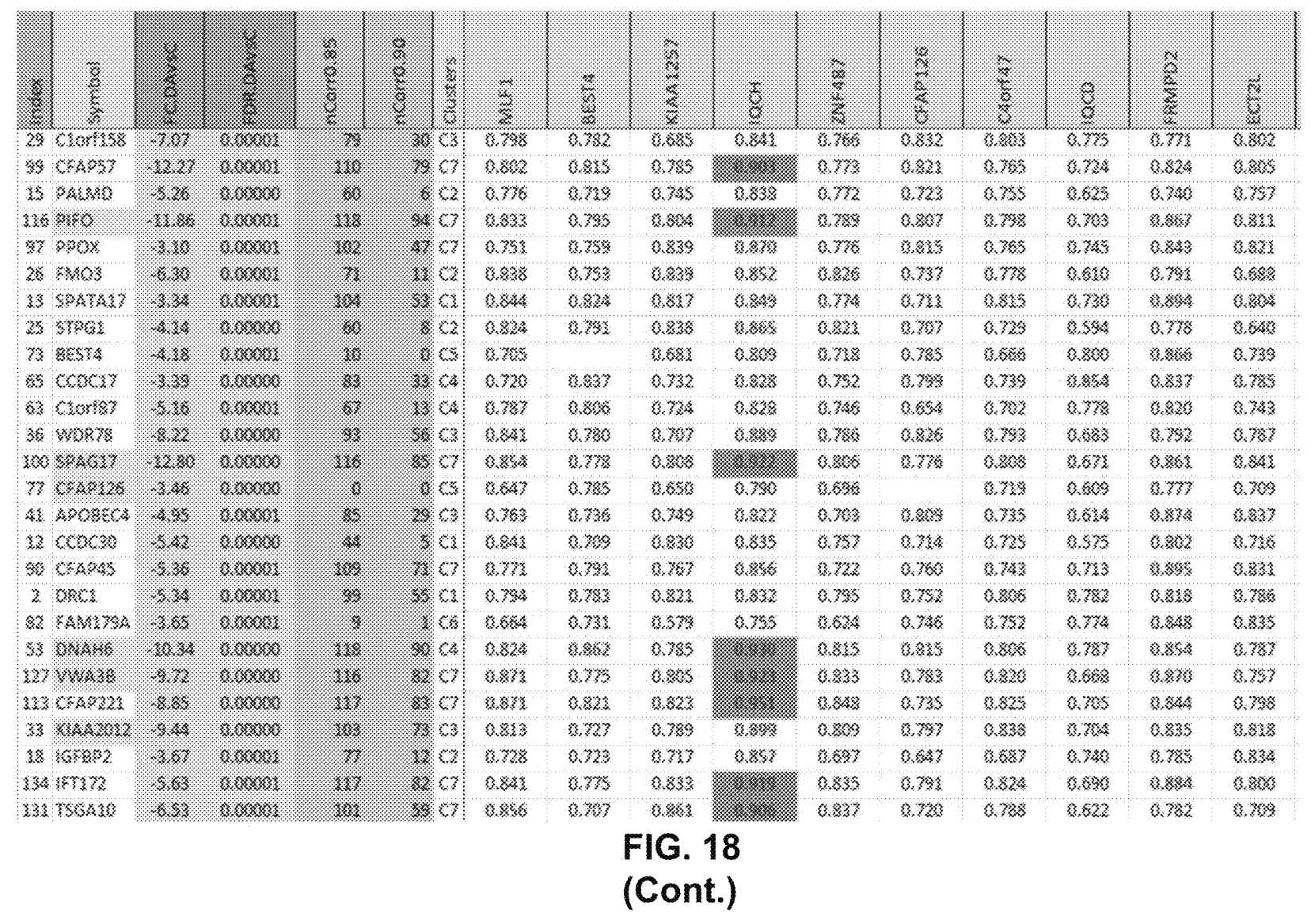
Figure 18:
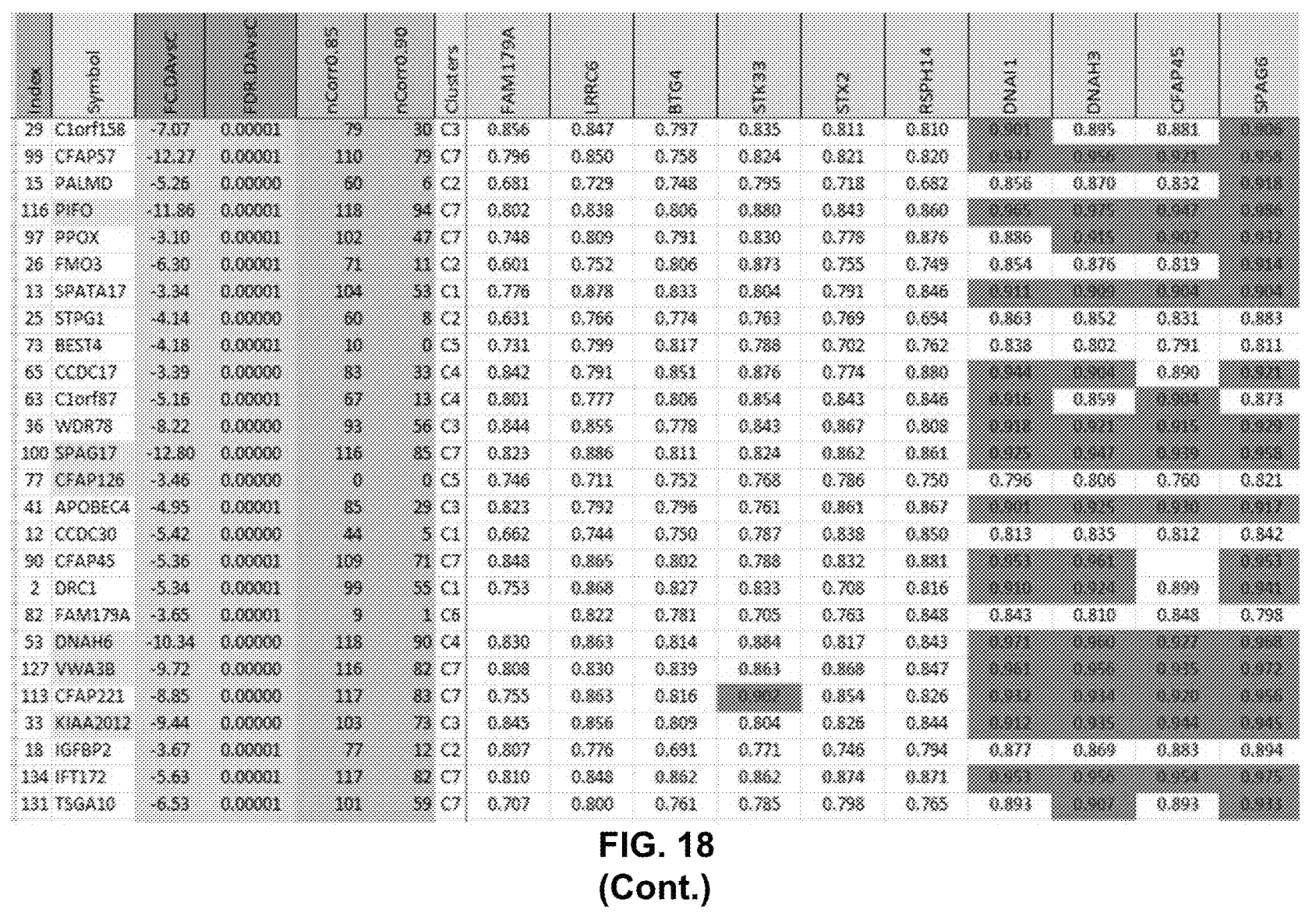
Figure 18:
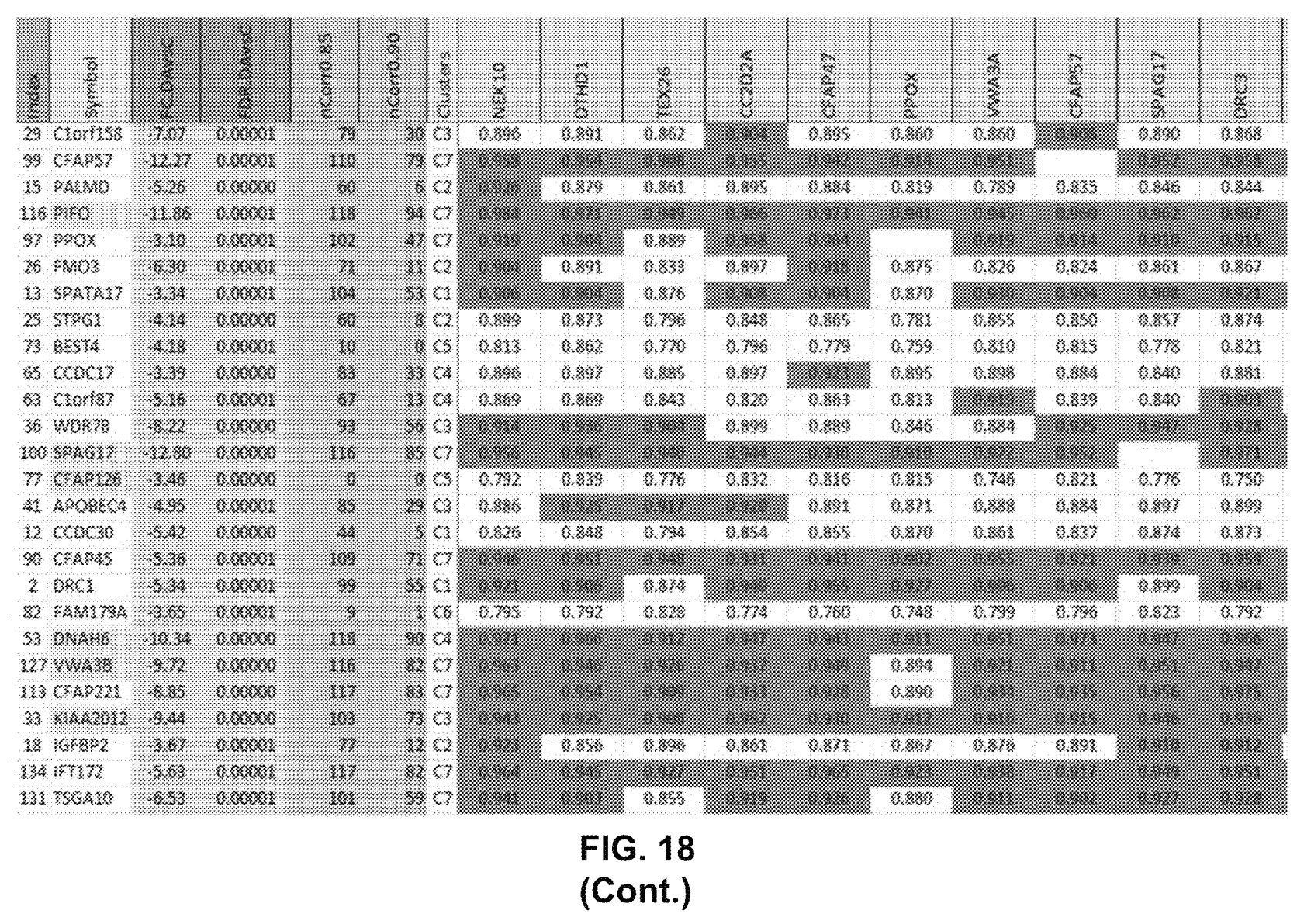
Figure 18:
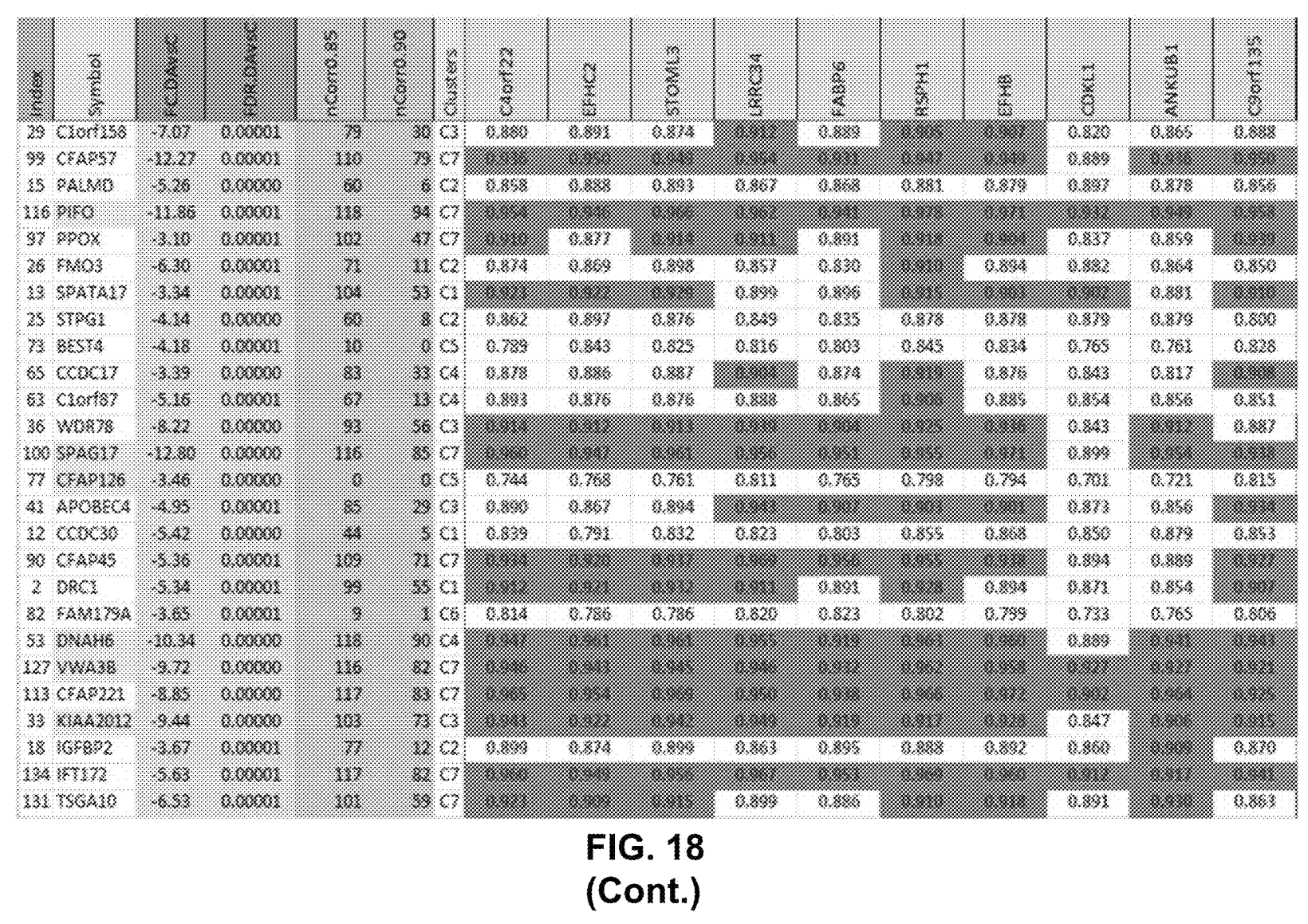
Figure 18:
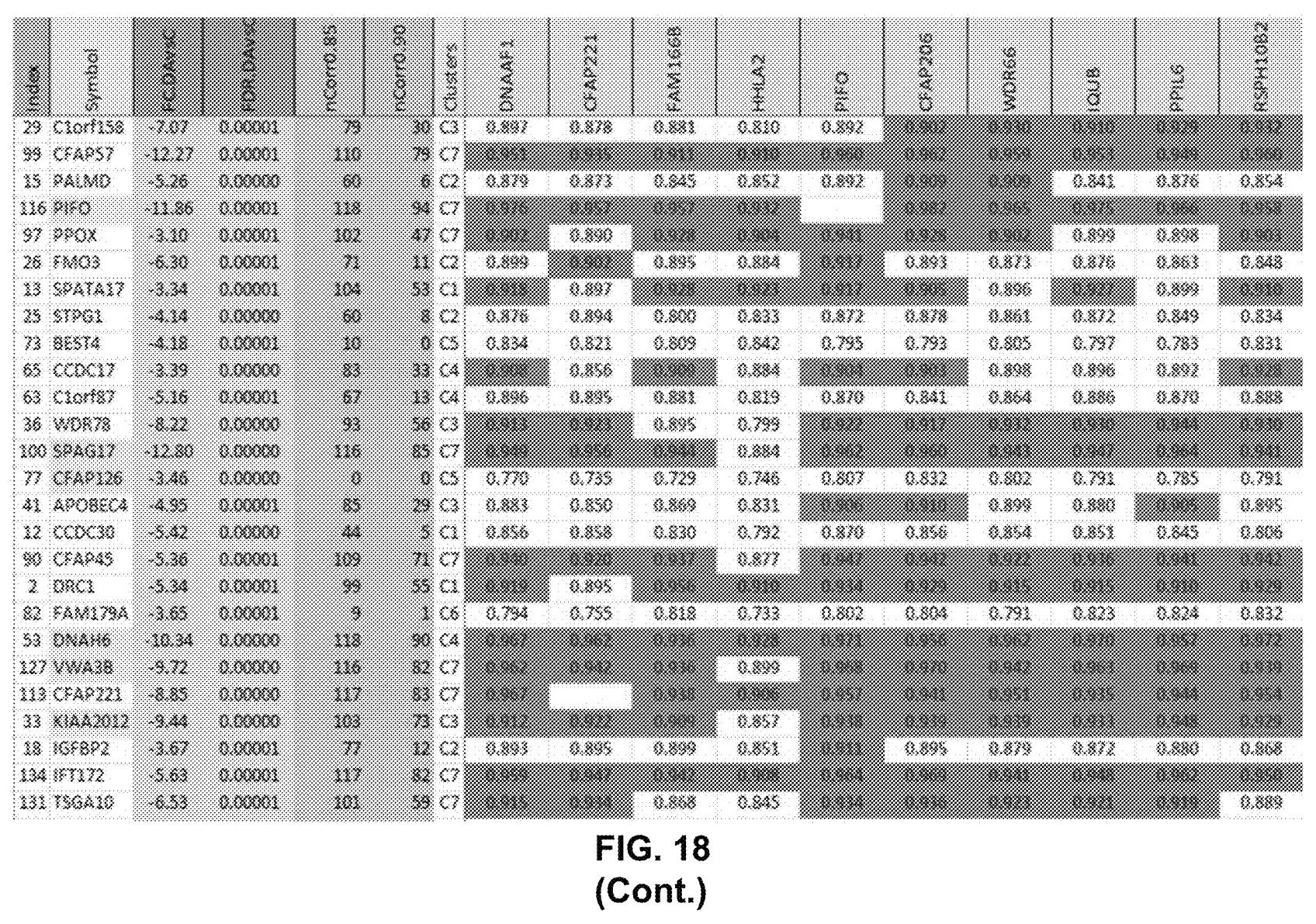
Figure 18:
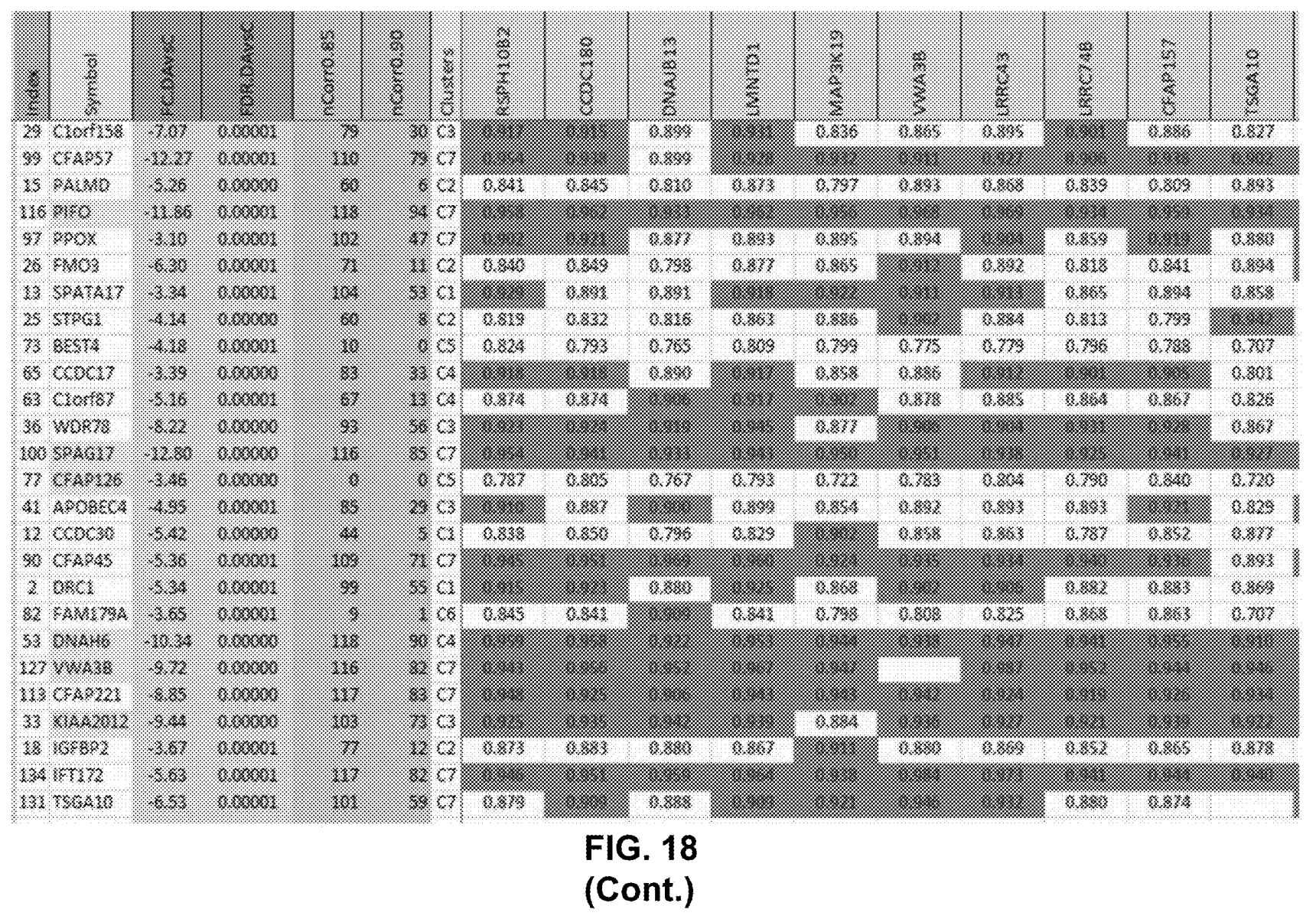
Figure 18:
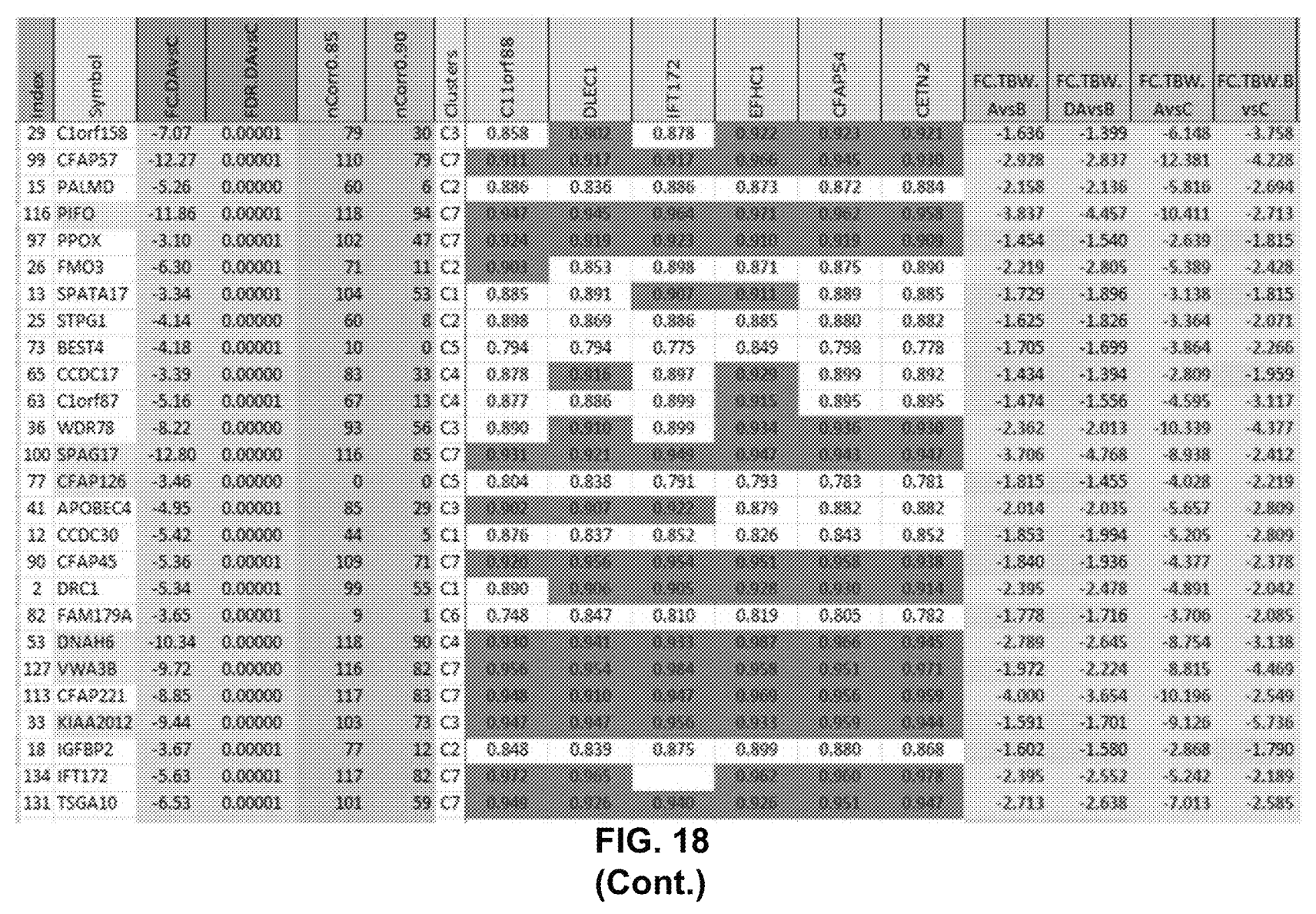
Figure 18:
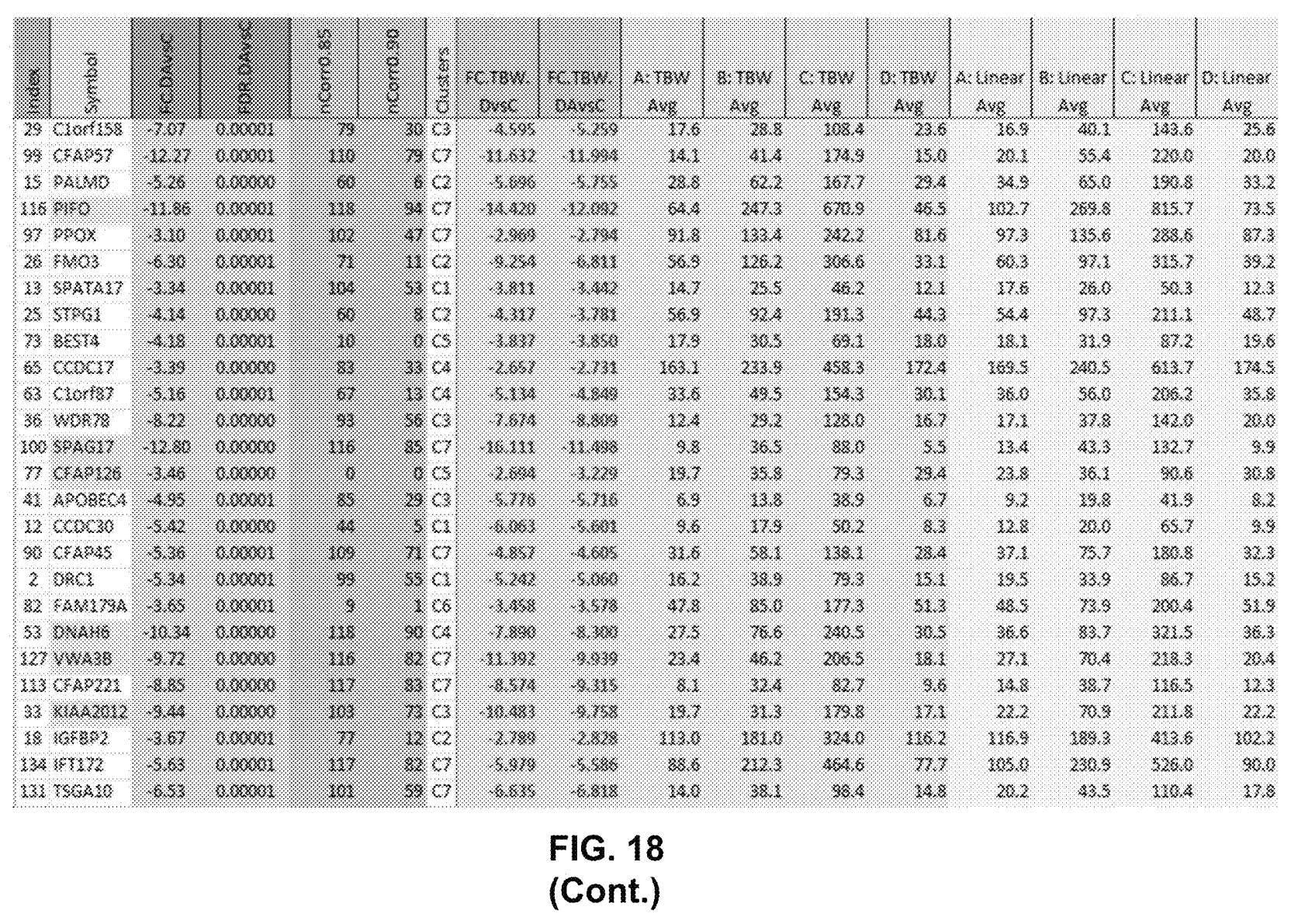
Figure 18:
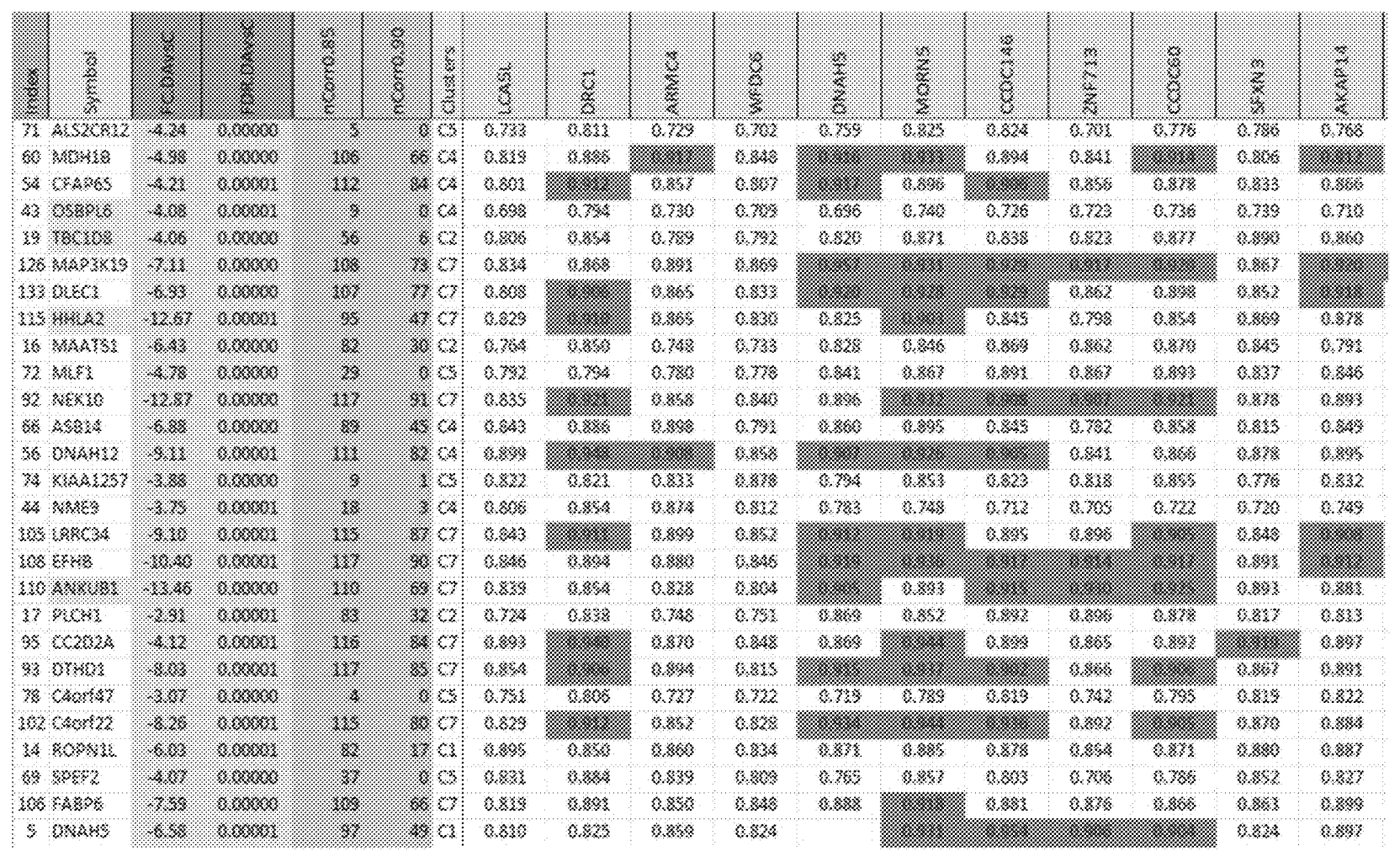
Figure 18:
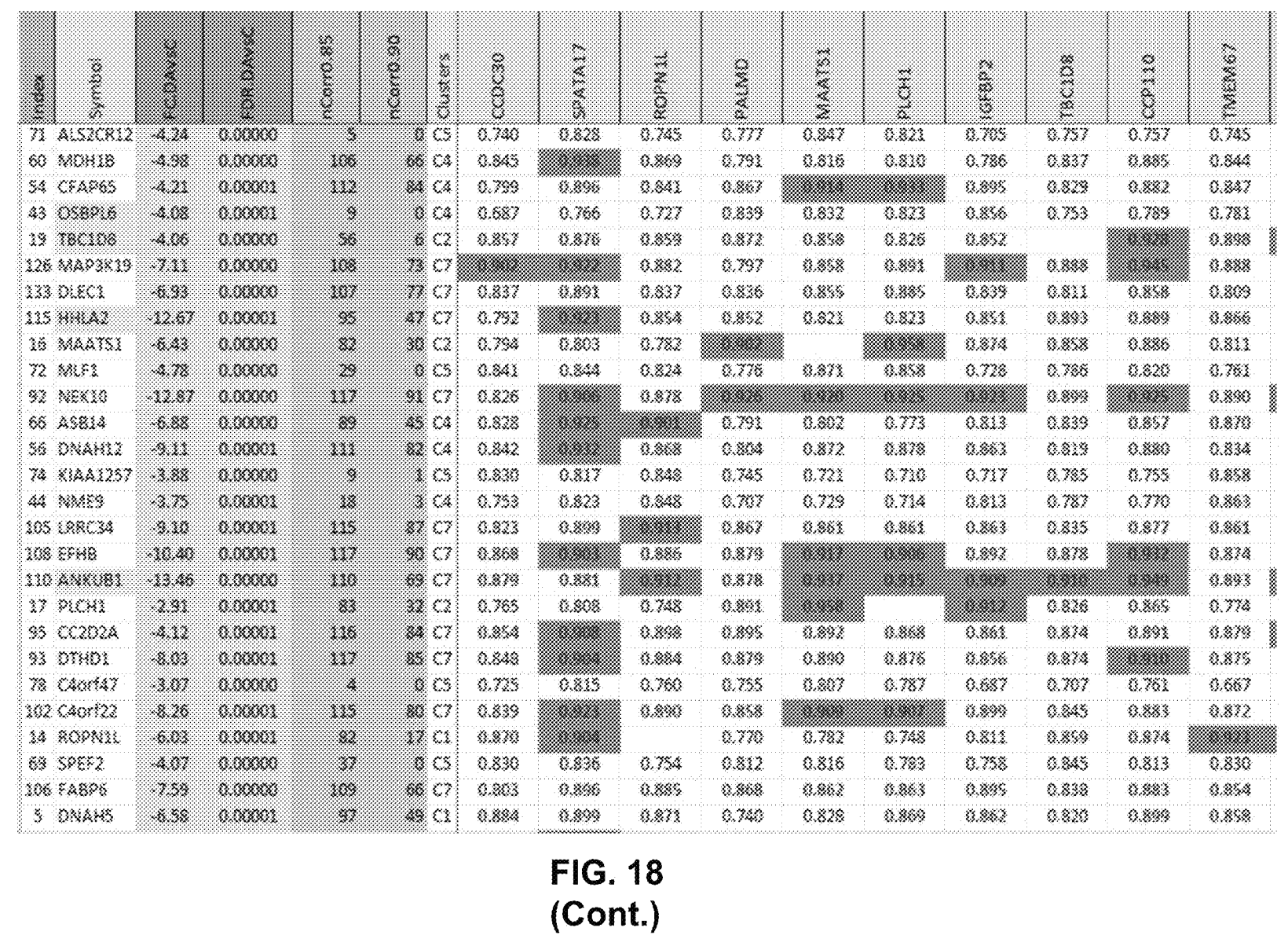
Figure 18:
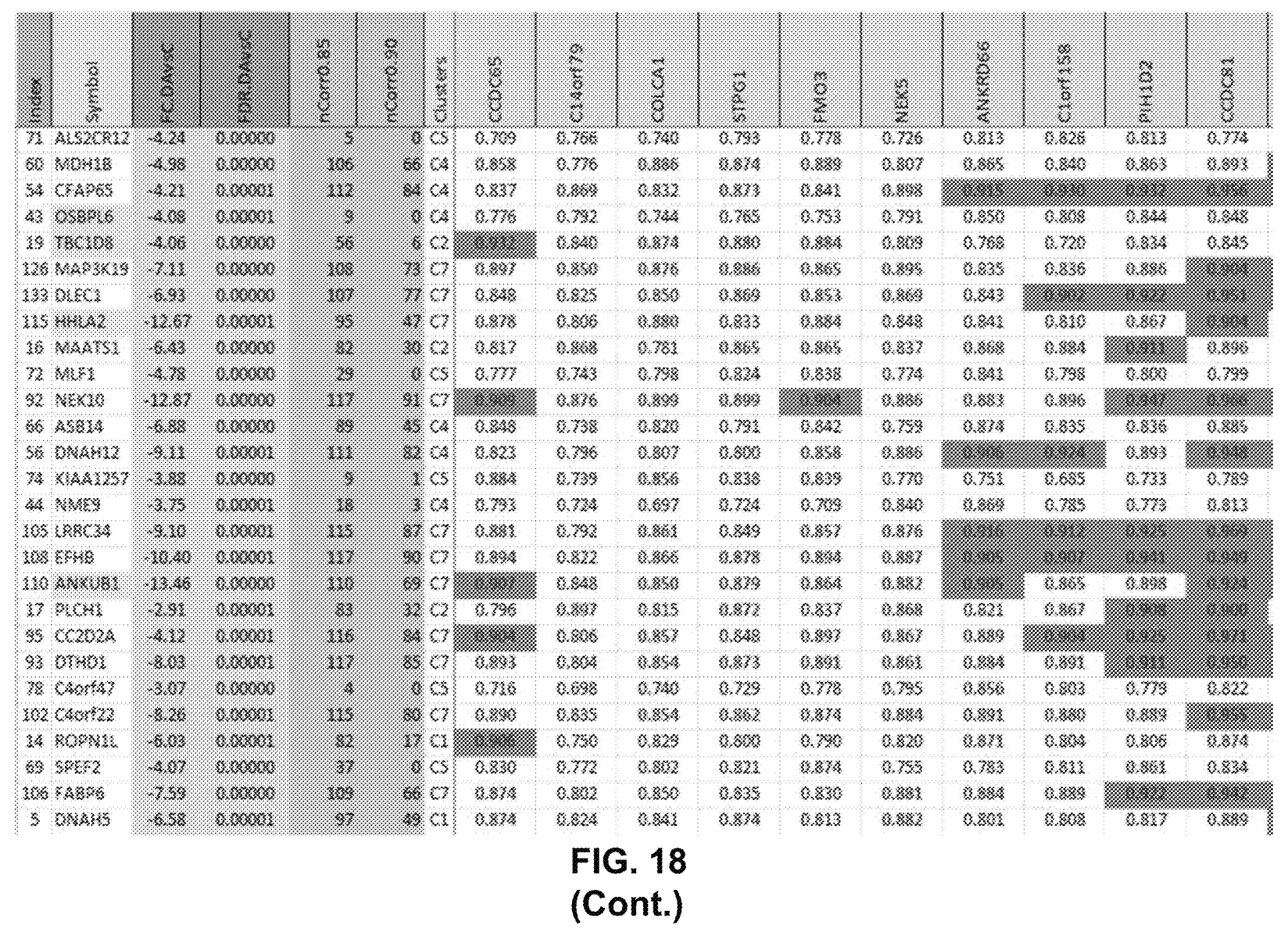
Figure 18:
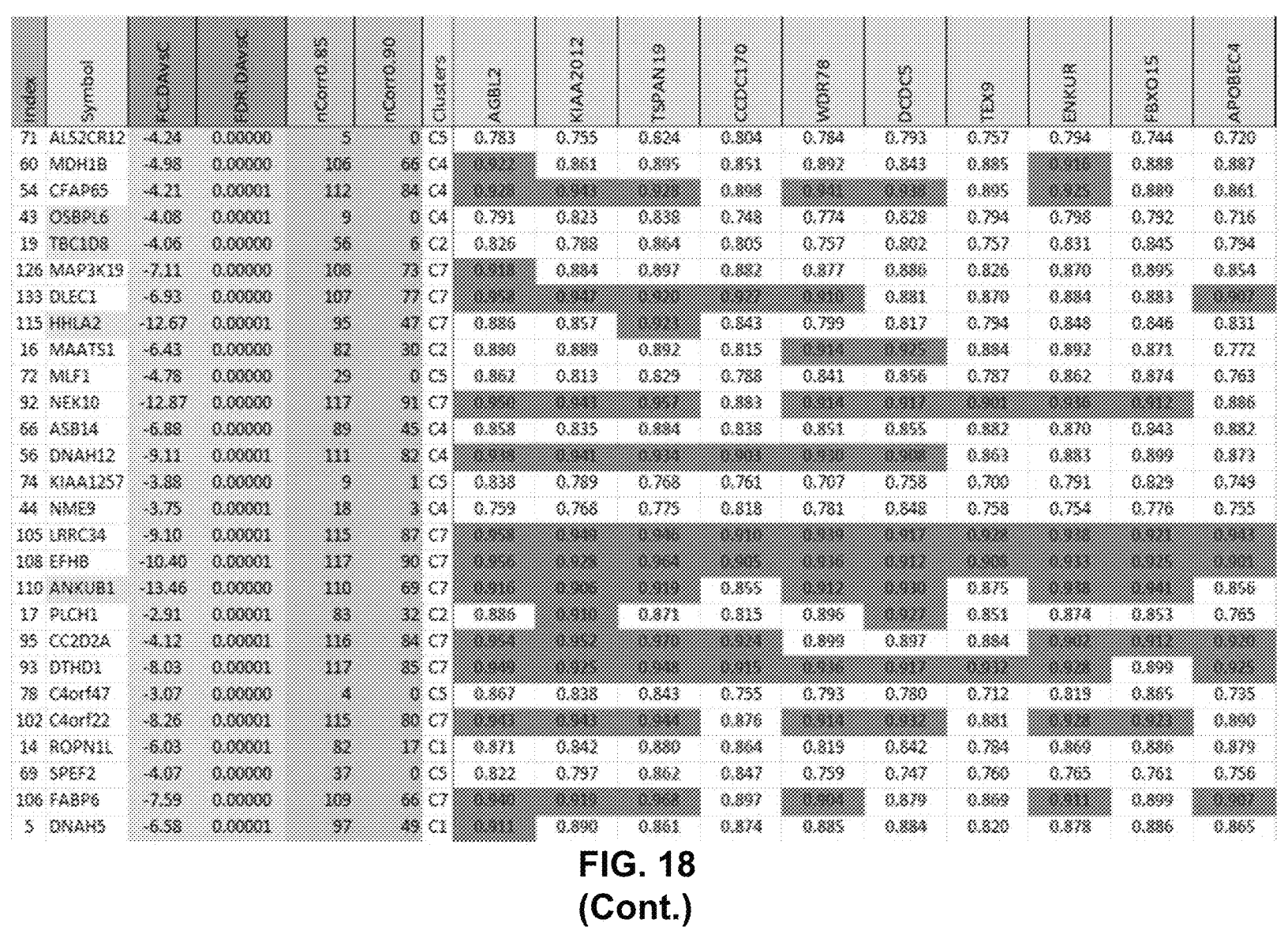
Figure 18:
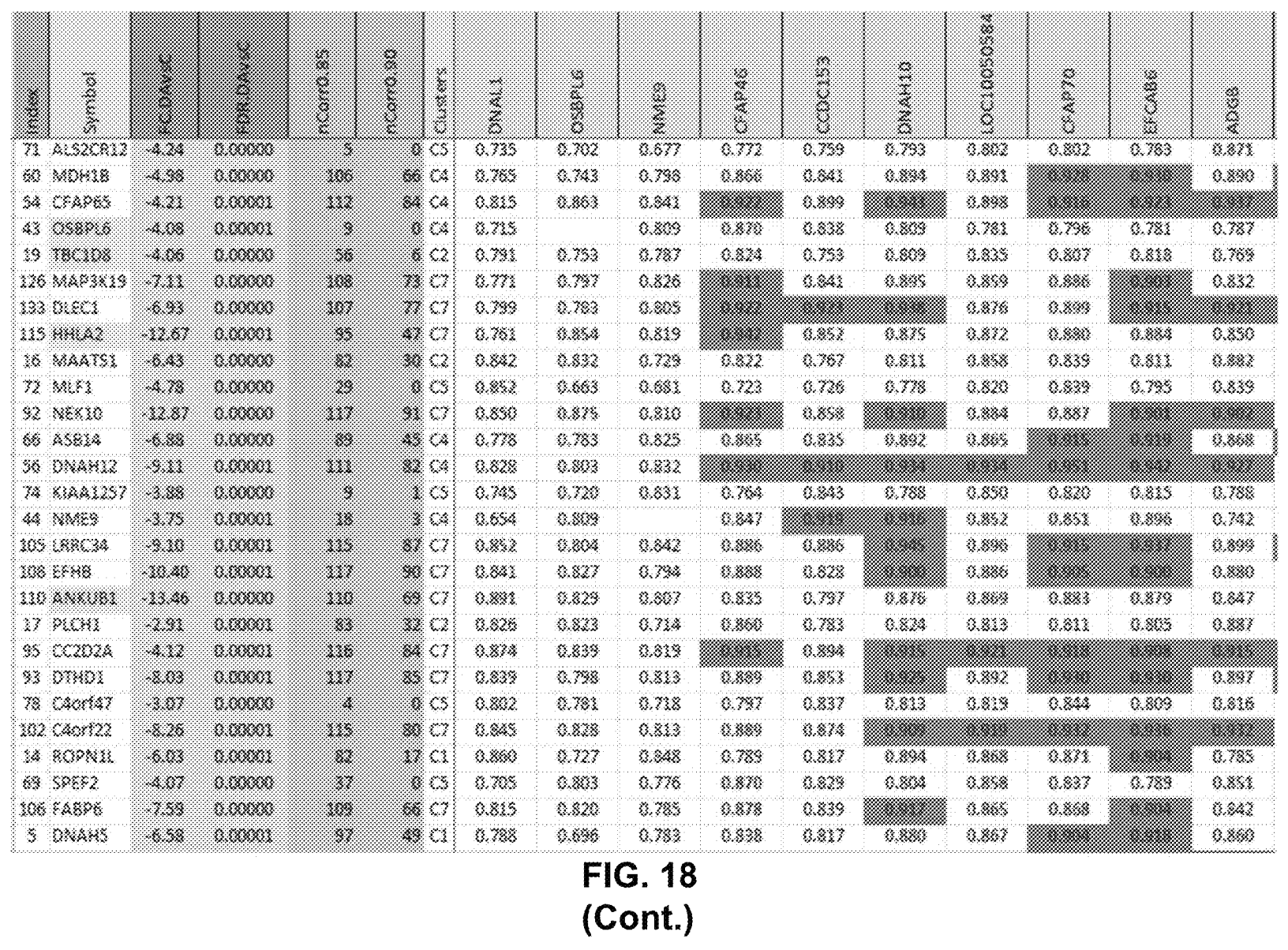
Figure 18:
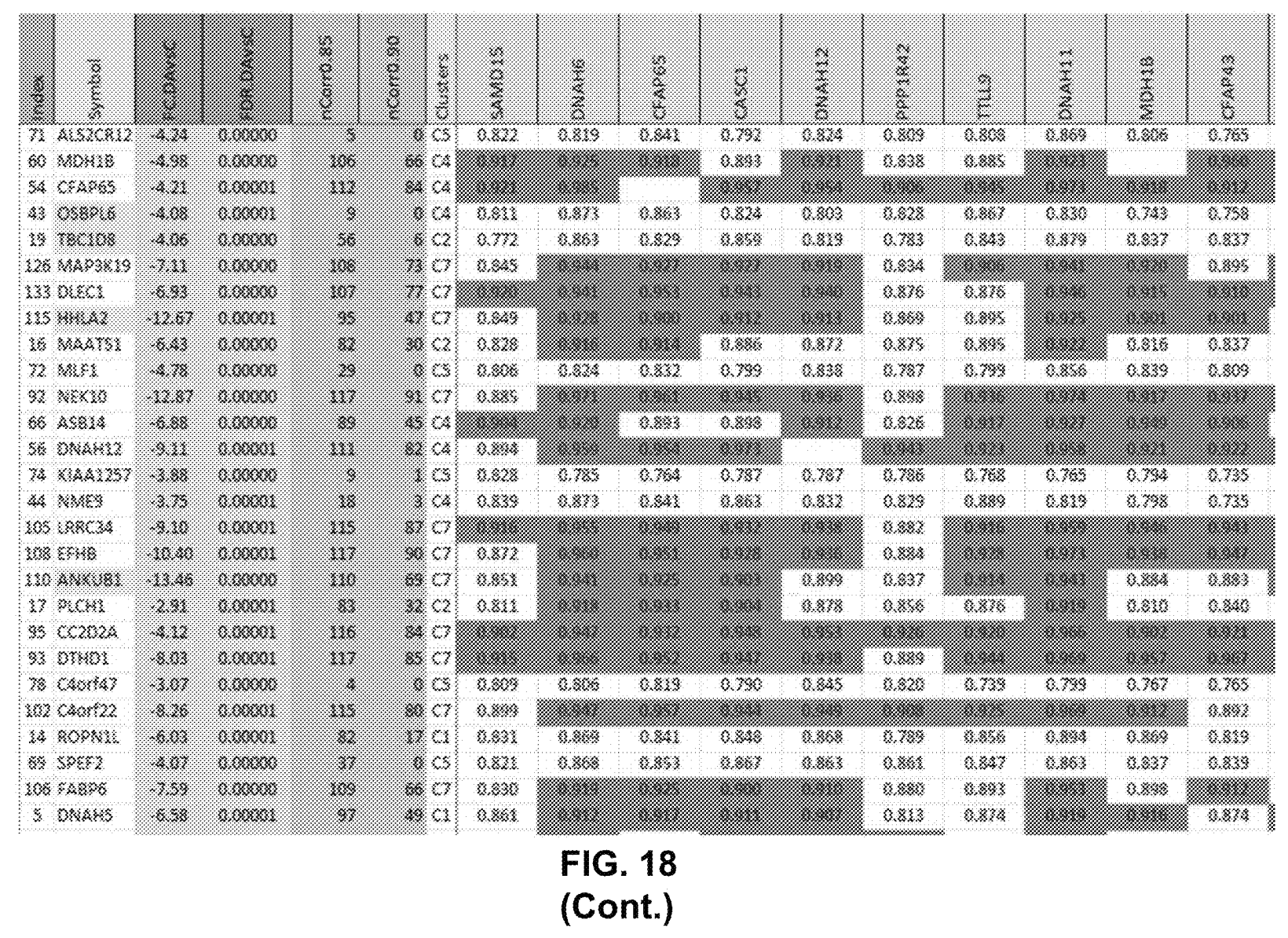
Figure 18:
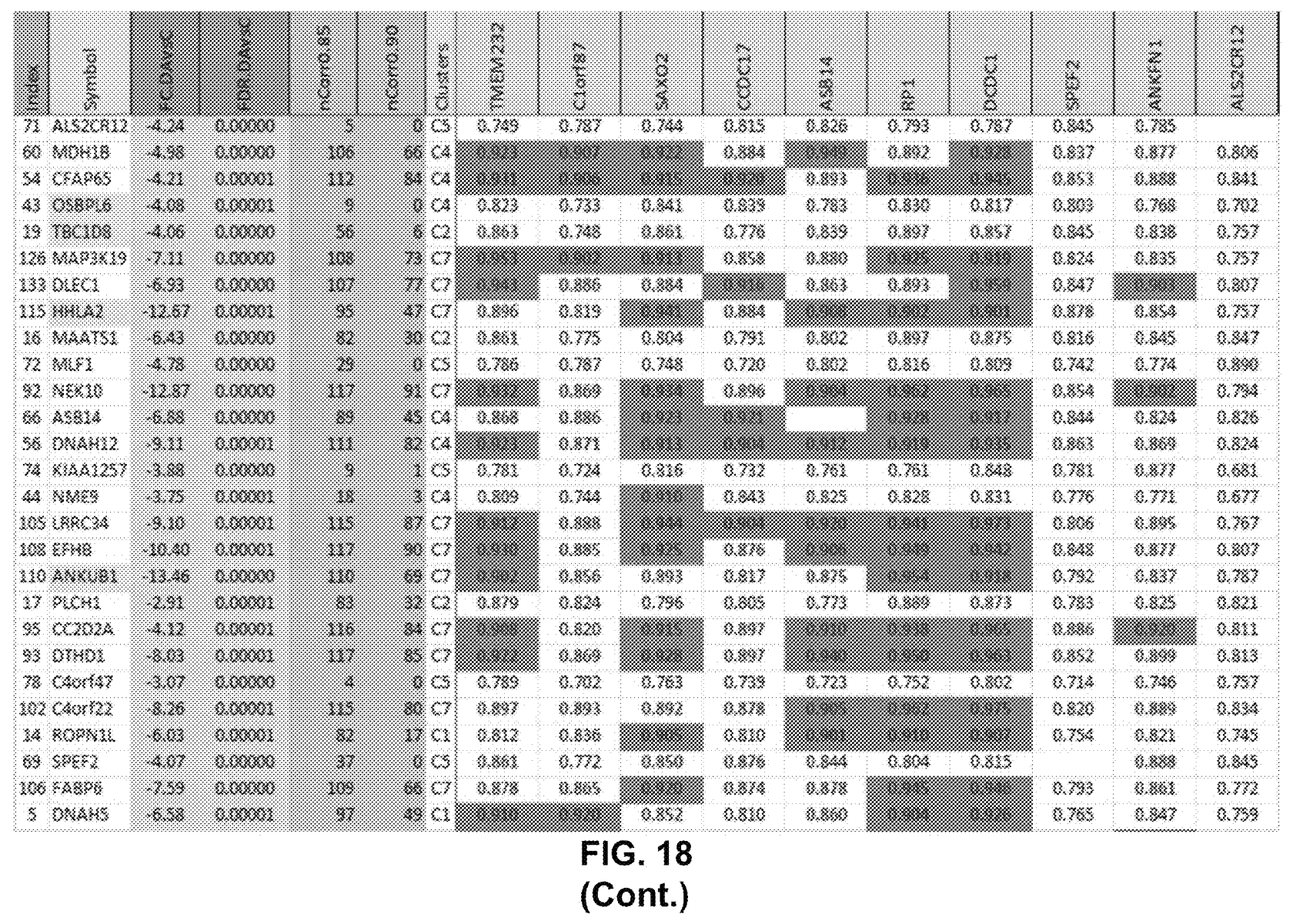
Figure 18:
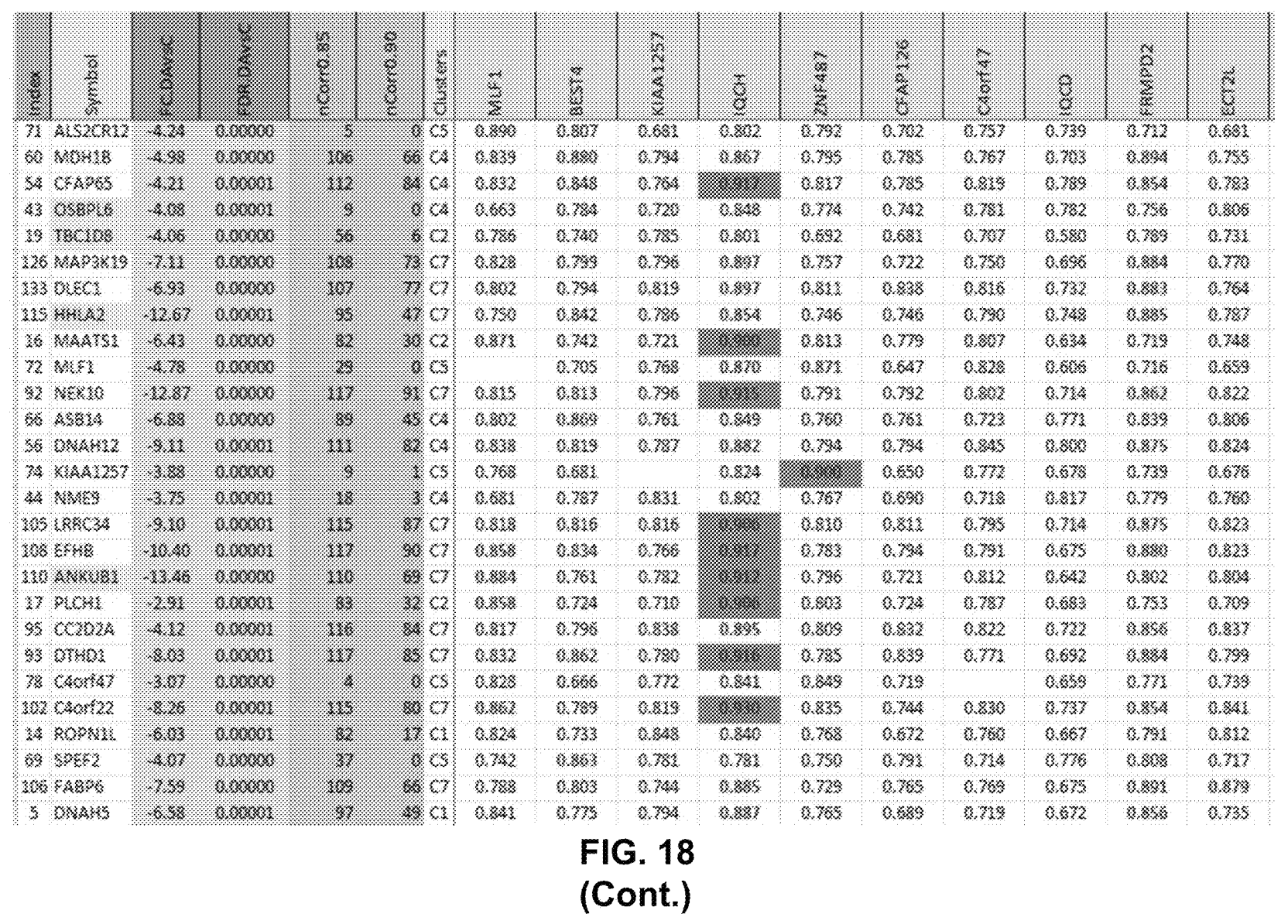
Figure 18:
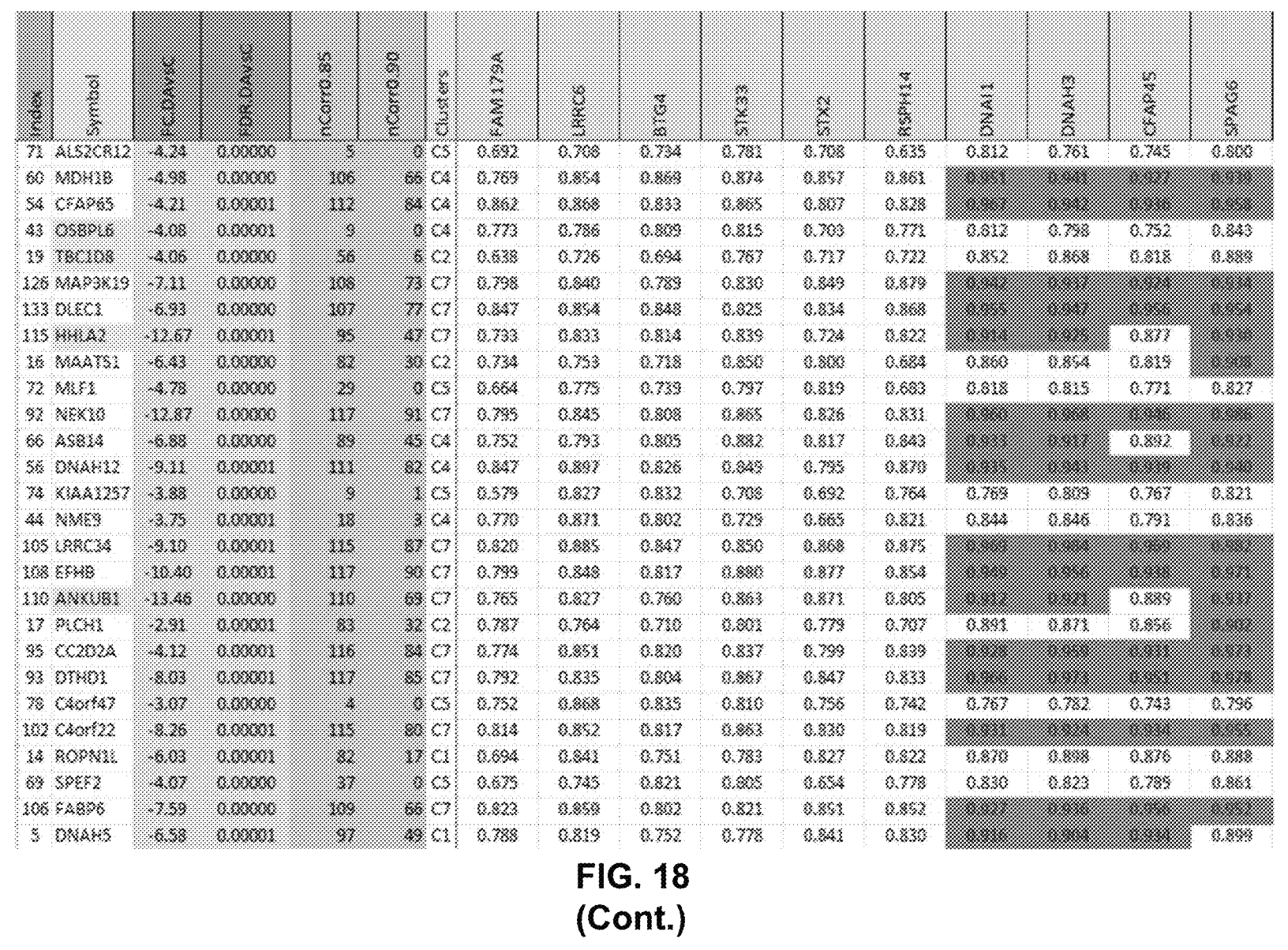
Figure 18:
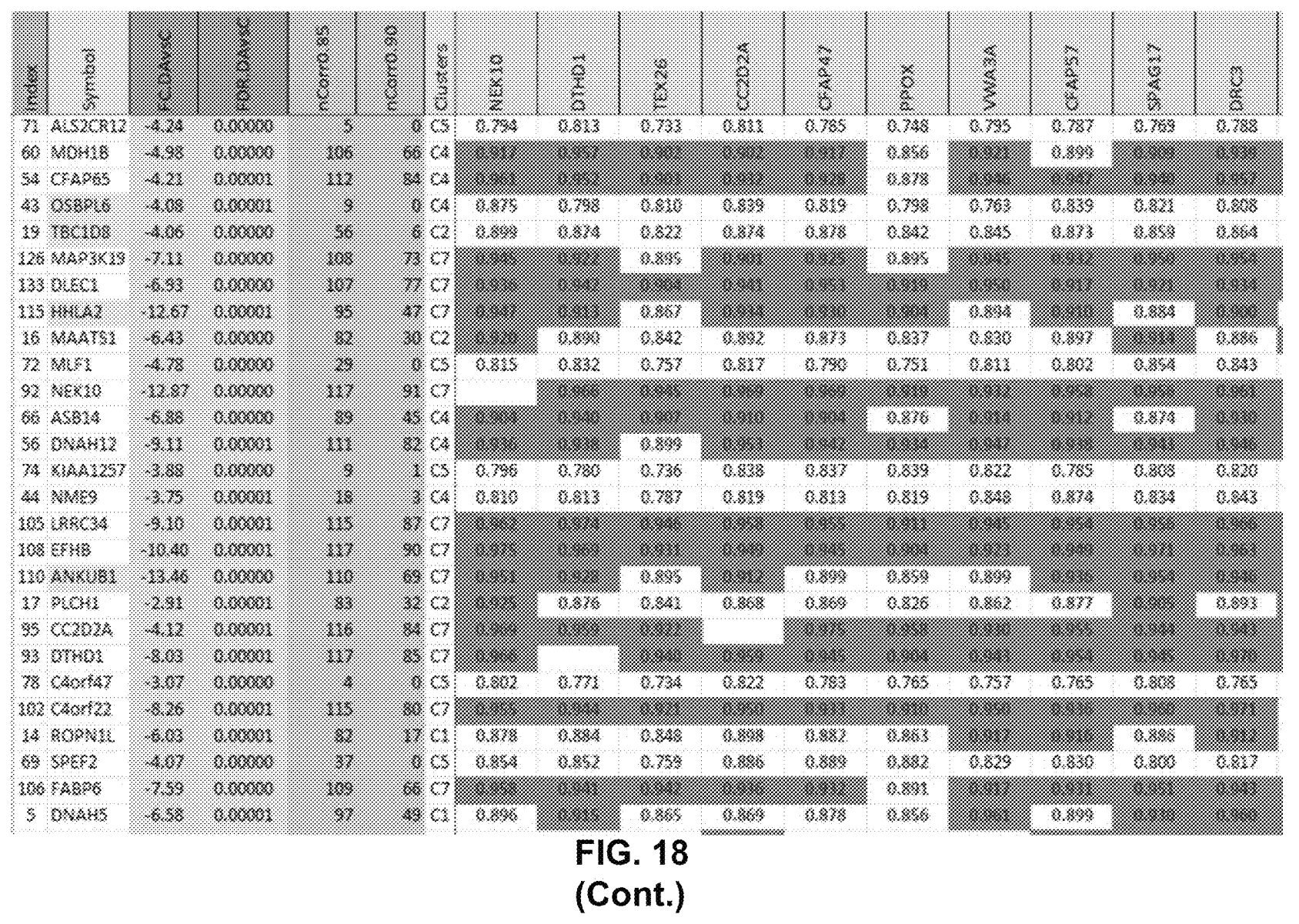
Figure 18:
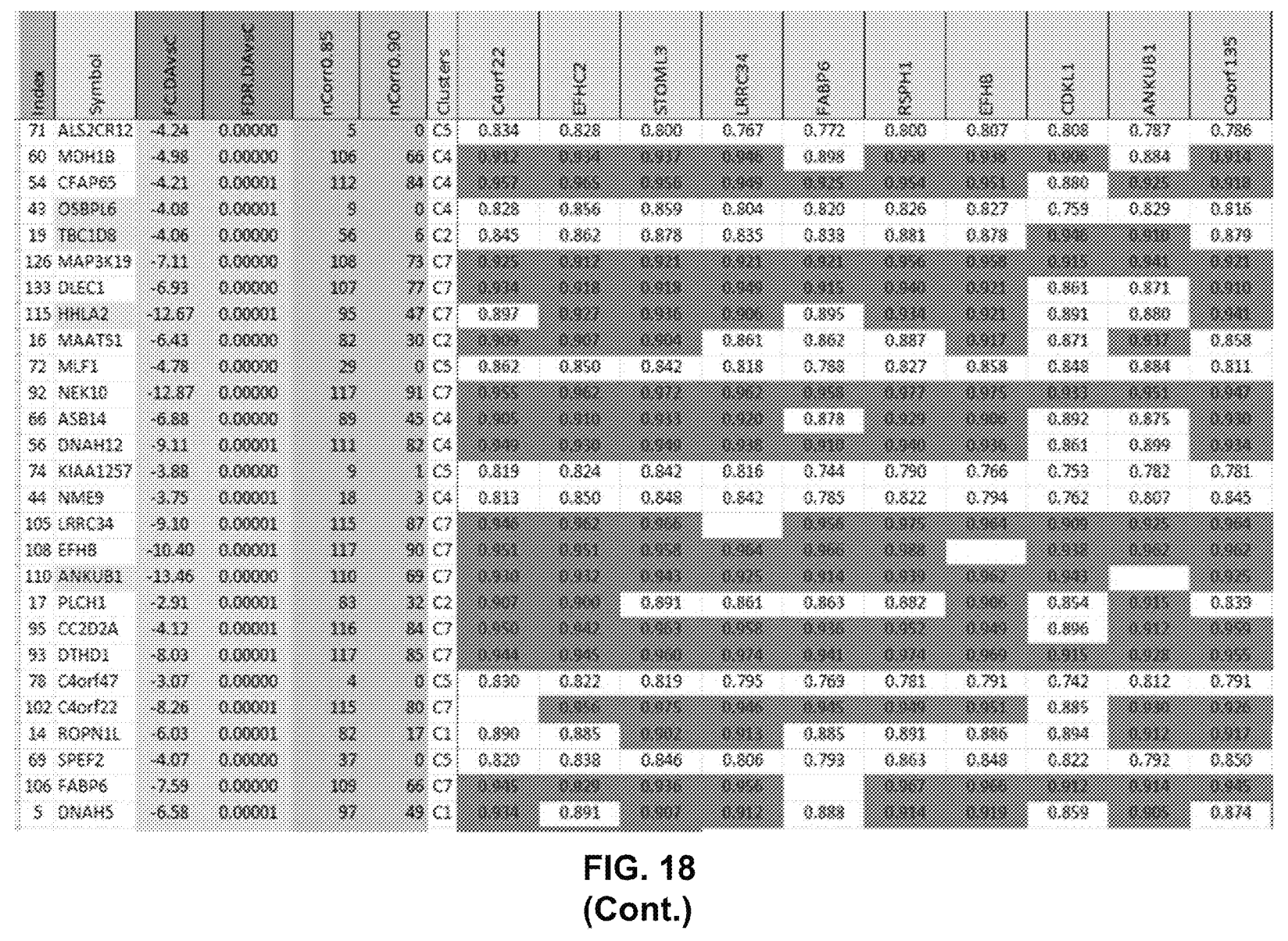
Figure 18:
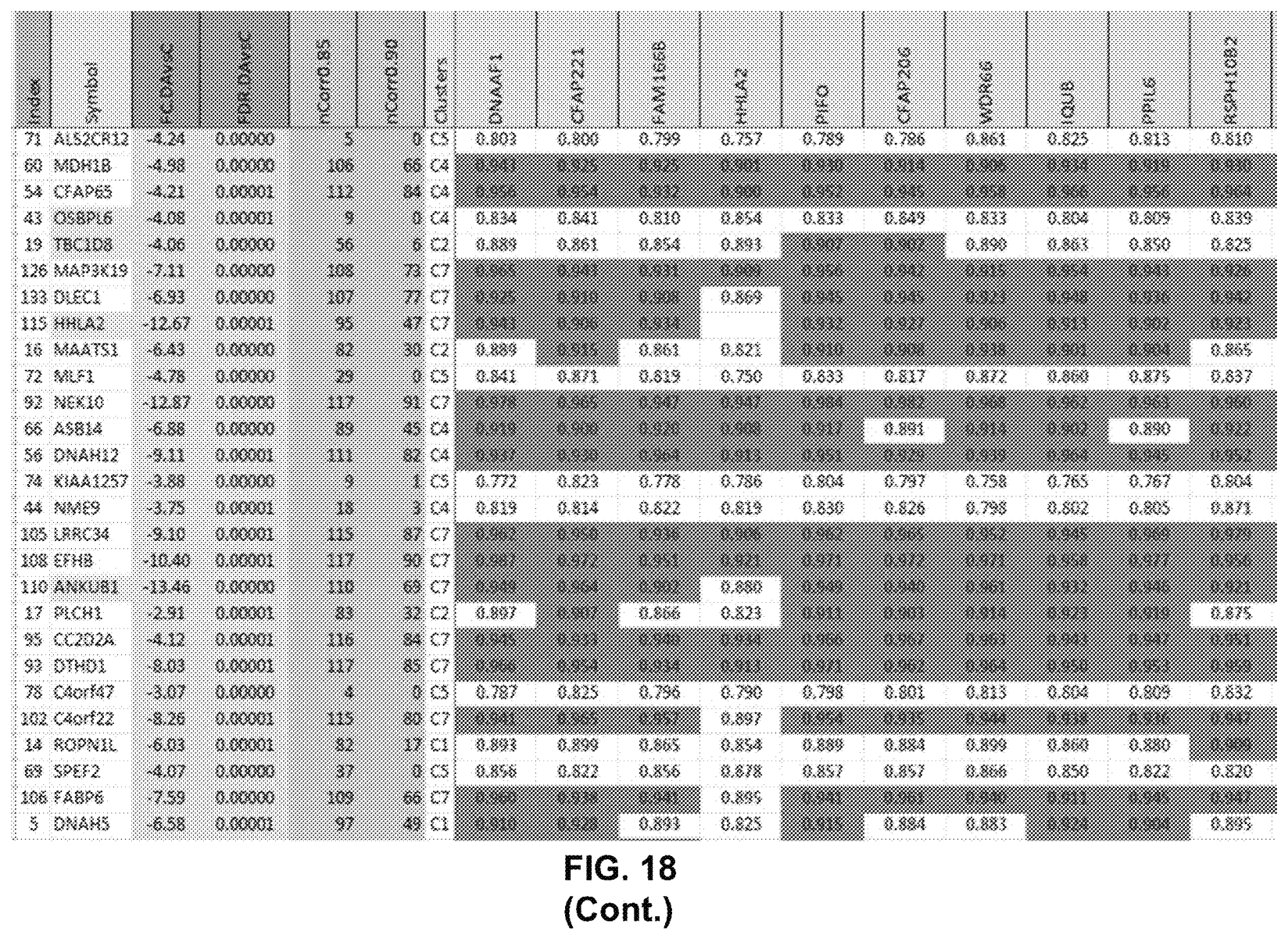
Figure 18:
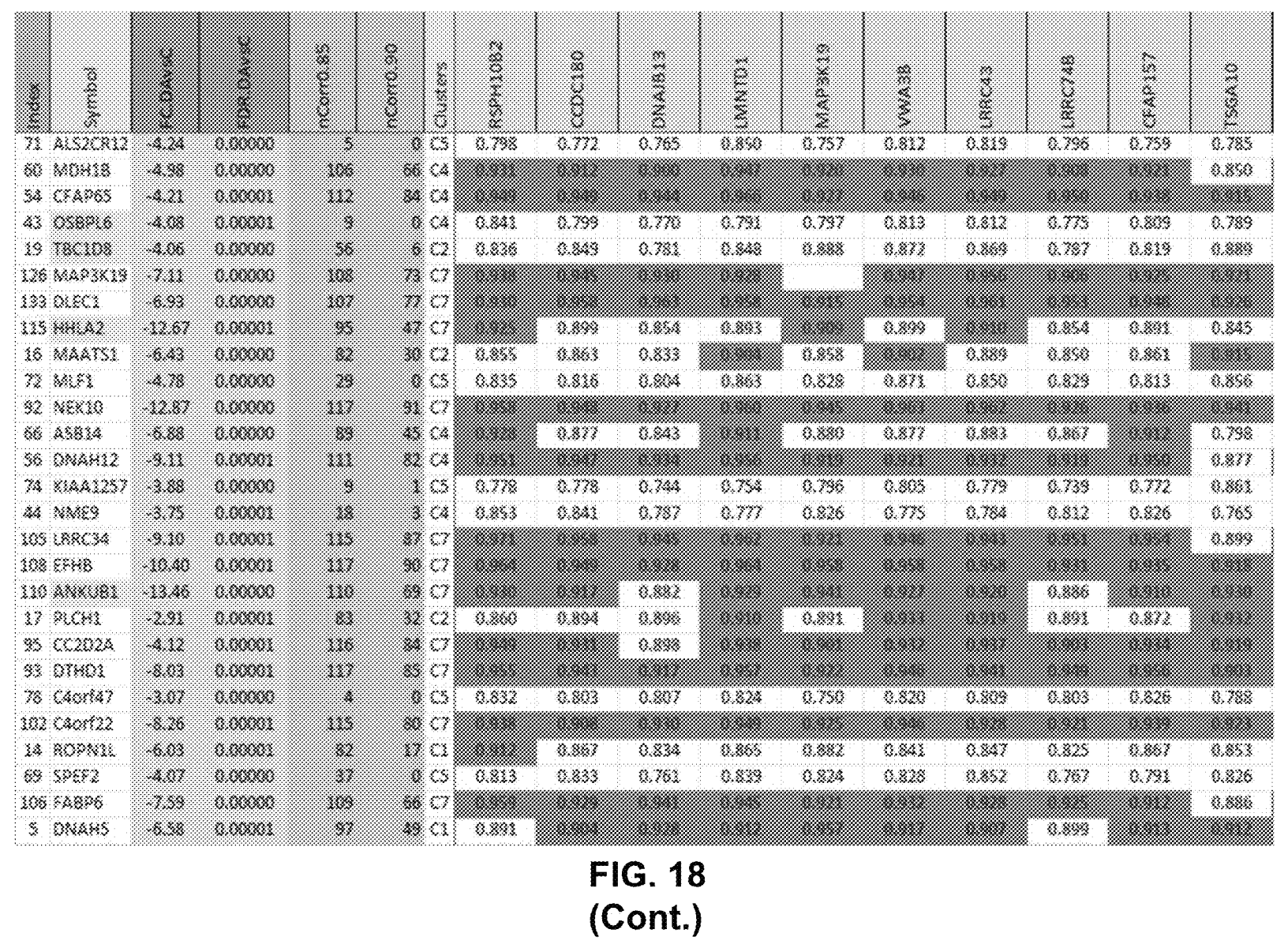
Figure 18:
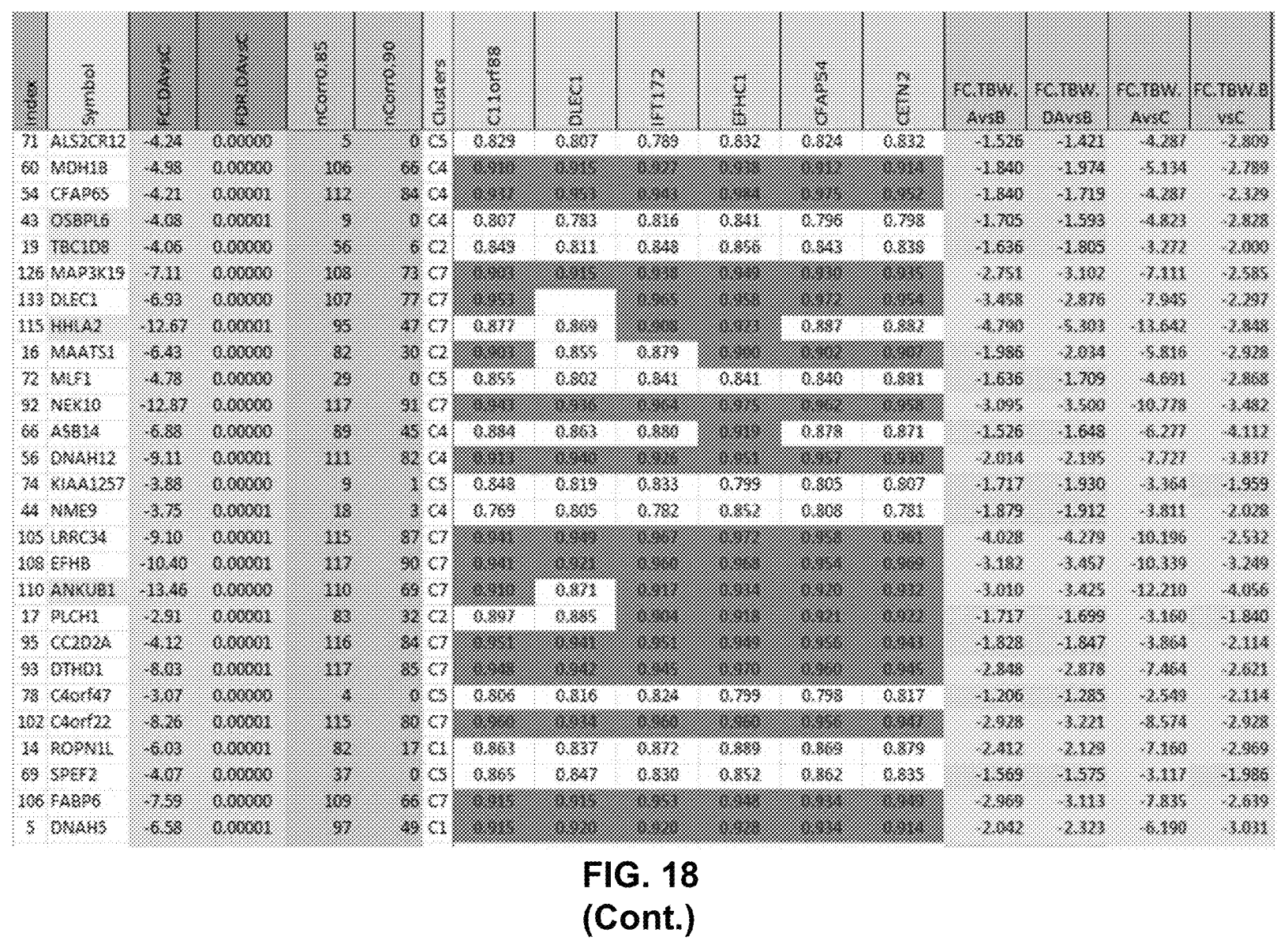
Figure 18:
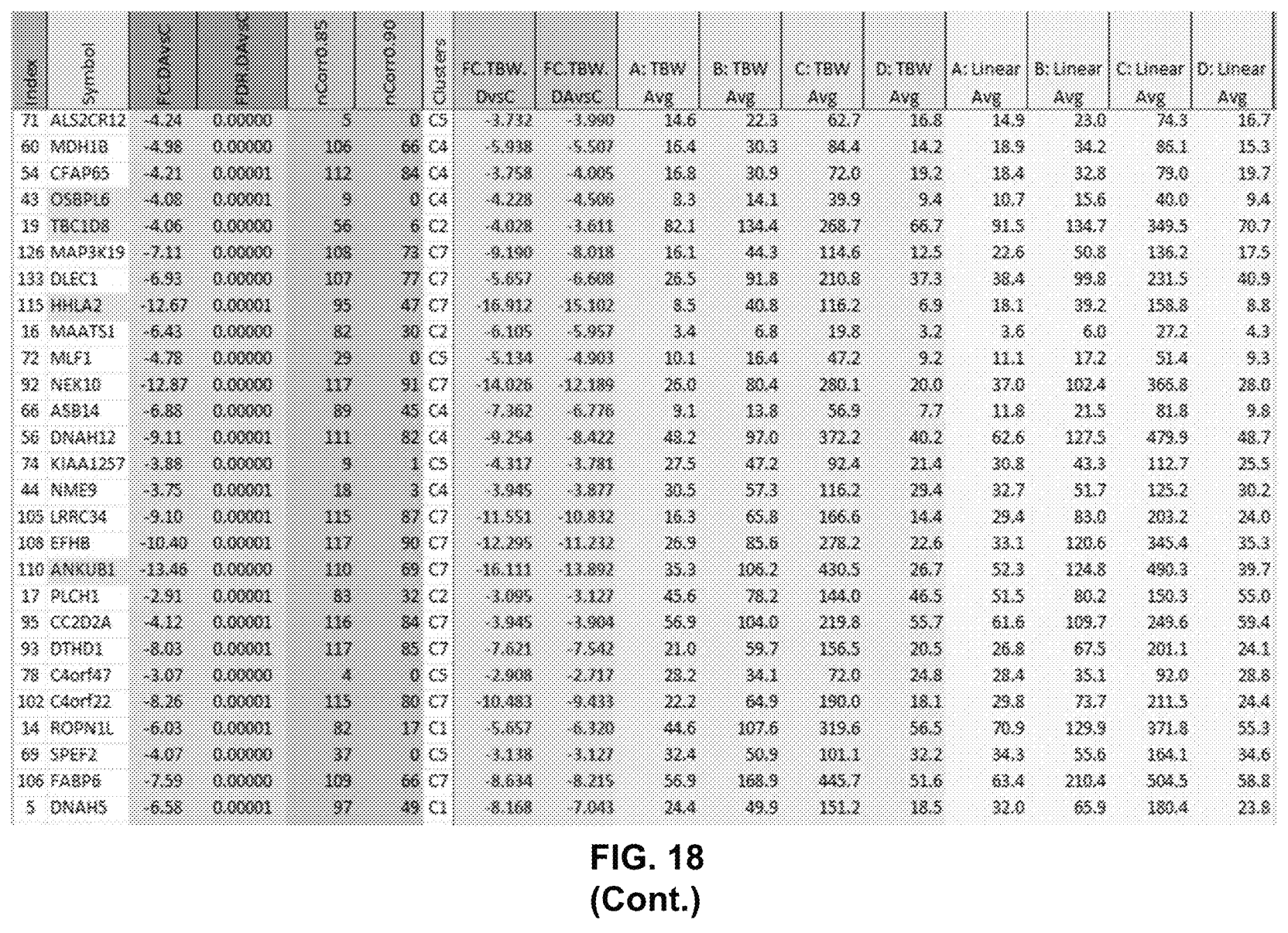
Figure 18:
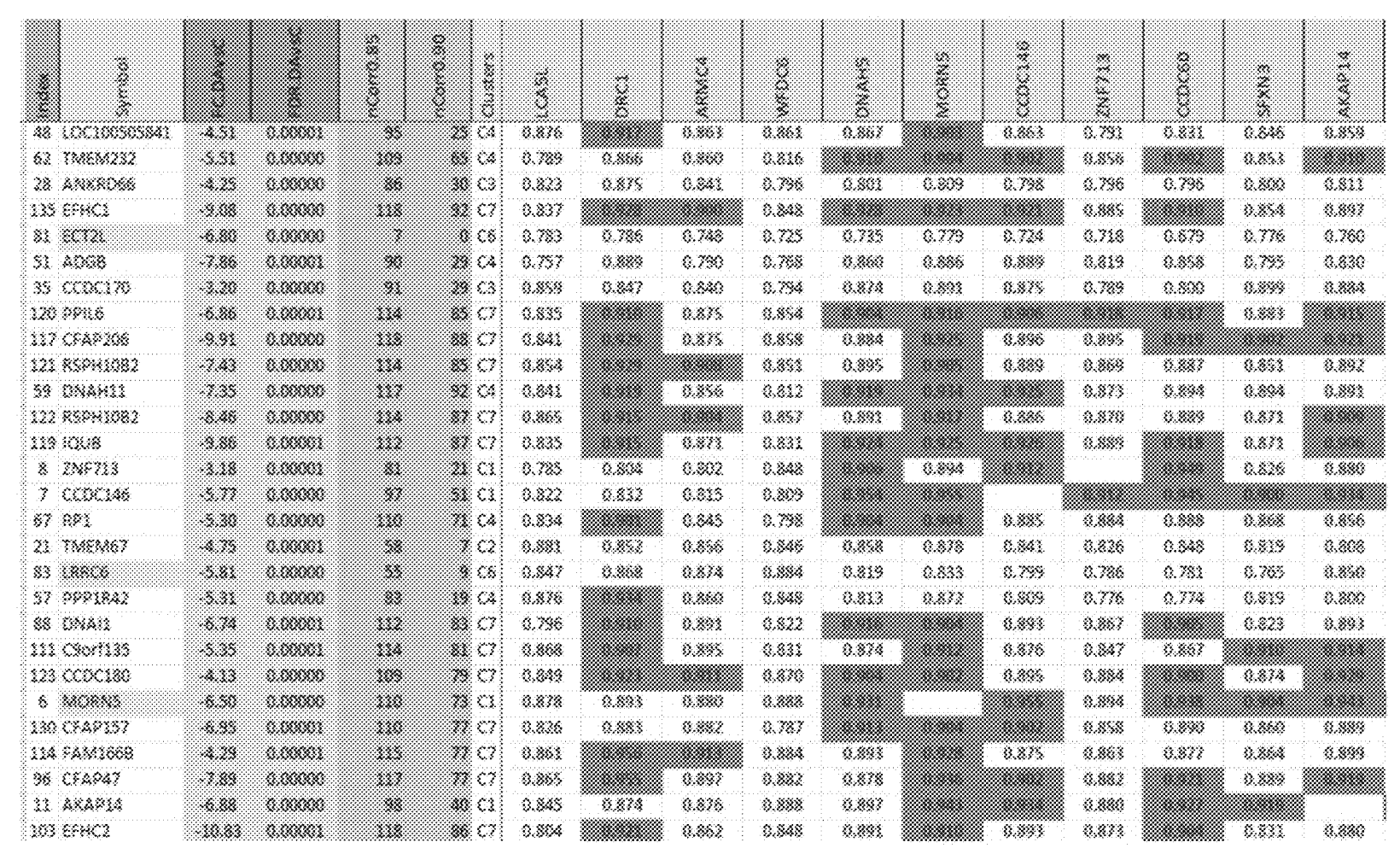
Figure 18:
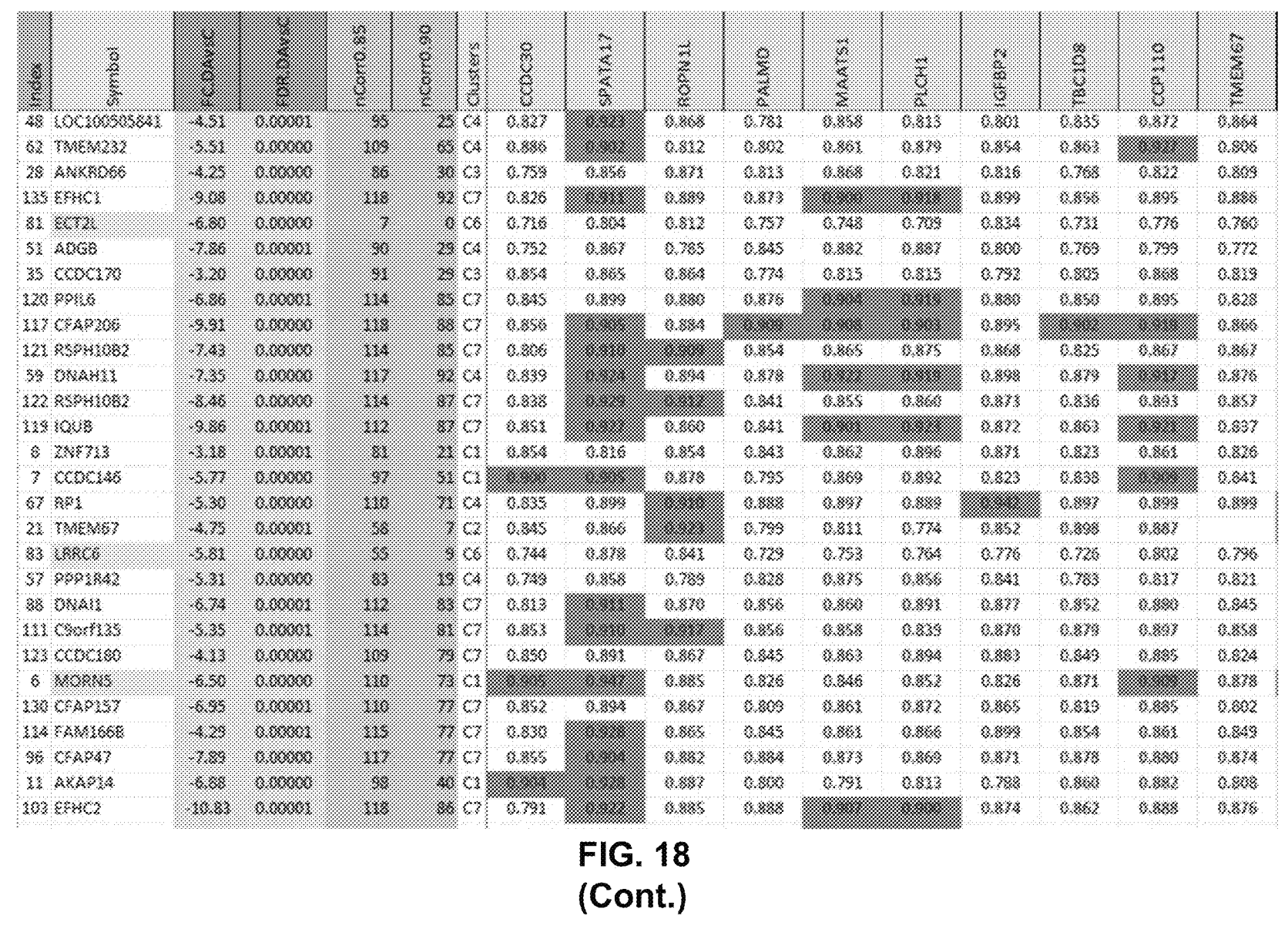
Figure 18:
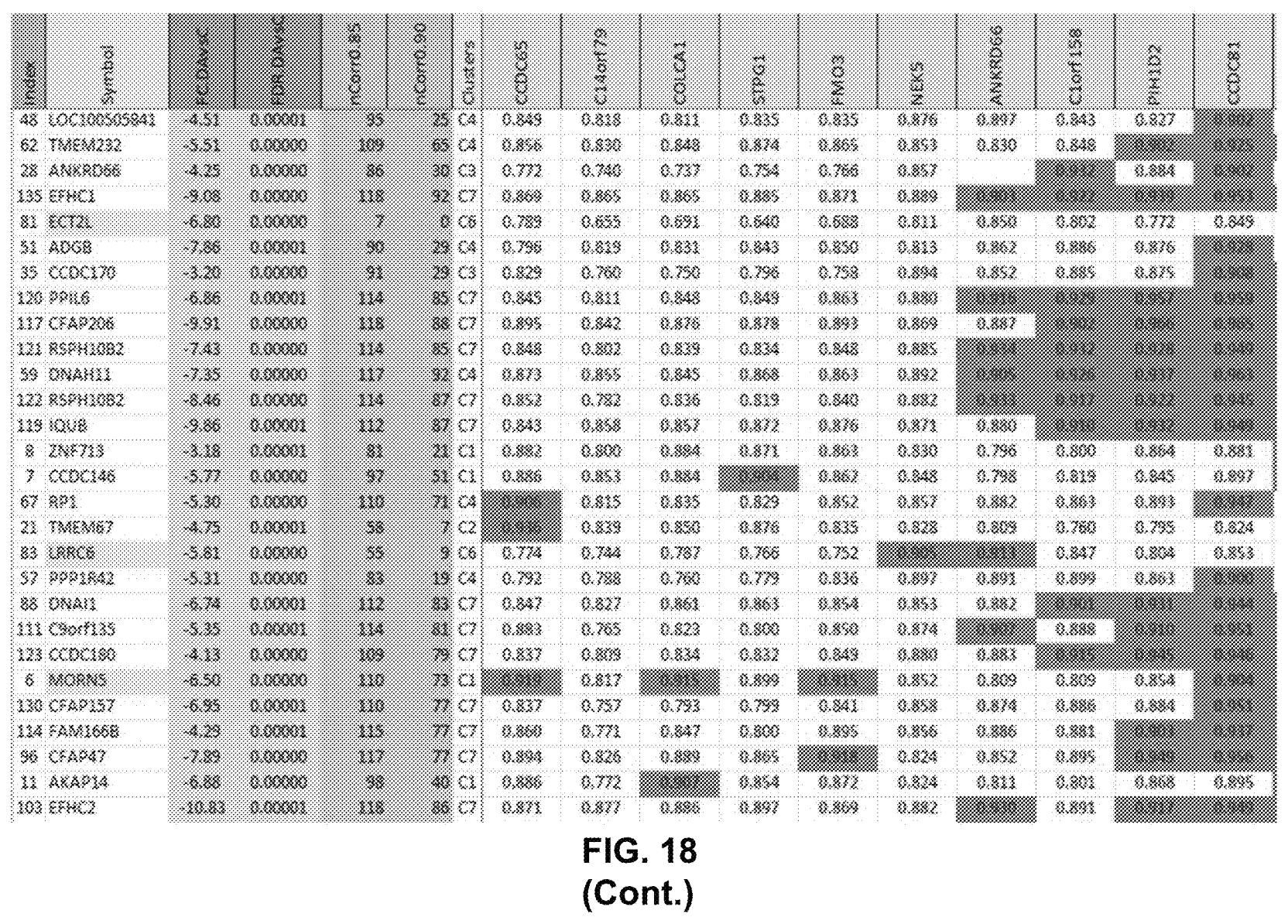
Figure 18:
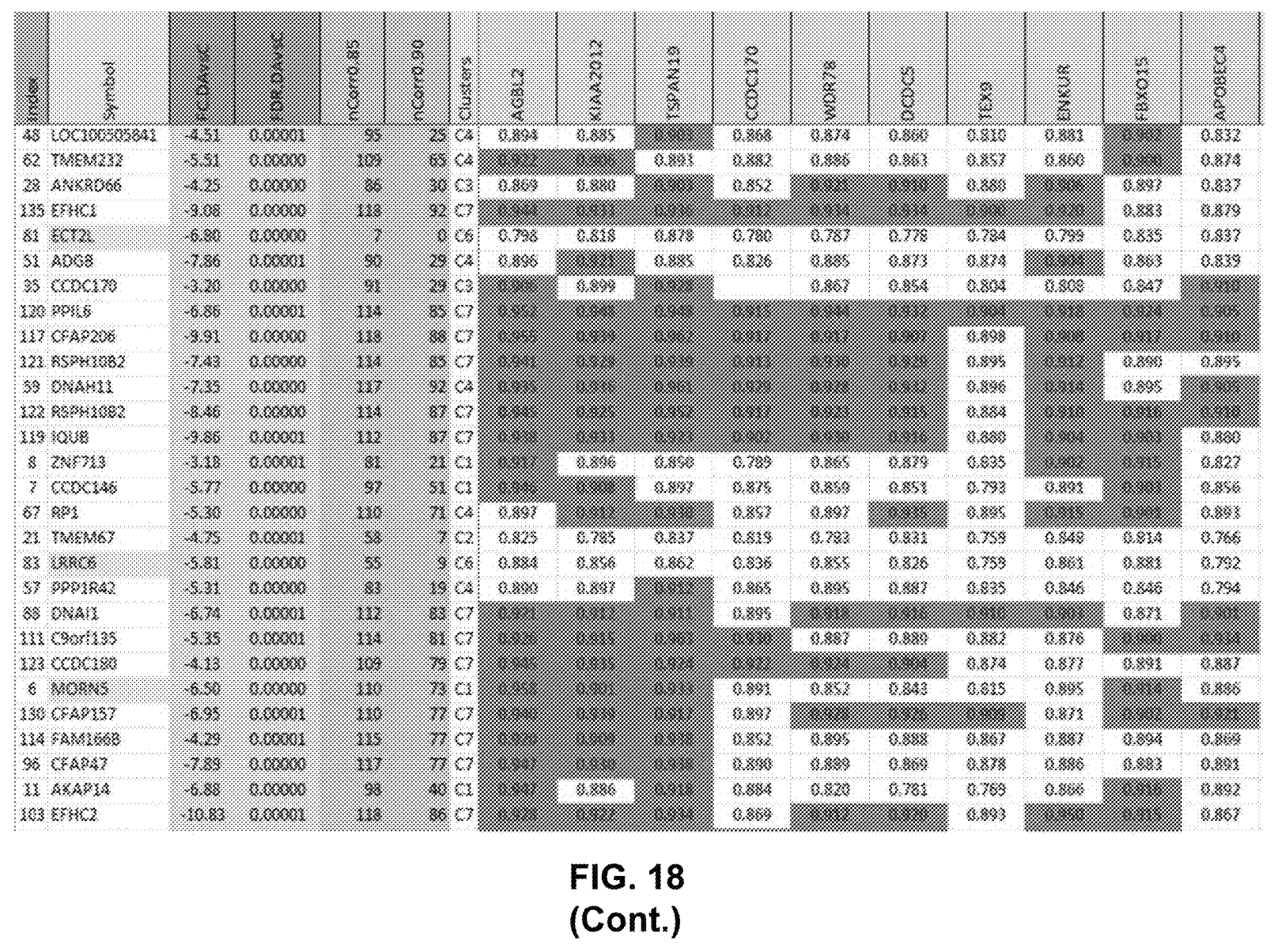
Figure 18:
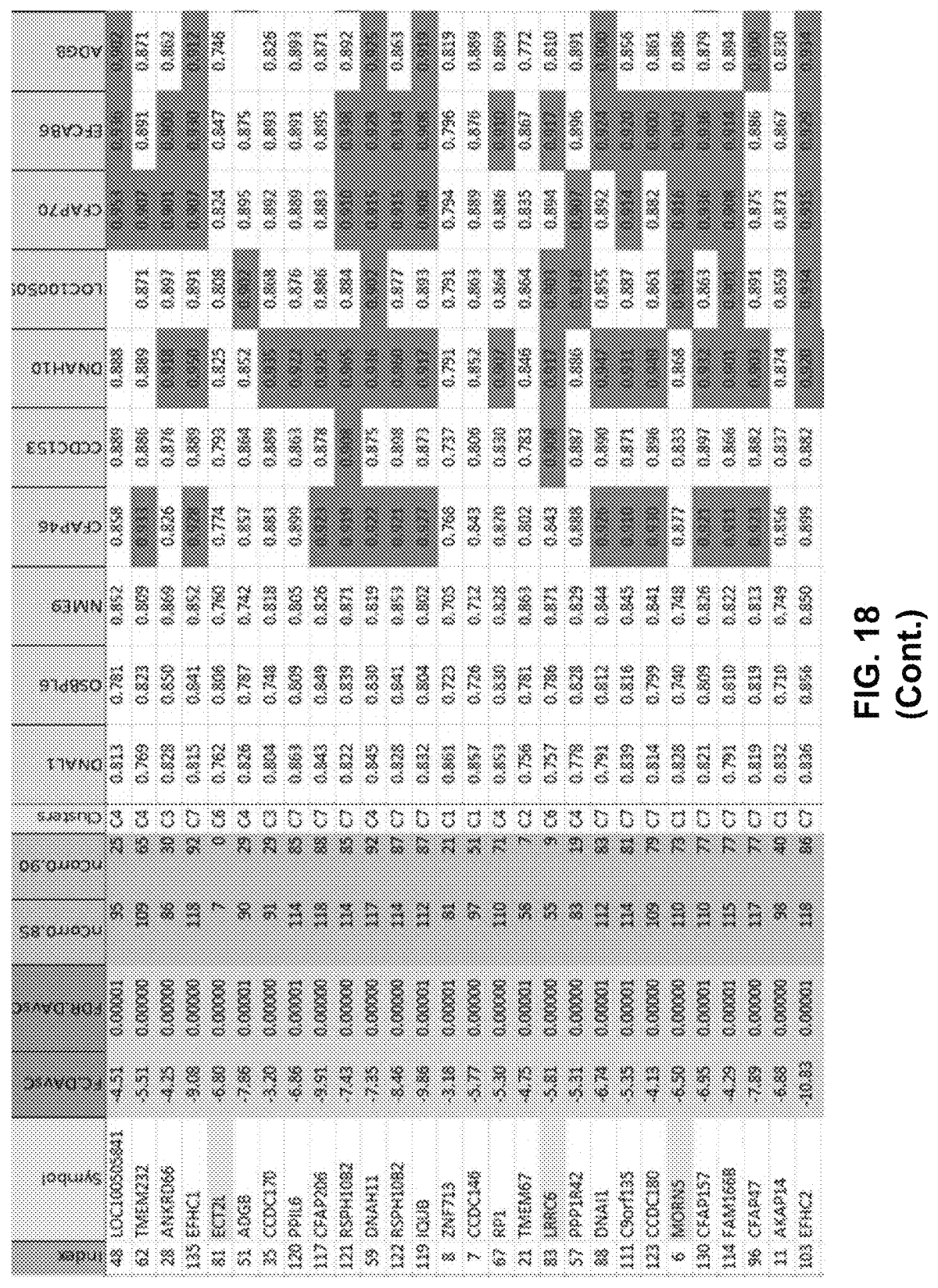
Figure 18:
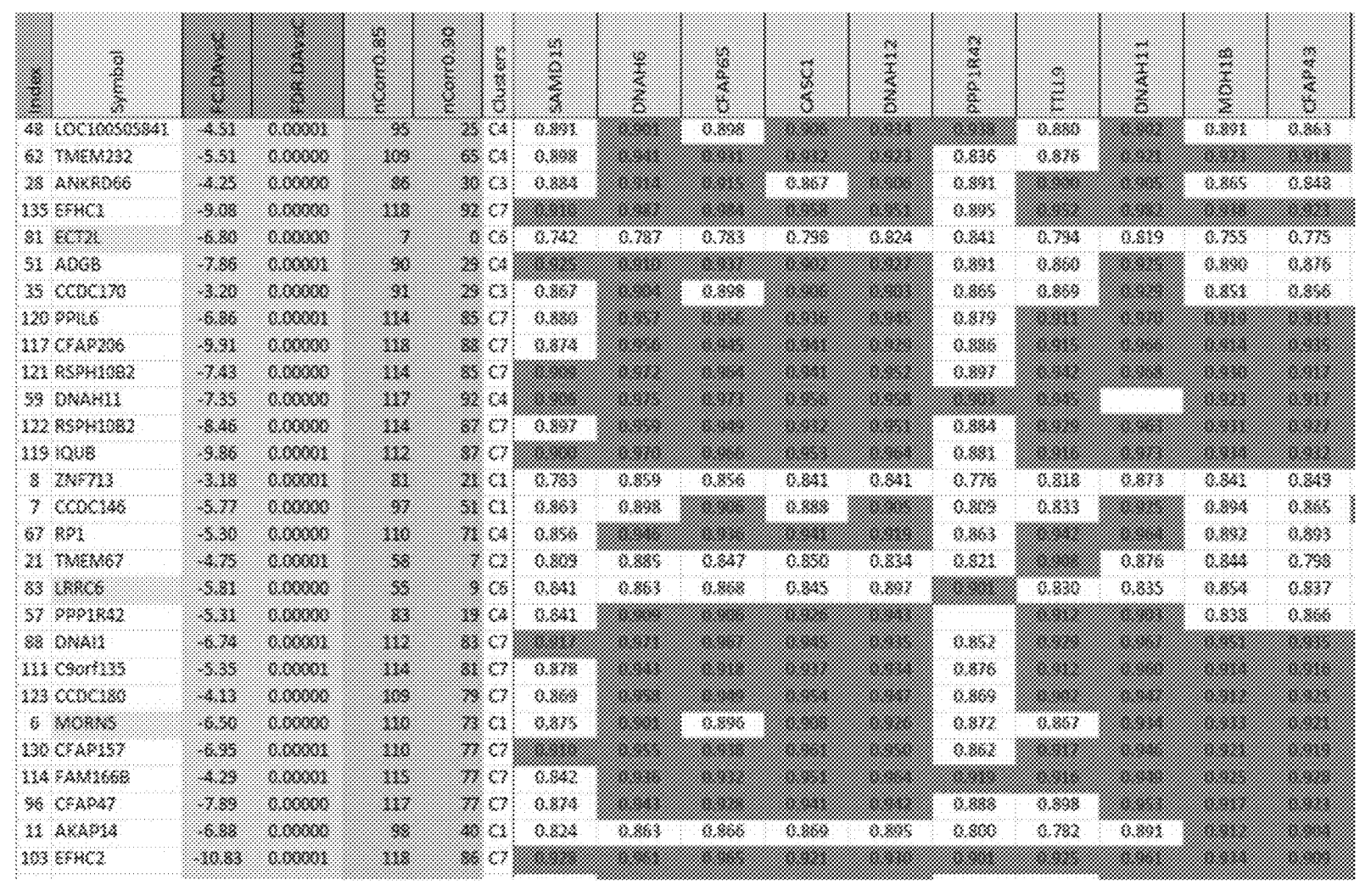
Figure 18:
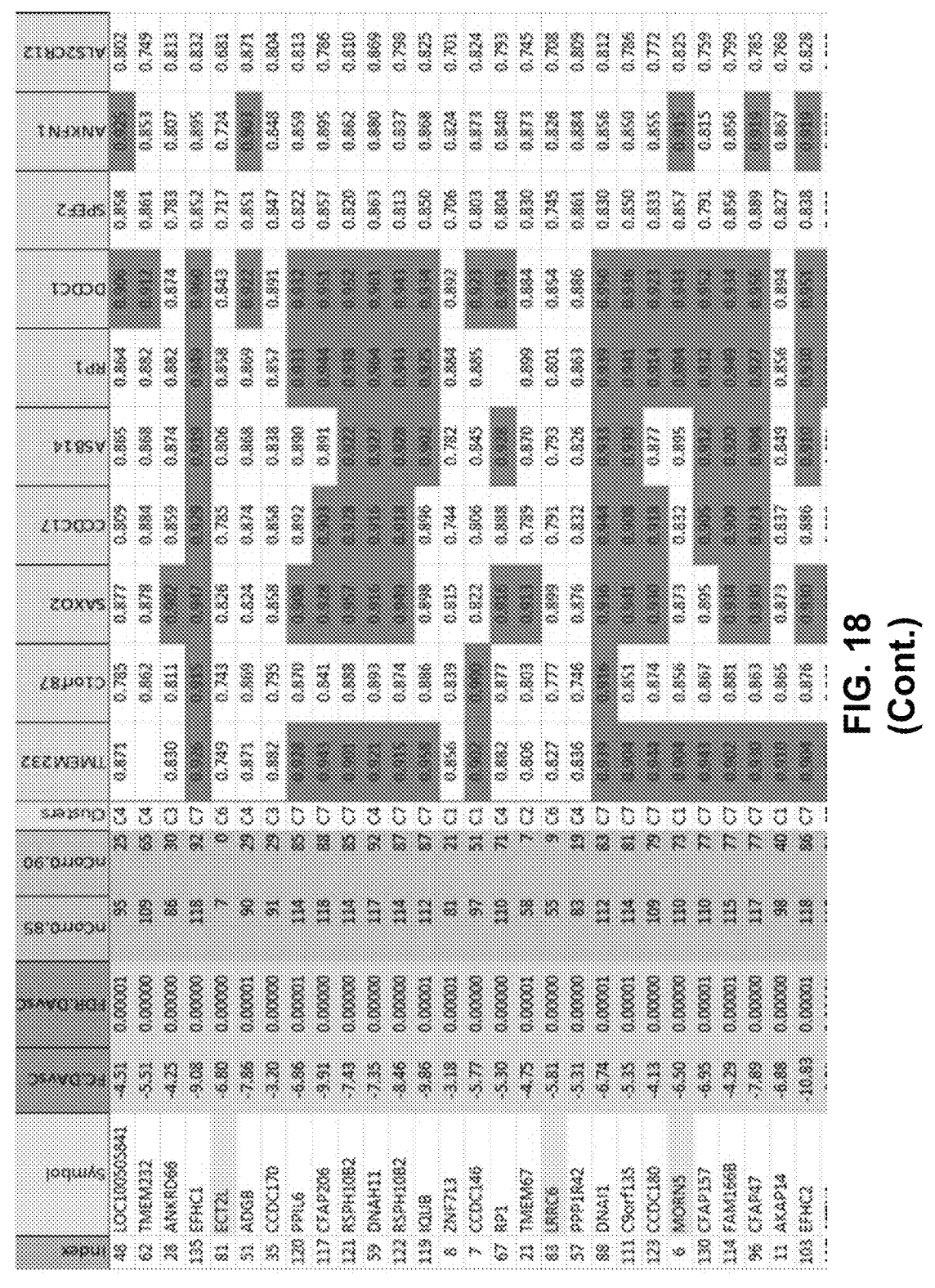
Figure 18:
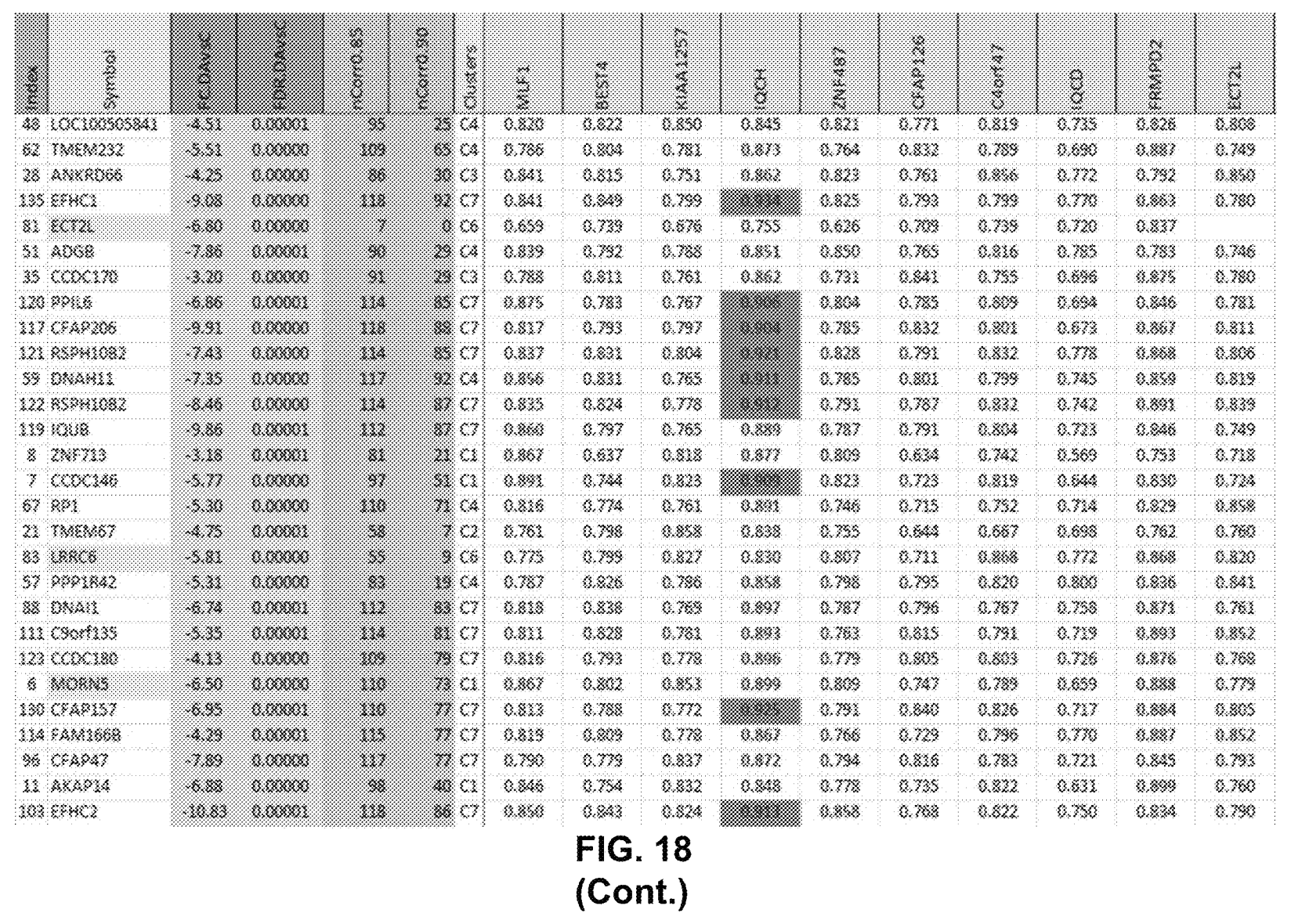
Figure 18:
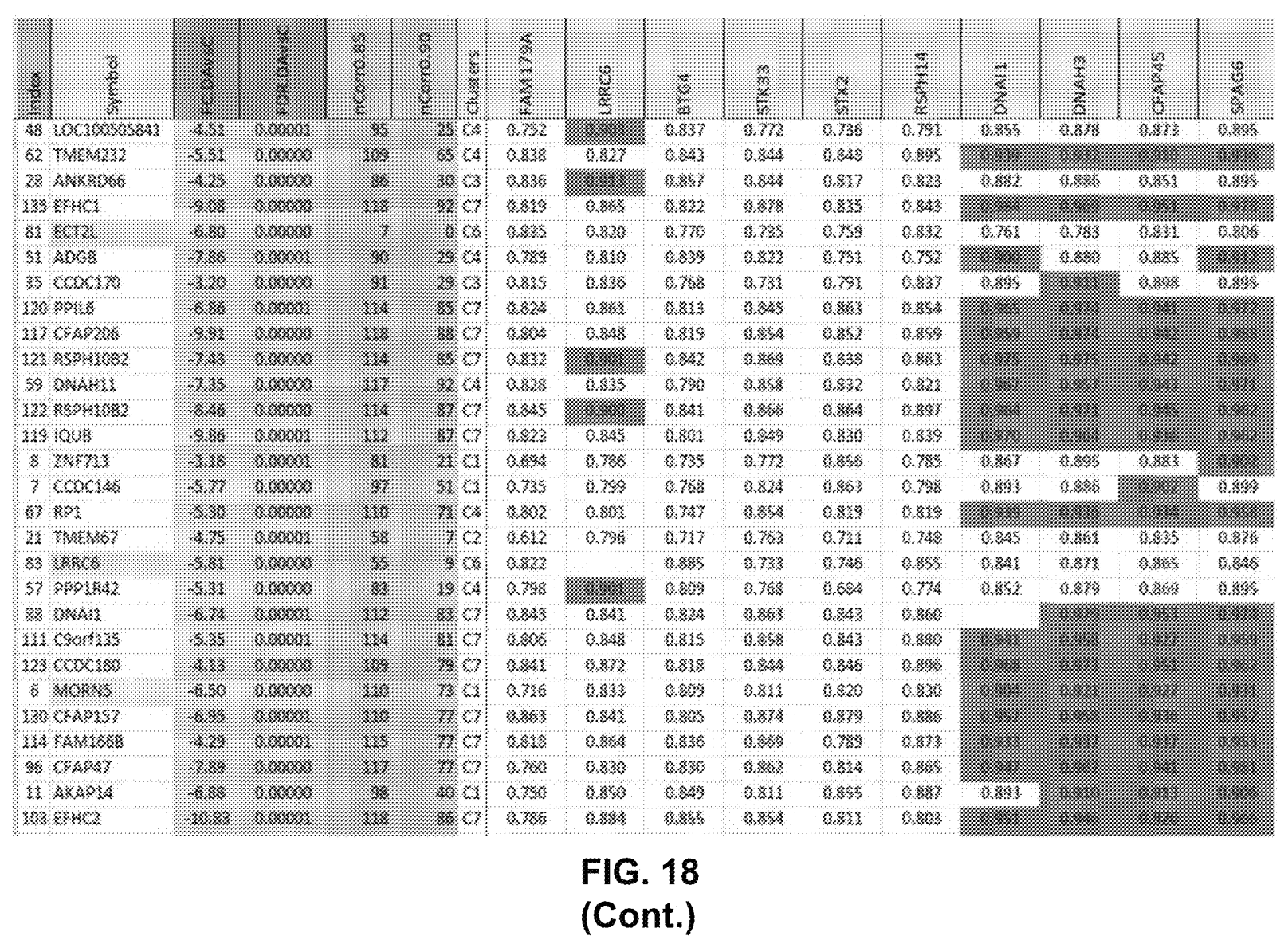
Figure 18:
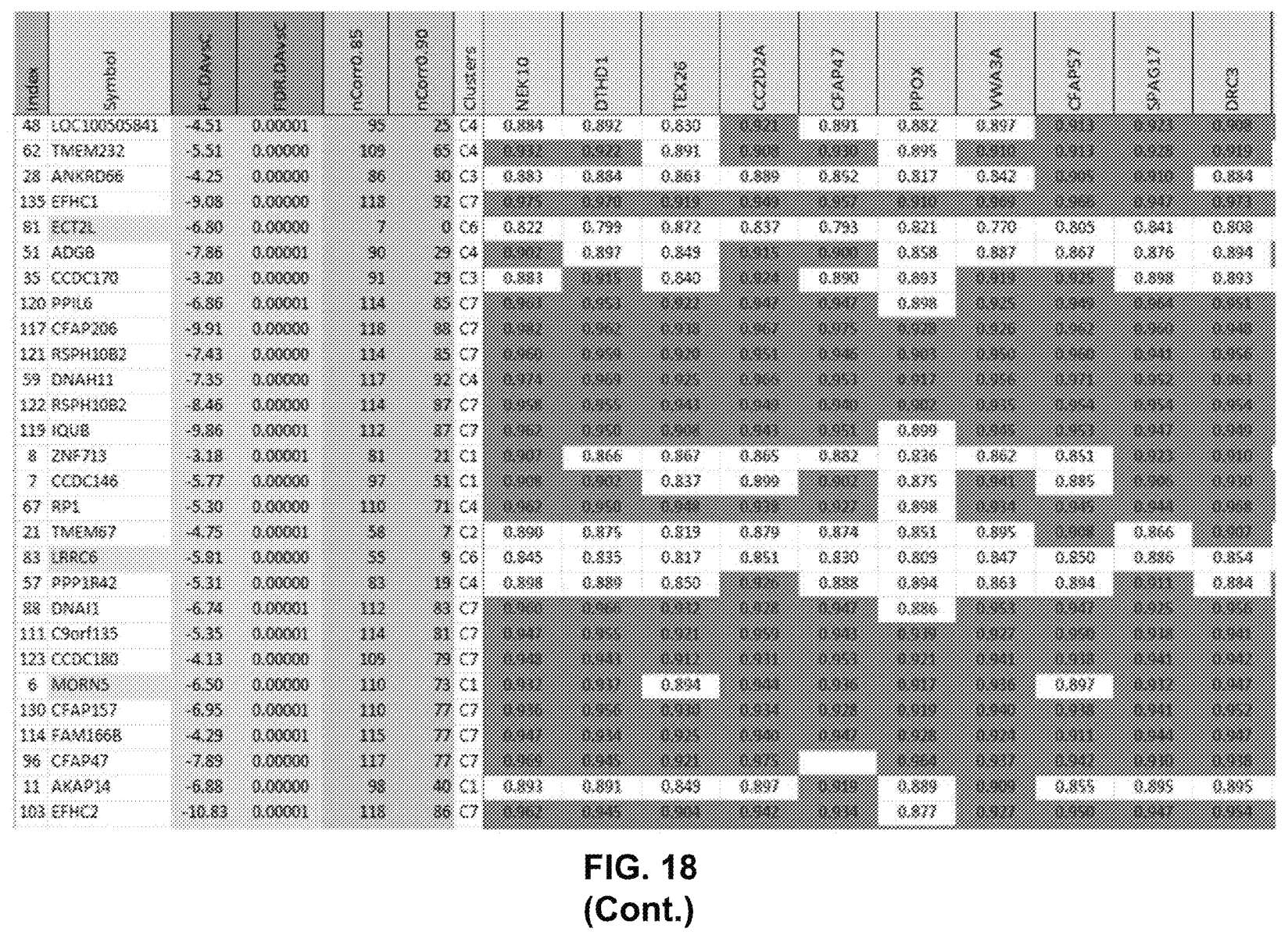
Figure 18:
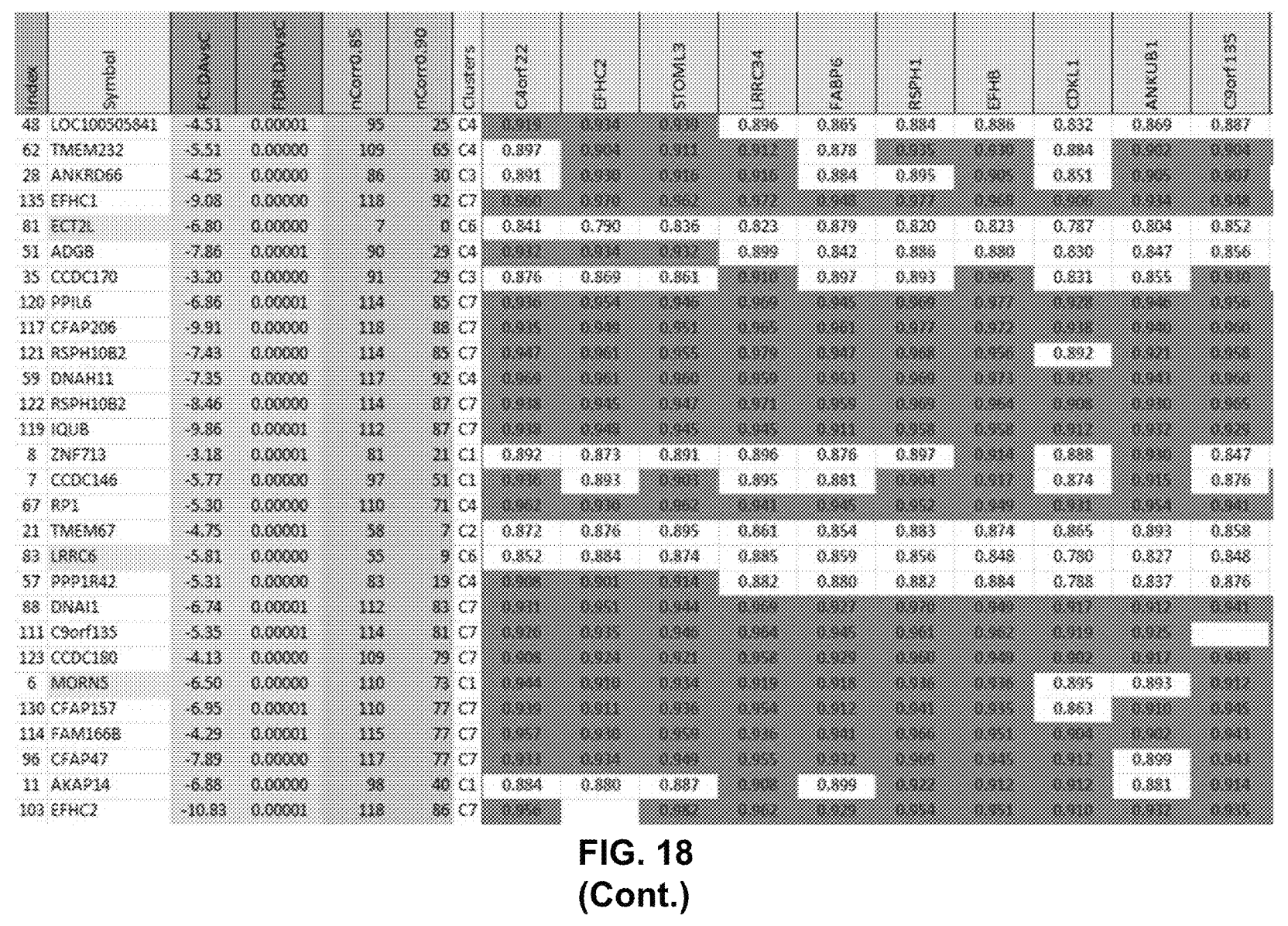
Figure 18:
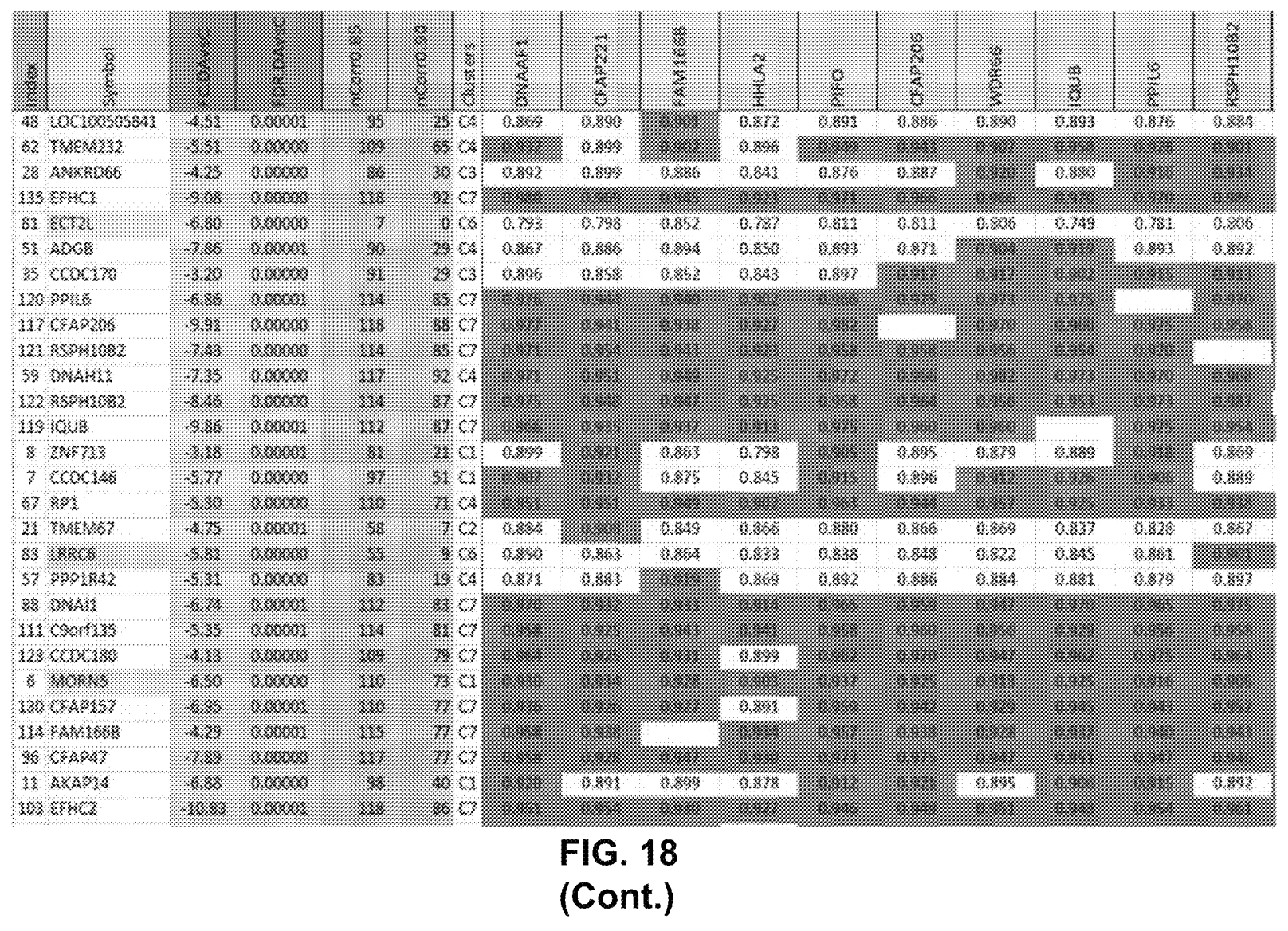
Figure 18:
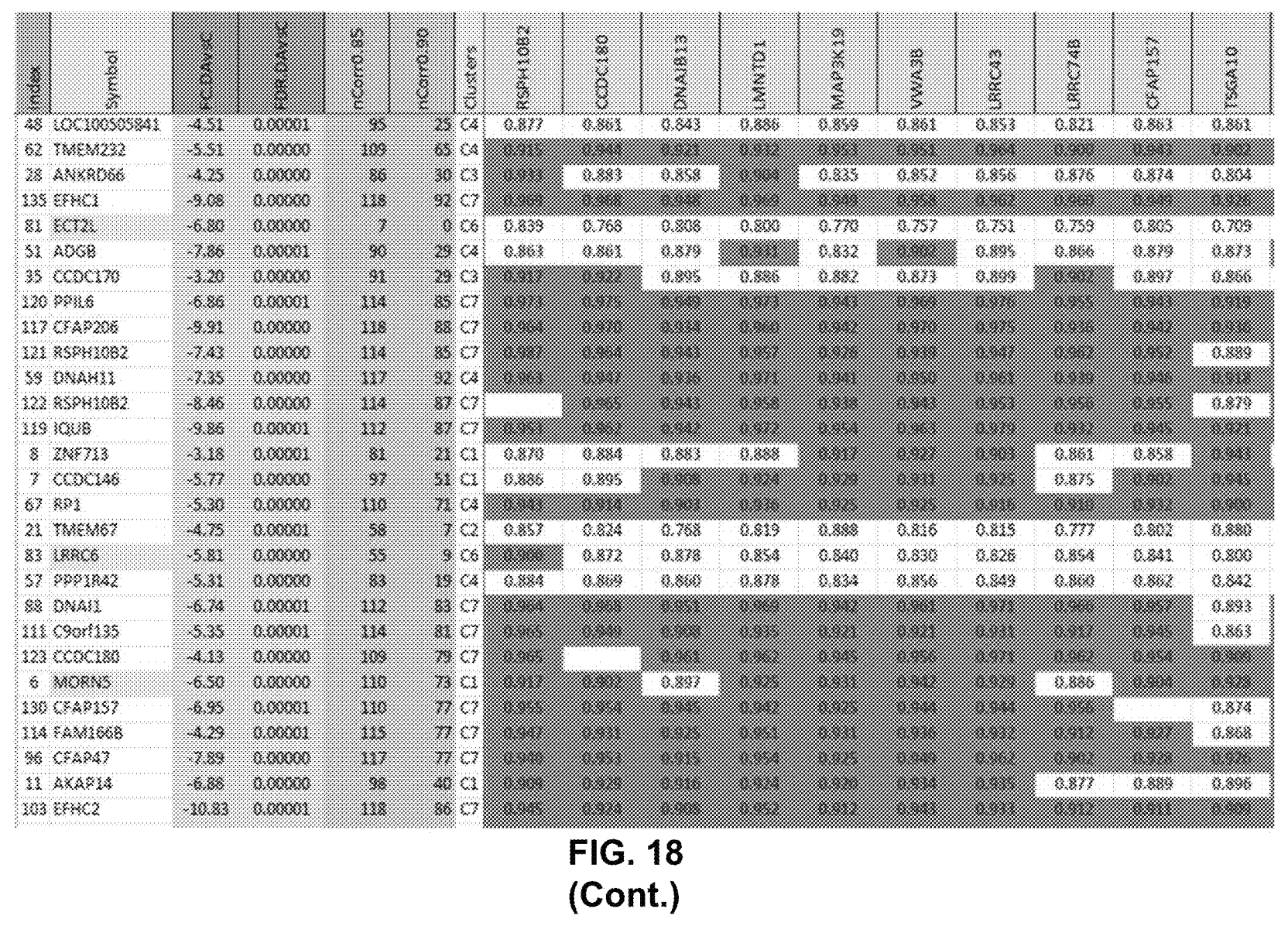
Figure 18:
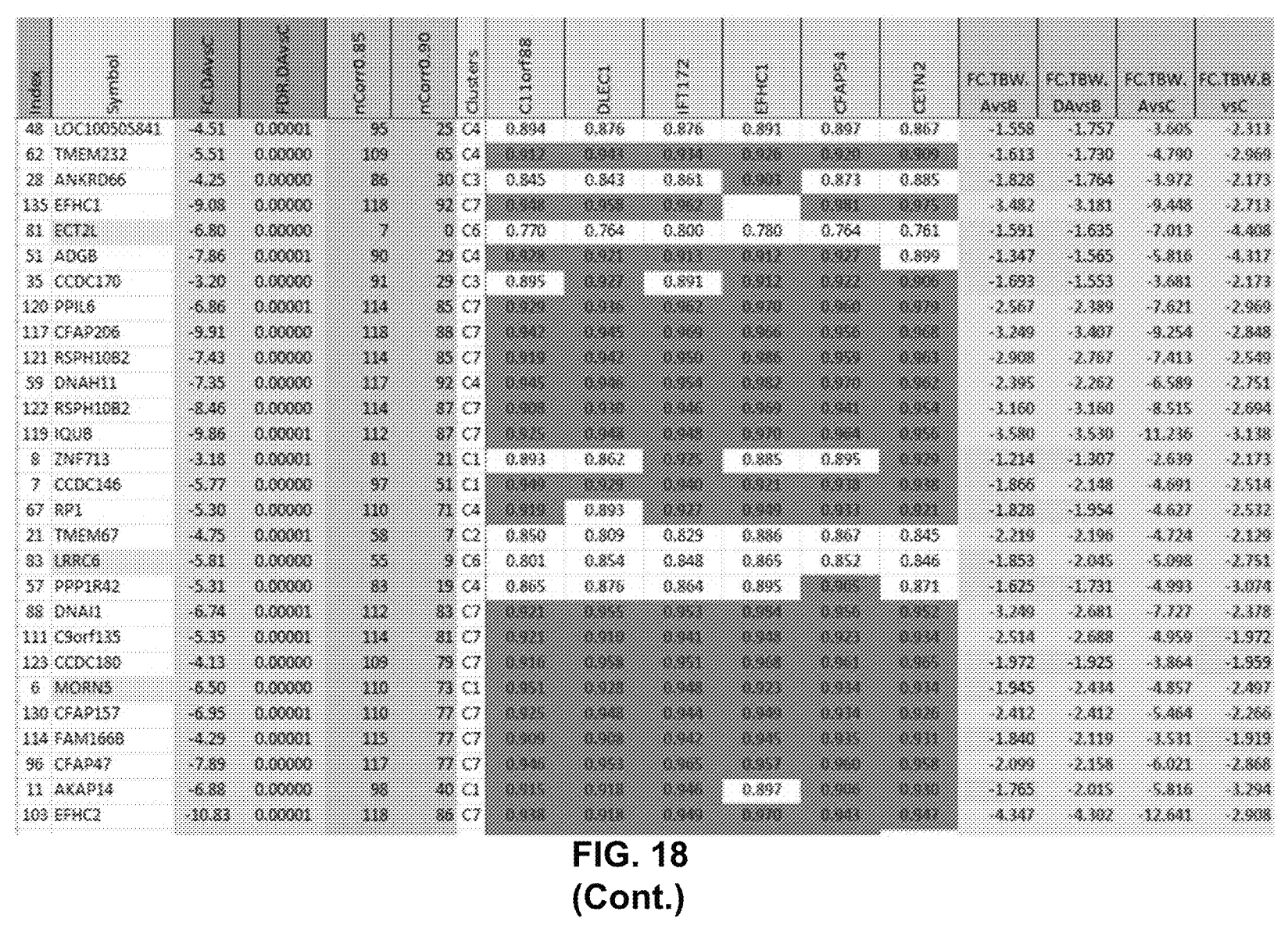
Figure 18:
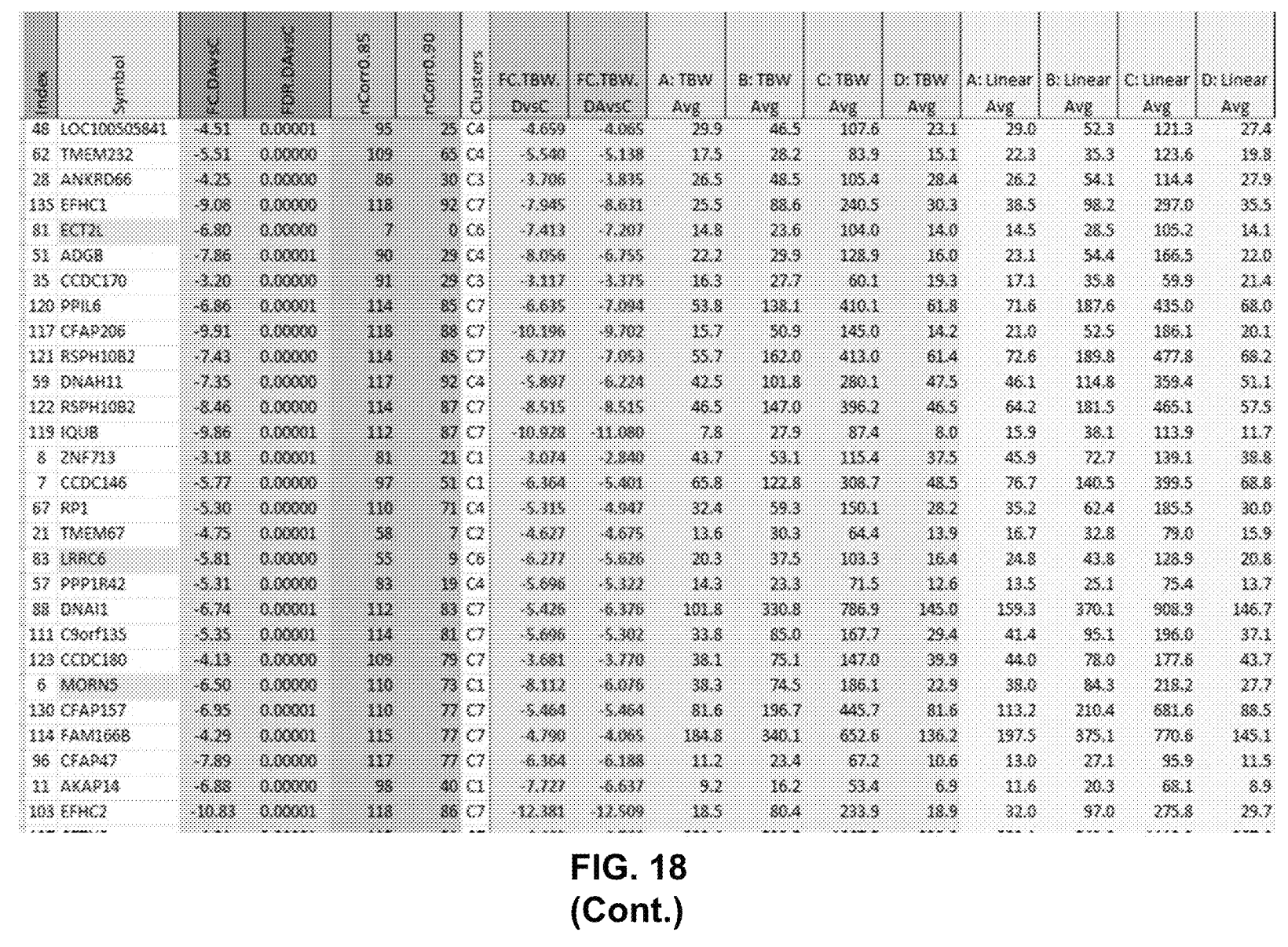
Figure 18:
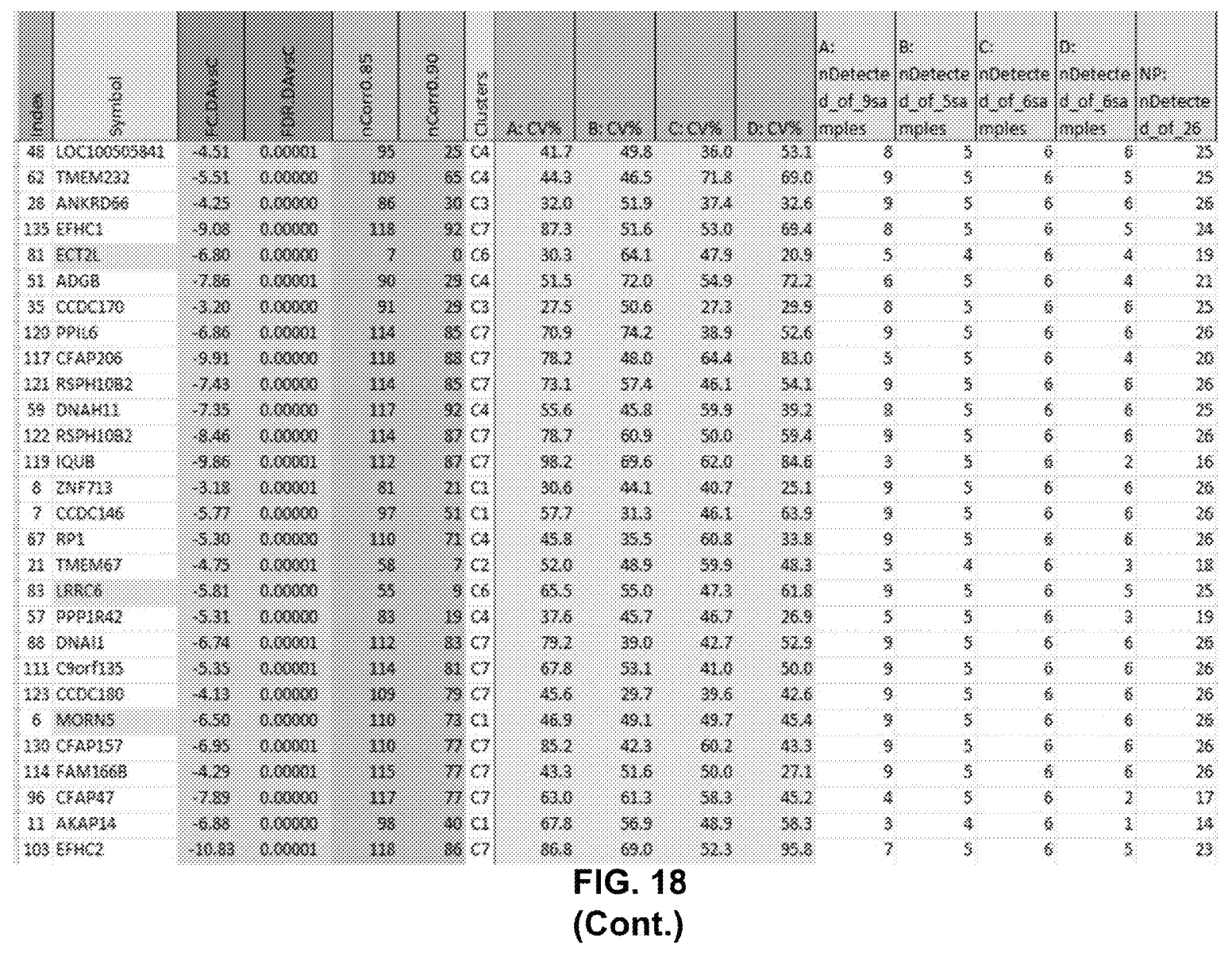
Figure 18:
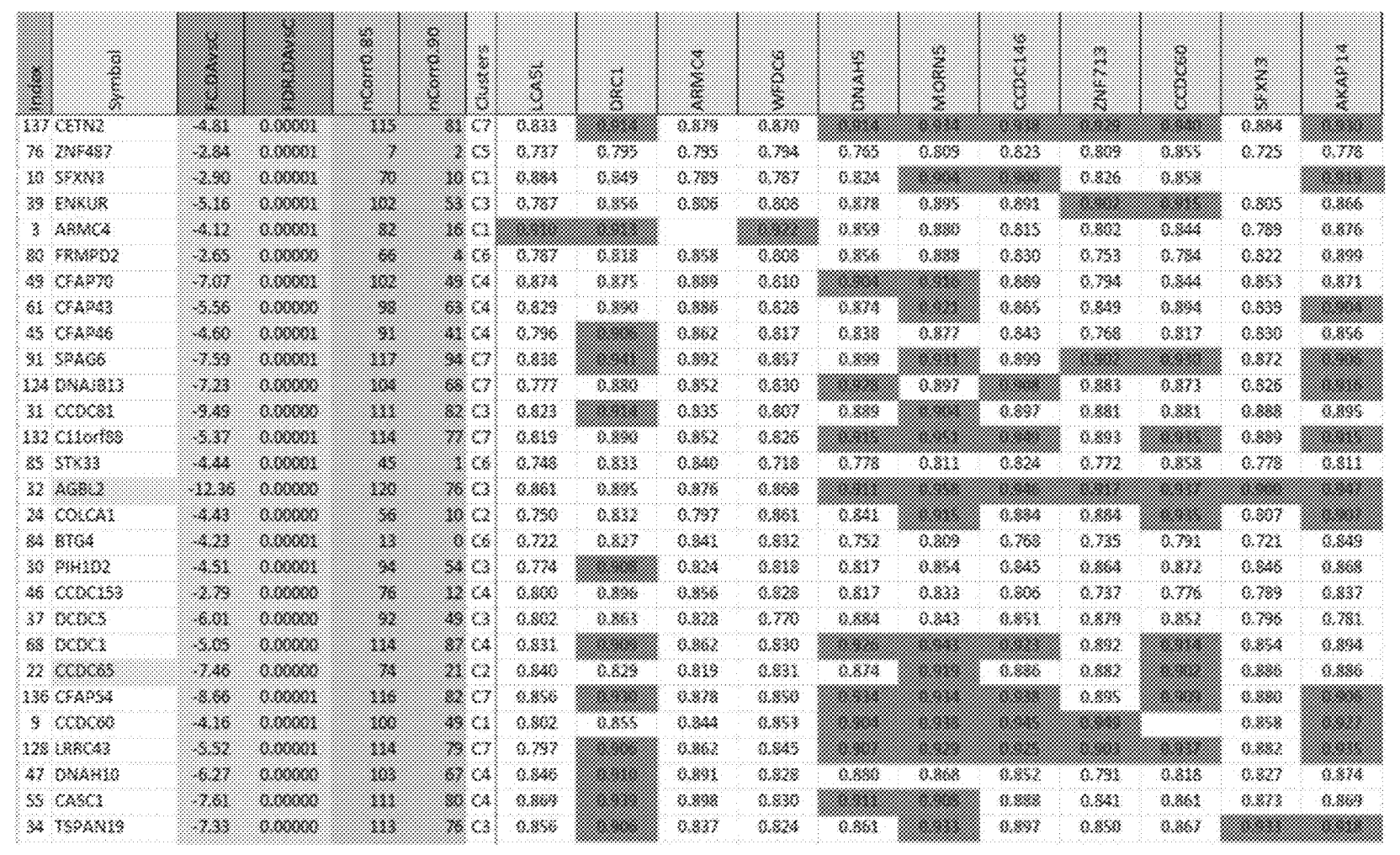
Figure 18:
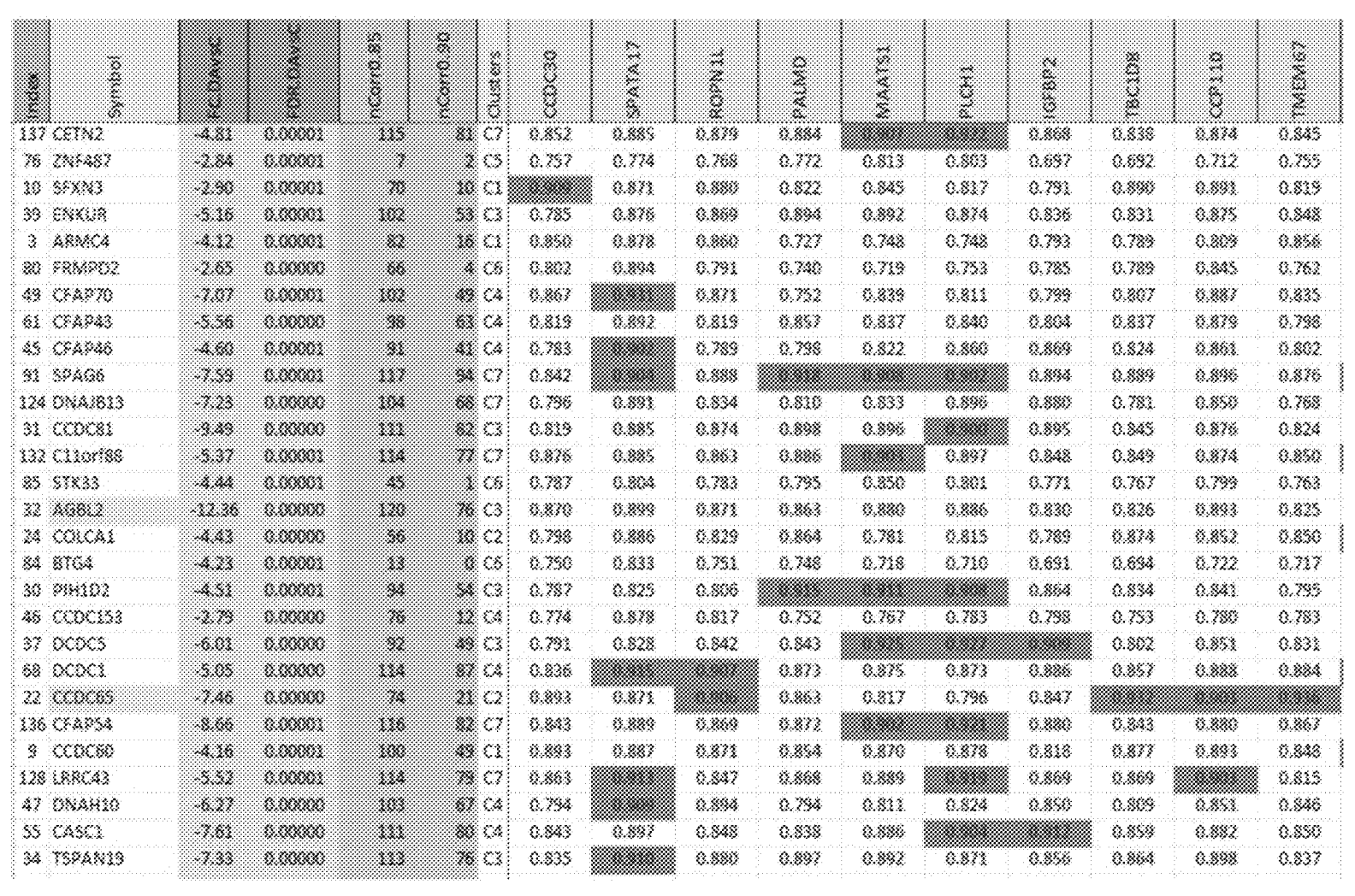
Figure 18:
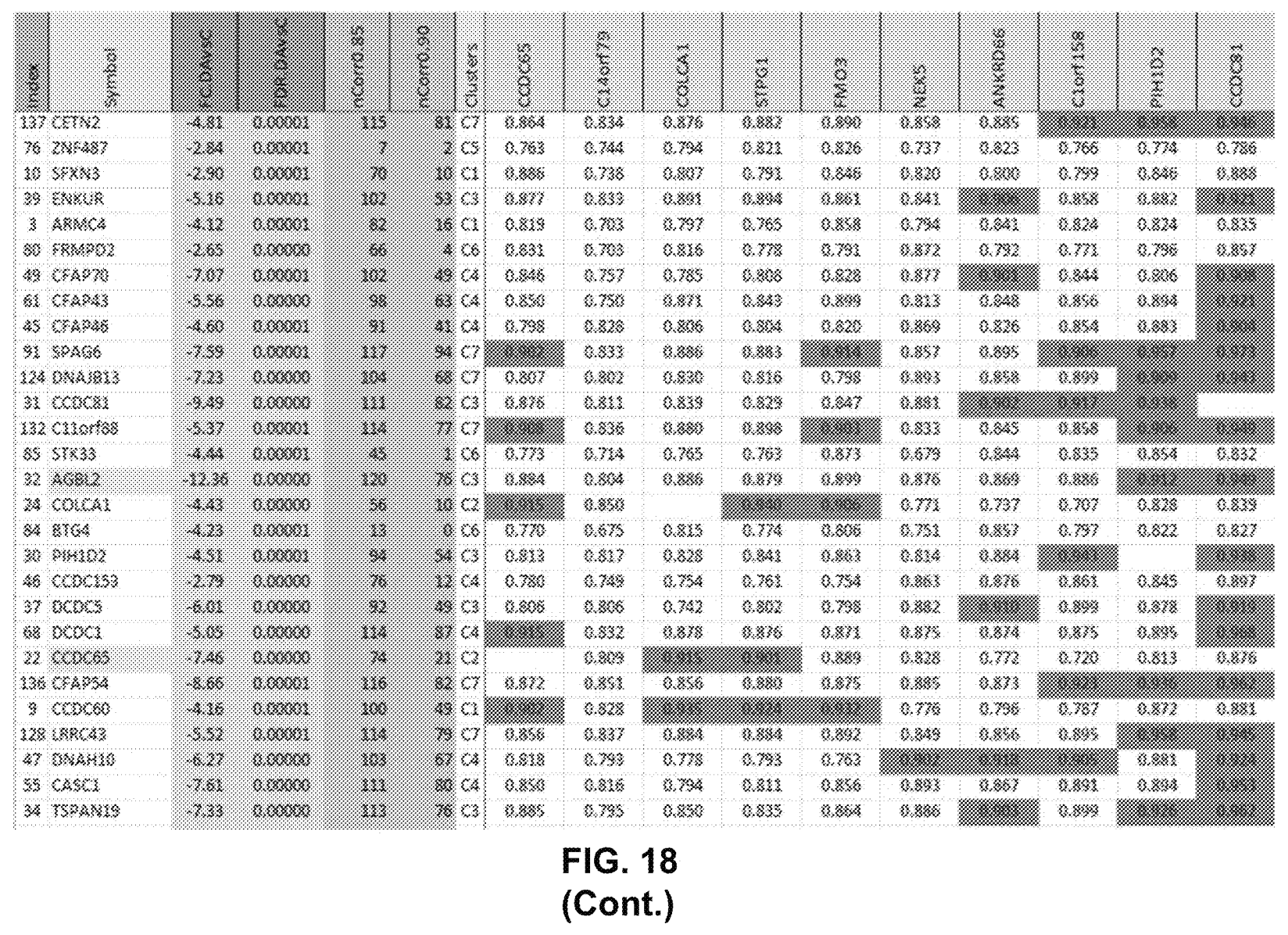
Figure 18:
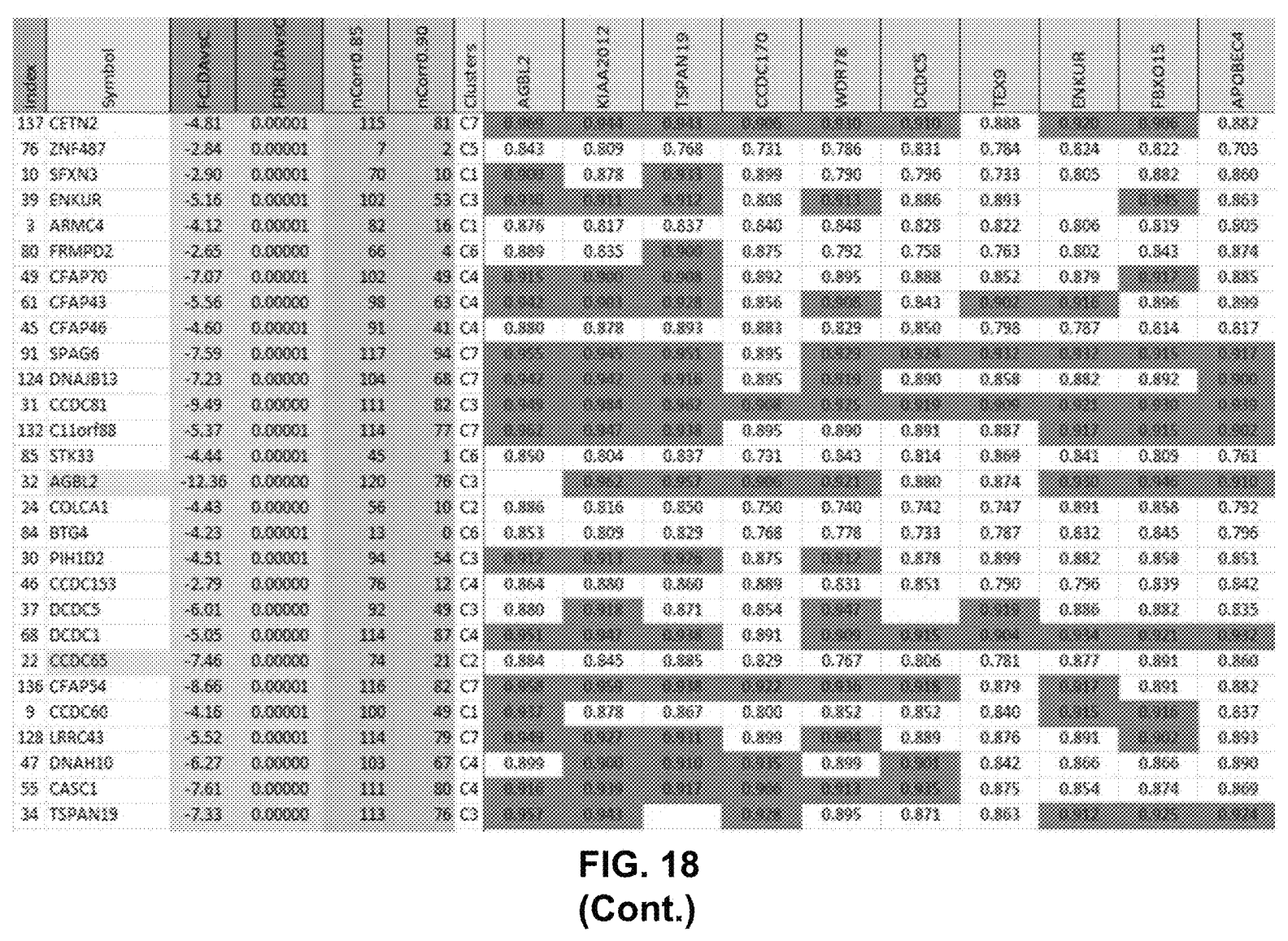
Figure 18:
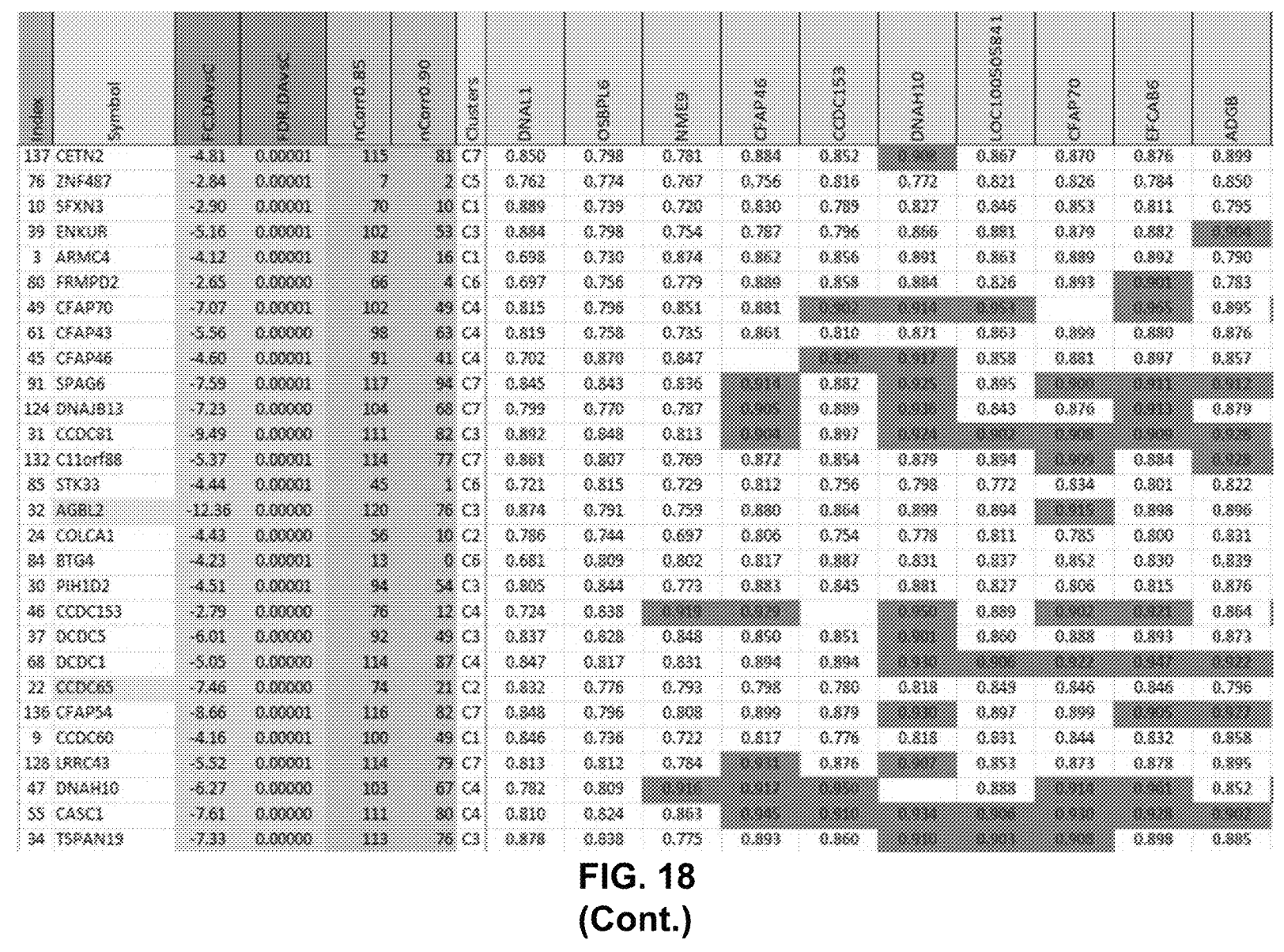
Figure 18:
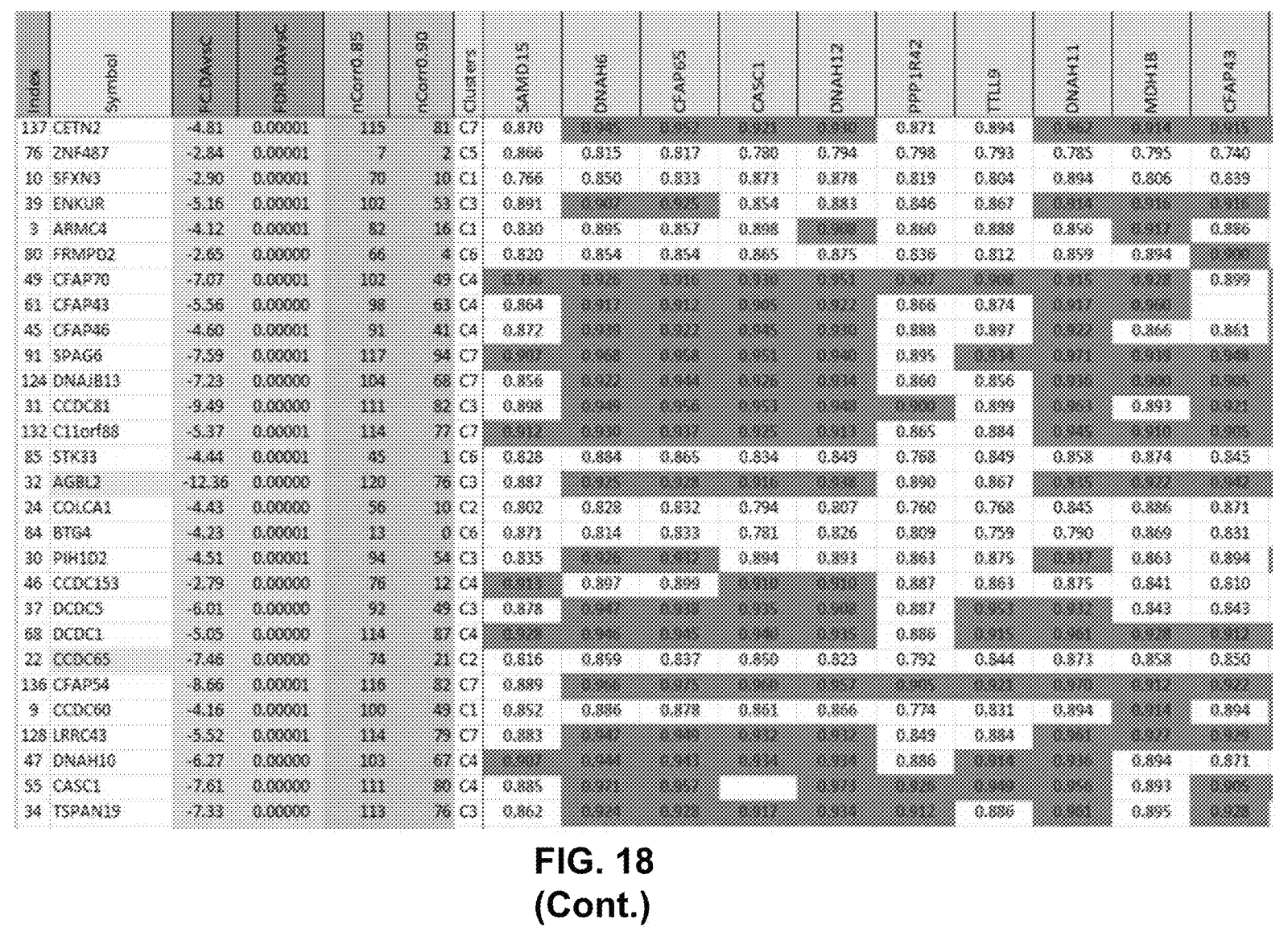
Figure 18:
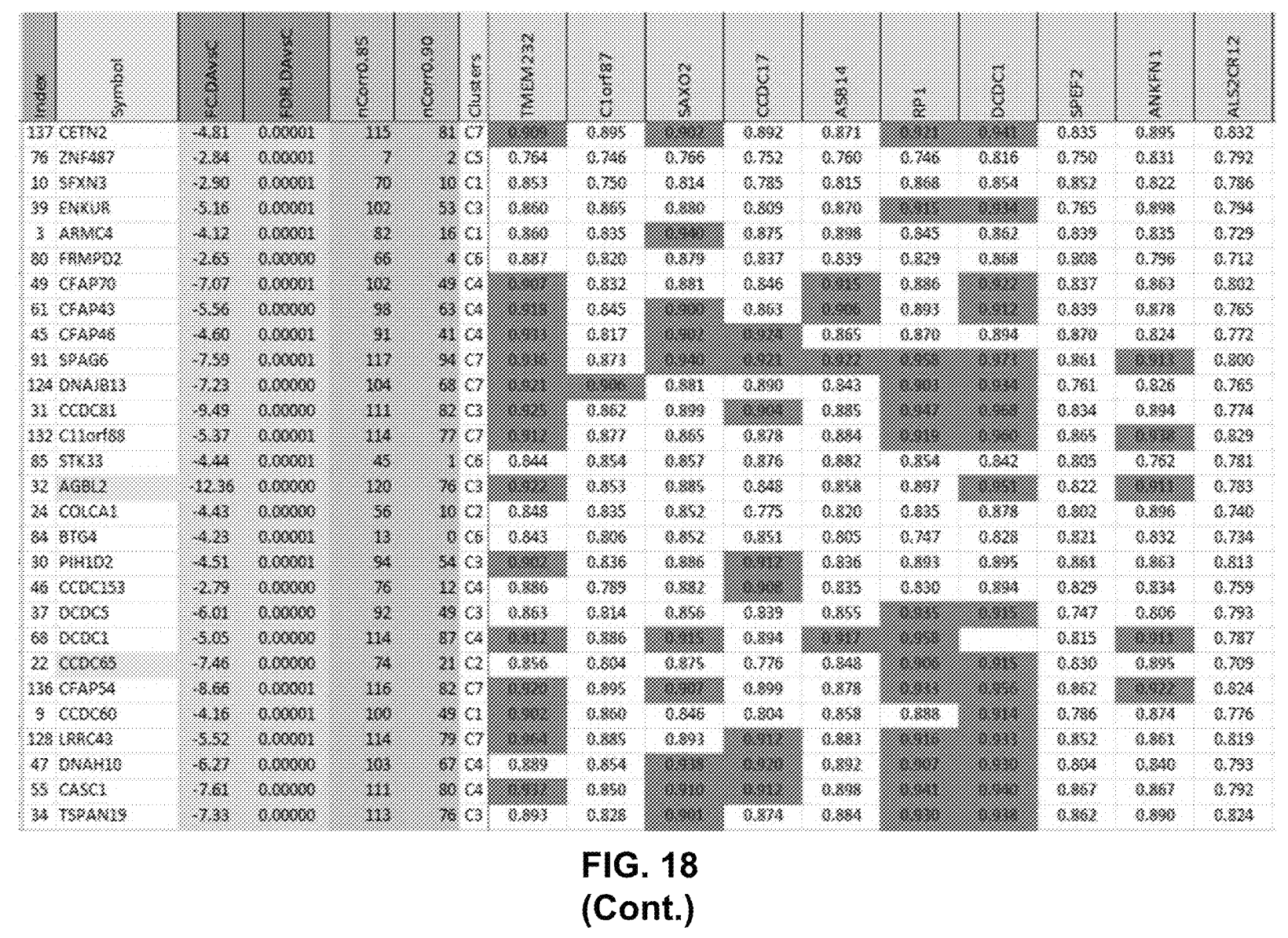
Figure 18:
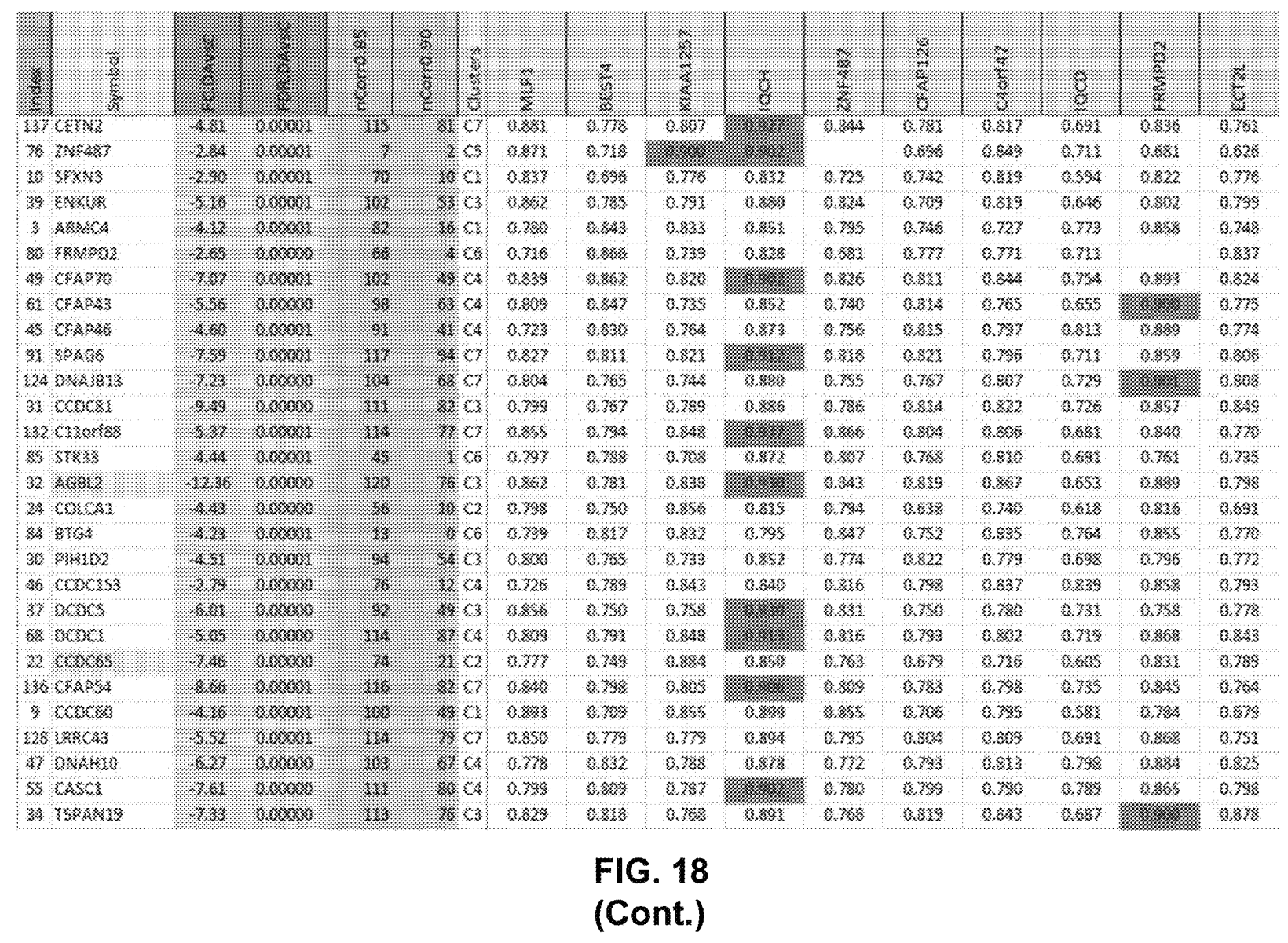
Figure 18:
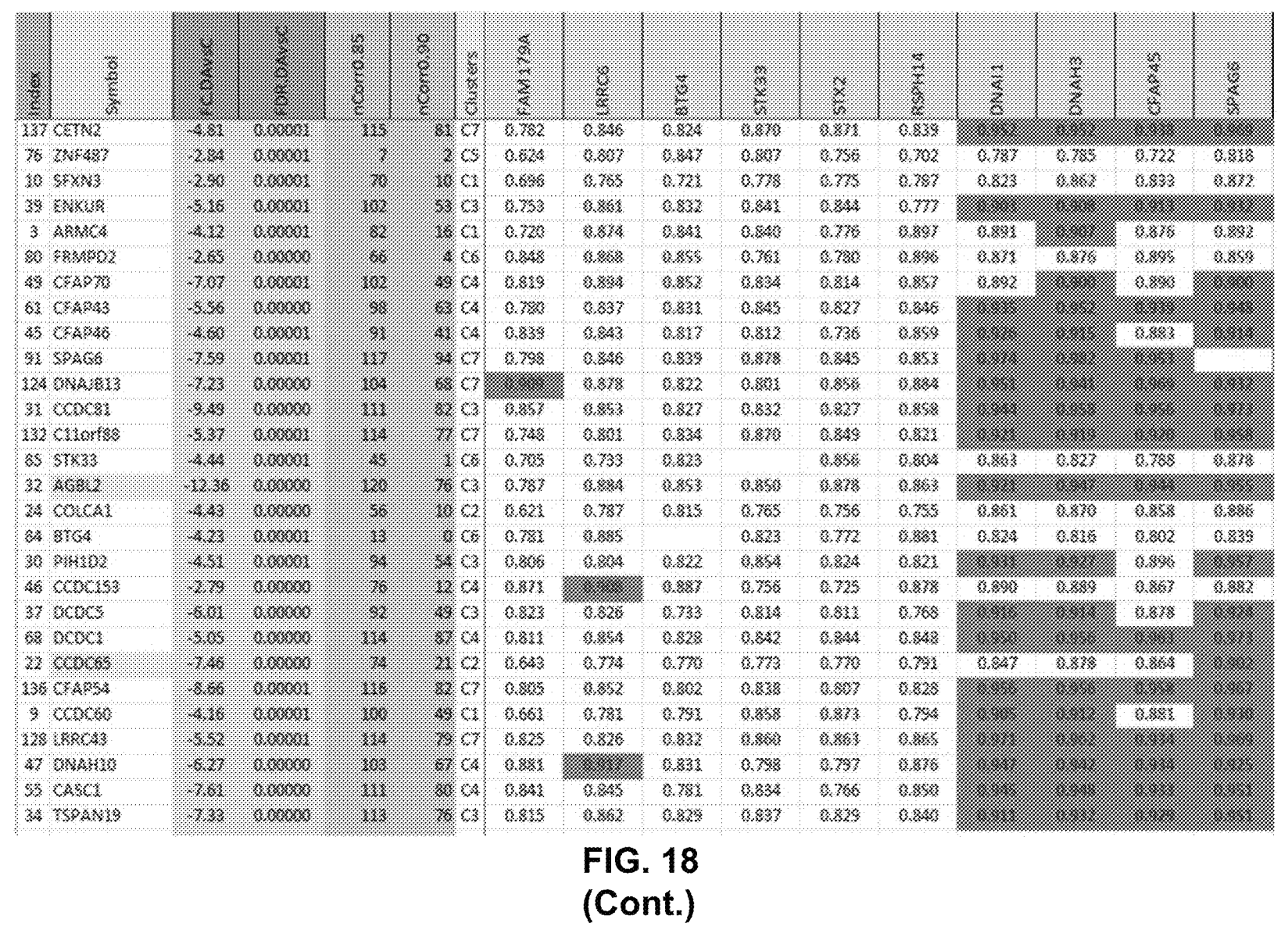
Figure 18:
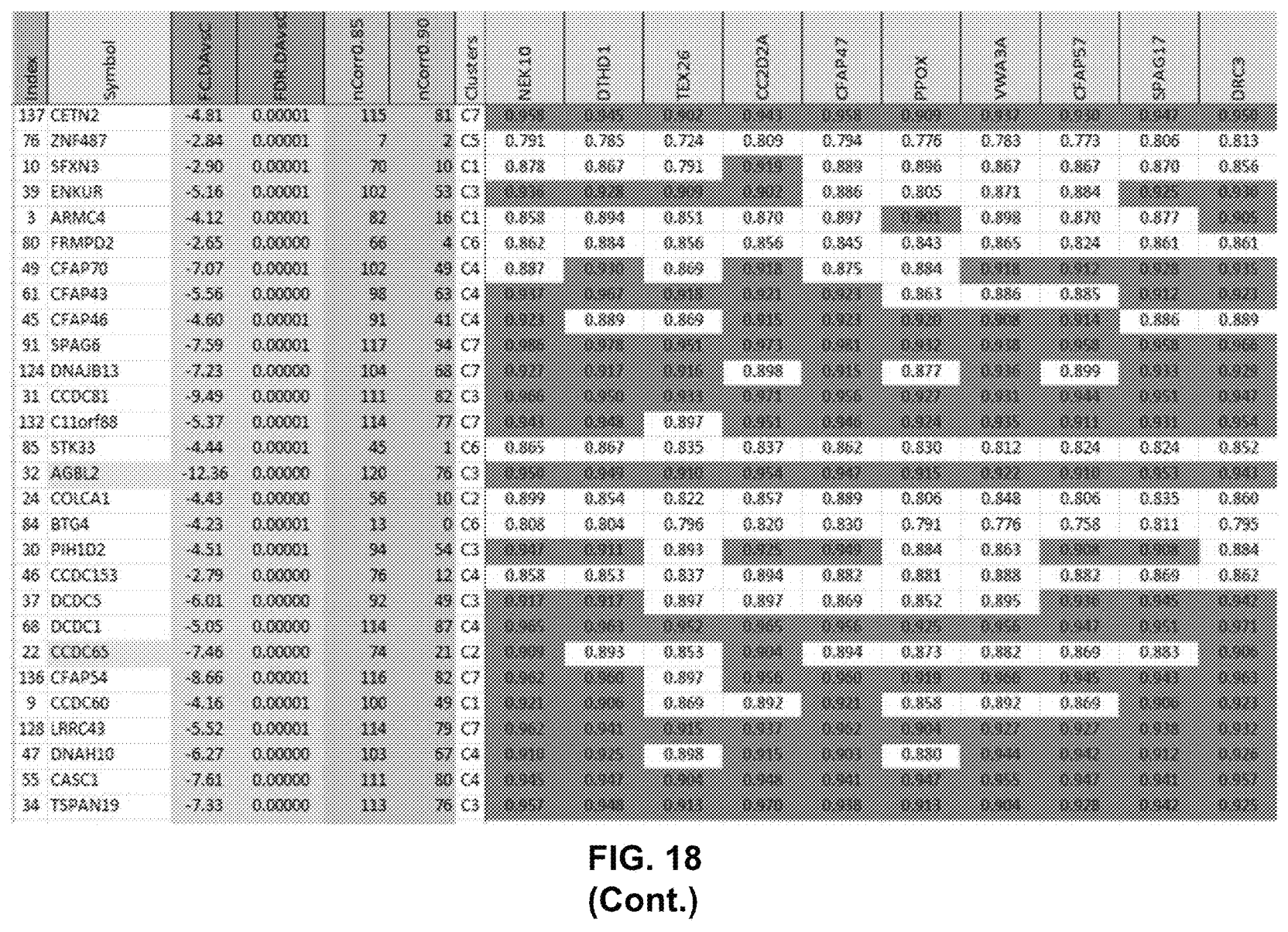
Figure 18:
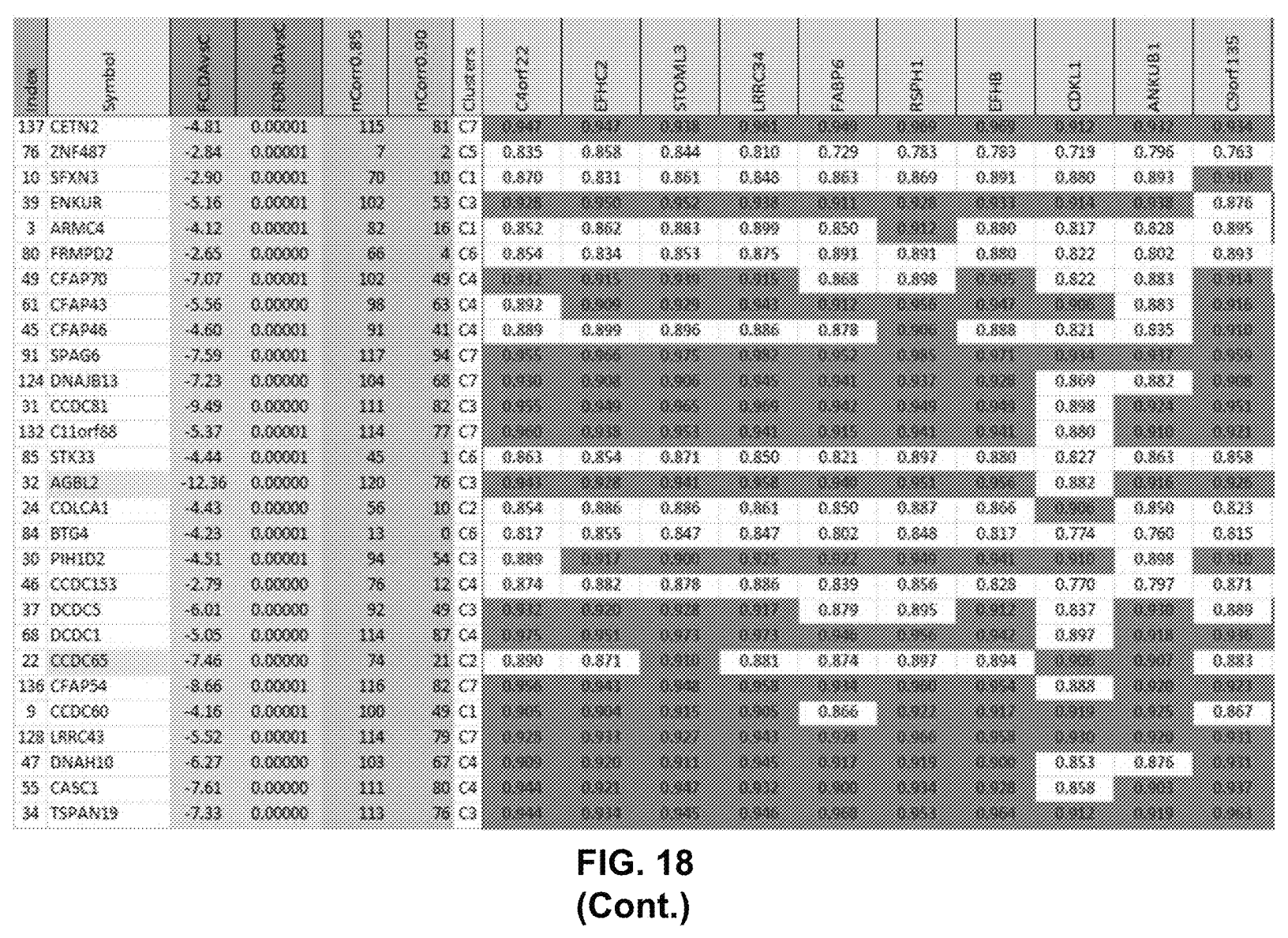
Figure 18:
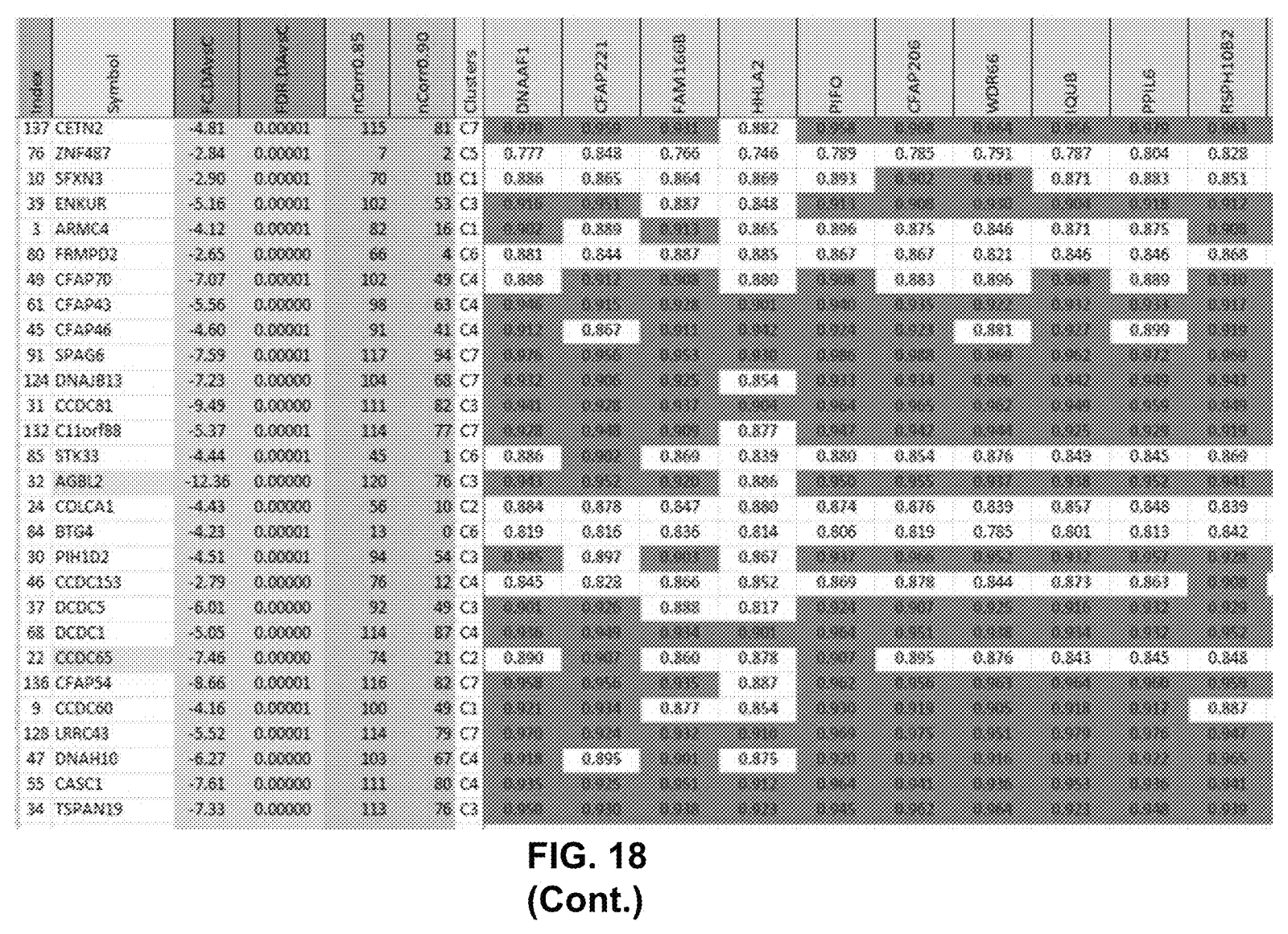
Figure 18:
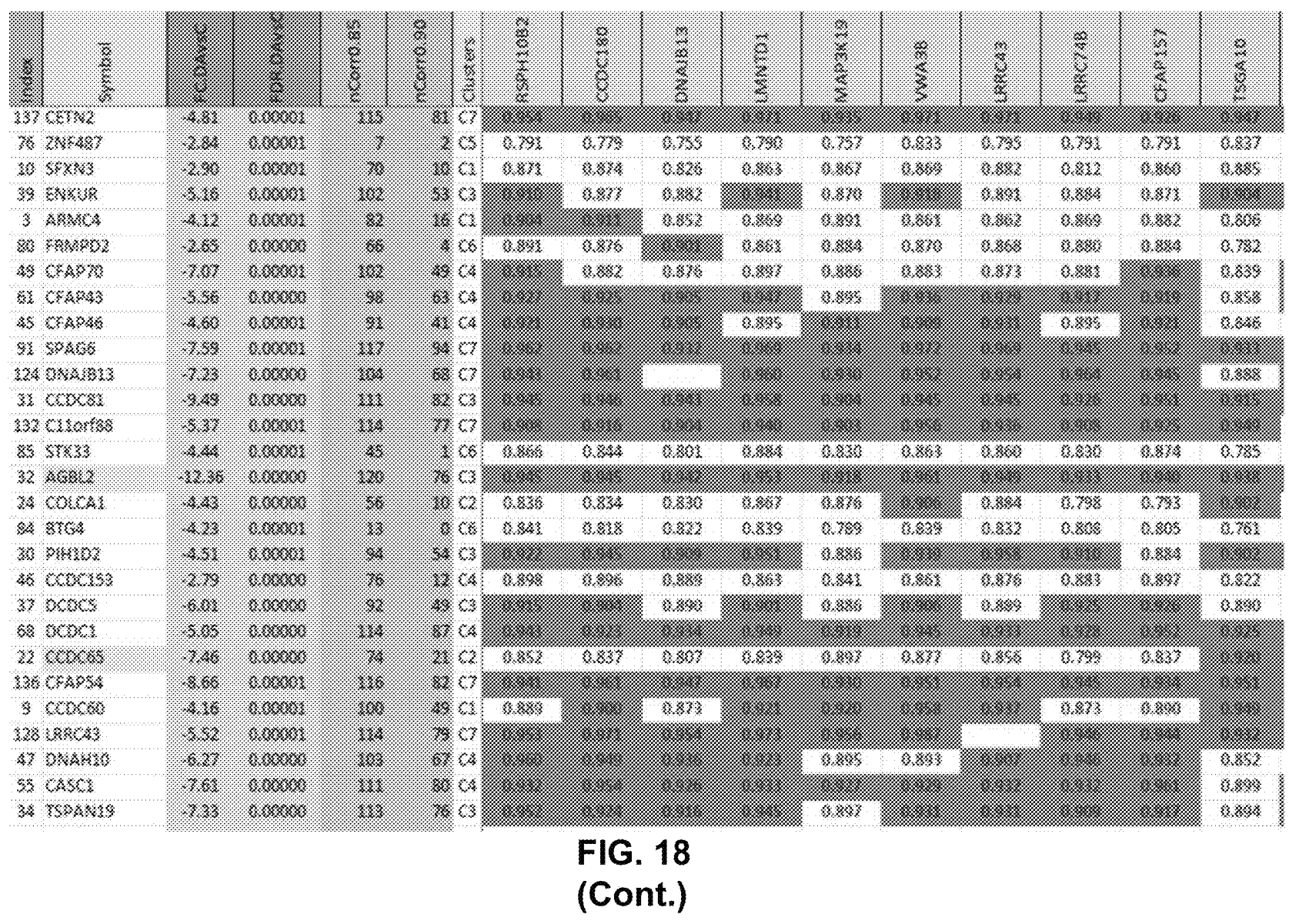
Figure 18:
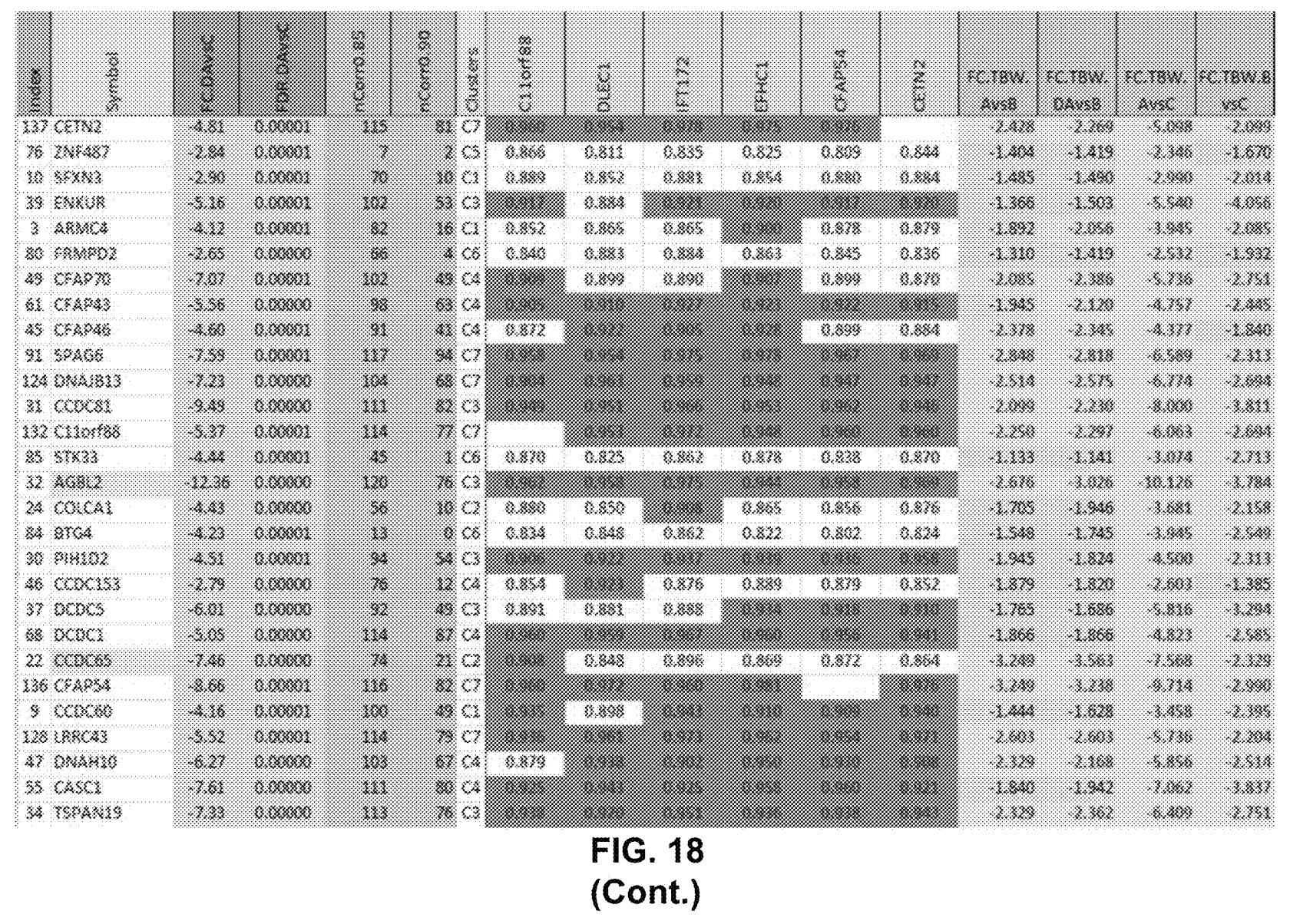
Figure 18:
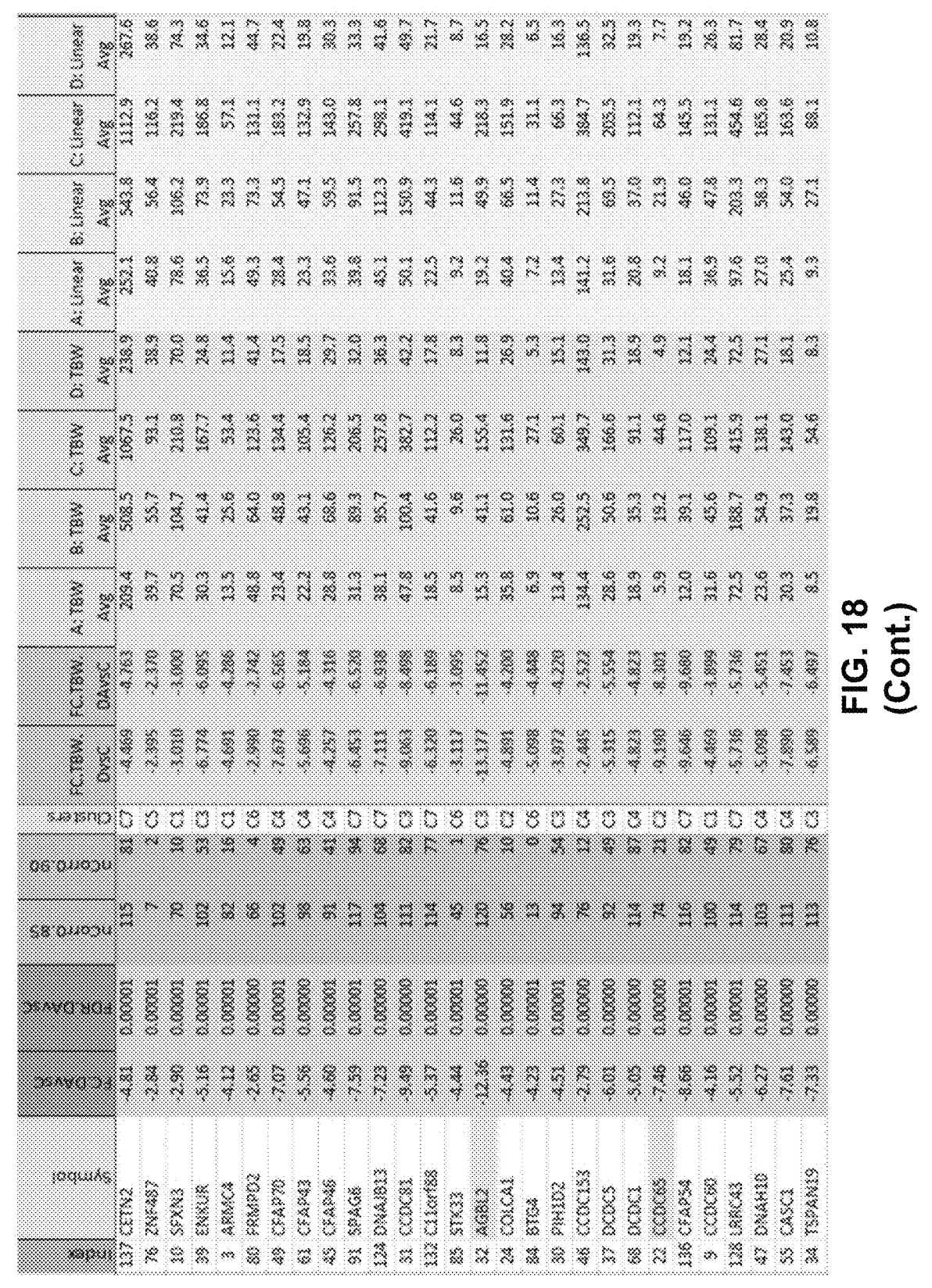
Figure 18:
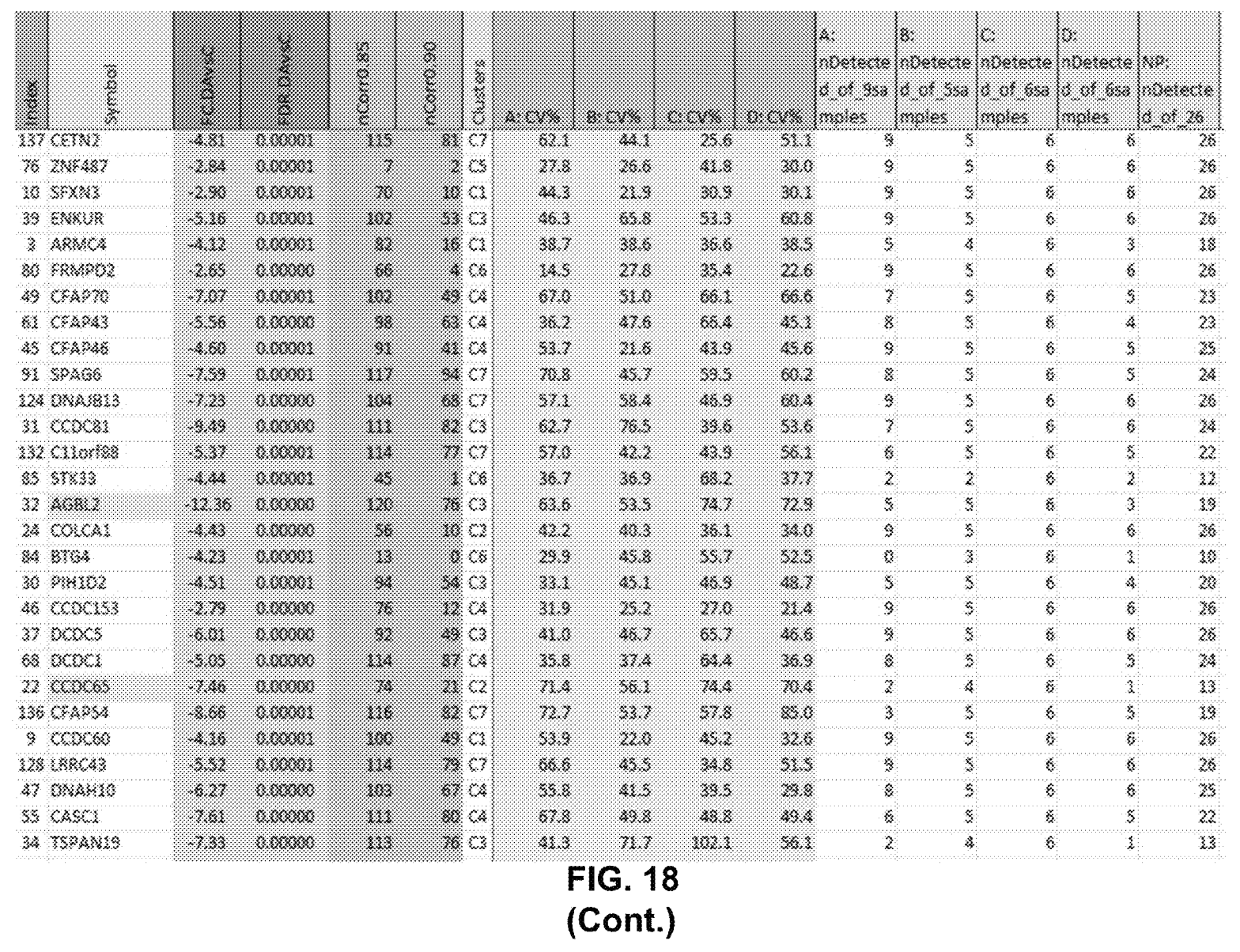
Figure 18:
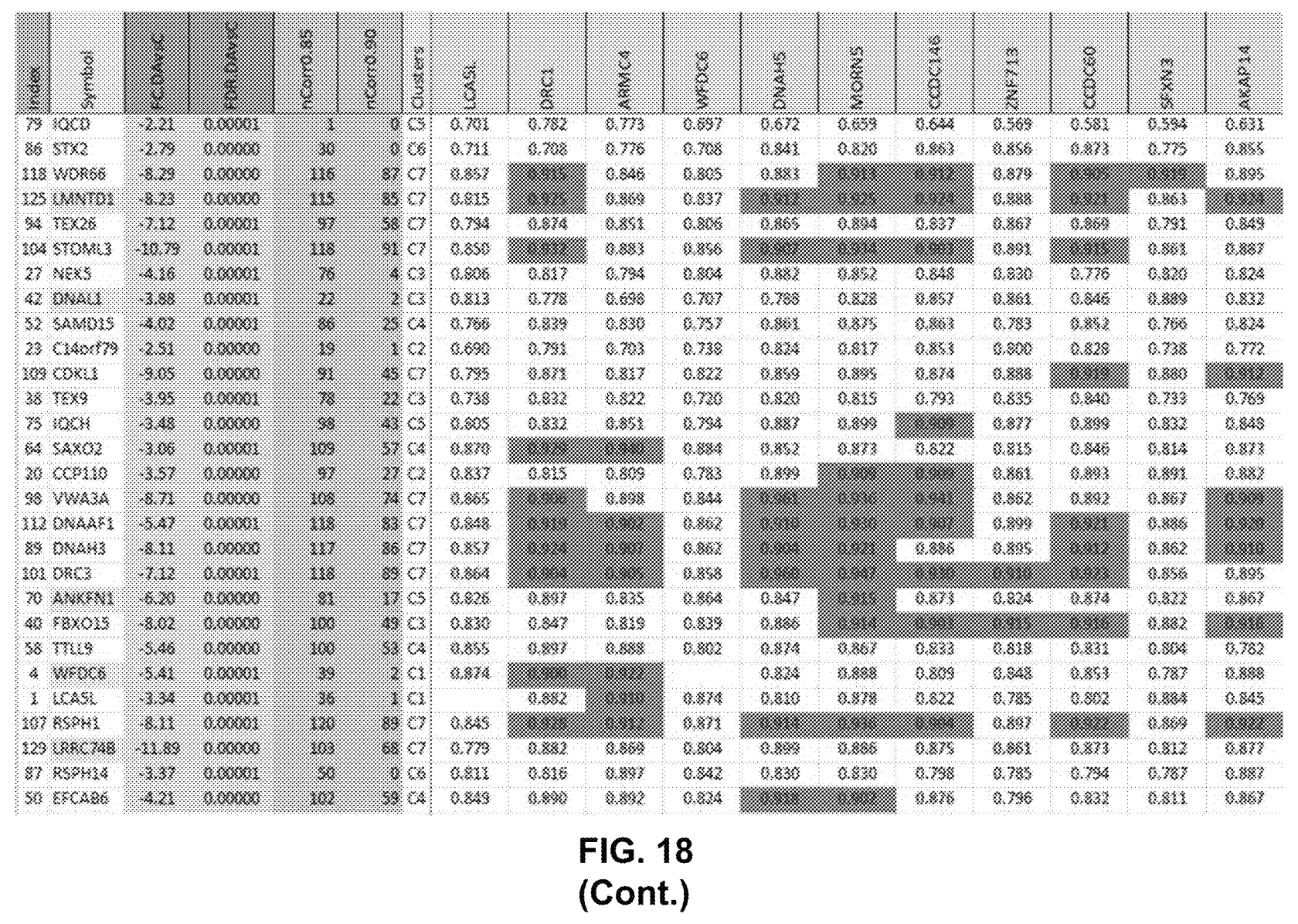
Figure 18:
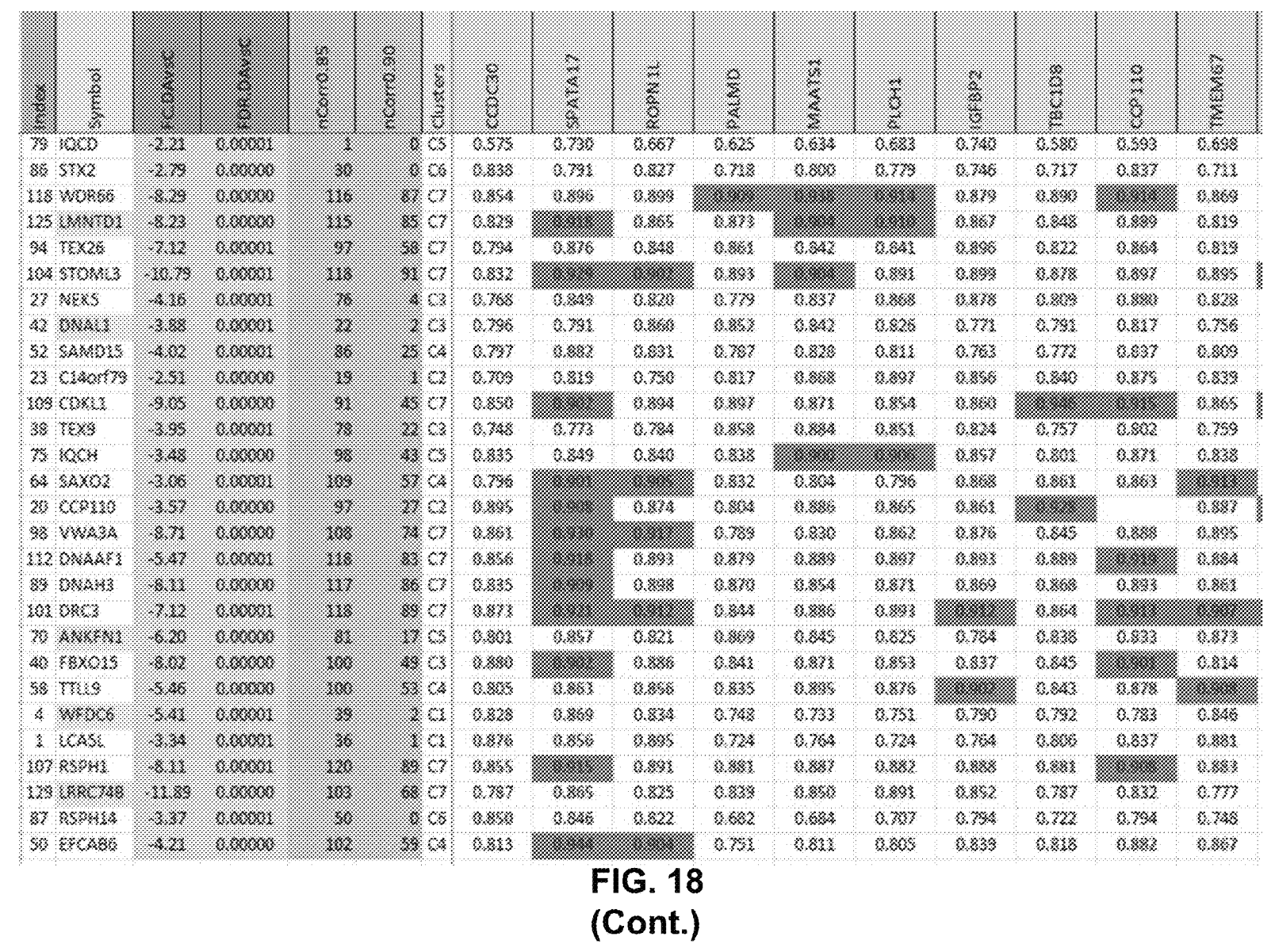
Figure 18:
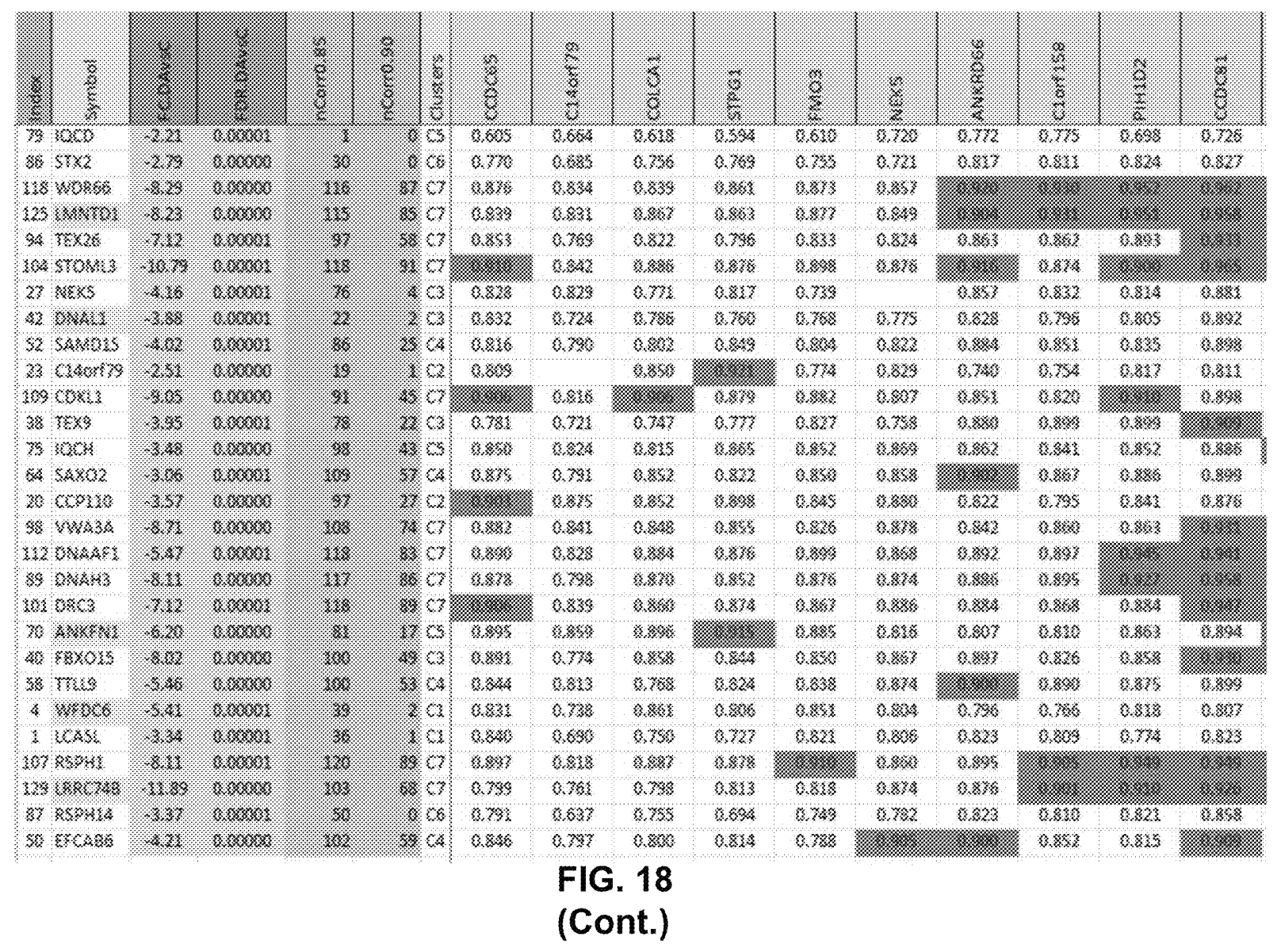
Figure 18:
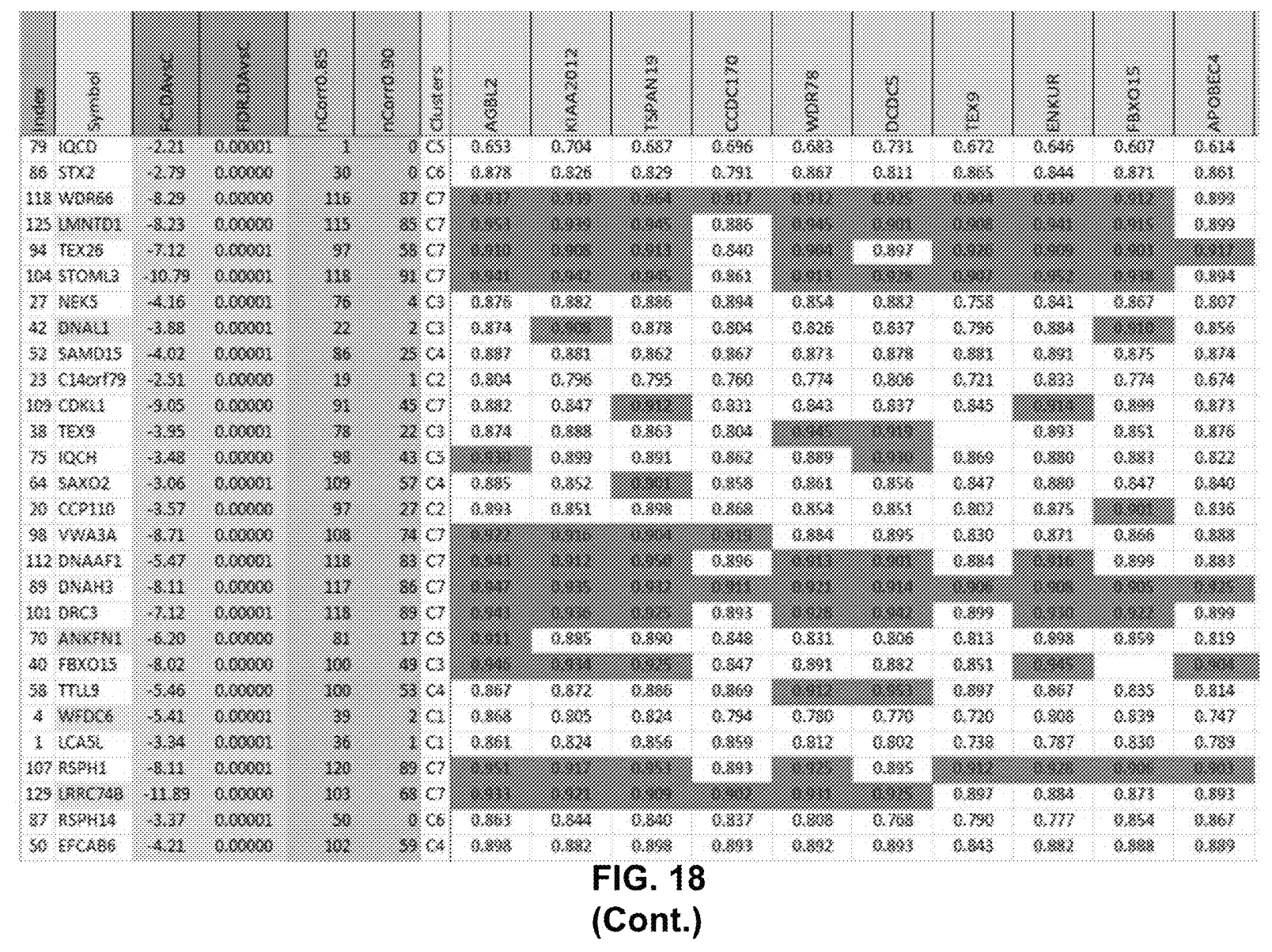
Figure 18:
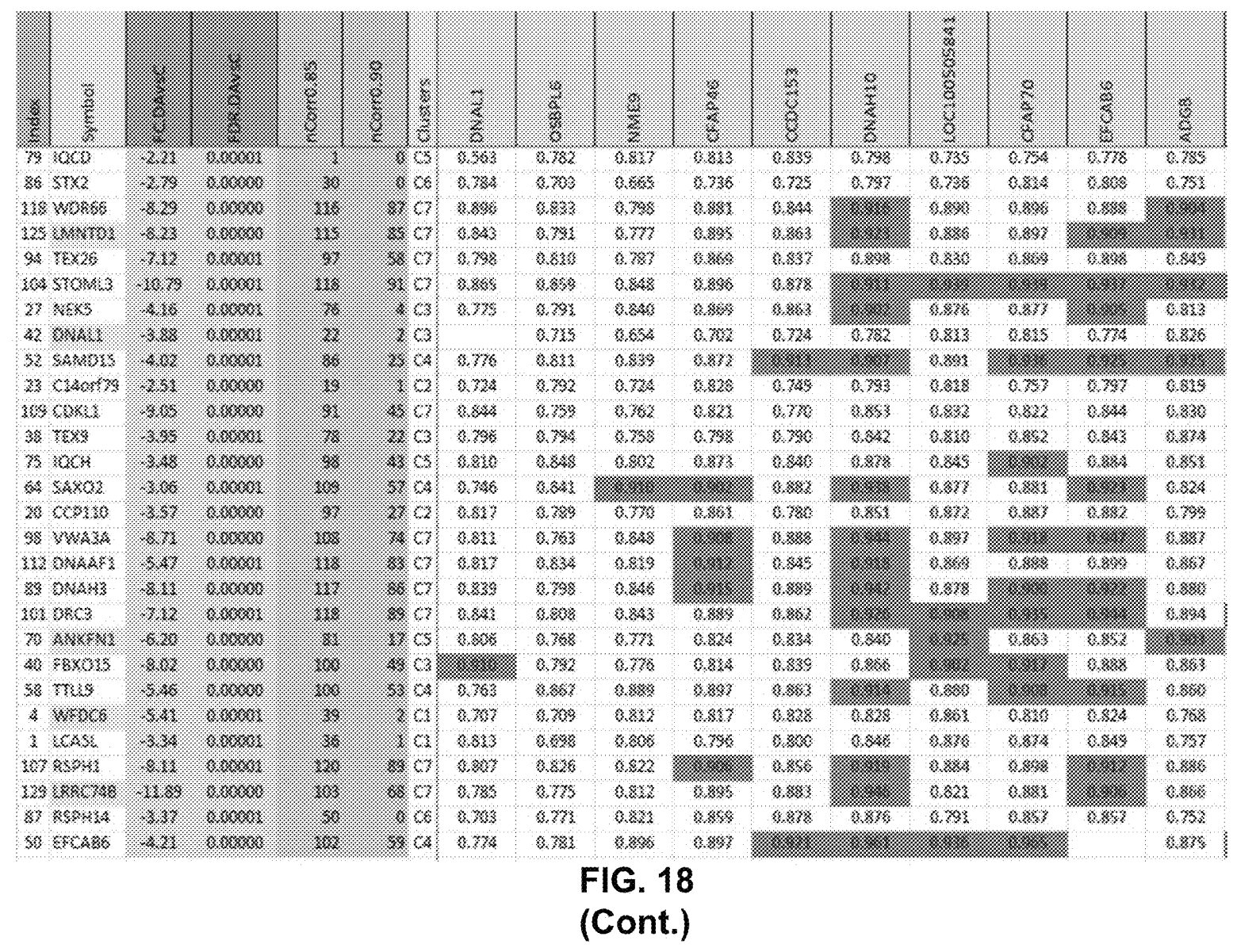
Figure 18:
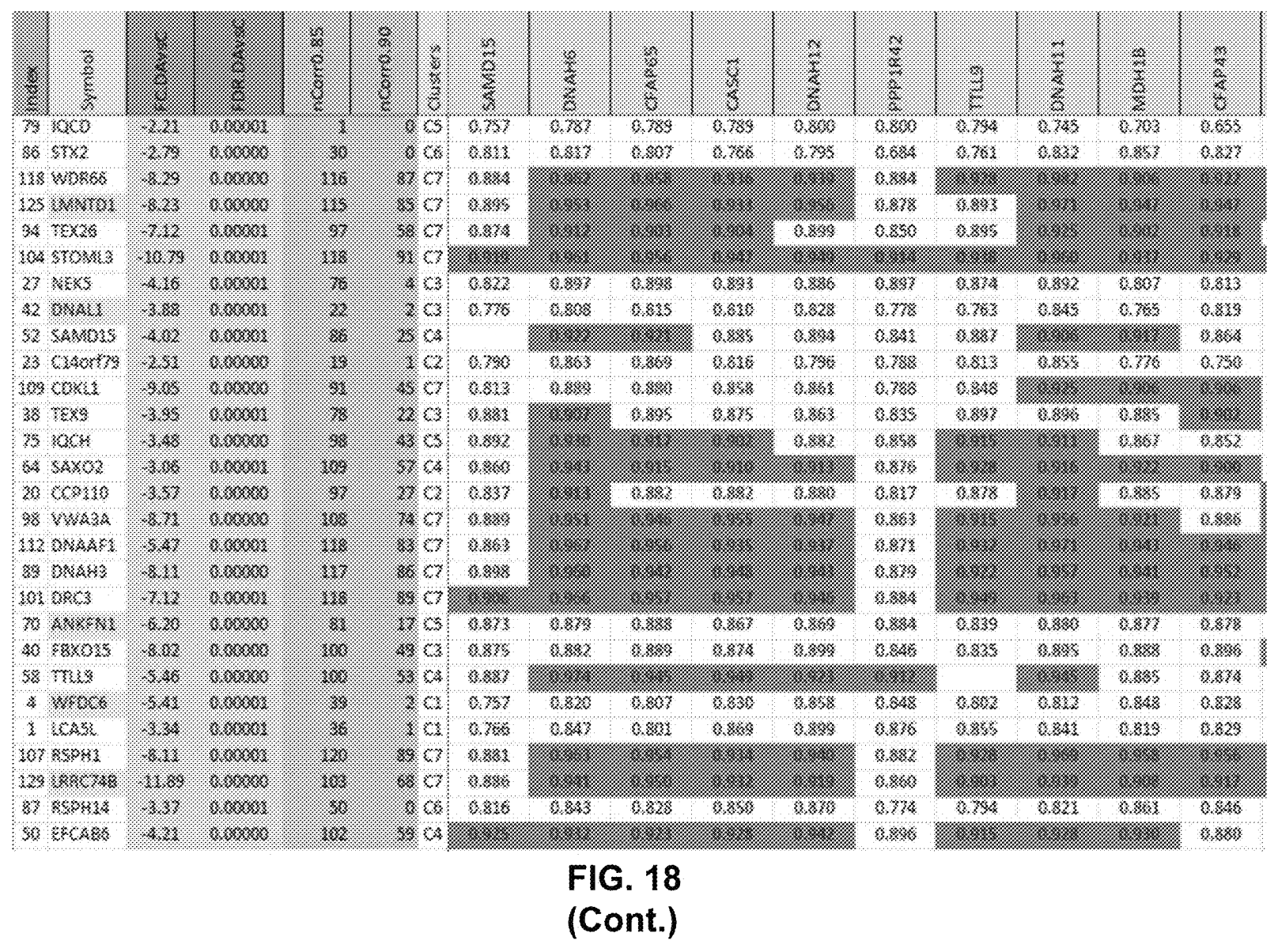
Figure 18:
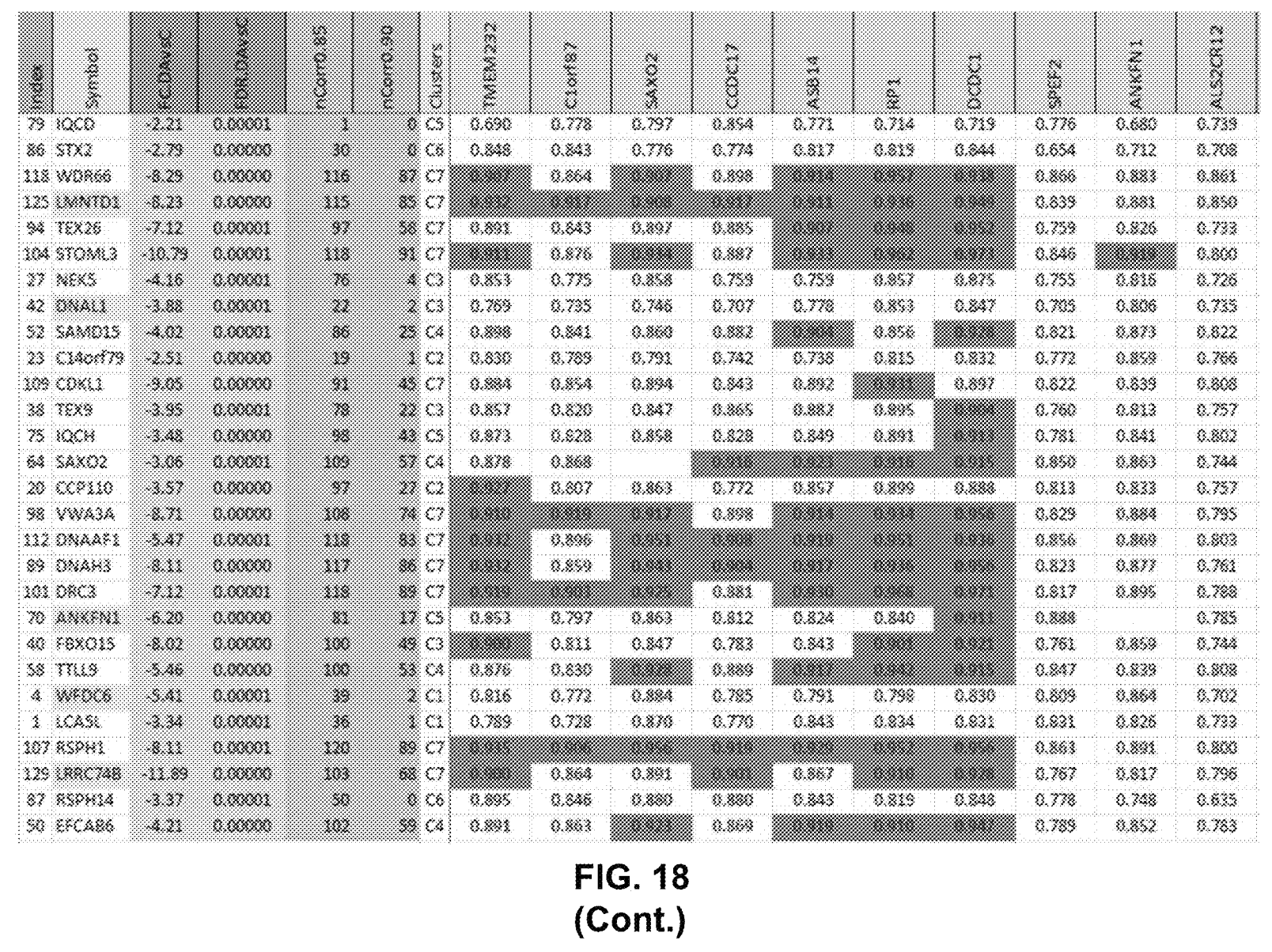
Figure 18:
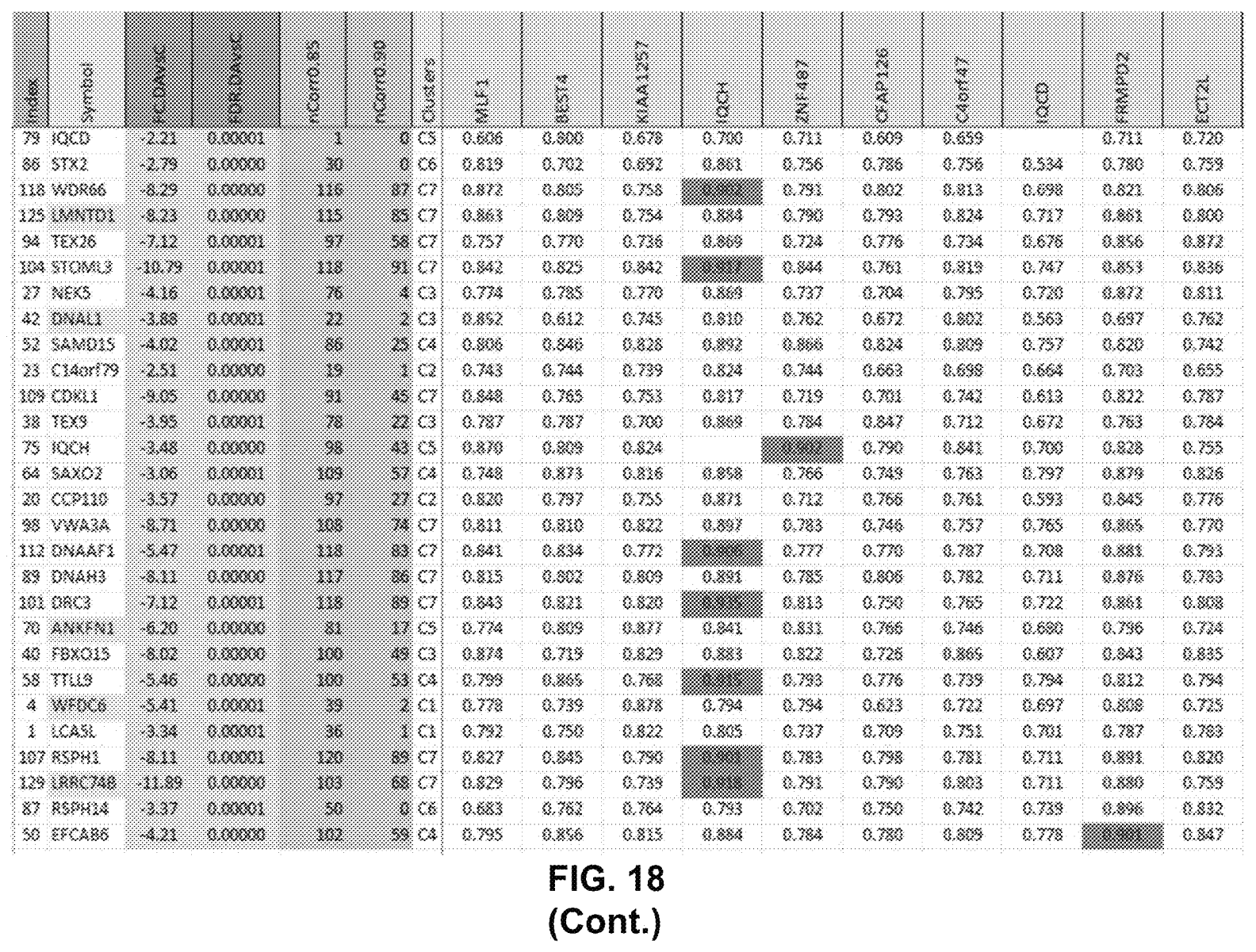
Figure 18:
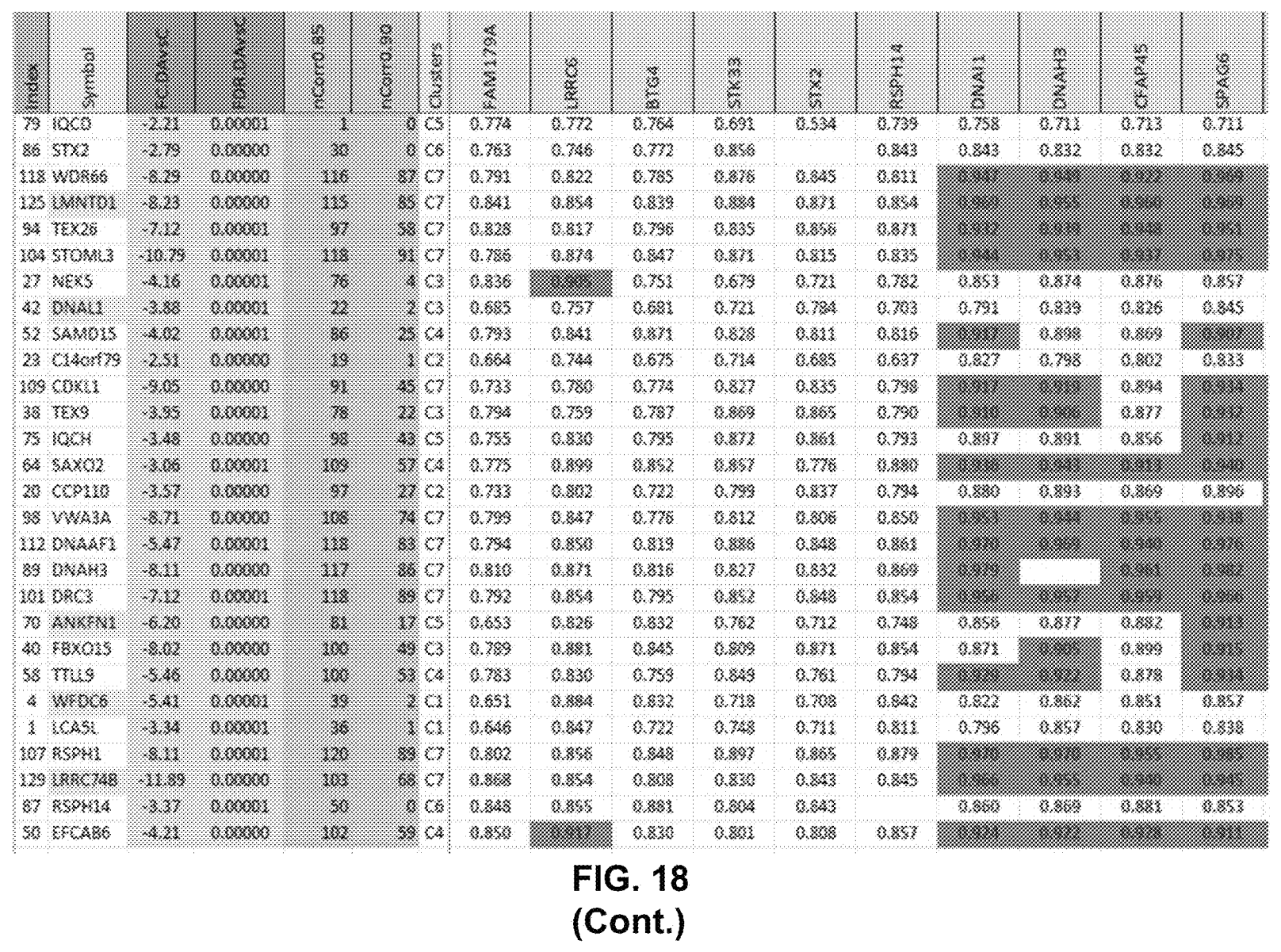
Figure 18:
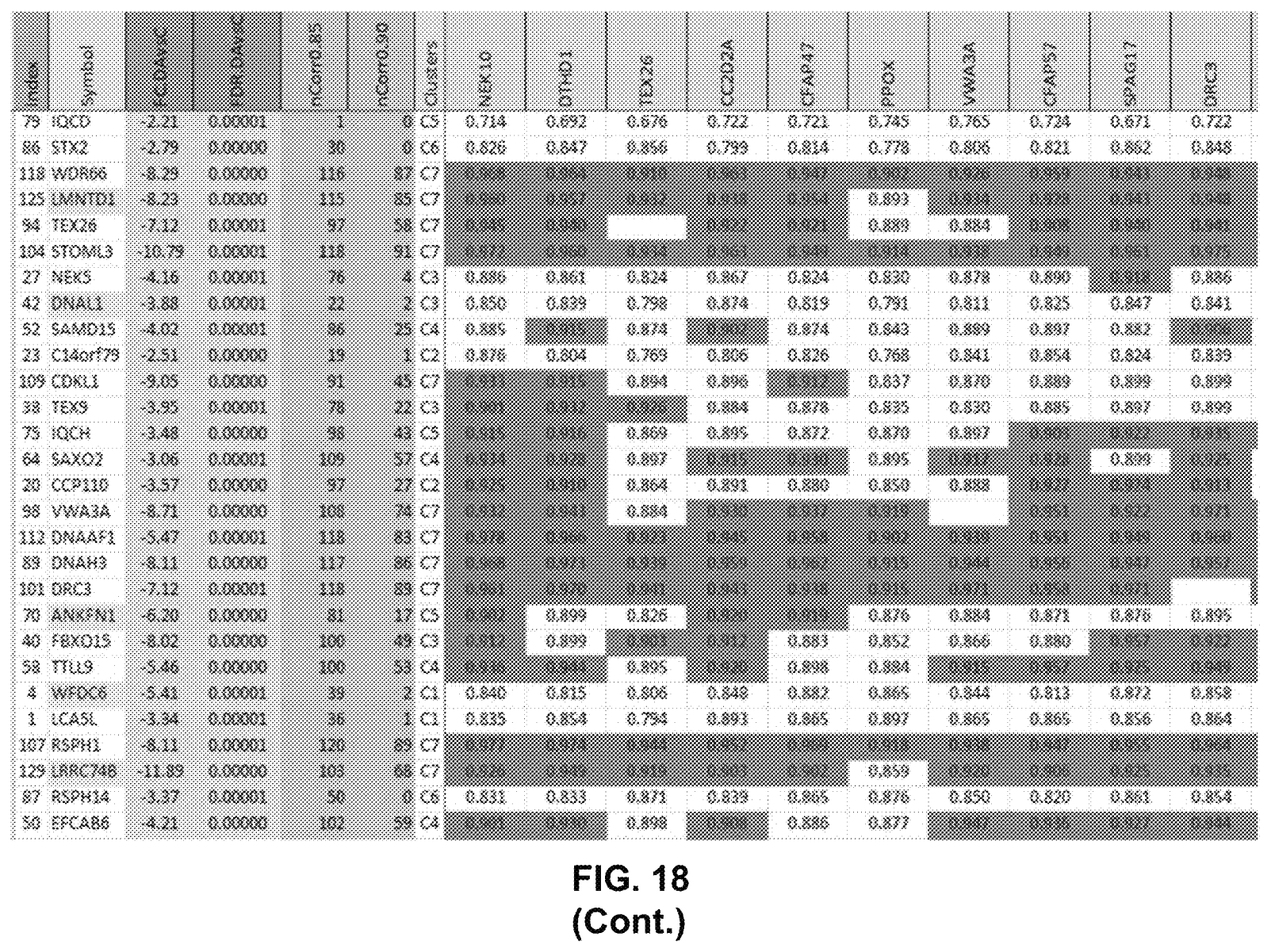
Figure 18:
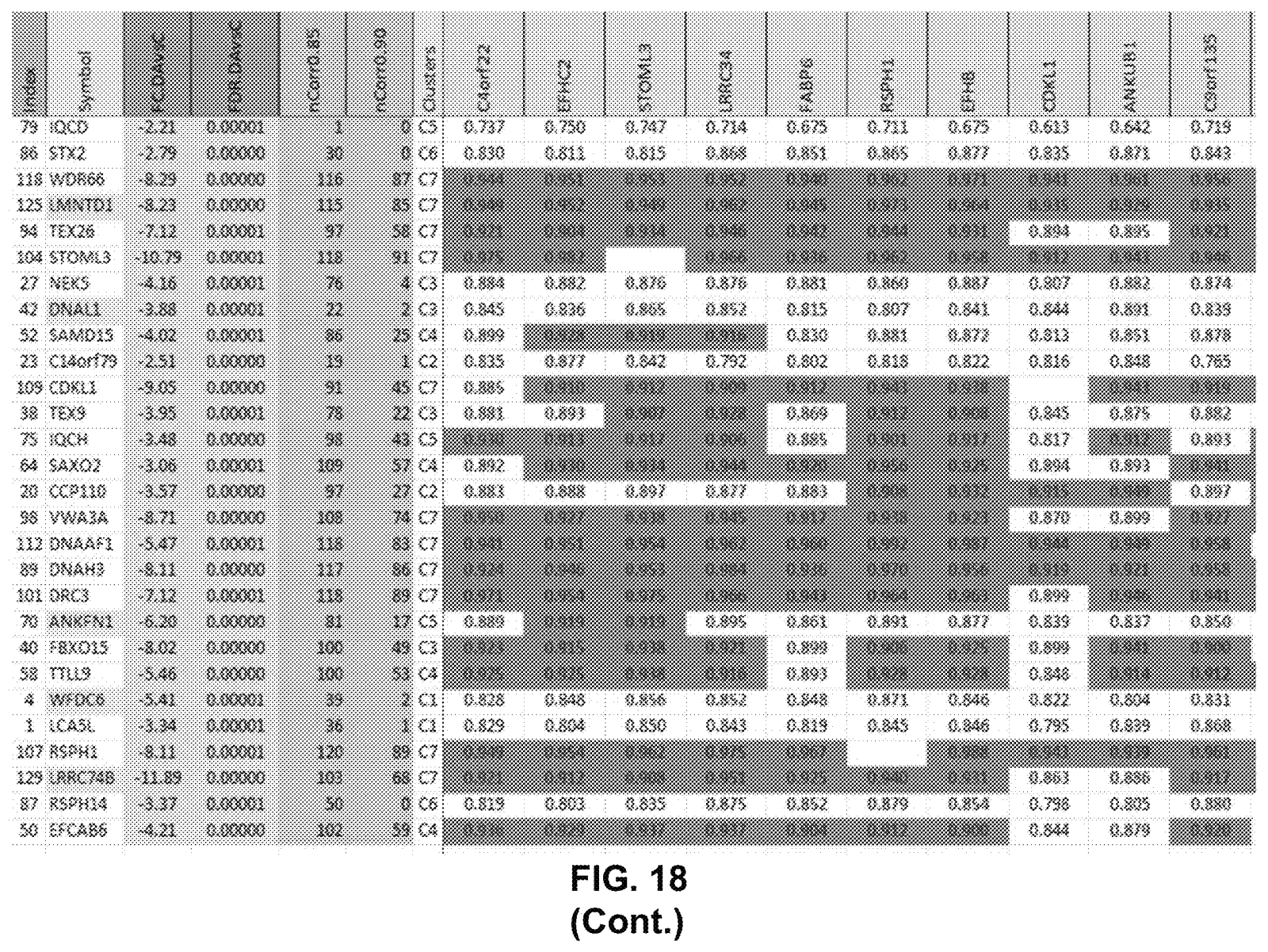
Figure 18:
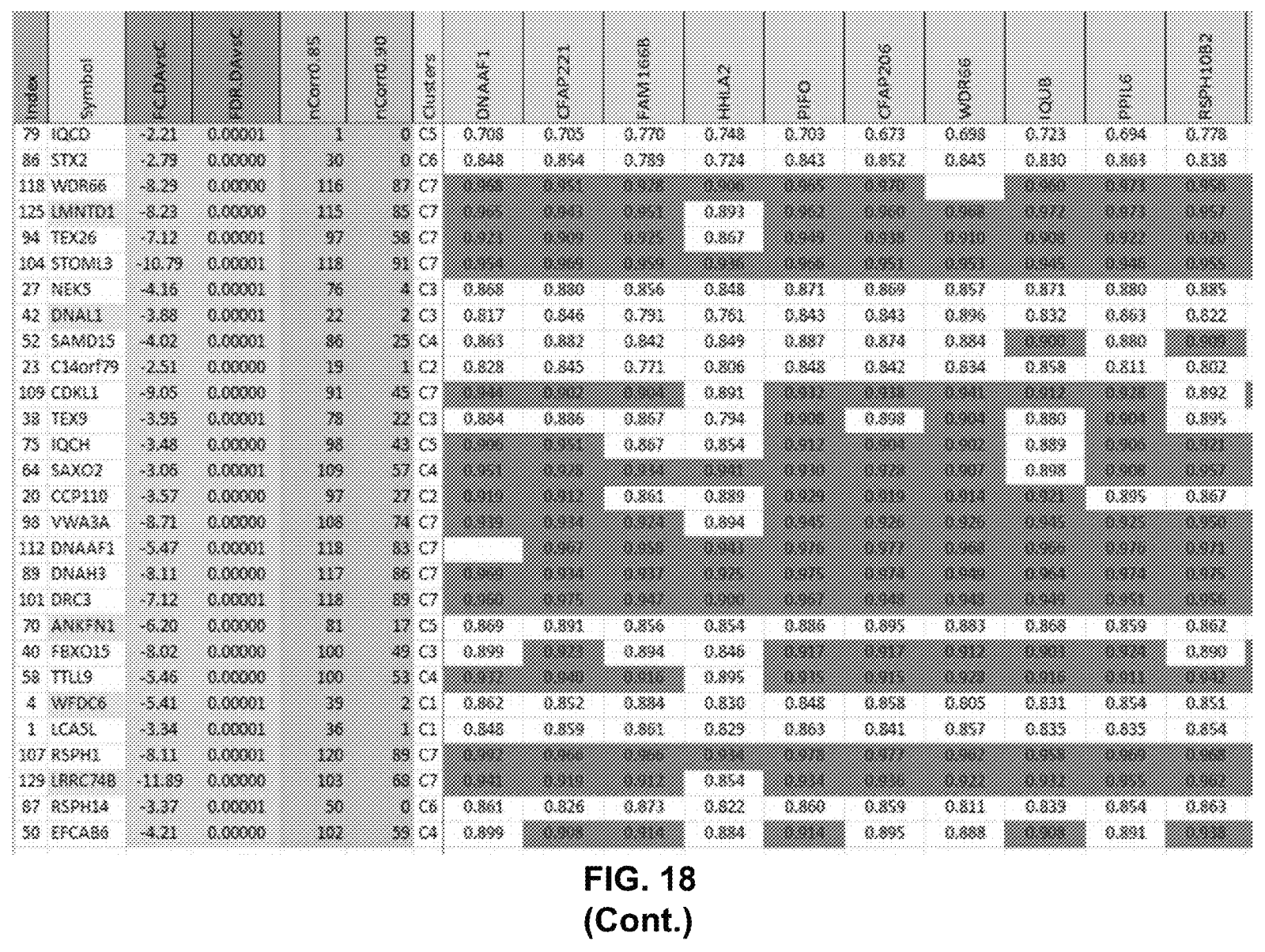
Figure 18:
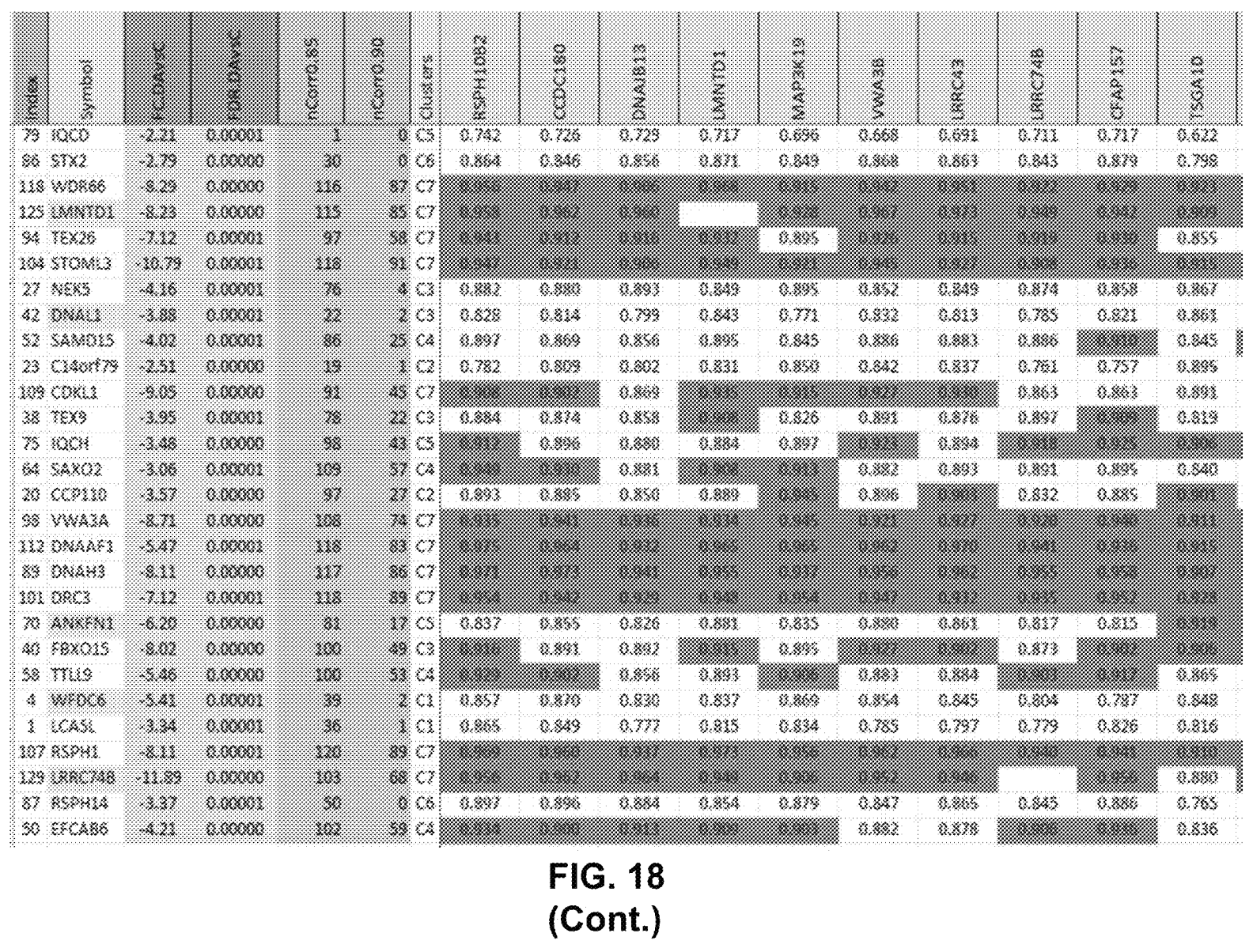
Figure 18:
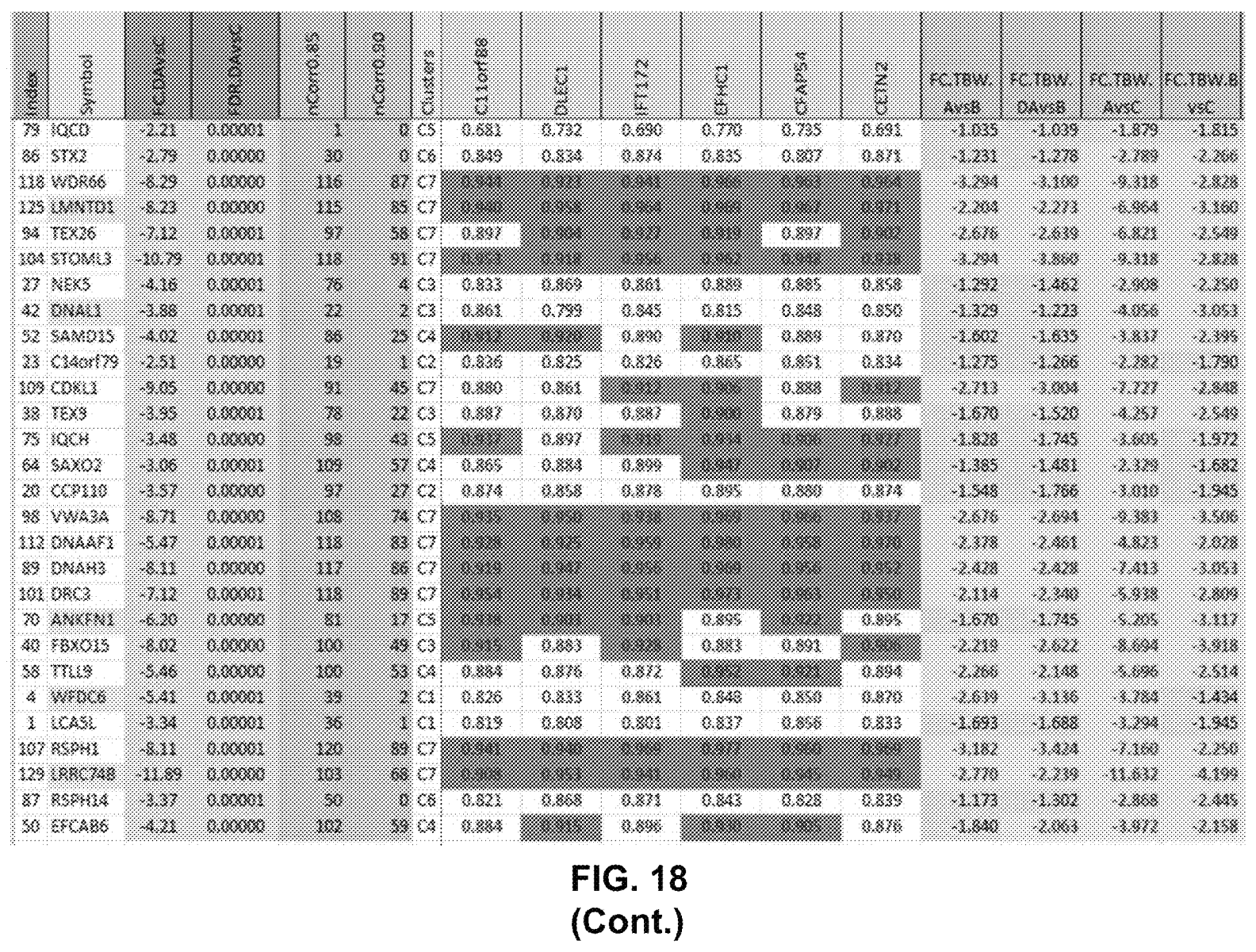
Figure 18:
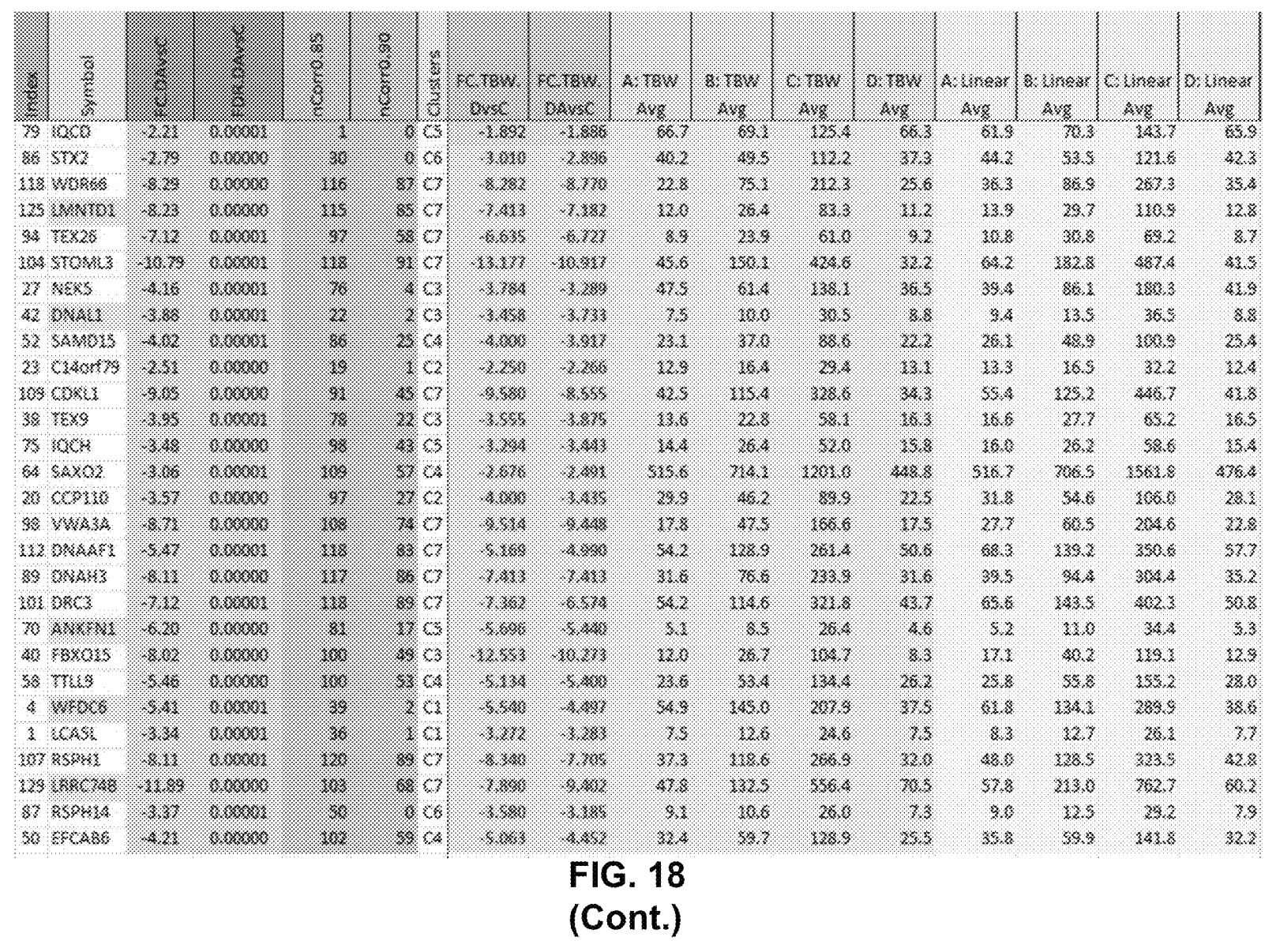
Figure 18:
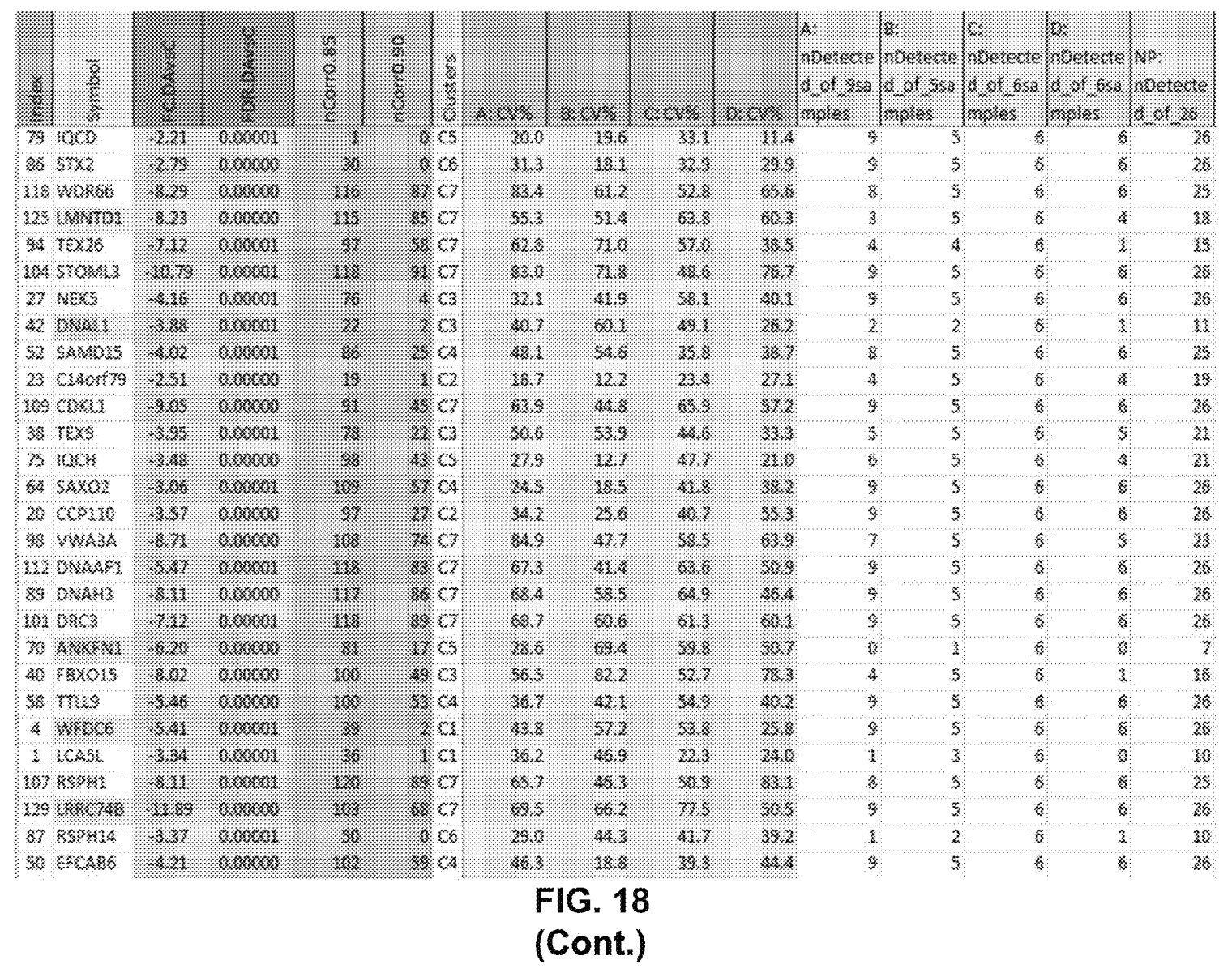

FIG. 18 shows an exemplary gene signature which includes 137 genes with decreased expression in symptomatic viral infections, FIG. 19 shows an exemplary gene signature which includes 25 genes with increased expression in symptomatic versus asymptomatic viral infections.

DETAILED DESCRIPTION OF THE INVENTION

Figure 1A:
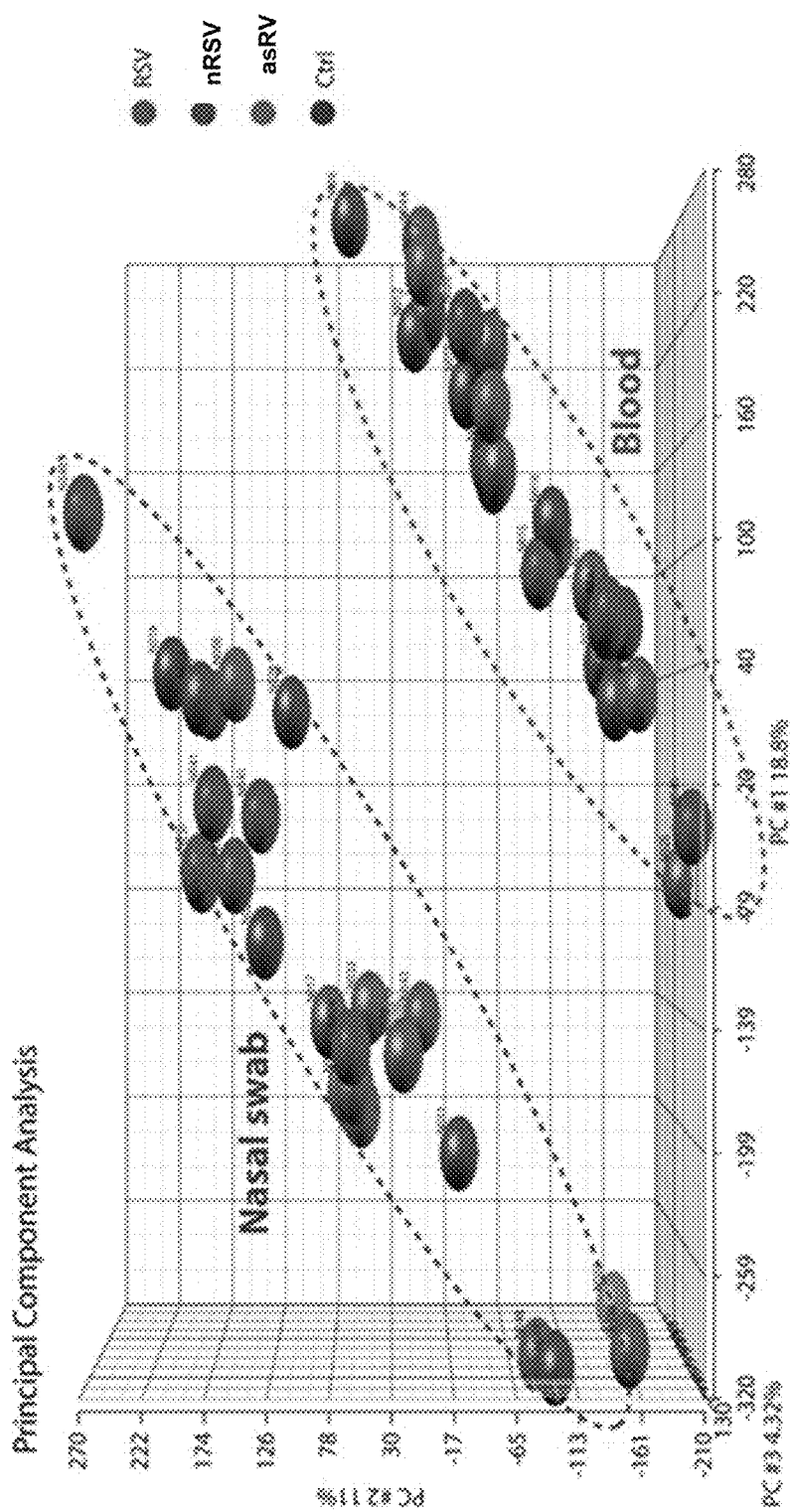
FIG. 1A, FIG. 1B, FIG. 1C, and FIG. 1D depict RNA and chip quality assessment.
Figure 1B:
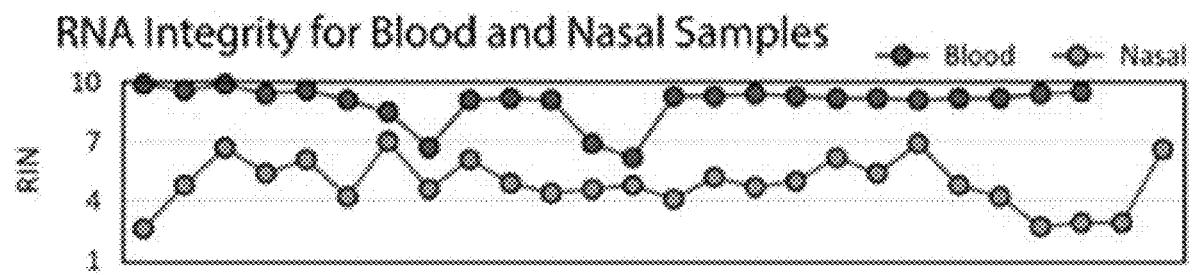
Figure 1C:
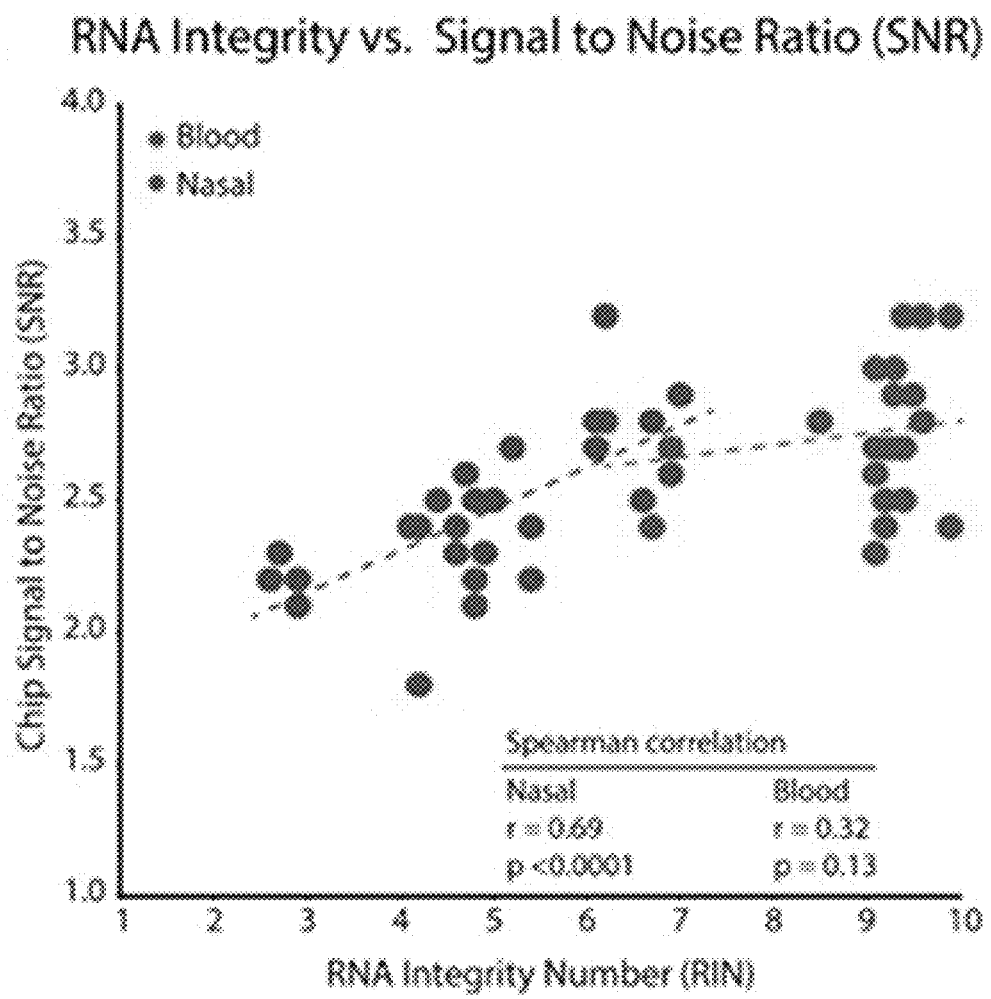
Figure 1D:
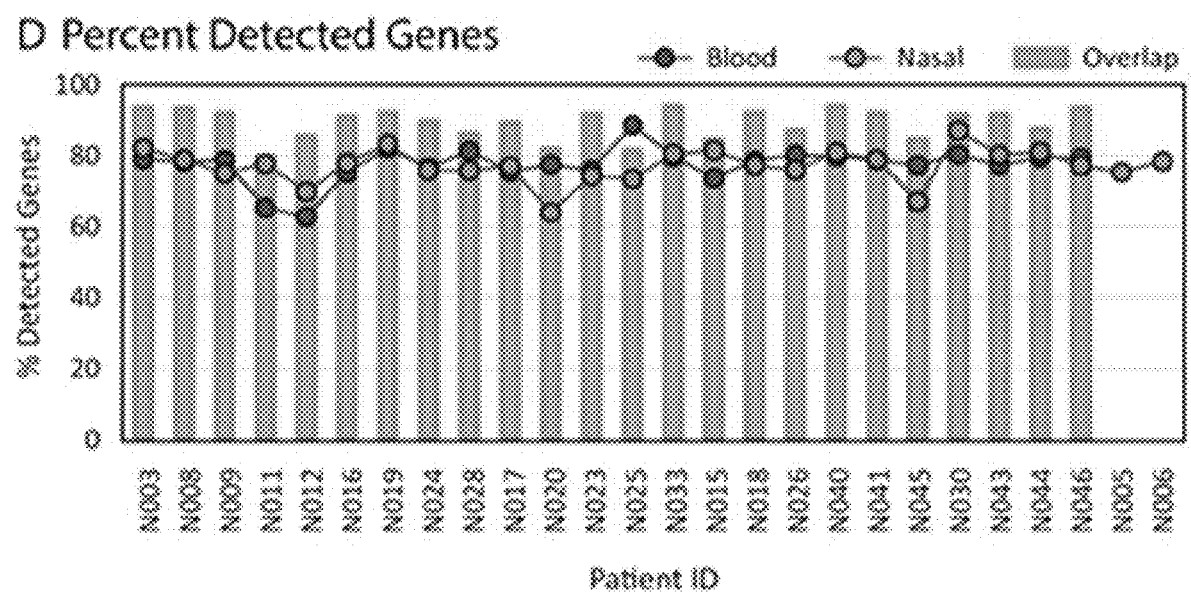

The present disclosure generally relates to molecular detection methods that overcome many of the limitations of current methods for the determination of the etiology of respiratory symptoms. In one aspect, the methods detect the host's response to an infectious agent or agents by measuring and analyzing the patterns of co-expressed host genes, or signatures. These gene expression signatures may be measured in a biological sample in a human or animal presenting with symptoms that are consistent with an acute respiratory infection (ARI) or in a human or animal that is at risk of developing (e.g., presymptomatic) an acute respiratory infection (e.g., during an epidemic or local disease outbreak). Measurement of the host response, as taught herein, differentiates between bacterial ARI, symptomatic viral ARI, asymptomatic viral ARI and a non-infectious cause of illness, and may also detect ARI resulting from co-infection with bacteria and virus.

The present disclosure optimizes treatment of subject having or suspected of having an ARI. As such, the present disclosure provides methods for guiding appropriate use of antimicrobials, thereby aiding against the rising tide of antimicrobial resistance. In one aspect, the present disclosure provides methods for epidemiological surveillance to identify and track outbreaks.

Additional aspects of the invention are described below.

(I) Methods

One aspect of the present disclosure encompasses determining the level of expression of genes which indicate a bacterial infection, symptomatic viral infection, asymptomatic viral infection and a non-infectious cause of illness in the respiratory tract of a subject. Suitable genes were identified according to example 1, and in exemplary embodiments, are genes used to detect an ARI in a subject. The present disclosure is not limited to the specific genes recited in the examples as a skilled artisan could identify other suitable genes using the techniques disclosed herein. Examining host gene signature induced by a symptomatic viral infection, an asymptomatic viral infection or non-infectious cause shows distinct biomarker profiles which can then be used to determine the etiology of the infection and guide treatment decisions.

(a) Host Gene Signatures

In various embodiments, a modulated host gene signature may comprise any gene with altered expression during the innate immune reaction of the host (e.g., the immune response of the respiratory tract or blood). In various embodiments, the modulated host gene may be any gene the expression of which changes in a subject having a respiratory infection relative to a subject that does not have a respiratory infection. In various embodiments, the modulated host gene is a cilium related gene, a cytokeratin gene, a mucin gene, an epithelial cell marker gene, a B cell marker gene, a T cell marker gene, a NK cell marker gene, an eosinophil marker gene, a basophil marker gene, a neutrophil marker gene, a dendritic cell marker gene, a monocyte marker gene, an Fc receptor gene, a leukocyte marker gene, a chemokine gene, an interferon or interferon-related gene, an anti-host gene, an anti-virus gene, an apoptosis related gene, a phagocytic gene, a cell cycle gene, a cell signaling gene, an immune signaling gene, a protein translation gene, an RNA transcription gene, a virus activity gene, a cilium assembly gene, a smoothened signaling gene, a protein localization gene, a polyglutamylation gene, a left/right symmetry gene, or a fatty acid oxidation gene. The term "signature" as used herein refers to a set of biological markers and the measurable quantities of said markers whose particular combination signifies the presence or absence of the specified biological state. These signatures are discovered in a plurality of subjects with known status (e.g., with a confirmed respiratory bacterial infection, respiratory viral infection, or suffering from non-infectious illness), and are discriminative (individually or jointly) of one or more categories or outcomes of interest. These measurable analytes, also known as biological markers, can be (but are not limited to) gene expression levels, protein or peptide levels, or metabolite levels.

In some embodiments as disclosed herein, the "signature" is a particular combination of genes whose expression levels discriminate a condition such as a bacterial ARI, a symptomatic viral ARI, an asymptomatic viral ARI or non-infectious illness. See, for example, Table 4, FIG. 2, FIG. 3, FIG. 6, FIG. 9 and FIG. 12. In some embodiments, the signature is agnostic to the species of respiratory virus or bacteria (i.e., while differentiating between virus or bacteria, it does not differentiate between particular genus or species of virus or bacteria) and/or agnostic to the particular cause of the non-infectious illness. In some embodiments, the gene signature as disclosed herein may be combined with testing to detect the etiology of the infection (e.g., culturing pathogens from host samples, detecting viral or bacterial proteins or nucleotides).

The nucleotide and amino acid sequence information for the various host genes suitable for use in the methods of the present disclosure can be found using a reference data base known in the art, for example, UniProt. In some embodiments, a modulated host gene suitable for use in the present methods includes one or more of, IFT81 (Intraflagellar Transport 81), MUC16 (Mucin 16, Cell Surface Associated), MUC15 (Mucin 15, Cell Surface Associated), MUCL1 (mucin like 1), BPIFB1 (BPI Fold Containing Family B Member 1), CDH1 (epithelial cadherin), CDHR3 (Cadherin Related Family Member 3), MS4A1 (Membrane Spanning 4-Domains A1), CD22 (cluster of differentiation-22), NCAM1 (Neural Cell Adhesion Molecule 1), KLRB1 (killer cell lectin like receptor B1), NCR1 (natural killer cell receptor NKp46), SIGLEC8 (Sialic acid-binding Ig-like lectin 8), CCR3 (C-C chemokine receptor type 3), CSF3R (Colony Stimulating Factor 3 Receptor), CXCR1 ((C-X-C Motif Chemokine Receptor 1)), CCR7 (C-C chemokine receptor type 7), CD83 (CD83 Molecule), SIRPA (Signal Regulatory Protein Alpha), CD14 (CD14 Molecule), CSF1R (Colony Stimulating Factor 1 Receptor), CCR5 (C-C chemokine receptor type 5), FCAR (Fc fragment of IgA receptor), FCER1A (Fc Fragment Of IgE, High Affinity I, Receptor For; Alpha Polypeptide), ITGAM (Integrin, Alpha M (Complement Component 3 Receptor 3 Subunit)), CR1 (Complement receptor type 1), OLR1 (oxidized low density lipoprotein (lectin-like) receptor 1), TNFSF13B (tumor necrosis factor (ligand) superfamily, member 13b), C3AR1 (complement component 3a receptor 1), CCRL2 (chemokine (C-C motif) receptor-like 2), TNFAIP6 (tumor necrosis factor, alpha-induced protein 6), SELL (selectin L), AQP9 (aquaporin 9), PROK2 (prokineticin 2), BCL2A1 (BCL2-related protein A1), FFAR2 (free fatty acid receptor 2), FPR1 (formyl peptide receptor 1), FCGR3B (Fc fragment of IgG, low affinity IIIb, receptor (CD16b)), IFITM2 interferon induced transmembrane protein 2), IFI6 (interferon, alpha-inducible protein 6), IFITM1 (interferon induced transmembrane protein 1), S100A12 (S100 calcium binding protein A12), FCER1G (Fc fragment of IgE, high affinity I, receptor for; gamma polypeptide), IFIT1 (interferon-induced protein with tetratricopeptide repeats 1), ISG15 (ISG15 ubiquitin-like modifier), RSAD2 (radical S-adenosyl methionine domain containing 2), DDX60L (DEAD (Asp-Glu-Ala-Asp) box polypeptide 60-like), IFIT3 (interferon-induced protein with tetratricopeptide repeats 3), WFDC6 (WAP four-disulfide core domain 6), MORN5 (MORN repeat containing 5), TBC1D8 (TBC1 domain family, member 8 (with GRAM domain)), CCDC65 (coiled-coil domain containing 65), AGBL2 (ATP/GTP binding protein-like 2), KIAA2012, DNAL1 (dynein, axonemal, light chain 1), OSBPL6 (oxysterol binding protein-like 6), DNAH6 (dynein, axonemal, heavy chain 6), ANKFN1 (ankyrin-repeat and fibronectin type III domain containing 1), CFAP126 (cilia and flagella associated protein 126), ECT2L (epithelial cell transforming 2 like), LRRC6 (leucine rich repeat containing 6), SPAG17 (sperm associated antigen 17), ANKUB1 (ankyrin repeat and ubiquitin domain containing 1), HHLA2 (HERV-H LTR-associating 2), PIFO (primary cilia formation), LMNTD1 (lamin tail domain containing 1), VWA3B (von Willebrand factor A domain containing 3B), LRRC74B (leucine rich repeat containing 74B), DTHD1 (death domain containing 1), FABP6 (fatty acid binding protein 6, ileal), EFHB (EF-hand domain family, member B), TIMP1 (TIMP metallopeptidase inhibitor 1), LIRA1 (leukocyte immunoglobulin-like receptor, subfamily A (with TM domain), member 1), LILRB2 (leukocyte immunoglobulin-like receptor, subfamily B (with TM and ITIM domains), member 2), SLC7A5 (solute carrier family 7 (amino acid transporter light chain, L system), member 5), GPR183 (G protein-coupled receptor 183), LILRB1 (leukocyte immunoglobulin-like receptor, subfamily B (with TM and ITIM domains), member 1), MYO1G (myosin IG), DOK2 (docking protein 2), EMP3 (epithelial membrane protein 3), CYBB (cytochrome b-245, beta polypeptide), SP140 (SP140 nuclear body protein), MLKL (mixed lineage kinase domain-like), DDX60L (DEAD (Asp-Glu-Ala-Asp) box polypeptide 60-like), FPR3 (formyl peptide receptor 3), MILR1 (mast cell immunoglobulin-like receptor 1), CD163 (CD163 molecule), CXorf21 (chromosome X open reading frame 21), TNFSF13B (tumor necrosis factor (ligand) superfamily, member 13b), CCR1 (chemokine (C-C motif) receptor 1), LGALS1 (lectin, galactoside-binding, soluble, 1), SLC15A3 (solute carrier family 15 (oligopeptide transporter), member 3), RELB (v-rel avian reticuloendotheliosis viral oncogene homolog B), FLNA (filamin A, alpha), FCER1G (Fc fragment of IgE, high affinity I, receptor for; gamma polypeptide), LY96 (lymphocyte antigen 96), SLAMF7 (SLAM family member 7), C3AR1 (complement component 3a receptor 1), CCRL2 (chemokine (C-C motif) receptor-like 2), TNFAIP6 (tumor necrosis factor, alpha-induced protein 6), SELL (selectin L) LILRB3 (leukocyte immunoglobulin-like receptor, subfamily B (with TM and ITIM domains), member 3), SIGLEC14 (sialic acid binding Ig-like lectin 14), DYSF (dysferlin), LAT2 (linker for activation of T-cells family member 2), CREB5 (cAMP responsive element binding protein 5), MNDA (myeloid cell nuclear differentiation antigen), SAMSN1 (SAM domain, SH3 domain and nuclear localization signals 1), PLEK (pleckstrin), CD53 (CD53 molecule), FCGR2A (Fc fragment of IgG, low affinity IIa, receptor (CD32) CSF2RB colony stimulating factor 2 receptor, beta, low-affinity (granulocyte-macrophage)), LINC01272 (long intergenic non-protein coding RNA 1272), PROK2 (prokineticin 2), SRGN (serglycin), AQP9 (aquaporin 9), BCL2A1 (BCL2-related protein A1FFAR2 free fatty acid receptor 2), FPR1 (formyl peptide receptor 1), CSRNP1 (cysteine-serine-rich nuclear protein 1), IER2 (immediate early response 2), PLAUR (plasminogen activator, urokinase receptor), FCGR3B (Fc fragment of IgG, low affinity IIIb, receptor (CD16b)), FCGR3A (Fc fragment of IgG, low affinity IIIa, receptor (CD16a)), ARHGAP25 (Rho GTPase activating protein 25), EVI2A (ecotropic viral integration site 2A), IFITM2 (interferon induced transmembrane protein 2), CD48 (CD48 molecule), RAC2 (ras-related C3 botulinum toxin substrate 2 (rho family, small GTP binding protein Rac2)), WAS (Wiskott-Aldrich syndrome), COTL1 (coactosin-like F-actin binding protein 1), FCGR1A (Fc fragment of IgG, high affinity 1a, receptor (CD64)), AIF1 (allograft inflammatory factor 1), GMFG (glia maturation factor, gamma), PTPRC (protein tyrosine phosphatase, receptor type, CCORO1A coronin, actin binding protein, 1A), MX2 (MX dynamin-like GTPase 2), IFIT1 (interferon-induced protein with tetratricopeptide repeats 1), ISG15 (ISG15 ubiquitin-like modifier), IFIT2 (interferon-induced protein with tetratricopeptide repeats 2), IFIT3 (interferon-induced protein with tetratricopeptide repeats 3), RSAD2 (radical S-adenosyl methionine domain containing 2), OASL (2-5-oligoadenylate synthetase-like IFI6 interferon, alpha-inducible protein 6), IFITM3 (interferon induced transmembrane protein 3), IFITM1 (interferon induced transmembrane protein 1), ISG20 (interferon stimulated exonuclease gene 20 kDa), C1orf158 (chromosome 1 open reading frame 158), CFAP57 (cilia and flagella associated protein 57), PALMD (palmdelphin), PPOX (protoporphyrinogen oxidase), FMO3 (flavin containing monooxygenase 3), SPATA17 (spermatogenesis associated 17), STPG1 (sperm-tail PG-rich repeat containing 1), BEST4 (bestrophin 4), CCDC17 (coiled-coil domain containing 17), C1orf87 (Chromosome 1 open reading frame 87), WDR78 (WD repeat domain 78), APOBEC4 (apolipoprotein B mRNA editing enzyme, catalytic polypeptide-like 4 (putative)), CCDC30 (coiled-coil domain containing 30), CFAP45 (cilia and flagella associated protein 45), DRC1 (dynein regulatory complex subunit 1), FAM179A (family with sequence similarity 179, member A), CFAP221 (cilia and flagella associated protein 221), IGFBP2 (insulin like growth factor binding protein 2), IFT172 (intraflagellar transport 172), TSGA10 (testis specific 10), ALS2CR12 (amyotrophic lateral sclerosis 2 chromosome region candidate 12), MDH1B (malate dehydrogenase 1B), CFAP65 (cilia and flagella associated protein 65), MAP3K19 (mitogen-activated protein kinase kinase kinase 19), DLEC1 (deleted in lung and esophageal cancer 1), MAATS1 (MYCBP-associated, testis expressed 1), MLF1 (myeloid leukemia factor 1), NEK10 (NIMA-related kinase 10), ASB14 (ankyrin repeat and SOCS box containing 14), DNAH12 (dynein, axonemal, heavy chain 12), KIAA1257, NME9 (NME/NM23 family member 9), LRRC34 (leucine rich repeat containing 34), EFHB (EF-hand domain family, member B), PLCH1 (phospholipase C, eta 1), CC2D2A (coiled-coil and C2 domain containing 2A), DTHD1 (death domain containing 1), C4orf47 (chromosome 4 open reading frame 47), C4orf22 (chromosome 4 open reading frame 22), ROPN1L (rhophilin associated tail protein 1-like), SPEF2 (sperm flagellar 2), FABP6 (fatty acid binding protein 6, ileal), DNAH5 (dynein, axonemal, heavy chain 5), LOC100505841 (zinc finger protein 474-like), TMEM232 (transmembrane protein 232), ANKRD66 (ankyrin repeat domain 66), EFHC1 (EF-hand domain (C-terminal) containing 1), ADGB (androglobin, CCDC170 coiled-coil domain containing 170), PPIL6 (peptidylprolyl isomerase (cyclophilin)-like 6), CFAP206 (cilia and flagella associated protein 206), DNAH11 (dynein, axonemal, heavy chain 11), RSPH10B2 (radial spoke head 10 homolog B2 (*Chlamydomonas*)), IQUB (IQ motif and ubiquitin domain containing), ZNF713 (zinc finger protein 713), CCDC146 (coiled-coil domain containing 146), RP1 (retinitis pigmentosa 1 (autosomal dominant)), TMEM67 (transmembrane protein 67), PPP1R42 (protein phosphatase 1, regulatory subunit 42), DNAI1 (dynein, axonemal, intermediate chain 1), C9orf135 (chromosome 9 open reading frame 135), CCDC180 (coiled-coil domain containing 180), CFAP157 (cilia and flagella associated protein 157), FAM166B (family with sequence similarity 166, member B), CFAP47 (cilia and flagella associated protein 47), AKAP14 (A kinase (PRKA) anchor protein 14), EFHC2 (EF-hand domain (C-terminal) containing 2), CETN2 (centrin 2, ZNF487 zinc finger protein 487), SFXN3 (sideroflexin 3), ENKUR (enkurin, TRPC channel interacting protein, ARMC4 armadillo repeat containing 4), FRMPD2 (FERM and PDZ domain containing 2), CFAP70 (cilia and flagella associated protein 70), CFAP43 (cilia and flagella associated protein 43), CFAP46 (cilia and flagella associated protein 46), SPAG6 (sperm associated antigen 6), DNAJB13 (DnaJ (Hsp40) homolog, subfamily B, member 13), CCDC81 (coiled-coil domain containing 81), C11orf88 (chromosome 11 open reading frame 88), STK33 (serine/threonine kinase 33), COLCA1 (colorectal cancer associated 1), BTG4 (B-cell translocation gene 4), PIH1D2 (PIH1 domain containing 2), CCDC153 (coiled-coil domain containing 153), DCDC5 (doublecortin domain containing 5), DCDC1 (doublecortin domain containing 1), CFAP54 (cilia and flagella associated 54), CCDC60 (coiled-coil domain containing 60), LRRC43 (leucine rich repeat containing 43), DNAH10 (dynein, axonemal, heavy chain 10), CASC1 (cancer susceptibility candidate 1), TSPAN19 (tetraspanin 19), IQCD (IQ motif containing D), STX2 (syntaxin 2), WDR66 (WD repeat domain 66), TEX26 (testis expressed 26), STOML3 (stomatin (EPB72)-like 3), NEK5 (NIMA-related kinase 5), SAMD15 (sterile alpha motif domain containing 15), C14orf79 (chromosome 14 open reading frame 79), CDKL1 (cyclin-dependent kinase-like 1 (CDC2-related kinase)), TEX9 (testis expressed 9), IQCH (IQ motif containing H), SAXO2 (stabilizer of axonemal microtubules 2), CCP110 (centriolar coiled coil protein 110 kDa), VWA3A (von Willebrand factor A domain containing 3A), DNAAF1 (dynein, axonemal, assembly factor 1), DNAH3 (dynein, axonemal, heavy chain 3), DRC3 (dynein regulatory complex subunit 3), FBXO15 (F-box protein 15), TTLL9 (tubulin tyrosine ligase-like family member 9), LCA5L (Leber congenital amaurosis 5-like), RSPH1 (radial spoke head 1 homolog (*Chlamydomonas*)), RSPH14 (radial spoke head 14 homolog (*Chlamydomonas*)), EFCAB6 (EF-hand calcium binding domain 6), ARHGAP25 (Rho GTPase activating protein 25), EVI2A (ecotropic viral integration site 2A), CCRL2 (chemokine (C-C motif) receptor-like 2), SIGLEC14 (sialic acid binding Ig-like lectin 14), EMP3 (epithelial membrane protein 3), CYBB (cytochrome b-245, beta polypeptide), LY96 (lymphocyte antigen 96), SLAMF7 (SLAM family member 7), IFITM2 (interferon induced transmembrane protein 2), MX2 (MX dynamin-like GTPase 2), IFIT2 (interferon-induced protein with tetratricopeptide repeats 2), APOBEC3A (apolipoprotein B mRNA editing enzyme, catalytic polypeptide-like 3A), OLR1 (oxidized low density lipoprotein (lectin-like) receptor 1), and FPR3 (formyl peptide receptor 3).

The methods may comprise determining the expression level of at least 1 gene, at least 2 genes, at least 3 genes, at least 4 genes, at least 5 genes, at least 6 genes, at least 6 genes, at least 7 genes, at least 8 genes, at least 9 genes, at least 10 genes, at least 11 genes, at least 12 genes, at least 13 genes, at least 14 genes, at least 15 genes, at least 16 genes, at least 17 genes, at least 18 genes, at least 19 genes, at least 20 genes, at least 21 genes, at least 22 genes, at least 23 genes, at least 24 genes, at least 25 genes, at least 26 genes, at least 27 genes, at least 28 genes, at least 29 genes, at least 30 genes, at least 31 genes, at least 32 genes, at least 33 genes, at least 34 genes, at least 35 genes, at least 36 genes, at least 37 genes, at least 38 genes, at least 39 genes, at least 40 genes, at least 41 genes, at least 42 genes, or at least 43 genes, at least 44 genes, at least 45 genes, at least 46 genes, at least 47 genes, at least 48 genes, at least 49 genes, at least 50 genes, at least 51 genes, at least 52 genes, at least 53 genes, at least 54 genes, at least 55 genes, at least 56 genes, at least 57 genes, at least 58 genes, at least 59 genes, at least 60 genes, at least 61 genes, at least 62 genes, at least 63 genes, at least 64 genes, at least 65 genes, at least 66 genes, at least 67 genes, at least 68 genes, at least 69 genes, at least 70 genes, at least 71 genes, at least 72 genes, at least 73 genes, at least 74 genes, at least 75 genes, at least 76 genes, at least 77 genes, at least 78 genes, at least 79 genes, at least 80 genes, at least 81 genes, at least 82 genes, at least 83 genes, at least 84 genes, at least 85 genes, at least 86 genes, at least 87 genes, at least 88 genes, at least 89 genes, at least 90 genes, at least 91 genes, at least 92 genes, at least 93 genes, at least 94 genes, at least 95 genes, at least 96 genes, at least 97 genes, at least 98 genes, at least 99 genes, at least 100 genes, at least 101 genes, at least 102 genes, at least 103 genes, at least 104 genes, at least 105 genes, at least 106 genes, at least 107 genes, at least 108 genes, at least 109 genes, at least 110 genes at least 111 genes, at least 112 genes, at least 113 genes, at least 114 genes, at least 115 genes, at least 116 genes, at least 117 genes, at least 118 genes, at least 119 genes, at least 120 genes, at least 121 genes, at least 122 genes, at least 123 genes, at least 124 genes, at least 125 genes, at least 126 genes, at least 127 genes, at least 128 genes, at least 129 genes, at least 130 genes, at least 131 genes, at least 132 genes, at least 133 genes, at least 134 genes, at least 135 genes, at least 136 genes, at least 137 genes, at least 138 genes, at least 139 genes, at least 140 genes, at least 141 genes, at least 142 genes, at least 143 genes, at least 144 genes, at least 145 genes, at least 146 genes, at least 147 genes, at least 148 genes, at least 149 genes, at least 150 genes, at least 151 genes, at least 152 genes, at least 153 genes, at least 154 genes, at least 155 genes, at least 156 genes, at least 157 genes, at least 158 genes, at least 159 genes, at least 160 genes, at least 161 genes, at least 162 genes, at least 163 genes, at least 164 genes, at least 165 genes, at least 166 genes, at least 167 genes, at least 168 genes, at least 169 genes, at least 170 genes, at least 171 genes, at least 172 genes, at least 173 genes, at least 174 genes, at least 175 genes, at least 176 genes, at least 177 genes, at least 178 genes, at least 179 genes, at least 180 genes, at least 181 genes, at least 182 genes, at least 183 genes, at least 184 genes, at least 185 genes, at least 186 genes, at least 187 genes, at least 188 genes, at least 189 genes, at least 190 genes, at least 191 genes, at least 192 genes, at least 193 genes, at least 194 genes, at least 195 genes, at least 196 genes, at least 197 genes, at least 198 genes, at least 199 genes, at least 200, at least 250, at least 300 or at least 350 genes.

"Rule in" or "rule out" tests (with threshold set for high positive predictive value or high negative predictive value respectively) support appropriate medical decision making and efficient utilization of resources when well-understood by health care providers. Various embodiments comprise a method to rule in respiratory infection using one or more host modulated genes but other embodiments may comprise determining the level of two, three or more modulated host genes as noted above. In certain embodiments, the disclosure provides a method comprising determining the level of two or more modulated host genes, the level of one or more of the modulated host genes may be measured as an indicator of sample quality. In some embodiments, tests to measure the level of two or more genes may be combined with tests for the presence of a virus or bacterium.

(b) Respiratory Infection

As used herein, the term "acute respiratory infection" or "ARI" refers to an infection, or an illness showing symptoms and/or physical findings consistent with an infection (e.g., symptoms such as coughing, wheezing, fever, sore throat, congestion; physical findings such as elevated heart rate, elevated breath rate, abnormal white blood cell count, low arterial carbon dioxide tension (PaCO2), etc.), of the upper or lower respiratory tract, often due to a bacterial or viral pathogen, and characterized by rapid progression of symptoms over hours to days. ARIs may primarily be of the upper respiratory tract (URIs), the lower respiratory tract (LRIs), or a combination of the two. ARIs may have systemic effects due to spread of the infection beyond the respiratory tract or due to collateral damage induced by the immune response. An example of the former includes *Staphylococcus aureus* pneumonia that has spread to the blood stream and can result in secondary sites of infection, including endocarditis (infection of the heart valves), septic arthritis (joint infection), or osteomyelitis (bone infection). An example of the latter includes influenza pneumonia leading to acute respiratory distress syndrome and respiratory failure. The term "respiratory virus" as used herein means a virus that can cause or does cause a respiratory virus infection in a patient. While the present disclosure is not limited to the detection of a specific pathogen, in some embodiments, the methods include detecting a non-respiratory syncytia virus (e.g. picornavirus infection). In some embodiments, the methods include detecting a rhinovirus infection.

(c) Biological Sample

In an aspect, the disclosure provides a method to detect aberrant host genes in a biological sample obtained from a subject. As used herein, the term "biological sample" means a biological material isolated from a subject. Any biological sample containing any biological material suitable for detecting the desired biomarkers, and may comprise cellular and/or non-cellular material obtained from the subject is suitable. Non-limiting examples include blood, plasma, serum, urine, and tissue. Frequently the sample will be a "clinical sample" which is a sample derived from a patient. Typical clinical samples include, but are not limited to, bodily fluid samples such as synovial fluid, sputum, blood, urine, blood plasma, blood serum, sweat, mucous, saliva, lymph, bronchial aspirates, peritoneal fluid, cerebrospinal fluid, and pleural fluid, and tissues samples such as blood-cells (e.g., white cells), tissue or fine needle biopsy samples and abscesses or cells therefrom. Biological samples may also include sections of tissues, such as frozen sections or formalin fixed sections taken for histological purposes.

In a specific embodiment, the sample is a respiratory sample. The term "respiratory sample" as used herein means any sample from a subject containing RNA or proteins a plurality of which is generated by cells in the upper or lower respiratory tract. Non-limiting examples include nasal swabs, nasopharyngeal swabs, nasopharyngeal aspirate, oral swab, oropharyngeal swab, pharyngeal (throat) swab, sputum, tracheal aspirate, bronchoalveolar lavage or saliva or transport medium exposed to any of these sample types. In one aspect, the sample is a nasopharyngeal sample. A "nasopharyngeal sample" as used herein means any sample from a subject containing RNA or proteins, a plurality of which is generated by cells in the upper respiratory tract. Non-limiting examples include nasal swabs, nasopharyngeal swabs, nasopharyngeal aspirate, oral swab, oropharyngeal swab, pharyngeal swabs, throat swabs, saliva or medium exposed to any of these sample types. In an exemplary embodiment, the biological sample is obtained using a mid-turbinate swab.

As will be appreciated by a skilled artisan, the method of collecting a biological sample can and will vary depending upon the nature of the biological sample and the type of analysis to be performed. Any of a variety of methods generally known in the art may be utilized to collect a biological sample. Generally speaking, the method preferably maintains the integrity of the sample such that the mRNA or protein can be accurately detected and the amount measured according to the disclosure.

In some embodiments, a single sample is obtained from a subject to detect a host gene signature in the sample. Alternatively, a host gene signature may be detected in samples obtained over time from a subject. As such, more than one sample may be collected from a subject over time. For instance, 2, 3, 4, 5, 6, 7, 8, 9, 10, 11, 12, 13, 14, 15, 16 or more samples may be collected from a subject over time. In some embodiments, 2, 3, 4, 5, or 6 samples are collected from a subject over time. In other embodiments, 6, 7, 8, 9, or 10 samples are collected from a subject over time. In yet other embodiments, 10, 11, 12, 13, or 14 samples are collected from a subject over time. In other embodiments, 14, 15, 16 or more samples are collected from a subject over time.

When more than one sample is collected from a subject over time, samples may be collected every 0.5, 1, 2, 3, 4, 5, 6, 7, 8, 9, 10, 11, 12 or more hours. In some embodiments, samples are collected every 0.5, 1, 2, 3, or 4 hours. In other embodiments, samples are collected every 4, 5, 6, or 7 hours. In yet other embodiments, samples are collected every 7, 8, 9, or 10 hours. In other embodiments, samples are collected every 10, 11, 12 or more hours. Additionally, samples may be collected every 1, 2, 3, 4, 5, 6, 7, 8, 9, 10, 11, 12 or more days. In some embodiments, a sample is collected about every 6 days. In some embodiments, samples are collected every 1, 2, 3, 4, or 5 days. In other embodiments, samples are collected every 5, 6, 7, 8, or 9 days. In yet other embodiments, samples are collected every 9, 10, 11, 12 or more days.

(d) Detecting Host Genes

Methods for assessing an amount of host gene expression in samples are well known in the art, and all suitable methods for assessing an amount of nucleic acid or protein expression known to one of skill in the art are contemplated within the scope of the invention. By the phrase "determining the level of expression" is meant an assessment of the absolute or relative quantity of a biomarker in a sample at the nucleic acid or protein level, using technology available to the skilled artisan to detect a sufficient portion of any marker.

The term "amount of nucleic acid expression" or "level of nucleic acid expression" as used herein refers to a measurable level of expression of the nucleic acids, such as, without limitation, the level of mRNA transcript expressed or a specific variant or other portion of the RNA. The term "nucleic acid" includes DNA and RNA and can be either double stranded or single stranded. Non-limiting examples of suitable methods to assess an amount of nucleic acid expression may include arrays, such as microarrays, PCR, such as RT-PCR (including quantitative RT-PCR), nuclease protection assays and Northern blot analyses. In a specific embodiment, determining the amount of a RNA comprises, in non-limiting examples, measuring the level of mRNA expression, tRNA expression, rRNA expression, snRNA expression miRNA expression, lncRNA expression, tmRNA expression, and/or snoRNA expression.

In one embodiment, the amount of nucleic acid expression may be determined by using an array, such as a microarray. Methods of using a nucleic acid microarray are well and widely known in the art. For example, a nucleic acid probe that is complementary or hybridizable to an expression product of a target gene may be used in the array.

The term "hybridize" or "hybridizable" refers to the sequence specific non-covalent binding interaction with a complementary nucleic acid. In a preferred embodiment, the hybridization is under high stringency conditions. Appropriate stringency conditions which promote hybridization are known to those skilled in the art, or can be found in Current Protocols in Molecular Biology, John Wiley & Sons, N.Y. (1989), 6.3.1 6.3.6. The term "probe" as used herein refers to a nucleic acid sequence that will hybridize to a nucleic acid target sequence. In one example, the probe hybridizes to an RNA product of the nucleic acid or a nucleic acid sequence complementary thereof. The length of probe depends on the hybridization conditions and the sequences of the probe and nucleic acid target sequence. In one embodiment, the probe is at least 8, 10, 15, 20, 25, 50, 75, 100, 150, 200, 250, 400, 500 or more nucleotides in length.

In general the methods include any know techniques for amplifying nucleic acids, including but not limited to PCR, loop-mediated isothermal amplification, and nucleic acid sequence-based amplification (NASBA). In one aspect, the amount of nucleic acid expression may be determined using PCR. A nucleic acid may be amplified using cDNA, mRNA or genomic DNA as a template and appropriate oligonucleotide primers according to standard PCR amplification techniques. Methods of PCR are well and widely known in the art, and may include quantitative PCR, semi-quantitative PCR, multiplex PCR, or any combination thereof. Specifically, the amount of nucleic expression may be determined using quantitative RT-PCR. Methods of performing quantitative RT-PCR are common in the art. In such an embodiment, the primers used for quantitative RT-PCR may comprise a forward and reverse primer for a target gene. The term "primer" as used herein refers to a nucleic acid sequence, whether occurring naturally as in a purified restriction digest or produced synthetically, which is capable of acting as a point of synthesis when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less or more. The factors involved in determining the appropriate length of primer are readily known to one of ordinary skill in the art.

The amount of nucleic acid expression may be measured by measuring an entire RNA transcript for a nucleic acid sequence, or measuring a portion of the RNA transcript for a nucleic acid sequence. For instance, if a nucleic acid array is utilized to measure the amount of RNA expression, the array may comprise a probe for a portion of the RNA of the nucleic acid sequence of interest, or the array may comprise a probe for the full RNA of the nucleic acid sequence of interest. Similarly, in a PCR reaction, the primers may be designed to amplify the entire cDNA sequence of the nucleic acid sequence of interest, or a portion of the cDNA sequence. One of skill in the art will recognize that there is more than one set of primers that may be used to amplify either the entire cDNA or a portion of the cDNA for a nucleic acid sequence of interest. Methods of designing primers are known in the art. Methods of extracting RNA from a biological sample are known in the art.

The level of expression may or may not be normalized to the level of a control nucleic acid. Such a control nucleic acid should not specifically hybridize with an RNA nucleotide sequence of the invention. This allows comparisons between assays that are performed on different occasions.

In other embodiments, a method of the disclosure comprises detecting the expression levels of one or more host genes at the protein level. In essence, a host protein may be detected using methods normally used in the art for detecting a specific protein in a sample. As such, non-limiting examples of methods of detecting a protein adduct may include chromatography, mass spectrometry, an antibody-based detection method, or a combination thereof, and may be as discussed in Ausubel et al. (2003) Current Protocols in Molecular Biology, John Wiley & Sons, New York, NY, or Sambrook et al. (1989) Molecular Cloning: A Laboratory Manual, Cold Spring Harbor Press, Cold Spring Harbor, NY.

In some embodiments, host protein levels are detected using mass spectrometry. Mass spectrometry may be tandem mass spectrometry, quadrupole mass spectrometry, MALDI-TOF mass spectrometry, inductively coupled plasma-mass spectrometry (ICP-MS), accelerator mass spectrometry (AMS), thermal ionization-mass spectrometry (TIMS), and spark source mass spectrometry (SSMS). In specific embodiments, host protein levels are detected using a mass spectrometry method capable of detecting a specific protein. Non-limiting examples of mass spectrometry methods capable of detecting a specific protein include MALDI-TOF mass spectrometry and high-resolution tandem mass spectrometry.

In other embodiments, host protein levels may be detected in a sample using methods based on epitope binding agents. Non-limiting examples of suitable epitope binding agents, depending upon the target molecule, include agents selected from the group consisting of an aptamer, an antibody, an antibody fragment, a double-stranded DNA sequence, modified nucleic acids, nucleic acid mimics, a ligand, a ligand fragment, a receptor, a receptor fragment, a polypeptide, a peptide, a coenzyme, a coregulator, an allosteric molecule, and an ion.

In some specific alternatives of the embodiments, an epitope binding agent is an antibody, and an host protein levels are detected using antibody based methods. Non-limiting examples of antibodies that may be used include polyclonal antibodies, ascites, Fab fragments, Fab' fragments, monoclonal antibodies, single chain antibodies, humanized antibodies, and other fragments that contain the epitope binding site of the antibody. Antibody based methods that may be used to detect a protein are known in the art. Non-limiting examples of methods based on antibodies may include Western blotting, enzyme-linked immunosorbent assays (ELISA), or other solid phase immunoassays, a sandwich immunoassay, radioimmunoassay, nephelometry, electrophoresis, immunofluorescence, immunoblot, flow cytometry, immunohistochemistry, an array or other methods (see Ausubel, F. M. et al., eds., Current Protocols in Molecular Biology, John Wiley & Sons, including supplements through 2001).

In general, an antibody-based method of detecting and measuring an amount of a protein comprises contacting some or all of the sample comprising a protein with an antibody specific for the protein under conditions effective to allow for formation of a complex between the antibody and the protein. Typically, the entire sample is not needed, allowing one skilled in the art to repeatedly detect and measure the amount of one or more proteins in the sample over time. The method may occur in solution, or the antibody or protein may be immobilized on a solid surface. Non-limiting examples of suitable surfaces include microtitre plates, test tubes, beads, resins, and other polymers. Attachment to the substrate may occur in a wide variety of ways, as will be appreciated by those in the art. For example, the substrate and the antibody may be derivatized with chemical functional groups for subsequent attachment of the two. For example, the substrate may be derivatized with a chemical functional group including, but not limited to, amino groups, carboxyl groups, oxo groups or thiol groups. Using these functional groups, the antibody may be attached directly using the functional groups or indirectly using linkers. The antibody may also be attached to the substrate non-covalently. For example, a biotinylated antibody may be prepared, which may bind to surfaces covalently coated with streptavidin, resulting in attachment. Alternatively, an antibody may be synthesized on the surface using techniques such as photopolymerization and photolithography.

Contacting the sample with an antibody under effective conditions for a period of time sufficient to allow formation of a complex generally involves adding the antibody composition to the sample and incubating the mixture for a period of time long enough for the antibody to bind to any antigen present. After this time, the complex may be washed and then the complex is detected and the amount measured by any method well known in the art. Methods of detecting and measuring an amount of an antibody-polypeptide complex are generally based on the detection of a label or marker. The term "label", as used herein, refers to any substance attached to an antibody, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, stretpavidin, protein A, protein G, antibodies or fragments thereof, polyhistidine, $Ni^{2+}$, Flag tags, myc tags, heavy metals, and enzymes (including alkaline phosphatase, peroxidase, glucose oxidase and luciferase). Methods of detecting and measuring an amount of an antibody-polypeptide complex based on the detection of a label or marker are well known in the art.

In some embodiments, an antibody-based method is an immunoassay. Immunoassays can be run in a number of different formats. Generally speaking, immunoassays can be divided into two categories: competitive immmunoassays and non-competitive immunoassays. In a competitive immunoassay, an unlabeled analyte in a sample competes with labeled analyte to bind an antibody. Unbound analyte is washed away and the bound analyte is measured. In a non-competitive immunoassay, the antibody is labeled, not the analyte. Non-competitive immunoassays may use one antibody (e.g. the capture antibody is labeled) or more than one antibody (e.g. at least one capture antibody which is unlabeled and at least one "capping" or detection antibody which is labeled.) Suitable labels are described above.

In other embodiments, an antibody-based method is an immunoblot or Western blot. In yet other embodiments, an antibody-based method is flow cytometry. In different embodiments, an antibody-based method is immunohistochemistry (IHC). IHC uses an antibody to detect and quantify antigens in intact tissue samples. The tissue samples may be fresh-frozen and/or formalin-fixed, paraffin-embedded (or plastic-embedded) tissue blocks prepared for study by IHC. Methods of preparing tissue block for study by IHC, as well as methods of performing IHC are well known in the art.

In alternative embodiments, an antibody-based method is an array. An array comprises at least one address, wherein at least one address of the array has disposed thereon an antibody specific for a host gene as disclosed herein. Arrays may comprise from about 1 to about several hundred thousand addresses. Several substrates suitable for the construction of arrays are known in the art, and one skilled in the art will appreciate that other substrates may become available as the art progresses. Suitable substrates are also described above. In some embodiments, the array comprises at least one host protein antibody attached to the substrate is located at one or more spatially defined addresses of the array. For example, an array may comprise at least one, at least two, at least three, at least four, or at least five host protein specific antibodies, each antibody recognizing the same or different protein, and each antibody may be may be at one, two, three, four, five, six, seven, eight, nine, ten or more spatially defined addresses.

For each of the foregoing embodiments, a protein may be first isolated or enriched before detection. For instance, proteins may be enriched or isolated using liquid chromatography, by precipitation, electrophoresis, or affinity purification. In some embodiments, proteins are enriched or purified using liquid chromatography. In other embodiments, proteins are enriched or purified using electrophoresis.

In specific embodiments, proteins are enriched or purified by affinity purification before detection. In particularly specific embodiments, proteins are enriched or purified by affinity purification using antibodies with specificity to the protein. Methods of enriching a sample for a protein or purifying a protein using affinity purification are known in the art. In short, affinity purification comprises incubating a sample with a solid support, such as beads, a culture plate, or a membrane, that facilitates later steps. A solid support may be coated with antibodies specific to a protein, causing the protein to attach to the solid support. Alternatively, a sample may be incubated with a first antibody with specificity to a protein, and the protein-antibody complex may be isolated by incubating with a solid support coated with a second antibody with specificity against a second site on said first antibody, causing a protein-antibody complex to attach to the solid support. The proteins may then be purified or enriched by washing other material in the sample that is not bound to the solid support, or, if the solid support is superparamagnetic beads, proteins attached to the beads (expressing the antigen) may be separated from the sample by attraction to a strong magnetic field. Upon enrichment or purification of a protein, the protein may then be detected in the enriched or purified sample using any of the methods described above.

The disclosure also provides that multiple proteins in the same biological sample may be measured simultaneously. Additionally, the disclosure provides that the proteins and corresponding non-specific proteins may be detected in the same biological sample. As such, the disclosure provides a useful method for screening changes in synthesis and clearance of host proteins on a large scale (i.e., proteomics/metabolomics) and provides a sensitive means to detect and measure host gene signatures in response to infection.

(e) Classification of a Subject

"Classification" refers to a method of assigning a subject suffering from or at risk for acute respiratory symptoms to one or more categories or outcomes (e.g., a patient is infected with a pathogen or is not infected, another categorization may be that a patient is infected with a virus and/or infected with a bacterium). In some cases, a subject may be classified to more than one category. The outcome, or category, is determined by expression signature of the subject being tested, which may be compared to a reference signature, confidence level, or limit. In other scenarios, the probability of belonging to a particular category may be given.

In various embodiments the invention is directed to a method of detecting a respiratory infection in a subject. The method generally comprises collecting a subject's cells, cell debris, or cell free fluid and determining the level at least one modulated host gene and comparing the level of the modulated host gene with its respective reference level. A "reference level" of a biomarker means a level of the biomarker that is indicative of the absence of a particular disease state or phenotype. In some embodiments, when the level of a biomarker in a subject is above the reference level of the biomarker it is indicative of the presence of a particular disease state or phenotype. In some embodiments, when the level of a biomarker in a subject is above the reference level of the biomarker it is indicative of the lack of a particular disease state or phenotype. In some embodiments, when the level of a biomarker in a subject is below the reference level of the biomarker it is indicative of the presence of a particular disease state or phenotype. In some embodiments, when the level of a biomarker in a subject is below the reference level of the biomarker it is indicative of the lack of a particular disease state or phenotype. In some embodiments, when the level of a biomarker in a subject is within the reference level of the biomarker it is indicative of a lack of a particular disease state or phenotype.

As used herein, the term "indicative" when used with gene expression levels, means that the gene expression levels are up-regulated or down-regulated, altered, or changed compared to the expression levels in alternative biological states (e.g., bacterial ARI or viral ARI) or control.

The term "indicative" when used with protein levels means that the protein levels are higher or lower, increased or decreased, altered, or changed compared to the standard protein levels or levels in alternative biological states.

In some embodiments expression of the modulated host gene is determined by measuring mRNA. In other embodiments, expression is determined by measuring protein. In embodiments comprising the measurement of protein, a biological sample may be used in an immunoassay. In embodiments comprising the measurement of mRNA, a biological sample may be optionally centrifuged to form a pellet of cells and cell debris which is then added to lysis buffer. Total nucleic acid is isolated from the pellet and DNA is digested using, by way of non-limiting example, DNAse I. The RNA is then reverse transcribed into cDNA. The cDNA is then analyzed to determine the level of at least one modulated host gene. In some embodiments the level of the at least one modulated host gene is determined by reverse transcription quantitative polymerase chain reaction (rt-qPCR) although the skilled artisan will appreciate that there are other ways that the level of the at least one modulated host gene may be determined by the analysis of mRNA and these methods are encompassed by the invention in its various embodiments.

The present disclosure further provides methods for determining whether a patient has a respiratory illness due to a bacterial infection, a symptomatic viral infection, an asymptomatic viral infection or a non-infectious cause. The method for making this determination relies upon the host gene signature as taught herein. The methods may include: a) measuring the expression levels of pre-defined sets of modulated host genes (i.e., for one or more of the four signatures); optionally normalizing gene expression levels for the technology used to make said measurement; and b) comparing the levels of one or more host genes with a reference value. In some embodiments, when the level of the one or more host genes is above the reference level it is indicative of the presence of a bacterial infection. In some embodiments, when the level of the one or more host genes is below the reference level it is indicative of the presence of a bacterial infection. In some embodiments, when the level of the one or more host genes is above the reference level it is indicative of the presence of a bacterial infection. In some embodiments, when the level of the one or more host genes is above the reference level it is indicative of the presence of a symptomatic viral infection. In some embodiments, when the level of the one or more host genes is below the reference level it is indicative of the presence of a symptomatic viral infection. In some embodiments, when the level of the one or more host genes is above the reference level it is indicative of the presence of an asymptomatic viral infection. In some embodiments, when the level of the one or more host genes is below the reference level it is indicative of the presence of an asymptomatic viral infection. In some embodiments, when the level of the one or more host genes is above the reference level it is indicative of the presence of a non-infectious cause. In some embodiments, when the level of the one or more host genes is below the reference level it is indicative of the presence of a non-infectious cause. In some embodiments, when the level of the one or more host genes is within the reference level it is indicative of a subject that does not have an infection or respiratory illness.

In one aspect, the disclosure provides a method of detecting a symptomatic viral infection comprising measuring the level or one or more host genes selected from C1orf158, CFAP57, PALMD, PIFO, PPOX, FMO3, SPATA17, STPG1, BEST4, CCDC17, C1orf87, WDR78, SPAG17, CFAP126, APOBEC4, CCDC30, CFAP45, DRC1, FAM179A, DNAH6, VWA3B, CFAP221, KIAA2012, IGFBP2, IFT172, TSGA10, ALS2CR12, MDH1B, CFAP65, OSBPL6, TBC1D8, MAP3K19, DLEC1, HHLA2, MAATS1, MLF1, NEK10, ASB14, DNAH12, KIAA1257, NME9, LRRC34, EFHB, ANKUB1, PLCH1, CC2D2A, DTHD1, C4orf47, C4orf22, ROPN1L, SPEF2, FABP6, DNAH5, LOC100505841, TMEM232, ANKRD66, EFHC1, ECT2L, ADGB, CCDC170, PPIL6, CFAP206, RSPH10B2, DNAH11, RSPH10B2, IQUB, ZNF713, CCDC146, RP1, TMEM67, LRRC6, PPP1R4, DNAI1, C9orf135, CCDC180, MORN5, CFAP157, FAM166B, CFAP47, AKAP14, EFHC2, CETN2, ZNF487, SFXN3, ENKUR, ARMC4, FRMPD2, CFAP70, CFAP43, CFAP46, SPAG6, DNAJB13, CCDC81, C11orf88, STK33, AGBL2, COLCA1, BTG4, PIH1D2, CCDC153, DCDC5, DCDC1, CCDC65, CFAP54, CCDC60, LRRC43, DNAH10, CASC1, TSPAN19, IQCD, STX2, WDR66, LMNTD1, TEX26, STOML3, NEK5, DNAL1, SAMD15, C14orf79, CDKL1, TEX9, IQCH, SAXO2, CCP110, VWA3A, DNAAF1, DNAH3, DRC3, ANKFN1, FBXO15, TTLL9, WFDC6, LCA5L, RSPH1, LRRC74B, RSPH14, EFCAB6 TIMP1, APOBEC3A, LILRA1, LILRB2, S100A12, SLC7A5, OLR1, GPR183, LILRB1, MYO1G, DOK2, EMP3, CYBB, SP140, MLKL, DDX60L, FPR3, MILR1, CD163, CXorf21, TNFSF13B, CCR1, LGALS1, SLC15A3, RELB, FLNA, FCER1G, LY96, SLAMF7, C3AR1, CCRL2, TNFAIP6, SELL, LILRB3, SIGLEC14, DYSF, LAT2, CREB5, MNDA, SAMSN1, PLEK, CD53, FCGR2A, CSF2RB, LINC01272, PROK2, SRGN, AQP9, BCL2A1, FFAR2, FPR1, CSRNP1, IER2, PLAUR, FCGR3B, FCGR3A, ARHGAP25, EVI2A, IFITM2, CD48, RAC2, WAS, COTL1, FCGR1A, AIF1, GMFG, PTPRC, CORO1A, MX2, IFIT1, ISG15, IFIT2, IFIT3, RSAD2, OASL, IFI6, IFITM3, IFITM1, and ISG20.

In some embodiments, the subject is classified as having a symptomatic viral infection when one or more of TIMP1, APOBEC3A, LILRA1, LILRB2, S100A12, SLC7A5, OLR1, GPR183, LILRB1, MYO1G, DOK2, EMP3, CYBB, SP140, MLKL, DDX60L, FPR3, MILR1, CD163, CXorf21, TNFSF13B, CCR1, LGALS1, SLC15A3, RELB, FLNA, FCER1G, LY96, SLAMF7, C3AR1, CCRL2, TNFAIP6, SELL, LILRB3, SIGLEC14, DYSF, LAT2, CREB5, MNDA, SAMSN1, PLEK, CD53, FCGR2A, CSF2RB, LINC01272, PROK2, SRGN, AQP9, BCL2A1, FFAR2, FPR1, CSRNP1, IER2, PLAUR, FCGR3B, FCGR3A, ARHGAP25, EVI2A, IFITM2, CD48, RAC2, WAS, COTL1, FCGR1A, AIF1, GMFG, PTPRC, CORO1A, MX2, IFIT1, ISG15, IFIT2, IFIT3, RSAD2, OASL, IFI6, IFITM3, IFITM1, ISG20 are increased relative to a reference value and/or one or more of C1orf158, CFAP57, PALMD, PIFO, PPOX, FMO3, SPATA17, STPG1, BEST4, CCDC17, C1orf87, WDR78, SPAG17, CFAP126, APOBEC4, CCDC30, CFAP45, DRC1, FAM179A, DNAH6, VWA3B, CFAP221, KIAA2012, IGFBP2, IFT172, TSGA10, ALS2CR12, MDH1B, CFAP65, OSBPL6, TBC1D8, MAP3K19, DLEC1, HHLA2, MAATS1, MLF1, NEK10, ASB14, DNAH12, KIAA1257, NME9, LRRC34, EFHB, ANKUB1, PLCH1, CC2D2A, DTHD1, C4orf47, C4orf22, ROPN1L, SPEF2, FABP6, DNAH5, LOC100505841, TMEM232, ANKRD66, EFHC1, ECT2L, ADGB, CCDC170, PPIL6, CFAP206, RSPH10B2, DNAH11, RSPH10B2, IQUB, ZNF713, CCDC146, RP1, TMEM67, LRRC6, PPP1R42, DNAI1, C9orf135, CCDC180, MORN5, CFAP157, FAM166B, CFAP47, AKAP14, EFHC2, CETN2, ZNF487, SFXN3, ENKUR, ARMC4, FRMPD2, CFAP70, CFAP43, CFAP46, SPAG6, DNAJB13, CCDC81, C11orf88, STK33, AGBL2, COLCA1, BTG4, PIH1D2, CCDC153, DCDC5, DCDC1, CCDC65, CFAP54, CCDC60, LRRC43, DNAH10, CASC1, TSPAN19, IQCD, STX2, WDR66, LMNTD1, TEX26, STOML3, NEK5, DNAL1, SAMD15, C14orf79, CDKL1, TEX9, IQCH, SAXO2, CCP110, VWA3A, DNAAF1, DNAH3, DRC3, ANKFN1, FBXO15, TTLL9, WFDC6, LCA5L, RSPH1, LRRC74B, RSPH14, EFCAB6 are decreased relative to a reference value.

In some embodiments, the subject is classified as having a symptomatic viral infection when one or more of ISG15, FCER1G, S100A12, SELL, TNFAIP6, IFIT1, C3AR1, CD163, FCGR1A, IFI6, FCGR3B, CCRL2, PROK2, IFITM2, IFITM1, OLR1, TNFSF13B, AQP9, BCL2A1, FFAR2, FPR1 are increased relative to a reference value and/or one or more of SPAG17, LRRC74B, PIFO, CFAP126, DNAH6, VWA3B, KIAA2012, OSBPL6, TBC1D8, HHLA2, ANKUB1, ECT2L, LRRC6, MORN5, AGBL2, CCDC65, LMNTD1, DNAL1, ANKFN1, WFDC6 are decreased relative to a reference value.

In another aspect, the disclosure provides a method of detecting a symptomatic viral versus an asymptomatic infection comprising measuring the level or one or more host genes selected from ARHGAP25, EVI2A, C3AR1, CCRL2, TNFAIP6, SELL, S100A12, SIGLEC14, EMP3, FCER1G, CYBB, LY96, SLAMF7, IFITM2, MX2, IFIT1, ISG15, IFIT2, IFIT3, RSAD2, APOBEC3A, DDX60L, OLR1, FPR3, CD163 DNAI1, DNAH6, SPAG6, NEK10, DTHD1, DNAH3, CFAP45, CFAP47, DNAJB13, LMNTD1, LRRC74B, CFAP157, AGBL2, KIAA2012, FBXO15, APOBEC4, TEX26, WDR78, DCDC5, NEK5, ADGB, CCDC81, CASC1, DNAH12, DNAH10, CFAP70, VWA3A, CFAP57, TTLL9, DNAH11, FABP6, RSPH1, EFHB, CDKL1, ANKUB1, C9orf135, DNAAF1, CFAP221, PIFO, CFAP206, WDR66, IQUB, PPIL6, RSPH10B2, RSPH10B2, SPAG17, DRC3, C4orf22, EFHC2, STOML3, LRRC34, TSPAN19, CCDC65, HHLA2, DNAH5, MORN5, CCDC146, MAP3K19, VWA3B, LRRC43, TSGA10, C11orf88, DLEC1, IFT172, EFHC1, CFAP54, and CETN2.

In some embodiments, the subject is classified as having a symptomatic viral infection versus an asymptomatic viral infection when one or more of ARHGAP25, EVI2A, C3AR1, CCRL2, TNFAIP6, SELL, S100A12, SIGLEC14, EMP3, FCER1G, CYBB, LY96, SLAMF7, IFITM2, MX2, IFIT1, ISG15, IFIT2, IFIT3, RSAD2, APOBEC3A, DDX60L, OLR1, FPR3, CD163 are increased relative to a reference value and/or one or more of DNAI1, DNAH6, SPAG6, NEK10, DTHD1, DNAH3, CFAP45, CFAP47, DNAJB13, LMNTD1, LRRC74B, CFAP157, AGBL2, KIAA2012, FBXO15, APOBEC4, TEX26, WDR78, DCDC5, NEK5, ADGB, CCDC81, CASC1, DNAH12, DNAH10, CFAP70, VWA3A, CFAP57, TTLL9, DNAH11, FABP6, RSPH1, EFHB, CDKL1, ANKUB1, C9orf135, DNAAF1, CFAP221, PIFO, CFAP206, WDR66, IQUB, PPIL6, RSPH10B2, RSPH10B2, SPAG17, DRC3, C4orf22, EFHC2, STOML3, LRRC34, TSPAN19, CCDC65, HHLA2, DNAH5, MORN5, CCDC146, MAP3K19, VWA3B, LRRC43, TSGA10, C11orf88, DLEC1, IFT172, EFHC1, CFAP54, CETN2 are decreased relative to a reference value.

In some embodiments, the subject is classified as having a symptomatic viral infection versus an asymptomatic viral infection when one or more of ISG15, FCER1G, S100A12, SELL, TNFAIP6, IFIT1, C3AR1, CD163 RSAD2, DDX60L, IFIT3 are increased relative to a reference value and/or one or more of SPAG17, LRRC74B, EFHB, DTHD1, FABP6 are decreased relative to a reference value.

Generally speaking, a host gene as disclosed herein may be classified as differentially expressed or aberrant when it has an increased or decreased amount relative to a reference value. Any suitable reference value known in the art may be used. For example, a suitable reference value may be the amount of a host gene in a biological sample obtained from a subject, or group of subjects, of the same species that has no clinically detectable symptom of a respiratory infection. In another example, a suitable reference value may be the amount of a host gene in a biological sample obtained from a subject, or group of subjects, of the same species that has no detectable respiratory infection pathology. In another example, a suitable reference value may be the background signal of the assay as determined by methods known in the art. In another example, a suitable reference value may be a measurement of the amount of a host gene in a reference sample obtained from the same subject. The reference sample comprises the same type of biological sample as the test sample, and may be obtained from a subject when the subject had no clinically detectable symptom of a respiratory infection. A skilled artisan will appreciate that it is not always possible or desirable to obtain a reference sample from a subject when the subject is otherwise healthy. For example, when monitoring the effectiveness of a therapy or progression of disease, a reference sample may be a sample obtained from a subject before therapy or at an earlier point in the disease. In such an example, a subject may have a risk of infection but may not have other symptoms of an infection or the subject may have one or more other symptom of a respiratory infection. In an additional example, a suitable reference sample may be a biological sample from an individual or group of individuals that has been shown not to have a respiratory infection. In an embodiment, the reference value may be a sample of the same type of biological sample obtained from one or more individuals that has not been administered therapy but has a respiratory infection.

In certain embodiments, to classify the amount of a host gene as increased in a biological sample, the amount of the host gene in the biological sample compared to the reference value is increased at least 1-fold. For example, the amount of the host gene in the sample compared to the reference value is increased at least 1-fold, at least 1.25-fold, at least 1.5-fold, at least 1.75-fold, at least 2-fold, at least 5-fold, at least 10-fold, at least 15-fold, at least 20-fold, at least 25-fold, at least 30-fold, at least 35-fold, at least 40-fold, at least 45-fold, at least 50-fold, at least 100-fold, at least 200-fold, at least 300-fold, at least 400-fold, at least 500-fold, at least 1000-fold, at least 5000-fold, or at least 10000-fold. In a specific embodiment, the amount of the host gene in the sample compared to the reference value is increased at least 10-fold.

In certain embodiments, to classify the amount of a host gene as decreased in a biological sample, the amount of the host gene in the biological sample compared to the reference value is decreased at least 1-fold. For example, the amount of the host gene in the sample compared to the reference value is decreased at least 1-fold, at least 1.25-fold, at least 1.5-fold, at least 1.75-fold, at least 2-fold, at least 5-fold, at least 10-fold, at least 15-fold, at least 20-fold, at least 25-fold, at least 30-fold, at least 35-fold, at least 40-fold, at least 45-fold, at least 50-fold, at least 100-fold, at least 200-fold, at least 300-fold, at least 400-fold, at least 500-fold, at least 1000-fold, at least 5000-fold, or at least 10000-fold.

In another embodiment, the increase or decrease in the amount of a host gene is measured using p-value. For instance, when using p-value, a RNA is identified as being differentially expressed between a biological sample and a reference value when the p-value is less than 0.1, preferably less than 0.05, more preferably less than 0.01, even more preferably less than 0.005, the most preferably less than 0.001.

(f) Treatment

In another aspect, the disclosure provides a method of treating a subject exhibiting symptoms of a respiratory infection, the method comprising: a) measuring the expression levels of one or more modulated host gene; optionally normalizing gene expression level for the technology used to make said measurement; b) comparing the levels of one or more host genes with a reference value; and, wherein if the normalized level of the at least one host gene is above or below the reference level the subject is classified for the presence or absence of a respiratory infection. The method may further comprise, testing the subject for the presence of at least one respiratory virus or bacteria.

In another aspect, the invention provides a method of treating a subject exhibiting symptoms of a respiratory infection, the method comprising: a) measuring the expression levels of one or more modulated host gene; optionally normalizing gene expression level for the technology used to make said measurement; b) comparing the levels of one or more host genes with a reference value; and, wherein if the normalized level of the at least one host gene is above or below the reference level, the subject receives an appropriate treatment regimen for a respiratory infection. The method may further comprise, testing the subject for the presence of at least one respiratory virus or bacteria.

In certain aspects, a therapeutically effective amount of a pharmaceutical composition may be administered to a subject. Administration is performed using standard effective techniques, including peripherally (i.e. not by administration into the central nervous system) or locally to the central nervous system. Peripheral administration includes but is not limited to oral, inhalation, intravenous, intraperitoneal, intra-articular, subcutaneous, pulmonary, transdermal, intramuscular, intranasal, buccal, sublingual, or suppository administration. Local administration, includes but is not limited to via a lumbar, intraventricular or intraparenchymal catheter or using a surgically implanted controlled release formulation. The route of administration may be dictated by the disease or condition to be treated.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents, and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners.

For therapeutic applications, a therapeutically effective amount of a composition of the invention is administered to a subject. A "therapeutically effective amount" is an amount of the therapeutic composition sufficient to produce a measurable response. Actual dosage levels of active ingredients in a therapeutic composition of the invention can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, age, the symptoms, and the physical condition and prior medical history of the subject being treated. As used herein, the terms "treat", "treatment" and "treating" refer to the reduction or amelioration of the severity, duration and/or progression of a disease or disorder or one or more symptoms thereof resulting from the administration of one or more therapies. Such terms refer to a reduction in the replication of a virus or bacteria, or a reduction in the spread of a virus or bacteria to other organs or tissues in a subject or to other subjects. Treatment may also include therapies for ARIs resulting from non-infectious illness, such as allergy treatment, asthma treatments, and the like.

The term "effective amount" refers to an amount of a therapeutic agent that is sufficient to exert a physiological effect in the subject. The term "responsivity" refers to a change in gene expression levels of genes in a subject in response to the subject being infected with a virus or bacteria or suffering from a non-infectious illness compared to the gene expression levels of the genes in a subject that is not infected with a virus, bacteria or suffering from a non-infectious illness or a control subject.

The term "appropriate treatment regimen" refers to the standard of care needed to treat a specific disease or disorder. Often such regimens require the act of administering to a subject a therapeutic agent(s) capable of producing a curative effect in a disease state. For example, a therapeutic agent for treating a subject having bacteremia is an antibiotic which include, but are not limited to, penicillins, cephalosporins, fluroquinolones, tetracyclines, macrolides, and aminoglycosides. A therapeutic agent for treating a subject having a viral respiratory infection includes, but is not limited to, oseltamivir, RNAi antivirals, inhaled ribavirin, monoclonal antibody respigam, zanamivir, and neuraminidase blocking agents. The invention contemplates the use of the methods of the invention to determine treatments with antivirals or antibiotics that are not yet available. Appropriate treatment regimes also include treatments for ARIs resulting from non-infectious illness, such as allergy treatments, including but not limited to, administration of antihistamines, decongestants, anticholinergic nasal sprays, leukotriene inhibitors, mast cell inhibitors, steroid nasal sprays, etc.; and asthma treatments, including, but not limited to, inhaled corticosteroids, leukotriene modifiers, long-acting beta agonists, combinations inhalers (e.g., fluticasone-salmeterol; budesonide-formoterol; mometasone-formoterol, etc.), theophylline, short-acting beta agonists, ipratropium, oral and intravenous corticosteroids, omalizumab, and the like.

Often such regimens require the act of administering to a subject a therapeutic agent(s) capable of producing reduction of symptoms associated with a disease state. Examples such therapeutic agents include, but are not limited to, NSAIDS, acetaminophen, anti-histamines, beta-agonists, anti-tussives or other medicaments that reduce the symptoms associated with the disease process.

In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

The frequency of dosing may be daily or once, twice, three times or more per week or per month, as needed as to effectively treat the symptoms. The timing of administration of the treatment relative to the disease itself and duration of treatment will be determined by the circumstances surrounding the case. Treatment could begin immediately, such as at the site of the injury as administered by emergency medical personnel. Treatment could begin in a hospital or clinic itself, or at a later time after discharge from the hospital or after being seen in an outpatient clinic. Duration of treatment could range from a single dose administered on a one-time basis to a life-long course of therapeutic treatments.

Typical dosage levels can be determined and optimized using standard clinical techniques and will be dependent on the mode of administration.

A subject may be a rodent, a human, a livestock animal, a companion animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas, and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the subject is a human.

Additionally, a subject in need thereof may be a subject suffering from, suspected of suffering from or at risk of a respiratory infection.

(g) Kits

In still other aspects, the present invention provides articles of manufacture and kits containing materials useful for treating the conditions described herein. The article of manufacture may include a container of a composition as described herein with a label. Suitable containers include, for example, bottles, vials, and test tubes. The containers may be formed from a variety of materials such as glass or plastic. The container holds a composition comprising reagents to detect a respiratory illness in a patient and instructions for the use thereof, wherein the instructions comprise: analyzing one or more host genes to determine a level of at least one modulated host gene; comparing the level of the at least one modulated host gene with a predetermined reference level; and, wherein if the level of the at least one modulated host gene is above or below the respective reference level, the patient is determined to have a respiratory infection.

Definitions

When introducing elements of the present disclosure or the preferred aspects(s) thereof, the articles "a," "an," "the," and "said" are intended to mean that there are one or more of the elements. The terms "comprising," "including," and "having" are intended to be inclusive and mean that there may be additional elements other than the listed elements.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The terms "antimicrobial" or "antimicrobial agent" mean any compound with bactericidal or bacteriostatic activity which may be used for the treatment of bacterial infection. Non-limiting examples include antibiotics.

"Measuring" or "measurement," or alternatively "detecting" or "detection," means determining the presence, absence, quantity or amount (which can be an effective amount) of either a given substance within a clinical or subject-derived sample, including the derivation of qualitative or quantitative concentration levels of such substances, or otherwise determining the values or categorization of a subject's clinical parameters.

The terms "patient," "subject," "individual," and the like are used interchangeably herein, and refer to any animal or cells thereof whether in vitro or in situ, amenable to the methods described herein. In certain non-limiting embodiments, the patient, subject or individual is a human.

"Platform" or "technology" as used herein refers to an apparatus (e.g., instrument and associated parts, computer, computer-readable media comprising one or more databases as taught herein, reagents, etc.) that may be used to measure a signature, e.g., gene expression levels, in accordance with the present disclosure. Examples of platforms include, but are not limited to, an array platform, a thermal cycler platform (e.g., multiplexed and/or real-time PCR platform), a nucleic acid sequencing platform, a hybridization and multi-signal coded (e.g., fluorescence) detector platform, etc., a nucleic acid mass spectrometry platform, a magnetic resonance platform, and combinations thereof.

In some embodiments, the platform is configured to measure gene expression levels semi-quantitatively, that is, rather than measuring in discrete or absolute expression, the expression levels are measured as an estimate and/or relative to each other or a specified marker or markers (e.g., expression of another, "standard" or "reference," gene).

In some embodiments, semi-quantitative measuring includes "real-time PCR" by performing PCR cycles until a signal indicating the specified mRNA is detected, and using the number of PCR cycles needed until detection to provide the estimated or relative expression levels of the genes within the signature.

A real-time PCR platform includes, for example, a TaqMan® Low Density Array (TLDA), in which samples undergo multiplexed reverse transcription, followed by real-time PCR on an array card with a collection of wells in which real-time PCR is performed. A real-time PCR platform also includes, for example, a Biocartis Idylla™ sample-to-result technology, in which cells are lysed, DNA/RNA extracted and real-time PCR is performed and results detected. A real-time PCR platform also includes, for example, CyTOF analysis: CyTOF (Fludigm) is a recently introduced mass-cytometer capable of detecting up to 40 markers conjugated to heavy metals simultaneously on single cells.

A magnetic resonance platform includes, for example, T2 Biosystems® T2 Magnetic Resonance (T2MR®) technology, in which molecular targets may be identified in biological samples without the need for purification.

The terms "array," "microarray" and "micro array" are interchangeable and refer to an arrangement of a collection of nucleotide sequences presented on a substrate. Any type of array can be utilized in the methods provided herein. For example, arrays can be on a solid substrate (a solid phase array), such as a glass slide, or on a semi-solid substrate, such as nitrocellulose membrane. Arrays can also be presented on beads, i.e., a bead array. These beads are typically microscopic and may be made of, e.g., polystyrene. The array can also be presented on nanoparticles, which may be made of, e.g., particularly gold, but also silver, palladium, or platinum. See, e.g., Nanosphere Verigene® System, which uses gold nanoparticle probe technology. Magnetic nanoparticles may also be used. Other examples include nuclear magnetic resonance microcoils. The nucleotide sequences can be DNA, RNA, or any permutations thereof (e.g., nucleotide analogues, such as locked nucleic acids (LNAs), and the like). In some embodiments, the nucleotide sequences span exon/intron boundaries to detect gene expression of spliced or mature RNA species rather than genomic DNA. The nucleotide sequences can also be partial sequences from a gene, primers, whole gene sequences, non-coding sequences, coding sequences, published sequences, known sequences, or novel sequences. The arrays may additionally comprise other compounds, such as antibodies, peptides, proteins, tissues, cells, chemicals, carbohydrates, and the like that specifically bind proteins or metabolites.

An array platform includes, for example, the TaqMan® Low Density Array (TLDA) mentioned above, and an Affymetrix® microarray platform.

A hybridization and multi-signal coded detector platform includes, for example, NanoString nCounter® technology, in which hybridization of a color-coded barcode attached to a target-specific probe (e.g., corresponding to a gene expression transcript of interest) is detected; and Luminex® xMAP® technology, in which microsphere beads are color coded and coated with a target-specific (e.g., gene expression transcript) probe for detection; and Illumina® BeadArray, in which microbeads are assembled onto fiber optic bundles or planar silica slides and coated with a target-specific (e.g., gene expression transcript) probe for detection.

A nucleic acid mass spectrometry platform includes, for example, the *Ibis* Biosciences Plex-ID® Detector, in which DNA mass spectrometry is used to detect amplified DNA using mass profiles.

A thermal cycler platform includes, for example, the FilmArray® multiplex PCR system, which extract and purifies nucleic acids from an unprocessed sample and performs nested multiplex PCR; the RainDrop Digital PCR System, which is a droplet-based PCR platform using microfluidic chips; and the GenMark eSensor or ePlex systems.

The term "genetic material" refers to a material used to store genetic information in the nuclei or mitochondria of an organism's cells. Examples of genetic material include, but are not limited to, double-stranded and single-stranded DNA, cDNA, RNA, and mRNA.

The term "plurality of nucleic acid oligomers" refers to two or more nucleic acid oligomers, which can be DNA or RNA.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

As various changes could be made in the above-described materials and methods without departing from the scope of the invention, it is intended that all matter contained in the above description and in the examples given below, shall be interpreted as illustrative and not in a limiting sense.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1. Nasal Samples to Measure Host Gene Expression for the Diagnosis of Viral Respiratory Infection Introduction In recent years, there has been great interest in the potential use of host transcriptomic analysis to augment the diagnosis of infectious diseases (1, 2). One reason is the potential for discrimination between broad classes of infection, such as those caused by viruses vs bacteria (3-5). This capability would have enormous therapeutic utility, particularly if it could be employed in a rapid test format that would be practical to use at or near the point of care. Most studies to date have been directed at acute respiratory infections (6)

(7-16) (17), non-specific febrile illnesses (4, 18, 19), but other applications have included dengue (20), other tropical hemorrhagic fevers (21, 22), and tuberculosis (23, 24).

Most studies to date have analyzed the human transcriptomic response in peripheral blood leukocytes (ref's). However, there may be advantages in analyzing host response at the site of infection, for example the nose or nasopharynx in acute respiratory infection. One practical advantage is the possibility of developing an integrated diagnostic test that simultaneously detects the nucleic acid of pathogens while also analyzing host gene expression (25). In the case of respiratory viral infections, a fundamental difference relevant to the nasal and blood transcriptomic responses is the different cellular compositions of the two locations, with mainly epithelial cells in the nose versus leukocytes in the blood. An additional difference is that nasal cells may be directly infected by pathogens, whereas leukocytes in the blood are primarily manifesting an indirect response to the presence of an infection at a location outside the bloodstream. Finally, the microbial environment in the nose is more complex than that of the blood, including a rich resident microbiota that may also affect the host transcriptomic response.

To evaluate the potential for using nasal cells for the diagnostic evaluation of host response, we undertook a direct comparison of the host transcriptomic responses occurring in the nose and blood of young children experiencing symptomatic infection with two common respiratory viruses, non-respiratory syncytial virus (nRSV) and respiratory syncytial virus (RSV). We compared responses in children with symptomatic infection to those of asymptomatic children, including some who were positive by RT-PCR for (nRSV) and some who were negative for respiratory viruses.

Results
Subjects and Samples

Forty-six subjects were enrolled in the study between March 2016 and January 2017, including 17 with acute respiratory infection (9 with nRSV, 7 with RSV, 1 with parainfluenza virus), and 29 ambulatory control subjects. Molecular testing of the nasal samples from the 29 control subjects revealed 5 with nRSV without other viruses. These subjects were considered to have asRV. No other viruses were detected in any of the remaining control subjects. In accordance with pre-study plans to evaluate approximately 6 subjects in each category, RNA was selected for analysis from 6 of the subjects with RSV (all subjects with RSV were symptomatic), all 9 subjects with symptomatic nRSV, the 5 control subjects with nRSV (subsequently referred to as asRV, and 6 control subjects who were negative for respiratory viruses (subsequently referred to as negative controls). Two of the subjects with RSV did not have blood RNA samples available. Thus, in all, we analyzed RNA from 26 nasal swabs and 24 blood samples from 26 subjects. Demographic characteristics are shown in Table 1. The median age for all subject was 14.5 months. Asymptomatic subjects were older than symptomatic subjects (median ages of 26 months and 8 months). Male subjects were overrepresented among the negative controls. Mean total RNA recovery was 522 ng (range 77-2413) from the nasal swabs and 4,607 ng (range 230-12,346), from the blood samples, measured using the Agilent Bioanalyzer.

RNA Characteristics and Quality

Results of analysis of RNA quality are shown in FIG. 1. Analysis of 28,476 transcript clusters (TCs) by principal component analysis (PCA) revealed clear separation between nasal and blood samples (FIG. 1A). As expected, RNAs from nasal specimens were moderately degraded with RNA integrity numbers (RIN) ranging from 2.6 to 7.0, while RNAs from blood were of high quality with RIN scores of approximately 9 or higher for most samples (FIG. 1B). Nonetheless, all microarrays for nasal and blood RNA samples passed vendor-recommended key quality control parameters such as positive versus negative control AUC >0.8. The raw signal before normalization was very robust, with a signal-to-noise ratio (SNR)>1.5 for all samples in the study. There was a positive correlation between RIN and SNR for nasal ($r=0.69$, $P<0.0001$) but not for blood samples ($r=0.32$, $P=0.13$) (FIG. 1C). The percent of genes detected in nasal and blood samples was comparable, with an average of 76.3% (range 67.6% to 79.4%) for nasal samples and 79.6% (range 76.5% to 83.1%) for blood samples (FIG. 1D). Of note, RIN values did not correspond well to the percent of detected genes.

Cell Marker Gene Expression

Figure 2:
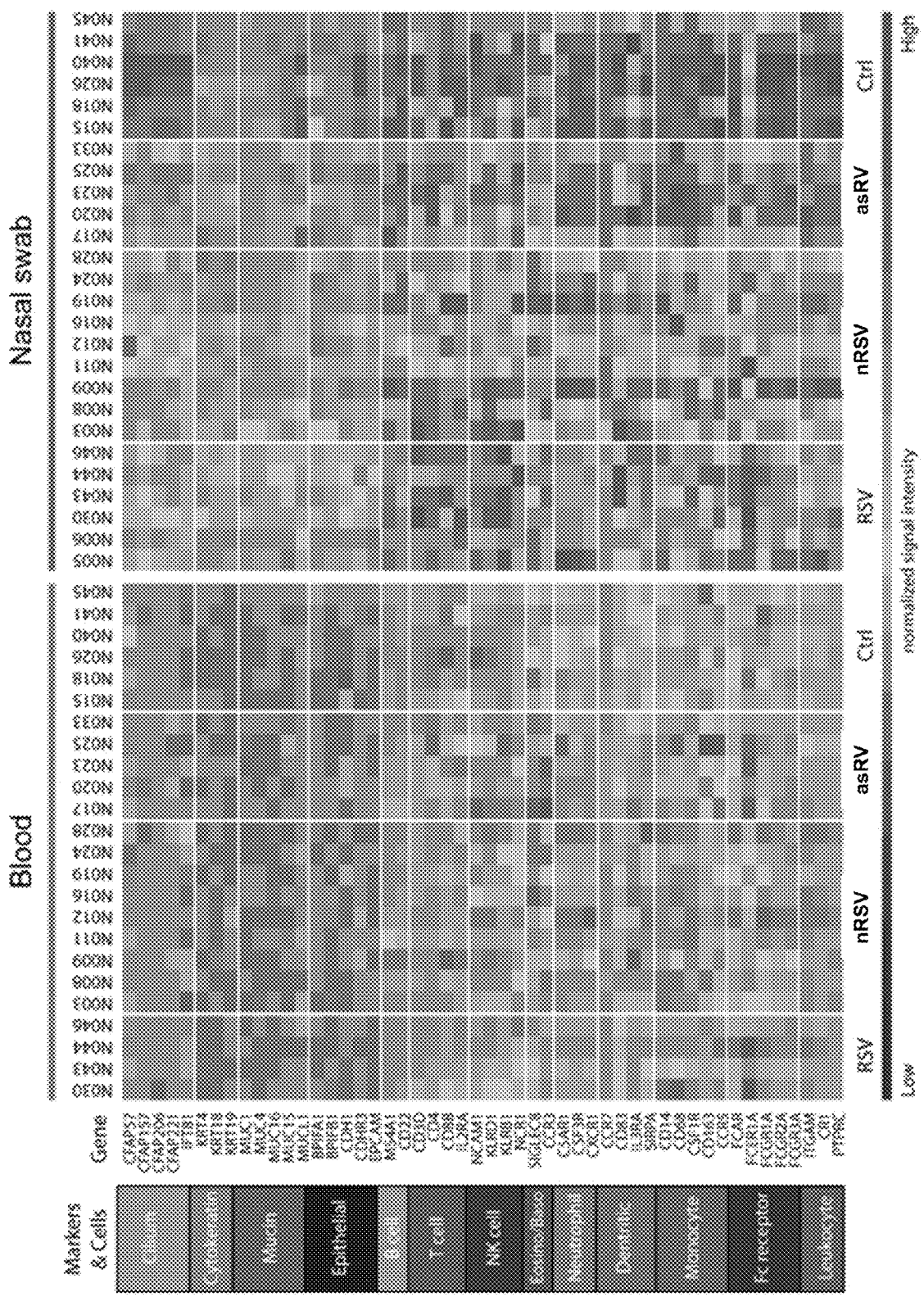
FIG. 2 depicts a heatmap for the expression profiles of 50 putative cell marker genes in both blood and nasal samples. Each column is for a sample with subject ID labeled at the top, and each row represents a marker gene whose expression value was normalized across these 50 genes by the z-score method.

To gain additional understanding of the differences in cellular composition between nasal and blood samples, we analyzed the two sample types with regard to the expression of 50 genes that encode putative epithelial and leukocyte markers (FIG. 2). The epithelial cell markers included cilia, mucin, cytokeratin, and several well-defined other epithelial markers such as BPIFA1, BPIFB1, CDH, CDHR3 and EPCAM. Leukocyte markers included all major leukocyte types, including B lymphocytes, T lymphocytes, NK cells, neutrophils, dendritic cells, monocytes and selected other general leukocyte markers. (Leukocyte markers were selected based upon cell marker information from Biolegend.com (Biolegend Inc, San Diego, CA). As expected, the overall expression of epithelial genes was higher in nasal than in blood samples, and the expression of leukocyte genes was higher in blood than in nasal samples.

Figure 3:
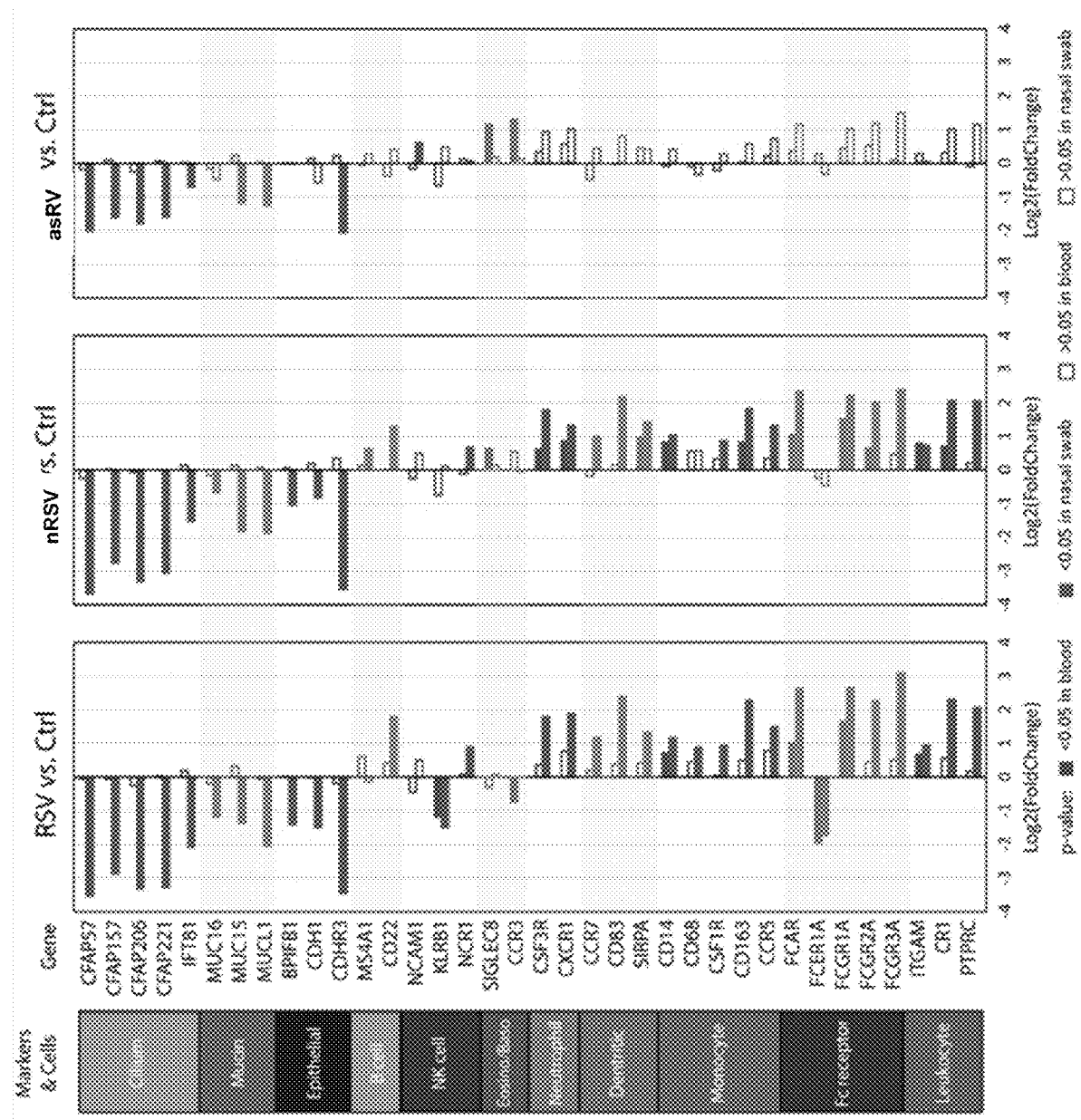
FIG. 3 shows the fold-change comparison between blood and nasal samples for 36 putative cell marker genes that were significantly different in at least 1 of the comparisons: respiratory syncytial virus infection (RSV) vs. Control (Ctrl), Symptomatic Non-Respiratory syncytial virus infection (nRSV) vs. Control (Ctrl), and Asymptomatic Rhinovirus (asRV) vs. Control (Ctrl).
Figure 9A:
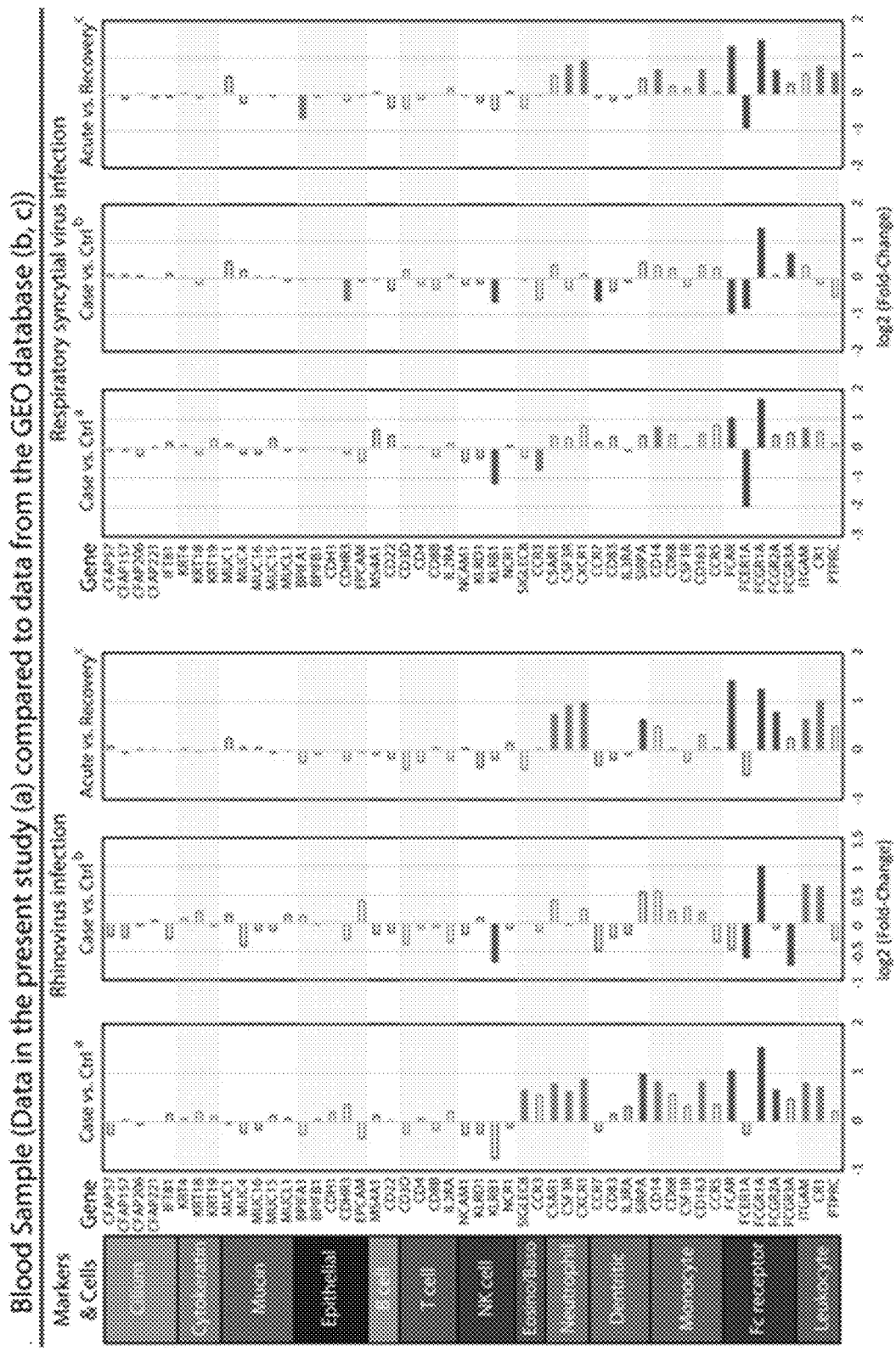
FIG. 9A and FIG. 9B depict differential expression of 50 putative cell marker genes in subjects with nRSV or respiratory syncytial virus infection. The overall consistent expression patterns of these marker genes are seen across different studies: (a) the present study, (b) GSE38900 (Ramilo 2013), (c) GSE97743 (Do 2018), (d) GSE11348 (Prout 2008), and (e) GSE41374 (Ramilo 2016, unpublished).
Figure 9B:
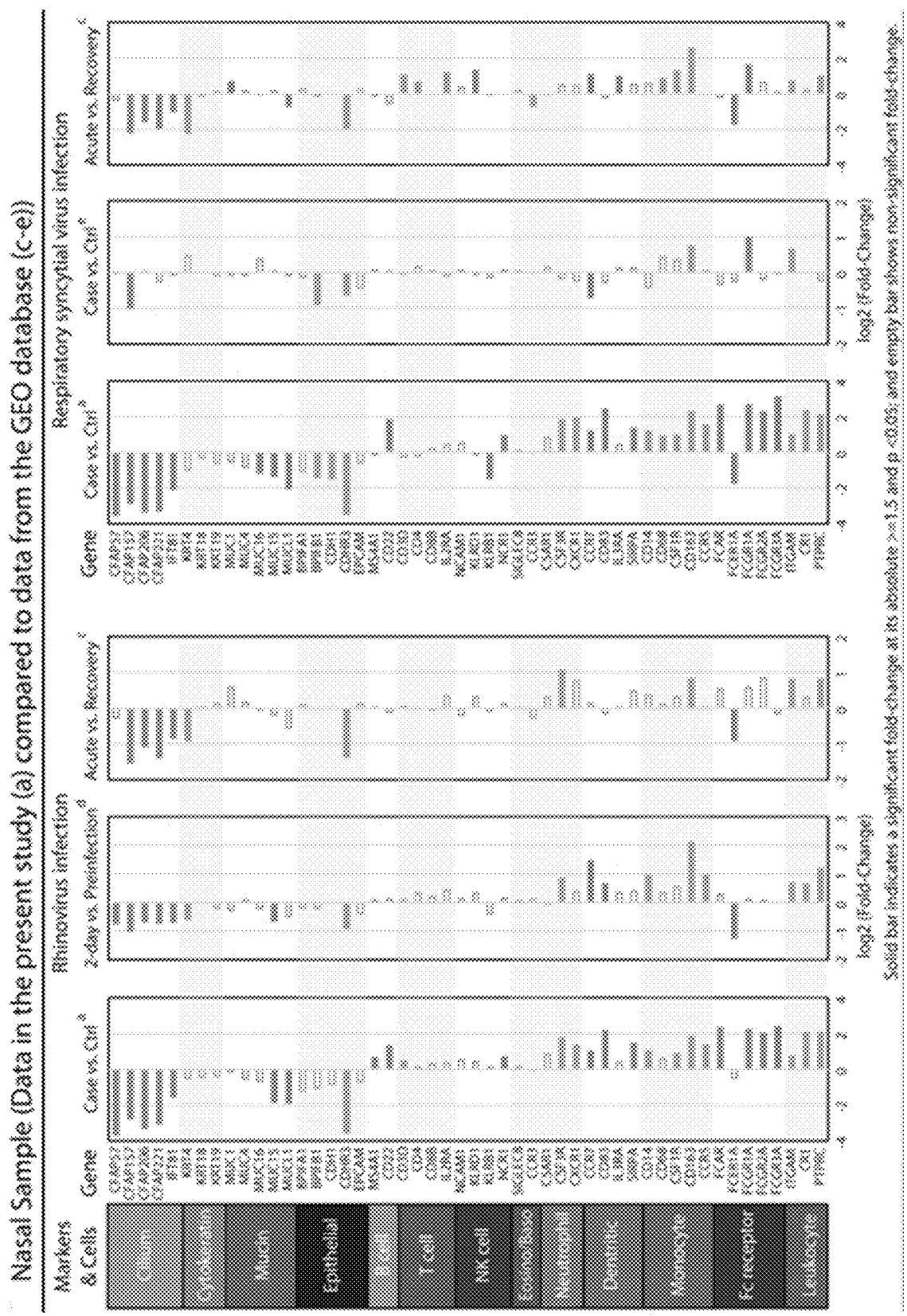

We also carried out between-group comparisons of these 50 genes in nasal and blood samples from subjects with RSV, nRSV, and asRV, each compared to negative controls. Of the 50 genes, 36 were significantly different in at least 1 of the comparisons. Results for those 36 genes are shown in FIG. 3. In virus-infected subjects, expression of genes encoding epithelial markers was broadly decreased in nasal samples. Also in the virus-infected subjects, expression of genes encoding leukocyte markers was generally increased in infected subjects compared to negative controls, more so in nasal samples than blood samples, consistent with leukocyte recruitment into the nasal mucosa of infected subjects. We extended the cell marker expression analysis to several public datasets at the GEO database to ensure the consistency of our findings with those from prior studies (11, 26, 27) (and GEO41374, unpublished). As shown in FIG. 9, overall expression patterns were consistent with previous studies of respiratory syncytial virus and symptomatic nRSV in both blood and nasal samples.

Deconvolution of Signal from Nasal Samples

Figure 4A:
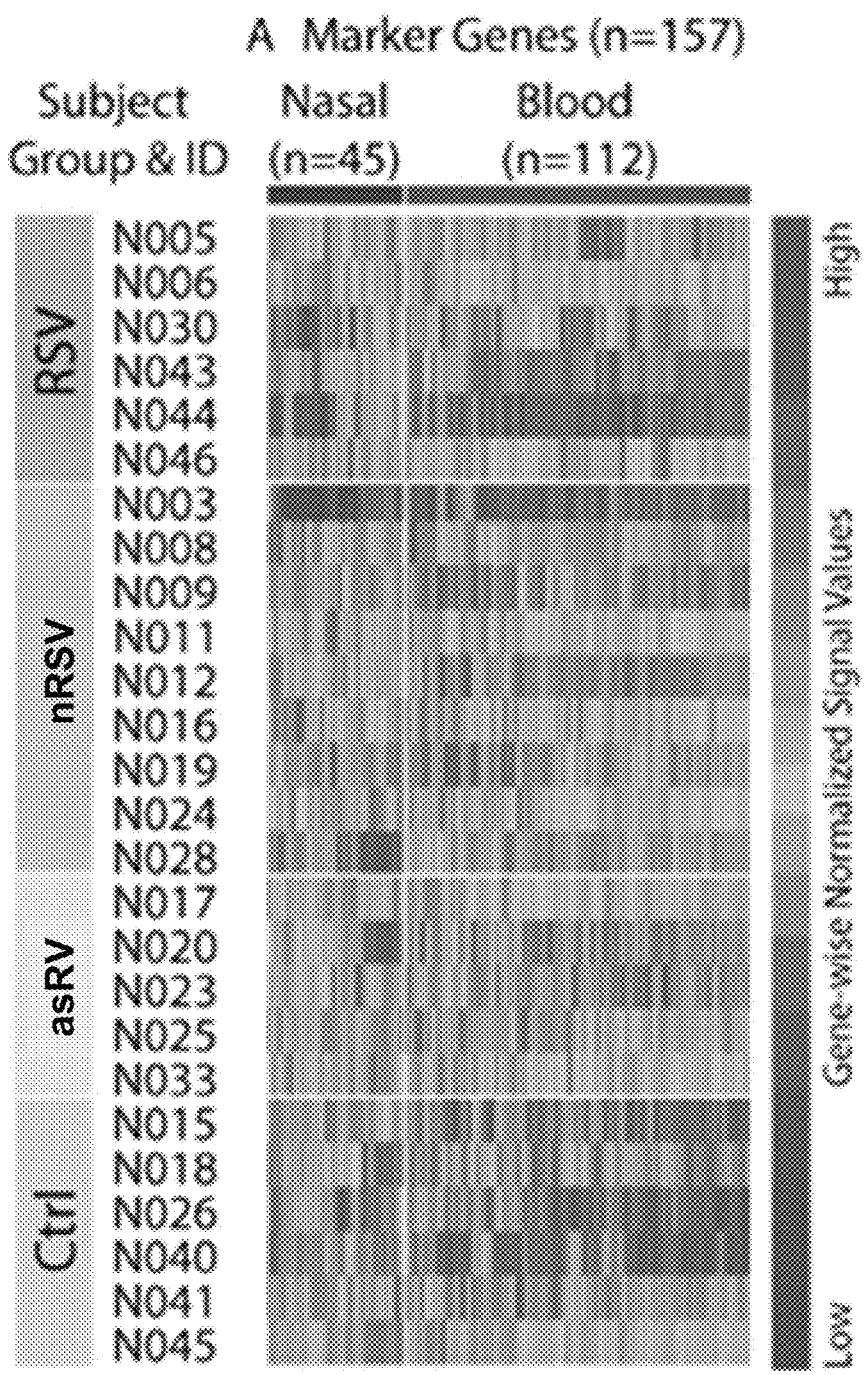
FIG. 4A and FIG. 4B depict cell type-specific signal deconvolution for nasal gene data set.
Figure 4B:
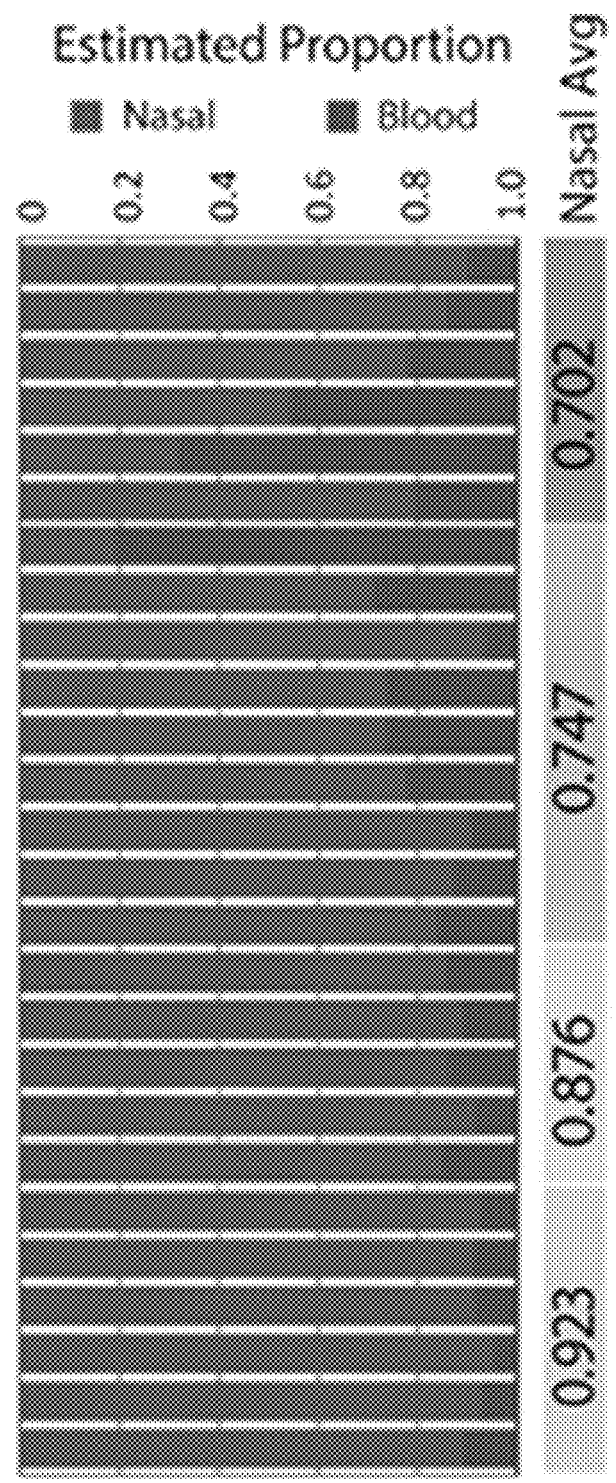
Figure 5A:
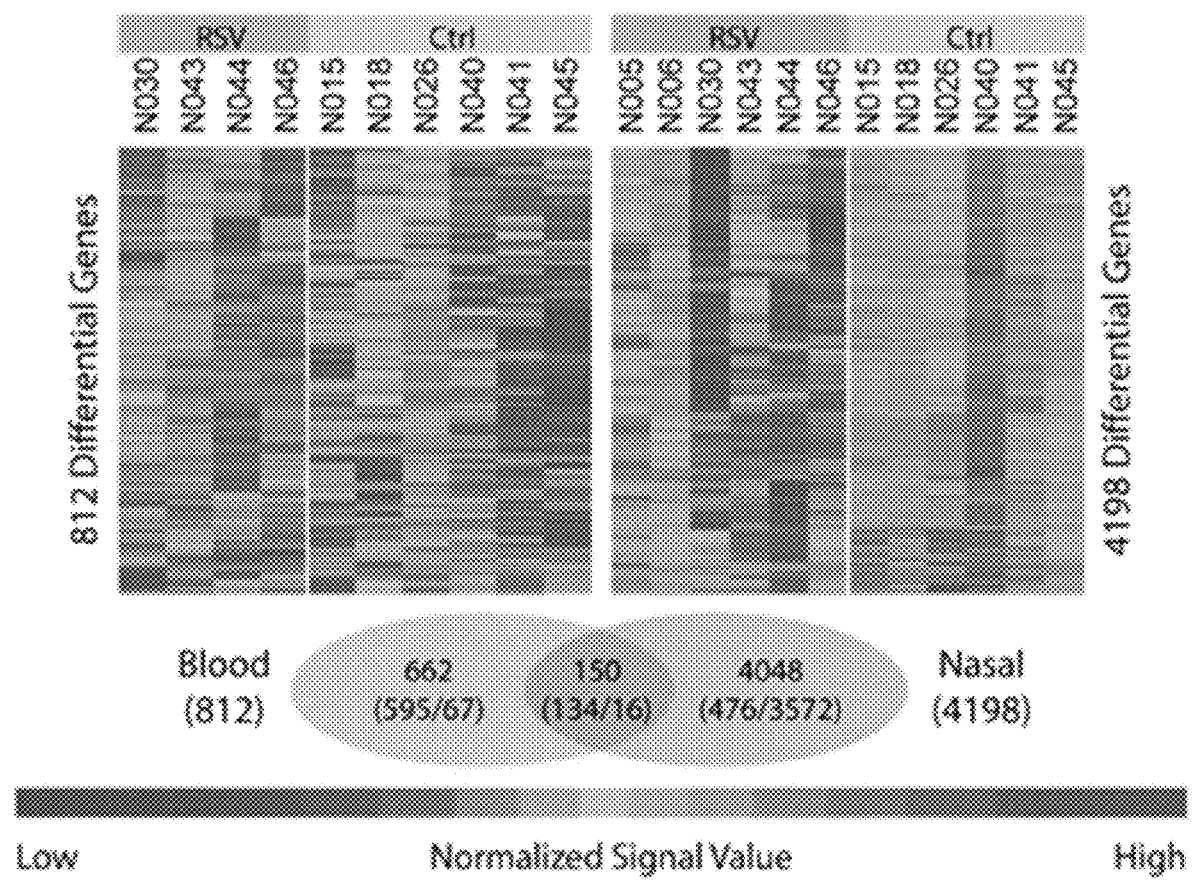
FIG. 5A, FIG. 5B, FIG. 5C and FIG. 5D depict heat maps and Venn diagrams for differentially expressed genes in comparisons between virus-infected groups and negative controls.
Figure 5B:
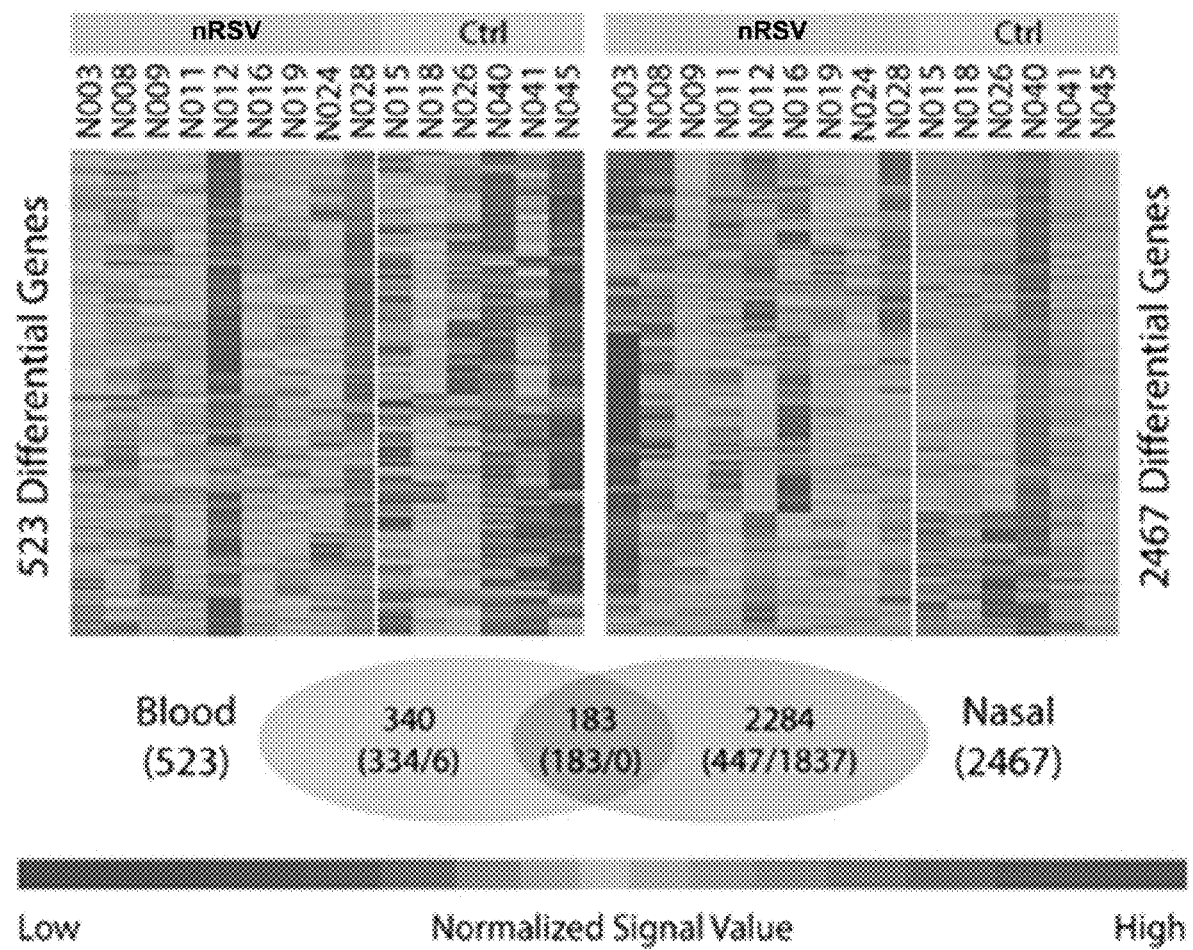
Figure 5C:
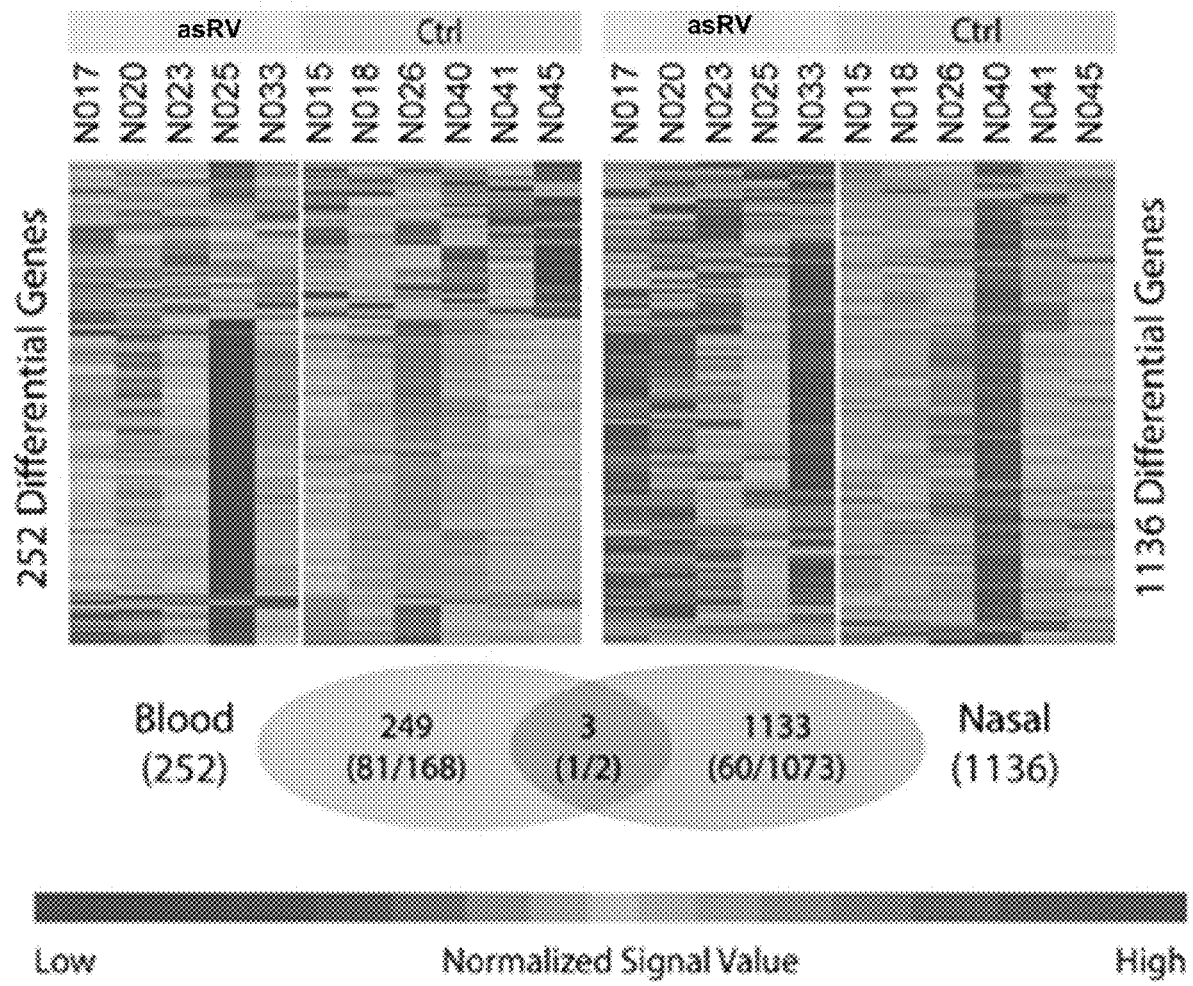
Figure 5D:
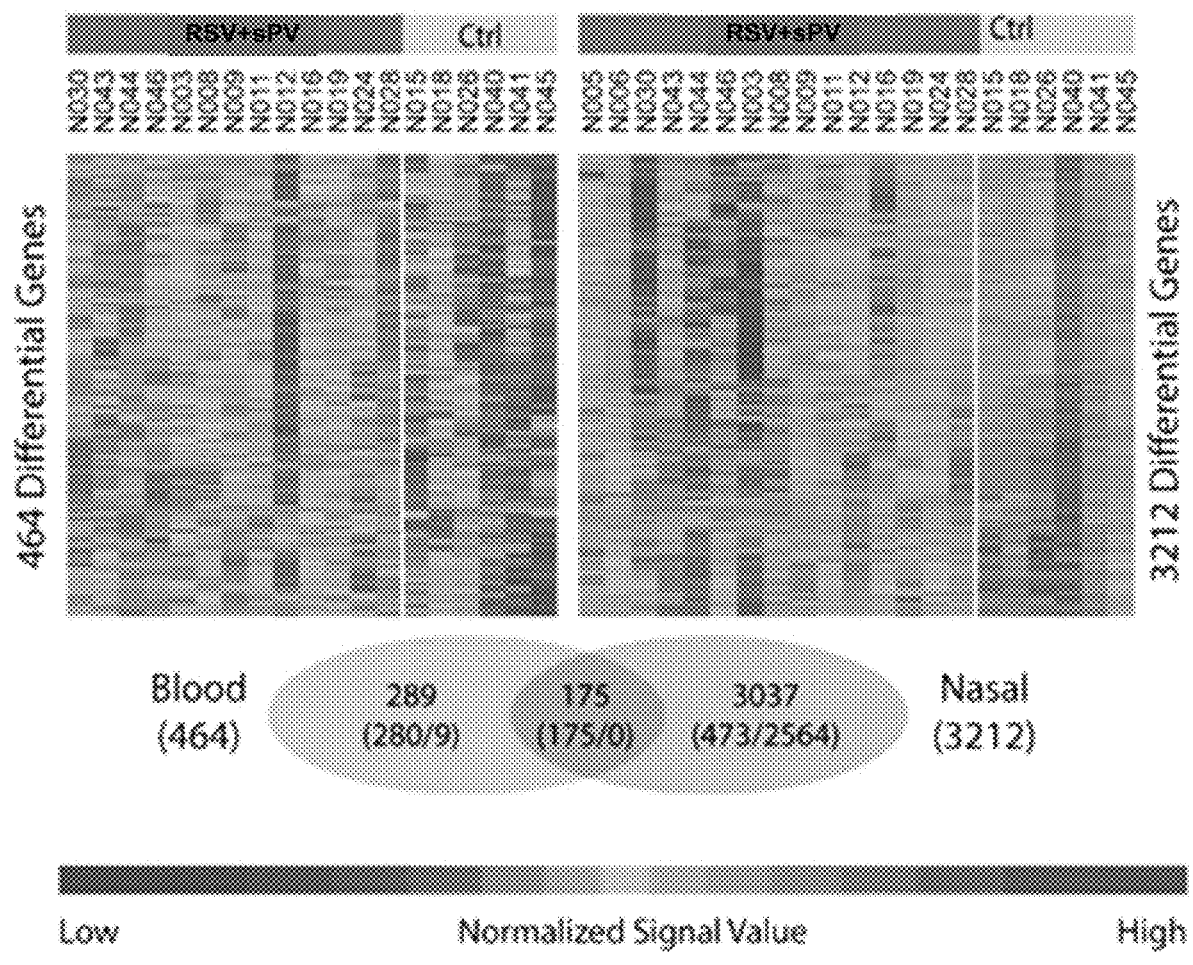
Figure 10B:
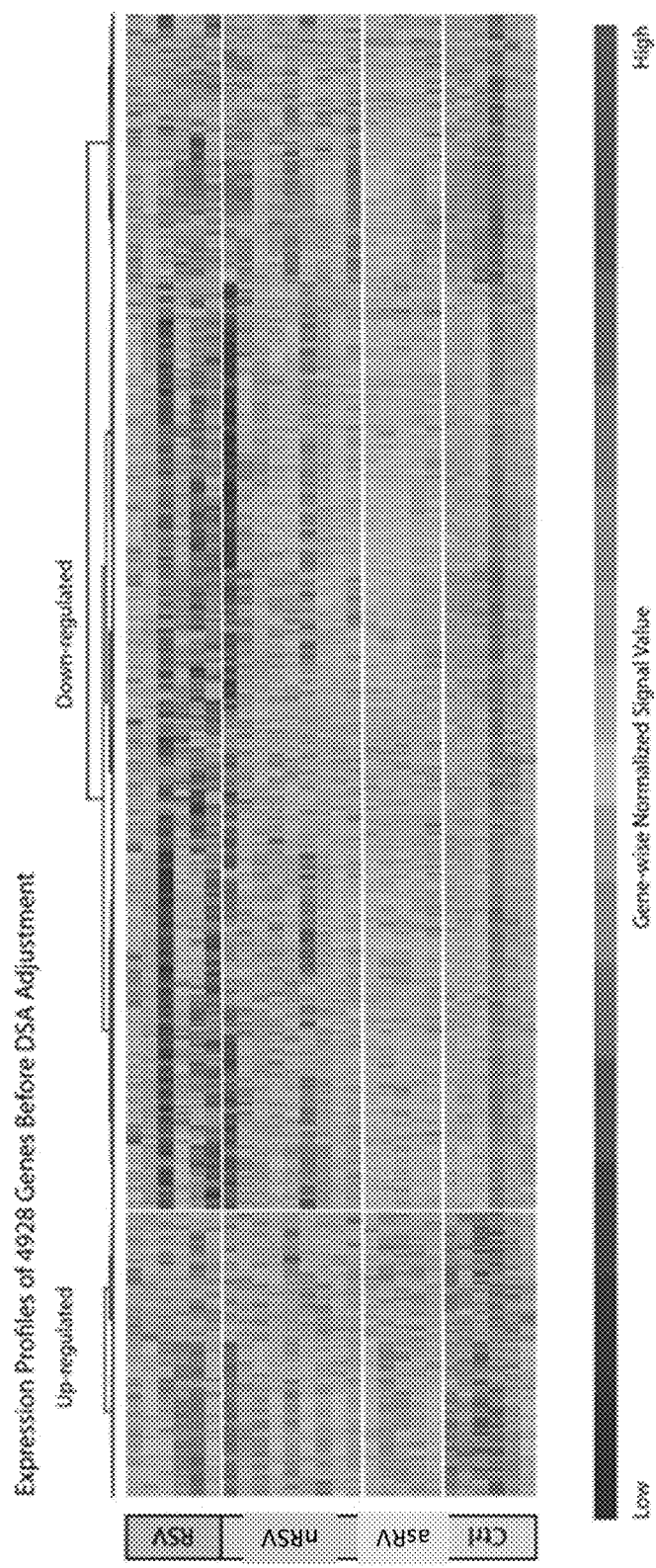
Figure 10C:
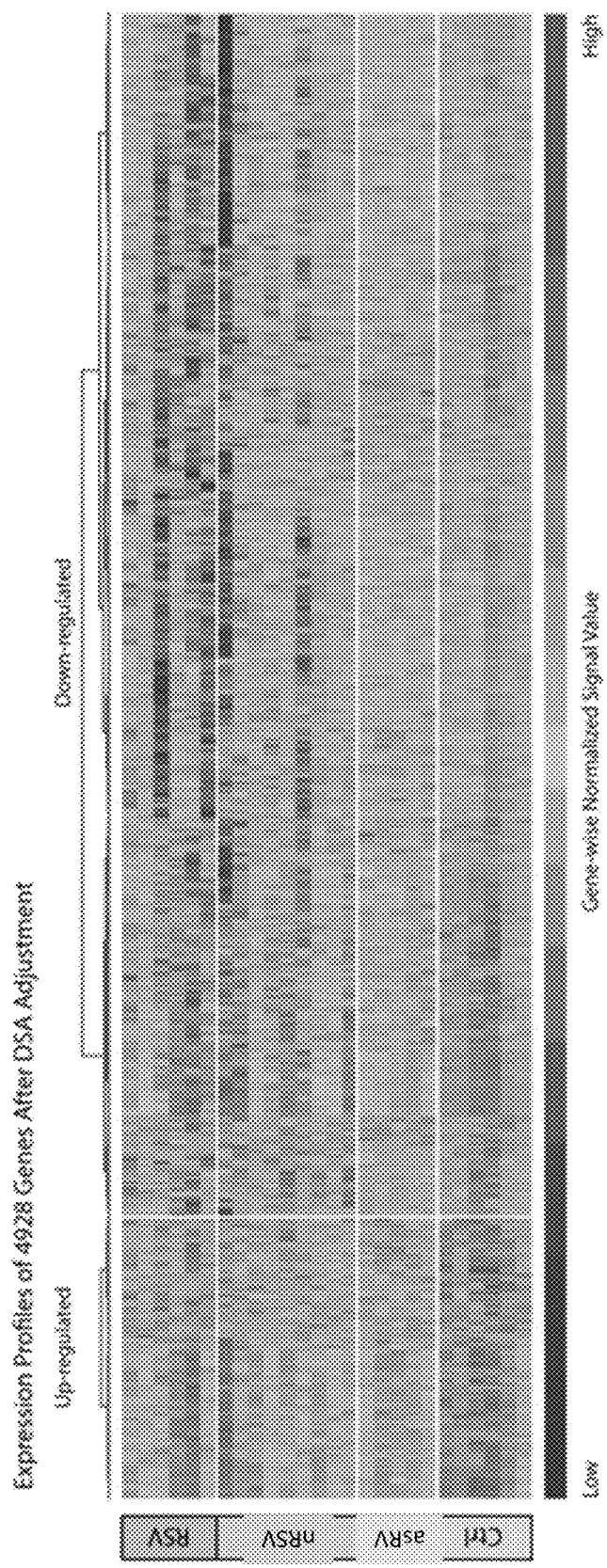

In order to further understand the implications of the mixed cell population in the nasal samples, we "deconvoluted" each nasal sample data set into epithelial and hematopoietic components by using the digital sorting algorithm (DSA) described by Zhong et al. (28). Using 157 selected cell-type-specific marker genes from the TIGER database we estimated the proportion of hematopoietic cells in the 26 nasal specimens (FIG. 4). The hematopoietic component showed considerable variability between subjects, but was generally larger in samples from symptomatic subjects (mean 27.1%, range 6.2 to 80.7%) compared to asymptomatic subjects (mean 9.9%, range 4.8-15.3%). It was also higher in subjects with RSV (mean 29.8%, range 9.6-67.9%)

compared to those with nRSV (mean 25.3%, range 6.2-80.7) and in subjects with asRV (mean 12.4%, range 8.1-15.3%) compared to negative controls (mean 7.7%, range 4.8-10.8%). We also compared the effect of deconvolution on the analysis of gene expression in the four subject groups (FIG. 10). Although application of DSA changed the patterns of gene expression, the distinctions among the four groups were similar in magnitude with and without application of DSA.

Differentially Expressed Genes

We examined blood and nasal gene expression by carrying out between-group comparisons (separately for nasal and blood samples) of mean normalized signal intensity for 19,837 protein-coding transcript clusters (19,655 genes) for each of the three subject groups with viral infection (RSV, nRSV, and asRV) versus the negative controls. We also carried out between-group comparisons for subjects with symptomatic versus asRV and for subjects with nRSV versus symptomatic RSV. Finally, we also compared subjects with symptomatic infection versus those with asymptomatic RV and versus the negative controls. For initial analysis, comparisons were based on genes with mean normalized signal intensity fold-change of at least 1.5 and uncorrected P value <0.05. The numbers of genes with differential gene expression according to these criteria and corresponding heat maps are shown in FIG. 5 and Table 3 for the comparisons of the virus-infected groups with negative controls. In these comparisons, the number of genes with differential expression was highest for RSV, followed by nRSV, with a smaller but still substantial number in asymptomatic RV. The nasal samples had more differentially expressed genes than did the blood samples. Of note, in the blood, most differentially expressed genes were increased while in nasal samples most differentially expressed genes were decreased. Overlap of genes with increased expression in nasal and blood samples was 11.1% for RSV and 19.0% for symptomatic RV; for genes with decreased expression, overlap was 0.7% for RSV and 0.2% for nRSV.

Biological Process and Pathway Analysis

Figure 6A:
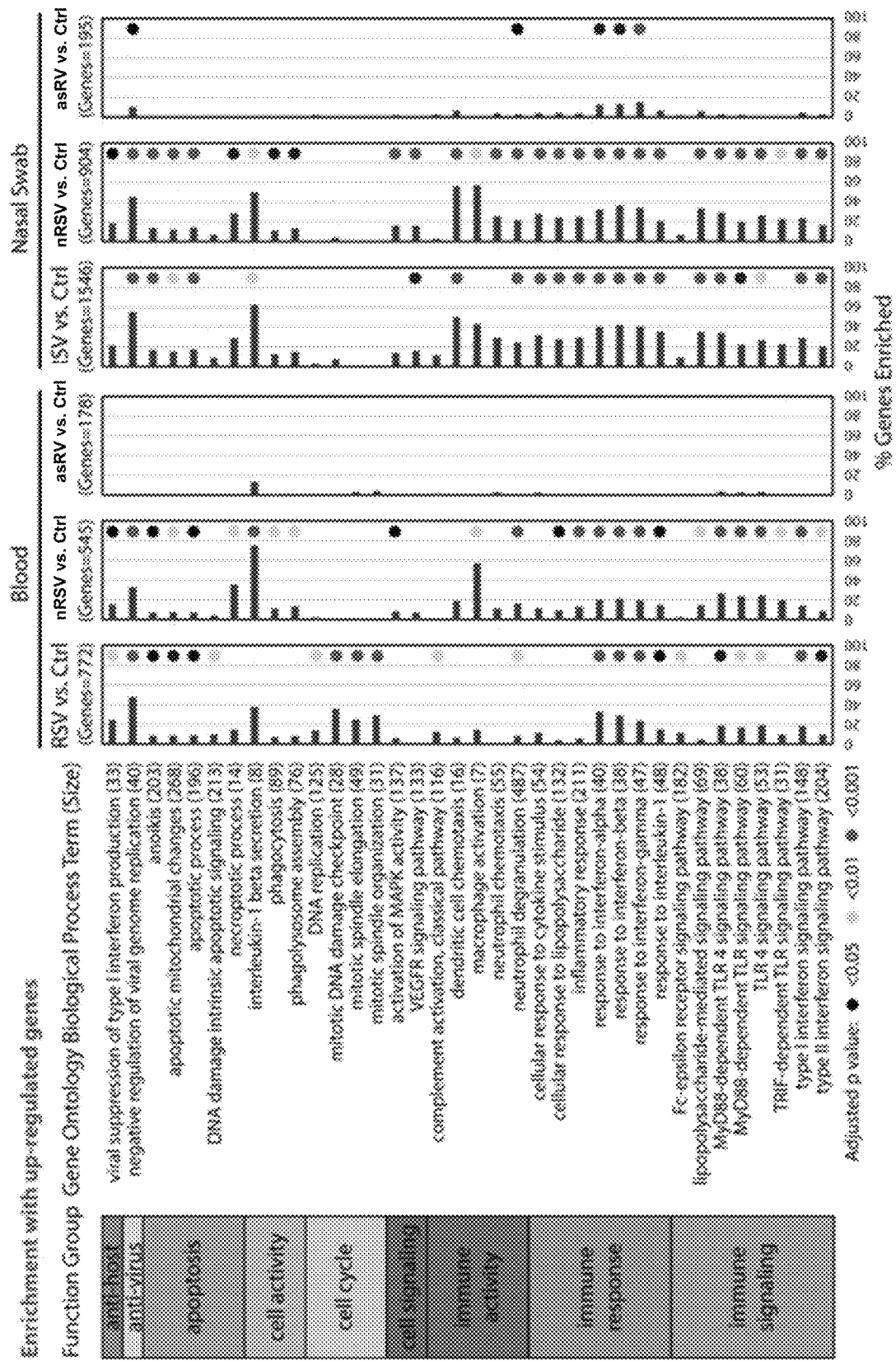
FIG. 6A and FIG. 6B depict gene ontology (GO) enrichment of genes with increased (FIG. 6A) and decreased expression (FIG. 6B).
Figure 6B:
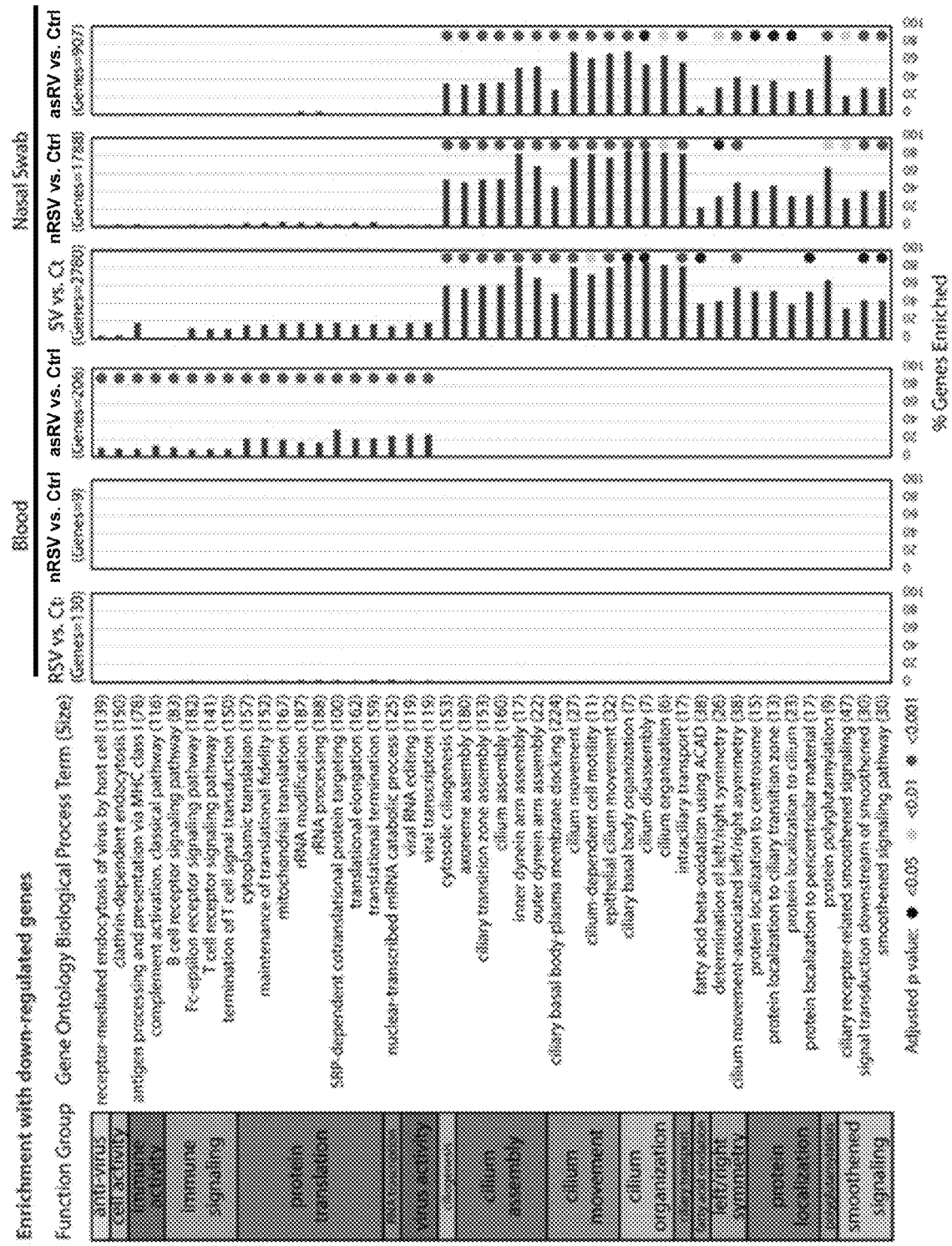
Figure 7A:
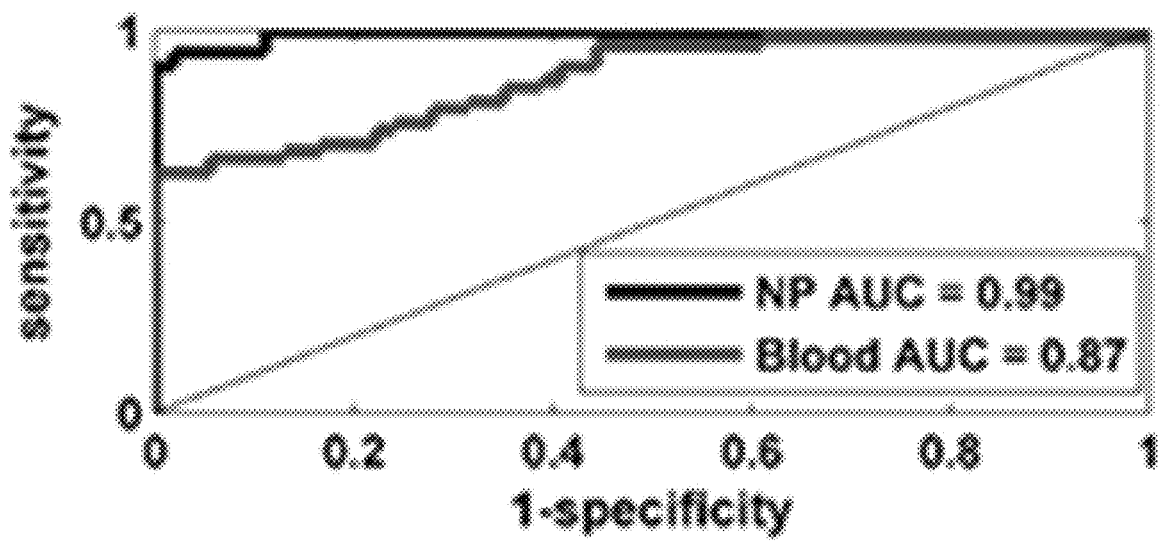
FIG. 7A, FIG. 7B, FIG. 7C, FIG. 7D, FIG. 7E and FIG. 7G show nested cross-validated (CV) ROC curves with AUC for the discriminatory genes based on a modified supervised principal components analysis. Panel (FIG. 7A) nRSV vs Ctrl, (FIG. 7B) nRSV vs asRV, (FIG. 7C) RSV vs Ctrl, (FIG. 7D) nRSV vs RSV, (FIG. 7E) asRV vs Ctrl, (FIG. 7F) RSV+nRSV vs Ctrl, (FIG. 7G) RSV+nRSV vs asRV. Genes were selected based on their univariate AUC and fold-change (estimated via Hodges-Lehmann median of all pairwise shifts in log expression), and then combined via their first principal component loadings. Thresholds for univariate AUC and fold-change were selected in the inner loop of nested CV, while the outer loop was used to estimate the ROC and AUC of the adaptive procedure. Note that the nested CV AUC in this figure is generally a bit lower than that reported in Table 2 since construction of full ROC curves requires the implicit comparison of subjects trained on different cross-validated training samples (unstratified AUC), whereas the nested CV AUC in Table 2 only compared pairs of subjects whose classification scores were built using the same training data (stratified AUC, which is preferable).
Figure 7B:
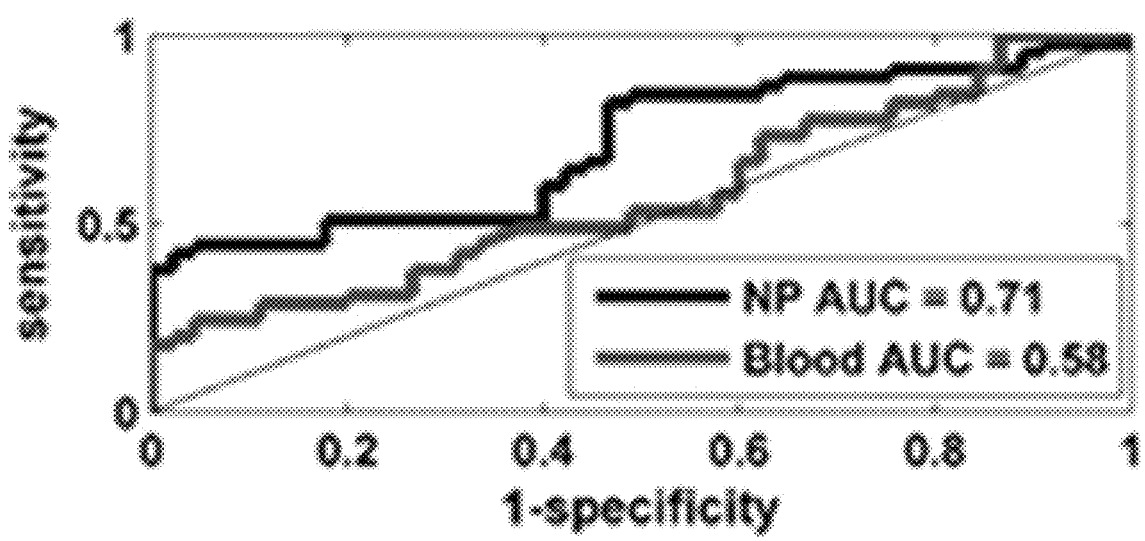
Figure 7C:
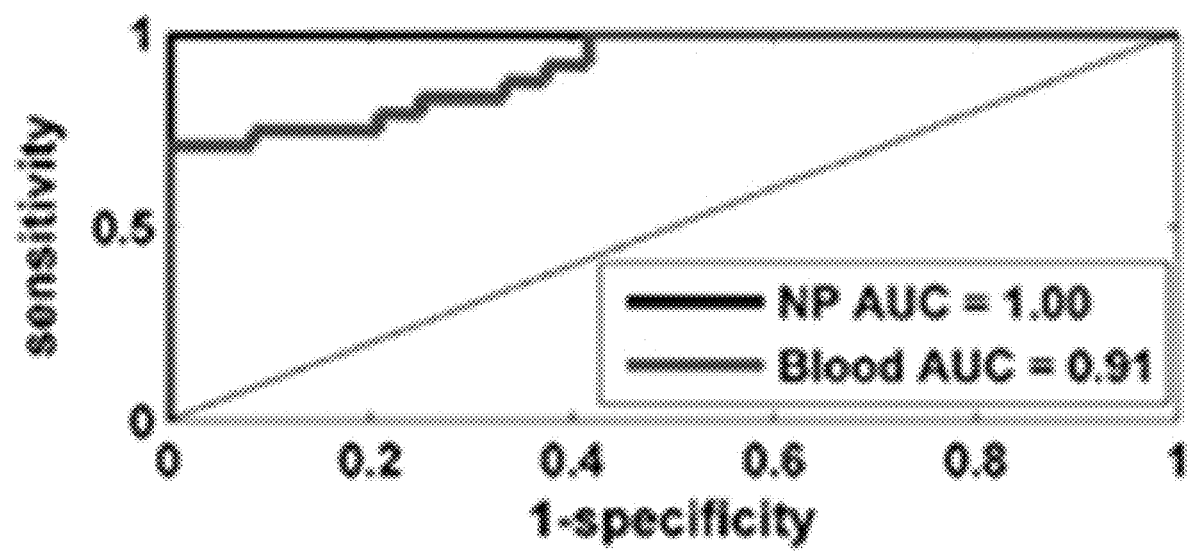
Figure 7D:
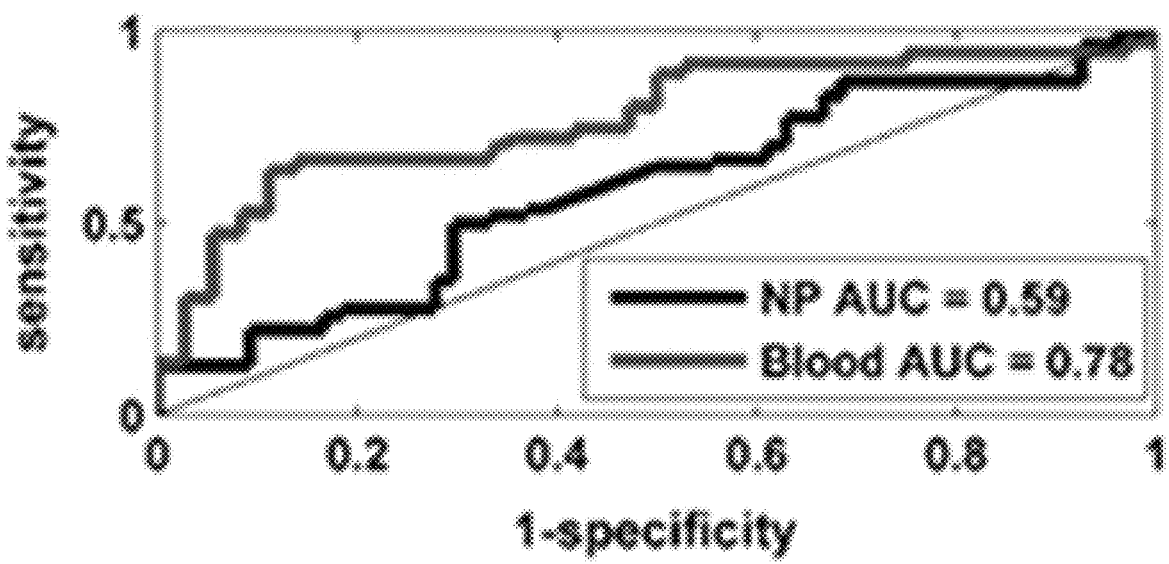
Figure 7E:
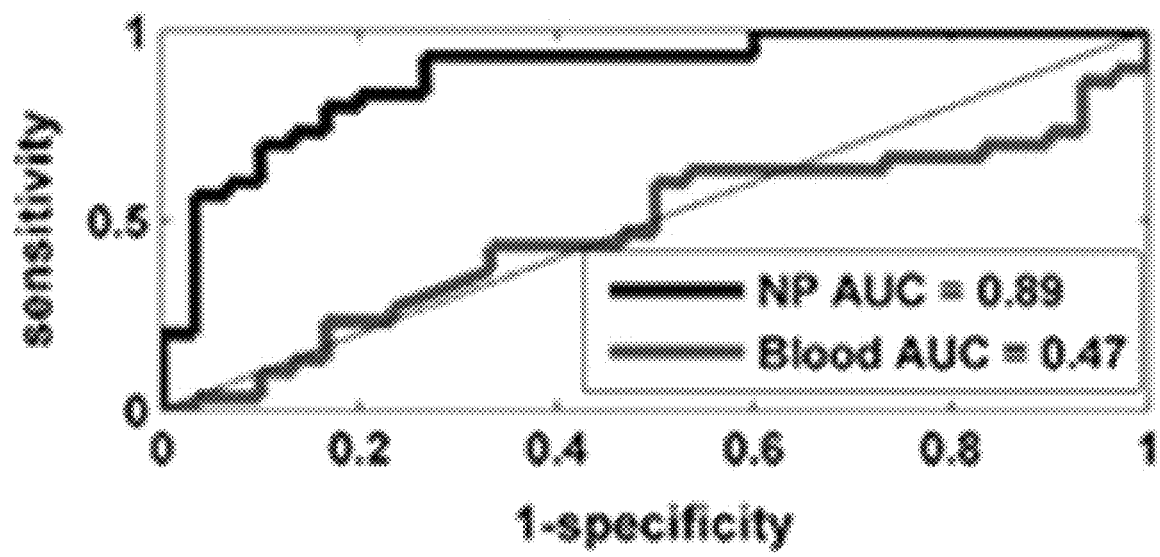
Figure 7F:
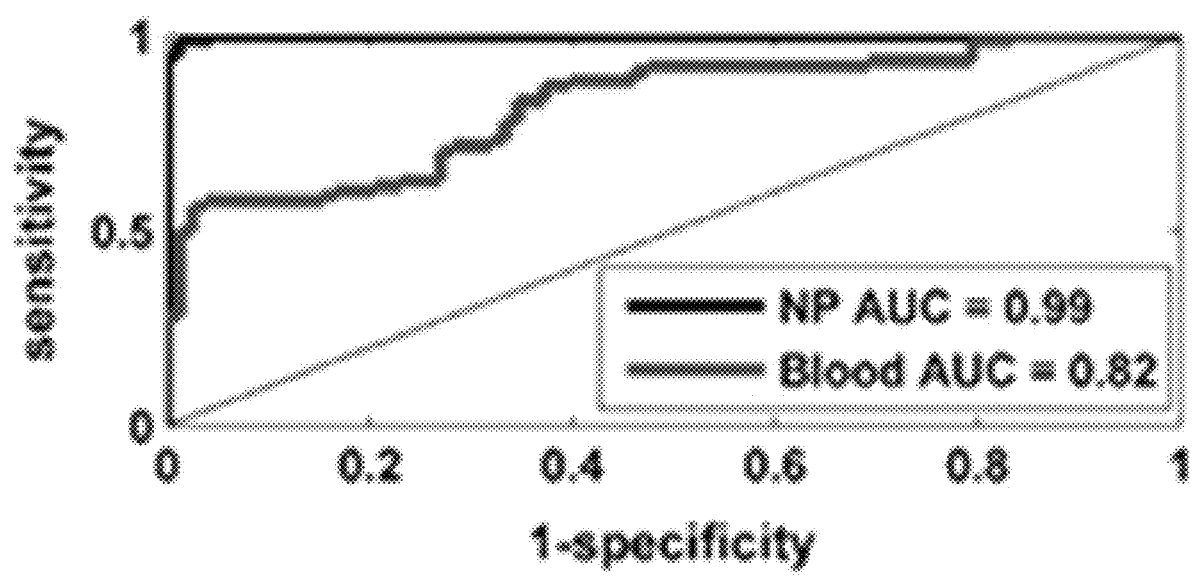
Figure 7G:
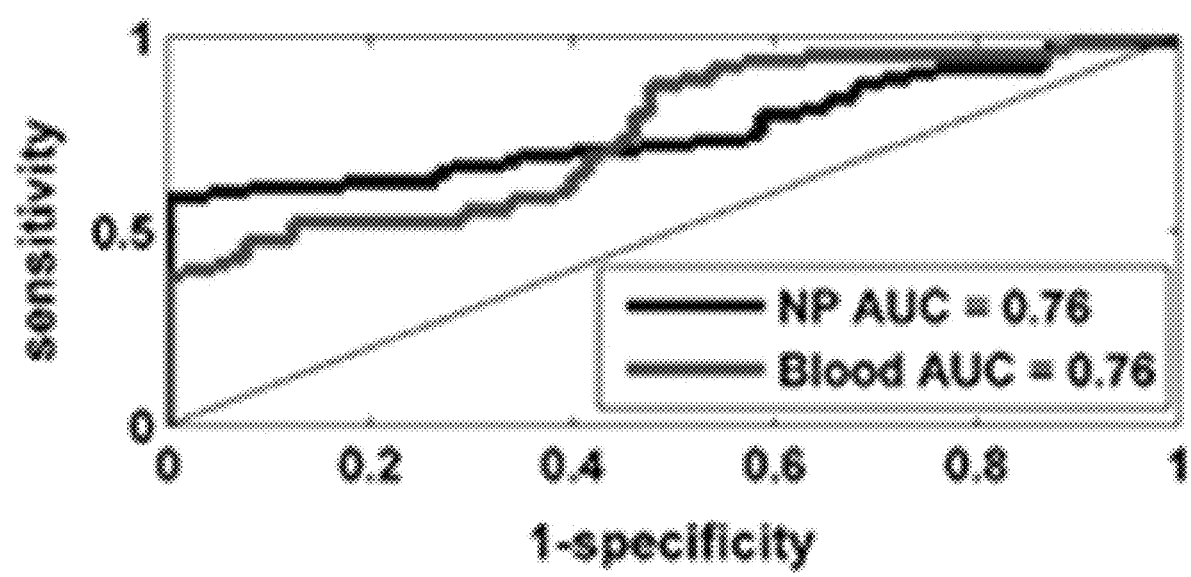

To explore the biological changes associated with respiratory viral infection, we examined the enrichment of Gene Ontology Biological Process terms using the genes with differential mean signal intensity identified from the subset of 28,476 TCs. Before analysis, the signal data for the nasal samples were adjusted by the DSA procedure in order to account for the variable contribution of inflammatory cells in each sample. Analysis was performed using the web tool "Enrichr" for comparisons of each of the three virus-infected groups with the negative controls in both blood and nasal data sets (FIG. 6). Separate analyses were carried out for the between-group comparisons of each of the groups of virus-infected subjects versus negative controls. Genes with increased mean signal intensity are shown in FIG. 6A and those with decreased mean signal intensity are shown in FIG. 6B. In the genes with increased mean signal intensity, similar process terms were enriched in the nasal and blood samples but the percent of genes corresponding to most of the processes examined was higher in the nasal samples. Enriched biological processes included anti-host, anti-virus, apoptosis, cell activity, cell cycle, cell signaling, immune activity, immune response and immune signaling. Enriched processes were generally similar for RSV and nRSV. An exception was cell cycle processes, which were enriched only for the subjects with RSV. Enrichment was markedly less for the subjects with asymptomatic RV compared to either of the symptomatic groups.

The striking finding in the genes with decreased expression in the nasal samples was very broad enrichment of cilia-related processes in the nasal samples from all three virus-infected groups, including those with asymptomatic RV infection. Other enriched processes were related to epithelial cell dysfunction including those involving nasopharynx cell structure and function, such as determination of left/right symmetry, smoothened (gene) signaling, and protein localization to cilium and related microstructures. In the blood samples, enrichment of decreased genes was limited mainly to subjects with asymptomatic RV, and included those related to RNA transcription and protein translation as well as immune cell activity and signaling pathways.

Figure 12:
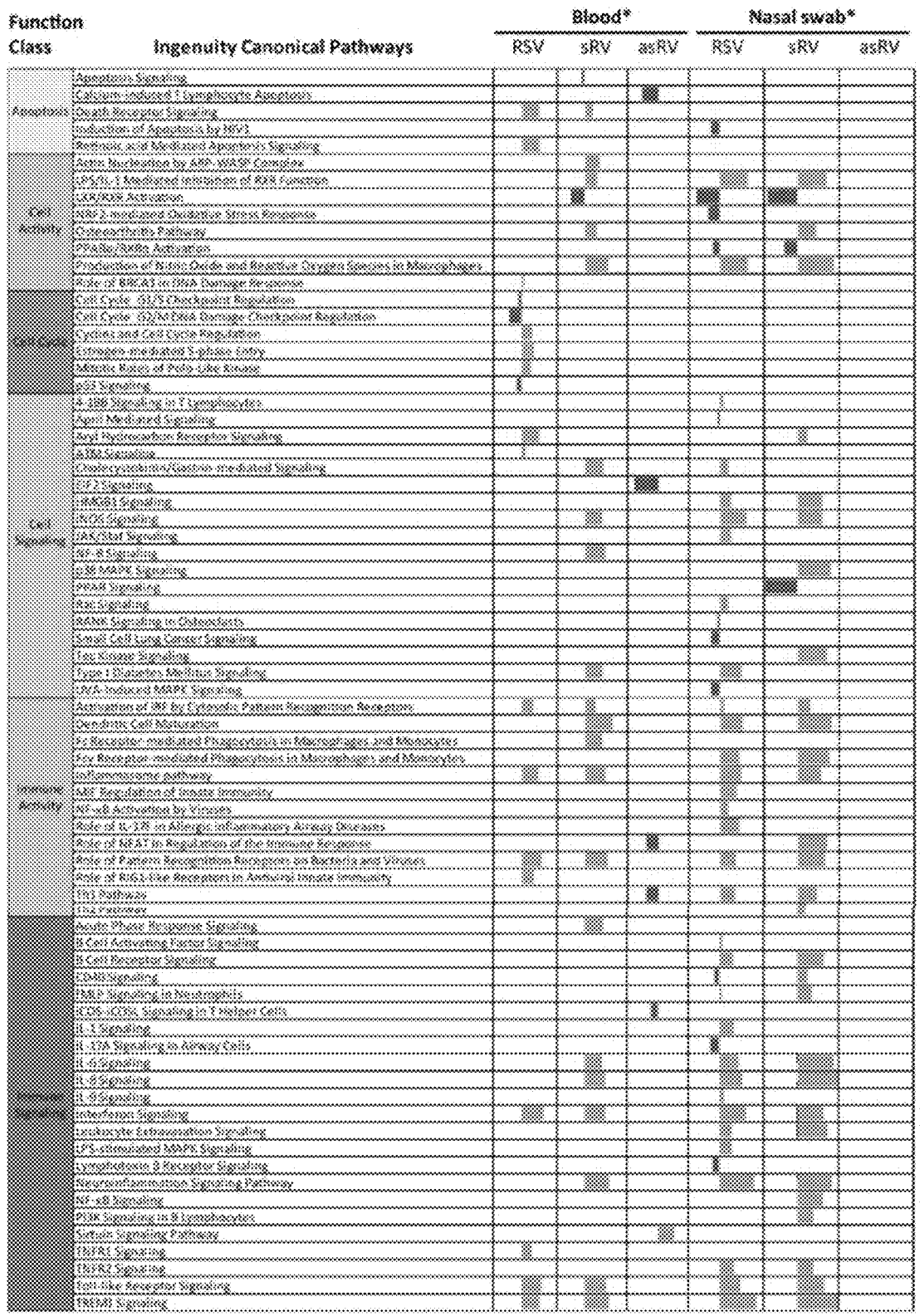
FIG. 12 depicts pathway activation and inhibition prediction from IPA pathway enrichment analysis. A positive z-score indicates an activated pathway (green bar) and a negative z-score signifies an inhibited pathway (red bar). The length of the bar reflects the absolute z-score. IPA analysis was done using genes with significant differential mean signal intensity (P<0.05) and absolute fold-change ≥1.5. The intensity values in the nasal data set were adjusted for cell type-specific signal using the R program "DSA" (Digital Sorting Algorithm) (28). The pathways shown are those significantly activated or inhibited (p<0.01) with mapping of at least 5% of genes. Whether the pathway is predicted to be activated or inhibited is based on the sign of the z-score value.

We also used Ingenuity Pathway Analysis (IPA) to identify activated and inhibited canonical pathways among the genes identified with differential mean signal intensity (FIG. 12). Activated pathways were predominantly related to cell signaling, immune activity, and immune signaling. Similar pathways were activated in blood and nasal samples, with greater activation in the nasal samples for many of the pathways. Although it was difficult to directly map the Go Process Terms to the IPA pathways, there appeared to be general consistency in the GO process terms enriched in up-regulated genes and activated IPA pathways. The GO processes that were enriched in the down-regulated genes (predominantly related to cilia structure and function) were not represented in the IPA pathways.

Construction and Cross-Validation of Polygenic Classification Scores Based on Modified Supervised Principal Components Analysis (SPCA).

From the clinical diagnostics standpoint, we wanted to investigate the extent to which the nasal samples might be as good or better than the blood samples for distinguishing (1) viral infection from healthy subjects, (2) different viral infections, and (3) symptomatic from asymptomatic infections. As shown in Table 2 and FIG. 7, the nasal samples outperformed the blood samples for 6 of the 7 comparisons, except for distinguishing between the two symptomatic viruses (nRSVnRSV vs. RSV): nested CV AUC=0.65 for nasal, based on 1 gene with >4 fold change; and nested CV AUC=0.79 for blood, based on 14 genes with >2 fold change each. Blood appeared incapable of distinguishing asymptomatic viral patients from healthy controls (nested CV AUC=0.48 for asRVasRV vs. Ctrl), in stark contrast to nasal (nested CV AUC=0.93, based on 77 genes with >2 fold change each), but both blood and nasal yielded reasonable signal (nested CV AUC >0.70) for 6 out of 7 comparisons. Symptomatic virus patients (nRSVnRSV and RSV) were most easily discriminated from virus negative controls by both sample types: nested CV AUC=100% for nasal, based on 3-6 genes with >16 fold change each; and nested CV AUC=92-94% for blood, based on 1-3 genes with >2-8 fold change each.

Figure 8A:
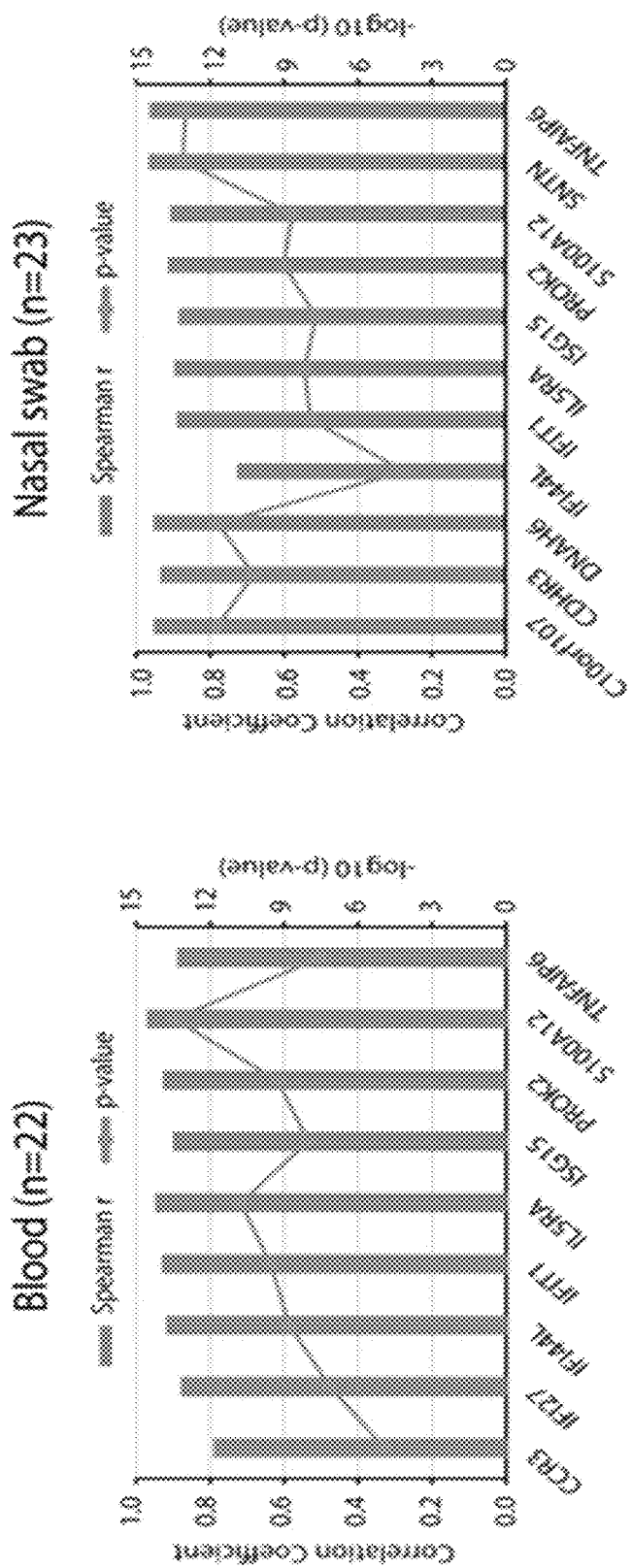
FIG. 8A, and FIG. 8B depict qRT-PCR validation. qRT-PCR assays were performed on 11 genes for nasal samples and 9 genes for blood samples, each of which showed a significant difference in microarray mean signal intensity in at least 1 of the 5 comparisons between the subject groups.
Figure 8B:
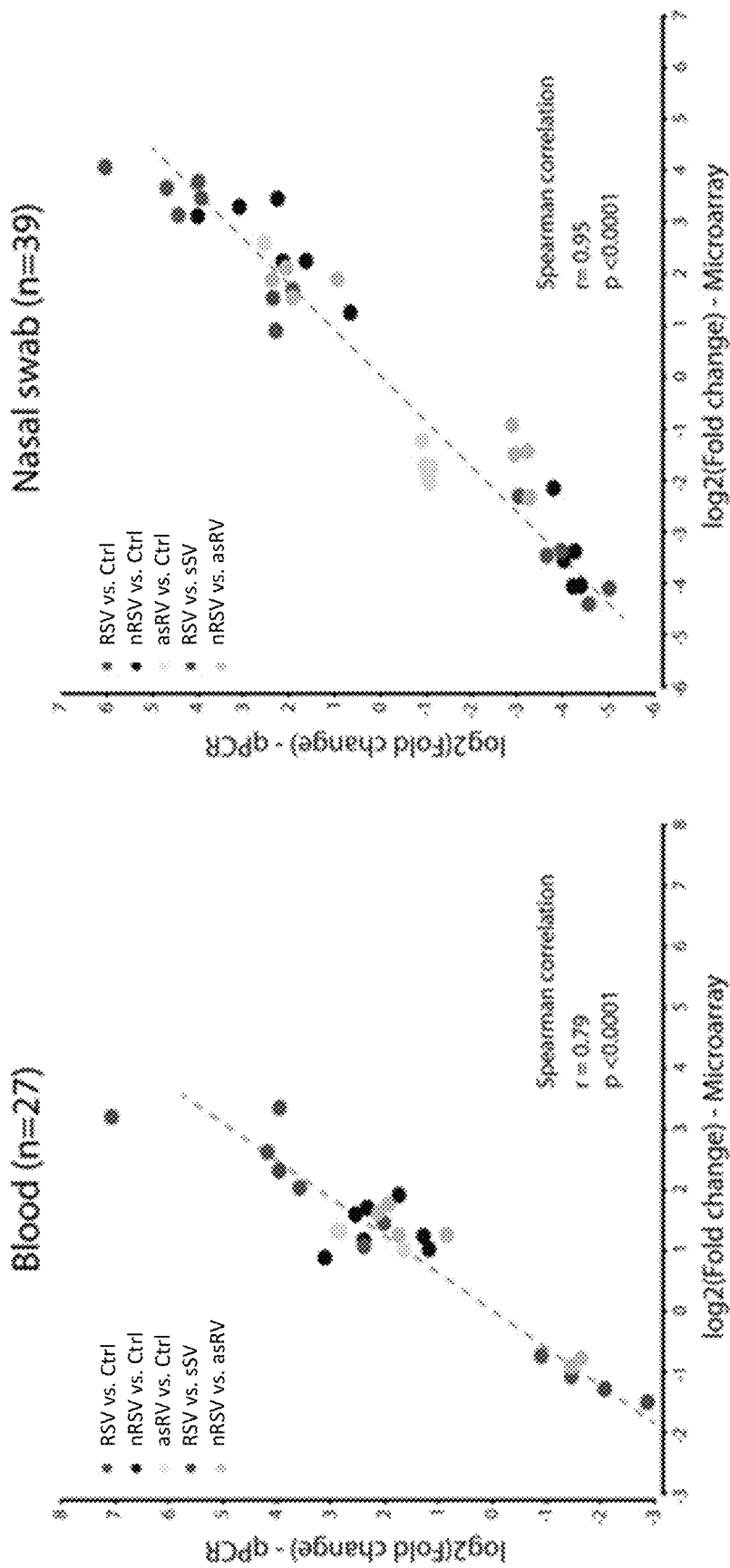
Figure 13A:
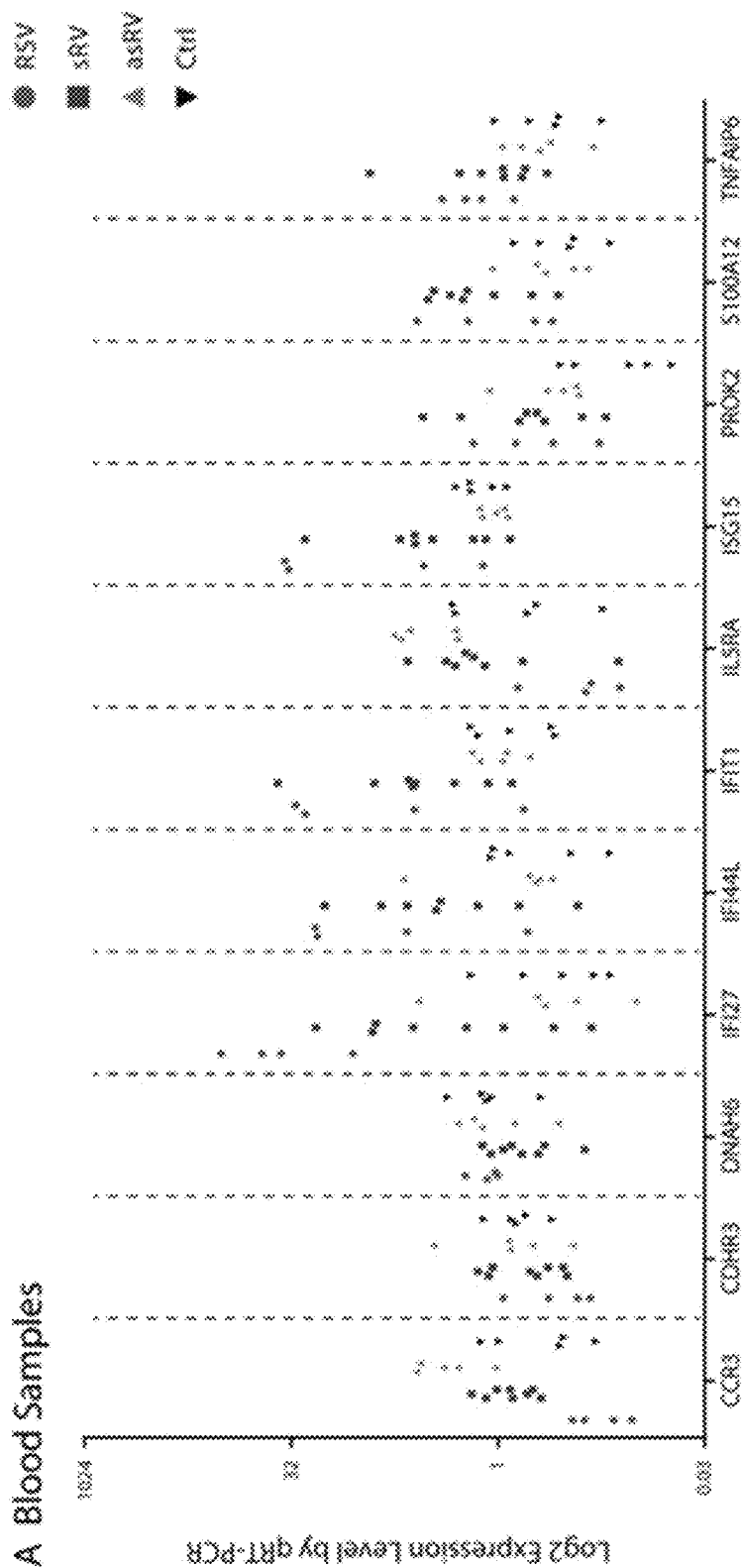
FIG. 13A and FIG. 13B show qRT-PCR testing of selected genes from blood (FIG. 13A) and nasal (FIG. 13B) samples.
Figure 13B:
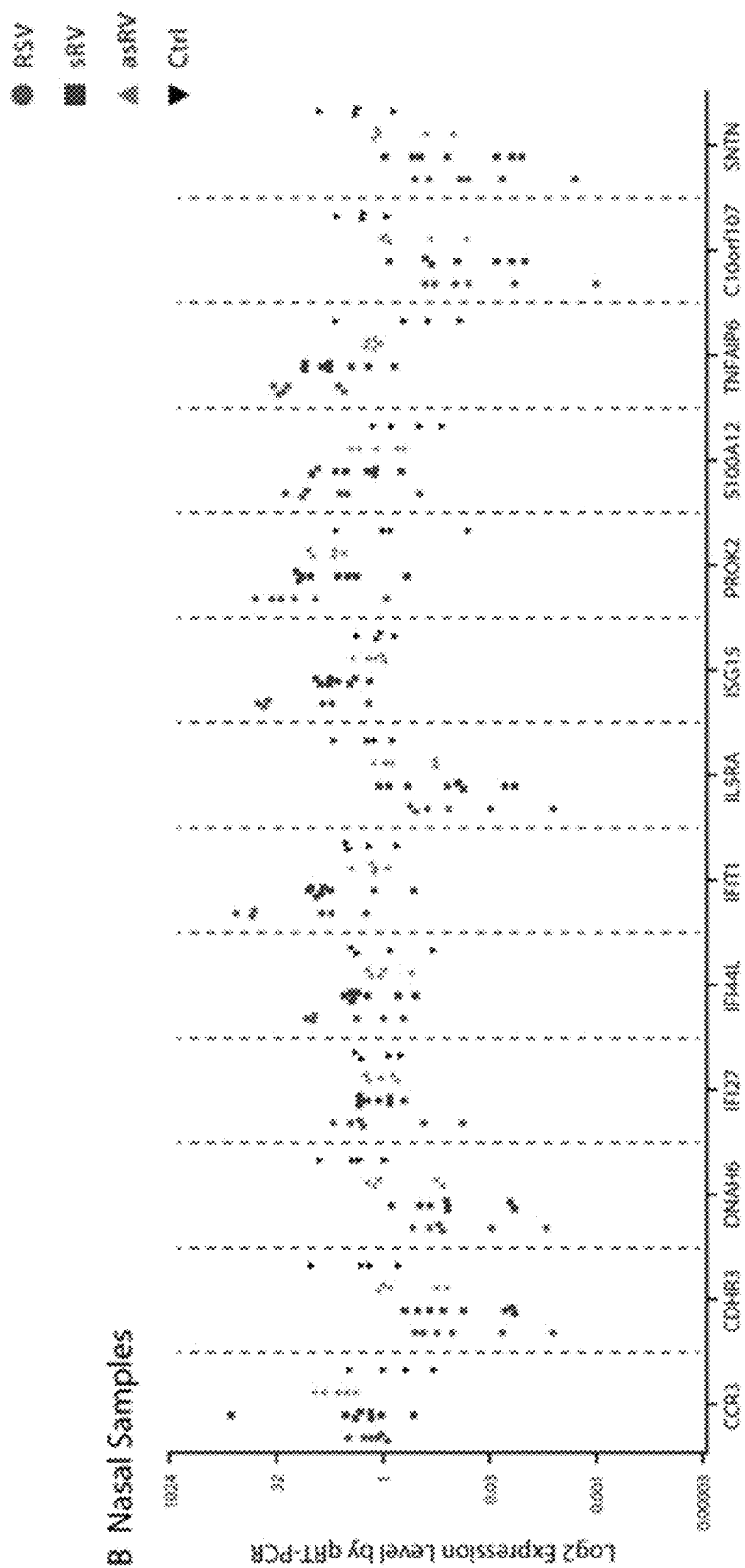
Figure 20:
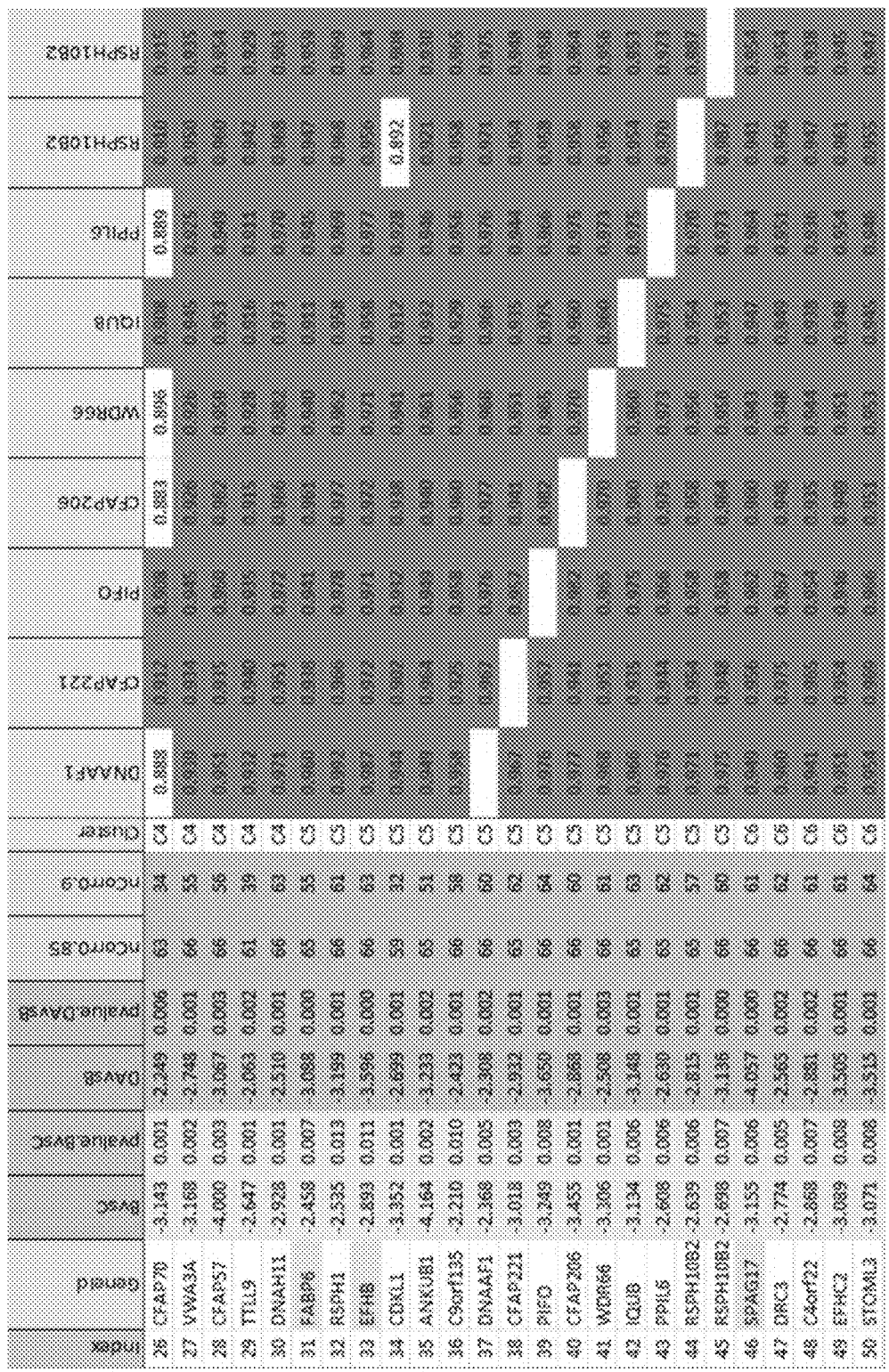
FIG. 20 shows an exemplary gene signature which includes 67 genes with decreased expression in symptomatic versus asymptomatic viral infections.

Identification of Classifiers Using Leave-One-Out Cross Validation Plus Shrinking Centroid Algorithm and k-Nearest Neighbor Algorithms Using the model selection tool in the Partek Genomics Suite software (v7.0, Partek Inc., St Louis, MO), we applied the 2-level nested 10-fold leave-one-out cross validation method to select the best model for classification of viral infection from healthy control subjects. The best classifier genes that were subjected to the cross validation were defined by the shrinking centroid algorithm. The classification was carried out by using the Euclidean distance-based k-nearest neighbor (kNN) algorithm with our microarray profiling data that were generated using the nasal swab specimens. The nasal gene classifiers selected are shown in Table 4.

qRT-PCR Validation qRT-PCR assays were conducted for 13 target and 1 reference (ACTB) genes using the same RNA samples used for microarray analysis. Of the 13 target genes with differential expression in the microarray data sets, 11 were differentially expressed in nasal and 9 in blood samples. These 13 genes were selected based on the magnitude of the fold-change difference between virus-infected subjects and negative controls, and most showed significant differential expression across multiple comparisons. The results of the comparison are shown in FIG. 8 and FIG. 13. The coefficient of variation (CV) for the 3 RT-PCR replicates performed for each comparison was less than 15% for 96.1% of the data points (range 0.1 to 14.8%, median 2%). The signal correlation between qRT-PCR and microarray was high (r=0.73-0.97, p<0.0001) for all genes (FIG. 8A), and fold-change concordance across the two platforms was also high (r=0.79, P<0.0001 for blood and r=0.95, P<0.0001 for nasal samples) (FIG. 8B).

Discussion

Analysis of the host transcriptomic response is emerging as an important tool for the diagnosis of infectious diseases (2, 29). Potential roles include rapid determination of the class of pathogen causing a patient's illness and assessment of the clinical significance of microbes detected by highly sensitive molecular assays that detect commensal organisms and other innocent bystanders in addition to disease-causing pathogens. Most studies of the transcriptomic response to date have measured the response in peripheral blood leukocytes. Our aim in this study was to evaluate nasal cells as an alternative. Use of nasal samples would circumvent the need for obtaining a blood sample and would allow the same sample to be tested for both presence of pathogens and host response. Our findings indicate that a rich transcriptomic response is measureable in nasal samples and provides information that is highly relevant to clinical diagnosis.

Nasal and blood samples differ in fundamental ways that affect evaluation of the host transcriptomic response. Most importantly, the cellular composition is different, with blood containing cells of hematopoietic origin whereas nasal samples are more heterogeneous, containing respiratory epithelial cells of different types (30) plus a variable contribution of leukocytes that migrate to the respiratory tract in response to inflammatory stimuli. Respiratory epithelial cells participate actively in the innate immune response to viral infection (31-33). The nasal transcriptome can be measured in cells recovered by swabbing the nasal passages (34) and has been validated as an indicator of the transcriptomic response of the airway epithelium (35, 36). The fact that respiratory epithelial cells are directly infected by respiratory viruses whereas blood cells are responding to signals generated from a localized site of infection, suggests that the transcriptomic responses would not be identical. An additional difference between the sample types is that nasal samples contain commensal bacterial and other microbial flora. This could be advantageous by allowing the same sample to be used for detection of potential pathogens as well as characterization of microbial genomes and transcriptomes (37, 38).

We were encouraged to find that nasal swab samples yielded host RNA that was analyzable by microarray. Measurements of RNA quality from the nasal swabs revealed more degradation than was present in RNA from blood samples, but the microarray signal from the two sample types was comparable in terms of number of genes detected. Expected differences in cell composition between nasal and blood samples were confirmed by analysis of expression of genes that serve to identify cell type. Our collection protocol involved nasal wash followed by swabbing of the nasal epithelium using a mid-turbinate flocked swab, which was placed immediately into RNA preservation media. We have not yet evaluated other collection protocols, especially those more similar to routine sample collection for virus detection that might be more practical in clinical practice.

Figure 11A:
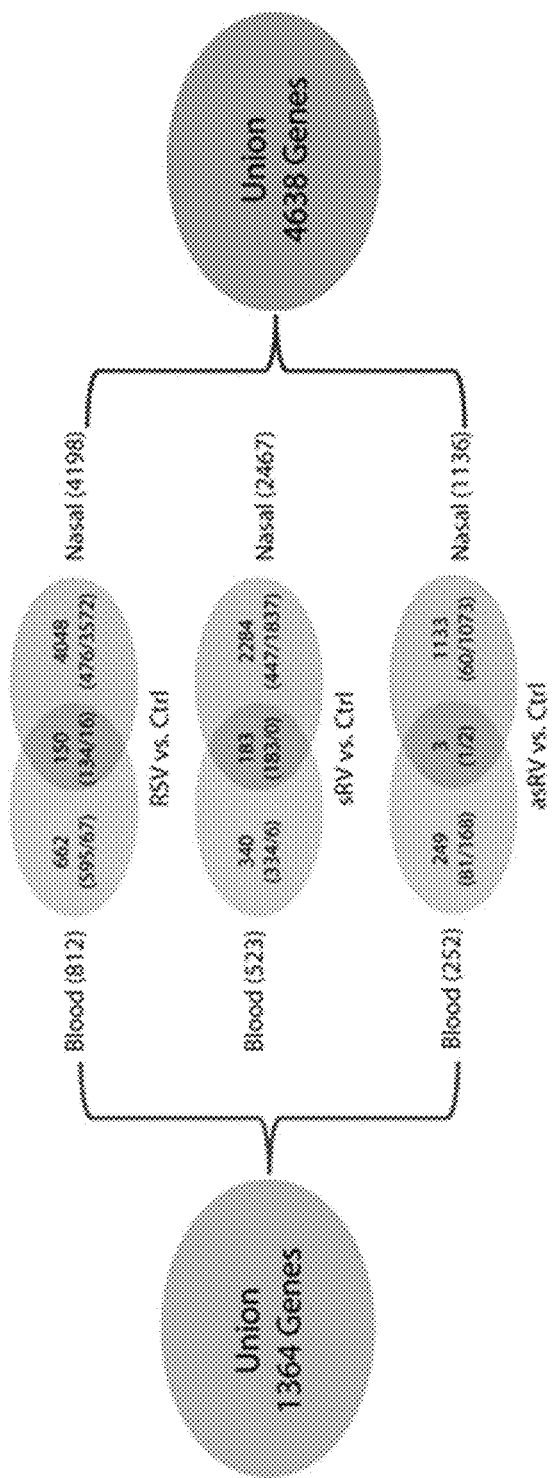
FIG. 11A, FIG. 11B and FIG. 11C depict genes with increased or decreased mean signal intensity in the comparisons of symptomatic non-respiratory syncytial virus infection (nRSV), asymptomatic rhinovirus infection (asRV) and respiratory syncytial virus infection (RSV), each versus the virus-negative controls (Ctrl) in blood and nasal samples.
Figure 11B:
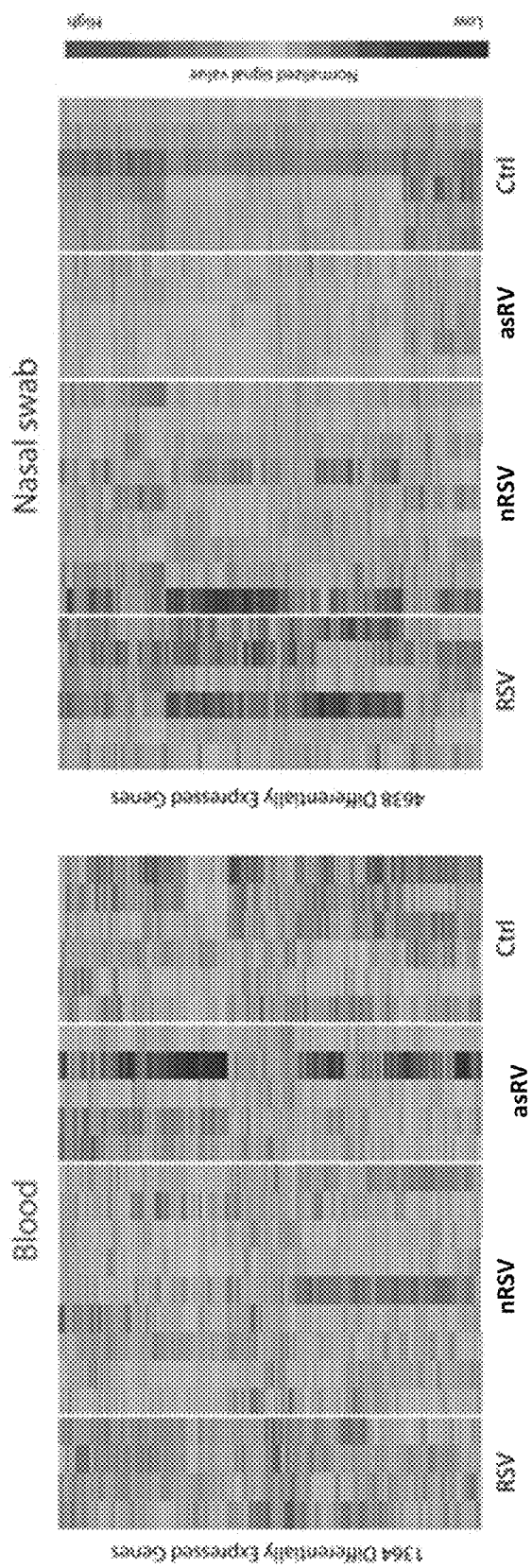
Figure 11C:
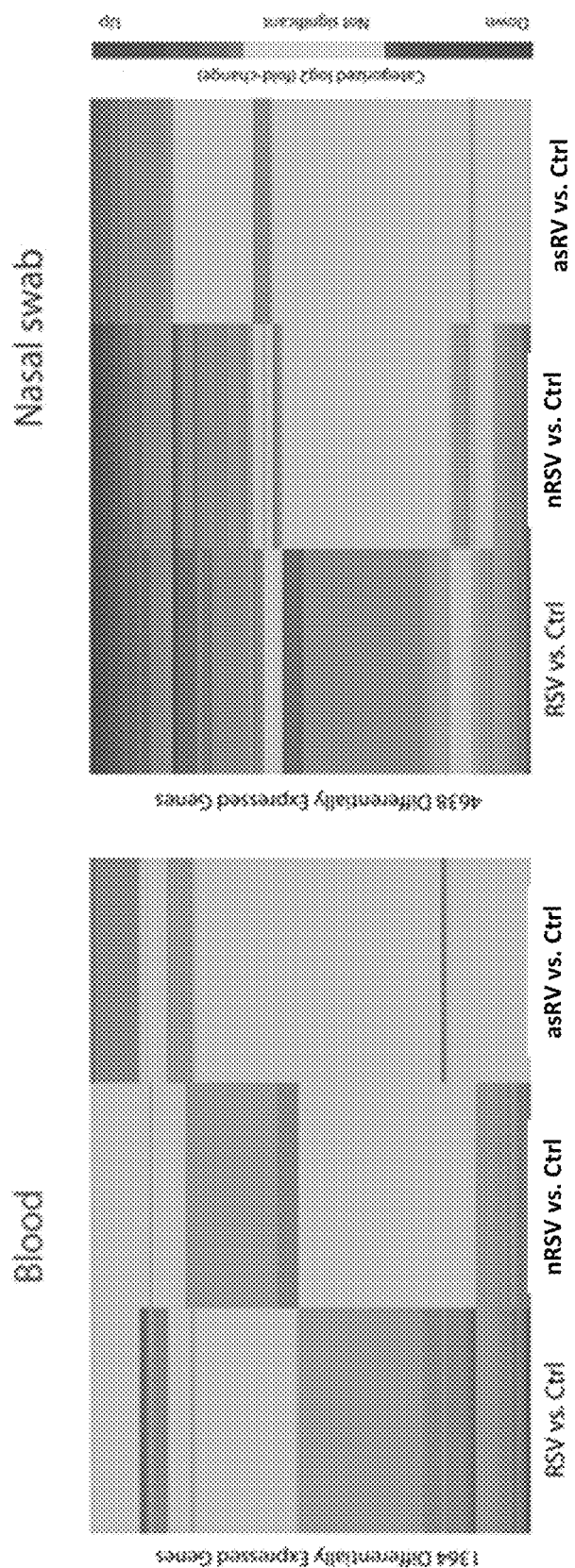

In light of the diversity of cell types represented in the nasal samples, we investigated whether digital signal deconvolution could provide additional useful information. Use of the digital sorting algorithm described by Zhong et al. (28) allowed us to estimate the proportion of epithelial and hematopoietic cells in each nasal swab. Not surprisingly, the proportion of hematopoietic cells was higher in samples from subjects with symptomatic viral infection compared to the asymptomatic virus-positive or virus-negative groups. However, as shown in FIG. 11, it appeared that application of DSA did not greatly change the ability of transcriptomic profiles to discriminate among the subject groups. However, further investigation is warranted to pursue the question of whether analysis of the transcriptomic response of specific cell types might improve the discriminatory capability of the transcriptomic profiles.

We found important similarities and differences between the nasal and blood transcriptomic responses to acute respiratory viral infection. The number of genes with increased expression in infected children was similar in nasal and blood transcriptomes, including overlap of 10-20% of the up-regulated genes. In contrast to Do et al. (27) we found more overlap of upregulated nasal and blood genes in nRSV infection compared to RSV infection. The reason for this discrepancy is not clear but could be related to different patient populations or to different comparator groups, which were asymptomatic uninfected children in our study and children in the recovery phase of acute infection in their study. Importantly, we found that enrichment of biological processes and functional pathways was greater overall in the nasal compared to the blood response, suggesting better capability of the nasal transcriptomic response to distinguish between infected and uninfected subjects. The biggest difference between nasal and blood transcriptomes was the large number of genes with decreased expression in the nasal samples, with strikingly decreased expression of genes involved in cilia structure and assembly. The decreased signal for these genes might be the result of specific transcriptional down-regulation, cellular destruction mediated by virus-induced apoptosis or necrosis, and/or dilution of the epithelial cell RNA by RNA from infiltrating inflammatory cells. The fact that cilia-related genes appeared to be disproportionately affected suggests that down-regulation may be responsible.

It may be important that decreased expression of many of these genes was observed in samples from children with asymptomatic as well as symptomatic nRSV infection. This finding raises questions about whether asymptomatic RV infection might have health consequences related to decreased ciliary activity. In addition, the fact that asymptomatic PV infection induces an active transcriptional response suggests that the virus may also interact with the immune system with potential induction of an immune response. Indeed, immune responses have been demonstrated in infants with asymptomatic RV infection (39).

Future studies are need to determine whether these interactions are positive by producing protective immunity or harmful by sensitizing the individual to future infections with adverse immunopathological consequences. The high frequency of asymptomatic RV infection in infants demonstrated recently (40) underscores the importance of understanding the pathophysiological consequences of these infections In the interest of finding a small number of genes that would be practical to incorporate into a rapid diagnostic test, we attempted to identify the smallest number of genes that could be used together to classify subjects among the 4 groups. We were able to identify fairly small groups of (1-77, but usually 3-14) genes that achieved accurate classification between pairs of groups. Consistent with the findings of biological process and pathway enrichments, nasal samples appeared to be better discriminators than blood samples for distinguishing between symptomatic infection and virus-negative controls and between symptomatic versus asymptomatic PV infection. The comparison between RSV and nRSVnRSV was the only one in which blood outperformed nasal classifiers. Because of small numbers of subjects, we were not able to have separate training and validation sets for our classifiers. Accordingly, these classifiers must be validated in additional studies.

Only a limited number of previous studies have analyzed the nasal transcriptome in respiratory virus infection (27, 28, 41, 42). Proud et al. (42) studied adult volunteers who underwent experimental infection. Comparing the results of nasal gene expression in our patients with symptomatic nRSV with that study, the pattern of expression of cell marker genes is similar as is the increased expression of interferon pathway genes and potential anti-viral genes. However, we did not observe the strong up-regulation of chemokine genes observed in that study. Do et al. (27) compared nasal and blood transcriptomes with a focus on pathophysiology and also observed more differentially expressed genes in nasal versus blood samples, with activation of innate immune response genes in both sample types. Two other recent studies (43, 44) evaluated expression of specific genes to confirm the presence of respiratory viruses. Yahya et al. (43) used PCR to evaluate nasal expression of myxovirus resistance protein A (MxA AKA Mx1), viperin (RSAD2), and tripartite-motif 21 in symptomatic and asymptomatic children with respiratory viruses. Viperin showed the best ability to distinguish symptomatic virus-positive children from asymptomatic virus-negative children and from asymptomatic virus-positive children. MxA levels also distinguished between infected and uninfected children, but showed more overlap between symptomatic and asymptomatic infected children. TRIM-21 expression did not differ significantly among the groups. Results from our study were consistent with these findings. Landry et al. (44) showed that expression of mRNAs of CXCL10, IFIT2, and OASL in nasal samples could accurately predict the presence of respiratory virus infection. These genes were among the ones that we found that could discriminate between subjects with RSV or nRSV and negative controls.

In summary, this study provides strong support for the use of nasal cells for assessing the host transcriptomic response to acute viral respiratory illness. This is important because use of nasal cells opens a path to diagnostic tests that do not require a blood sample and could allow the detection of pathogens and host response using the same test device. Our studies show a strong and informative host response measurable in nasal samples that originates from a mixture of resident epithelial cells plus leukocytes that migrate to site of infection. The pattern of host response identifies acute individuals with respiratory viral infection and can suggest whether or not the infection is symptomatic. The ability to make these distinctions is at least as good and possibly superior to the distinctions made using blood samples. In addition to a pattern of up-regulated genes largely related to the innate immune response, we have also identified a pattern of broad down-regulation of genes in nasal cells, with prominent involvement of genes related to assembly and function of cilia. The finding that these changes are present in children with asymptomatic as well as symptomatic infection should stimulate studies are needed to define whether there are immediate and/or long-term consequences of asymptomatic RV infection, now known to occur commonly in young infants (40). Our future vision includes tests with markers of both viral and bacterial infection and conversion to inexpensive rapid test formats that are currently in development (45, 46). If realized, this vision would provide the tool needed to limit the overuse of antibiotics for acute respiratory infections, most of which are viral (47)

Methods and Materials

Subjects and Samples

Symptomatic subjects in this study were children hospitalized for acute respiratory illness at St. Louis Children's Hospital (SLCH). Potential subjects were identified by reviewing positive results from a multiplex molecular test (FilmArray, BioFire, Salt Lake City, UT) performed on diagnostic samples submitted to the hospital laboratory. Inclusion criteria were in-patient status, multiplex molecular panel-positive for a single respiratory virus, age between 3 months and 18, and presence of a parent or guardian capable of providing informed consent. Exclusion criteria were any underlying medical condition that required regular medical care, receipt of immunosuppressive medications including corticosteroids within the preceding 30 days, and receipt of antibiotics within 7 days. If consent was granted, the nasopharynx was washed with normal saline by a trained study coordinator and a nasal swab was obtained using a mid-turbinate flocked swab (Copan Diagnostics, Inc., Murrieta, CA). The nasal swab was immediately placed in RNAprotect (Qiagen, Valencia, CA). In addition, a blood sample obtained by venipuncture was drawn into a Tempus tube (Applied Biosystems, Foster City, CA). Control subjects were recruited from children who were in the same age range as the ill subjects and were having ambulatory surgery for non-acute conditions at SLCH. Exclusion criteria were the same as for symptomatic subjects plus fever within the preceding 48 hours. Participating families were called 7 days after enrollment to determine whether any illness had occurred in the control subject during the 7 days following enrollment. Informed consent was obtained before the surgical procedure and samples were obtained at the time of anesthesia induction using procedures identical to those used for ill subjects, except that before the nasal wash an additional nasal swab was obtained using a mid-turbinate flocked swab and placed in universal transport media. That nasal swab was stored at −80° C. and was subsequently tested for respiratory viruses using a multiplex molecular test (Gen-Mark, Carlsbad, CA). Although this test was different from the one used by the hospital laboratory to test samples from ill subjects, it detected the same group of respiratory viruses. The nasal swab in RNAprotect was stored for 1-5 days at 4° C., after which cells were pelleted, suspended in lysis buffer containing BME, and homogenized by passing the lysate 10-12 times through a 28-gauge needle. RNA was extracted using the Absolutely RNA Miniprep Kit (Agilent Technologies, Santa Clara, CA) according to the manufacturer's instructions. Blood samples in Tempus tubes were stored at −80° C. until processing carried out according to the manufacturer's instructions. Concentrations were measured using a Bioanalyzer (Agilent, Santa Clara, CA). Extracted RNAs were stored at −80° C.

Microarray Sample Processing

Human gene expression data from blood and nasal RNA samples was generated using Affymetrix Human Clariom-D chips (Affymetrix, Santa Clara, CA). RNA samples were processed to prepare biotin-labeled cDNA targets using the Affymetrix GeneChip® Whole Transcript (WT) Pico Reagent Kit recommended by the manufacturer for use with partially degraded RNAs. In brief, 10 ng of RNA from each sample was input into the RNA amplification process that included first strand cDNA synthesis, T7-in vitro transcription cRNA amplification, 2nd-cycle single-stranded cDNA synthesis, and template RNA removal to generate single-stranded cDNAs. 5.5 μg of cDNA from each sample was fragmented and biotin-labeled. Chip hybridization was carried out at 45° C. in an Affymetrix Hybridization Oven with a rotating rate of 60 RPM overnight for 16 hours, followed by Affymetrix standard washing and staining procedures. An Affymetrix 7G Scanner was used to scan the chips to generate raw signal intensity files.

Microarray Data Processing

Off-scanner raw intensity values were processed with the Affymetrix Expression Console (v4.1) through robust multi-array averaging (RMA) background correction, median-polish probe signal summarization to probe set level of data, and quantile normalization across chips. Due to apparent different distributions of the expression data from blood and nasal samples, chip data were processed separately for blood and nasal samples, and a combined data set was also generated. The separate blood and nasal data sets were used for sample type-specific transcriptome analysis while the combined data set was used for general examination of transcriptome differences across and within sample types. Microarray probes were annotated with the Affymetrix transcript cluster (TC) annotation file for Clariom-D chips (NetAffx version na36). Signal detection calls were made based upon the chip negative control mean+1 standard deviation. Differential expression analysis between subject groups was performed using the R program "limma" (48) which uses a linear model for signal data fitting and an empirical Bayesian statistics (a moderated t-test). The Benjamini & Hochberg false-discovery rate (FDR) procedure (49) was implemented in the limma program to adjust initial p-values.

Of the 138,745 transcript clusters (TCs) included on the Clariom-D chip, 28,476 are annotated with an Entrez gene ID. To identify candidate gene classifiers, we eliminated non-coding RNAs including antisense RNAs, microRNA, pseudogenes, and other uncharacterized genes, leaving 19,847 TCs. Because of uneven gender allocation among our study groups, we excluded an additional 10 genes with strong gender effect because they are on chromosome X or Y, and had a large difference ($p<10-5$) in expression level between male and female subjects. From the remaining 19,837 TCs, we selected those with nominal p-value <0.05 and fold-change absolute value ≥1.5. Correction for multiple tests was not used at this stage because many of the differentially expressed genes are regulated in sets for pathways and biological processes, resulting in non-independent behavior, which would result in over-elimination using standard multiple comparison corrections such as Benjamini-Hochberg which assume independence.

Cell Type Deconvolution

We used the R program "DSA" (digital sorting algorithm) (28) to estimate the relative proportion of hematopoietic and epithelial cells present in nasal samples. DSA implements a quadratic programming procedure with constraint on the estimated parameter on linear regression, and requires a set of marker genes that are highly expressed in each cell type. To find marker genes, we used the Tissue-Specific Gene Expression and Regulation (TiGER) database (http://bioinfo.wilmer.jhu.edu/tiger/). A total of 505 hematopoietic cell marker genes and 371 laryngeal cell marker genes (the closest available to the nasal epithelium) were downloaded and reviewed. We excluded genes common to hematopoietic and laryngeal cells, genes showing no expression difference between hematopoietic and nasal cells, and genes not present in our data set, resulting in 229 cell-type specific markers. From these we selected 157 genes (112 hematopoietic and 45 laryngeal) based on their expression profiles distinguished by the hierarchical clustering procedure. The DSA-estimated proportion of epithelial cells in each nasal sample was utilized to adjust the nasal data sets, which were afterwards used in identification of significant biological processes in the nasal samples.

Construction and Cross-Validation of Polygenic Classification Scores Based on Modified Supervised Principal Components Analysis (SPCA)

Analyses for nasal and for blood were performed separately. For each, TCs undetectable in all subjects were removed from further consideration, leaving 18,523 TCs for NP and 18,435 TCs for blood. The goal was to develop classification scores based on the smallest number of TCs (genes) capable of distinguishing: nRSVnRSV vs. Ctrl, asRVasRV vs. Ctrl, RSV vs. Ctrl, nRSVnRSV vs. asRVasRV, nRSVnRSV vs. RSV; and, secondarily, RSV+nRSVnRSV vs Ctrl, and RSV+nRSVnRSV vs asRVasRV. All 14 (7 for NP and 7 for blood) classification scores were developed independently.

Given the very small sample sizes, including only 4 RSV subjects with TCs measured in the blood, coupled with the high-dimensional (18K TCs) feature vector, no standard multivariable regression method—e.g. logistic or linear models, even if constrained via LASSO or forward selection—would be capable of estimating multiple gene loading coefficients from the data while accounting for the correlation structure of the genes. Thus, we implemented a modified version of supervised principal components analysis (SPCA). This procedure: (1) selects a subset of candidate predictors based on their univariate associations with the outcome, typically a regression coefficient; (2) reduces the selected variables to their first few principal components; and (3) uses the resulting principal component scores as a low-dimensional set of derived predictors, typically in a regression model for the outcome. In order to avoid undue influence of potential outliers in the gene expression space, as well as the small-sample bias and instability of logistic regression, we modified step (1) from the usual regression coefficient to instead use a combination of univariate AUC (equivalent to an appropriately sample-size scaled Mann-Whitney-Wilcoxon statistic) and the accompanying robust yet efficient Hodges-Lehmann estimate of the $\log_2$ (fold change), the latter computed as the median of all $n_1 \times n_2$ pairwise differences. We used this combination since (a) fold-change alone is generally considered to be an unreliable way to rank genes and (b) AUC (and the Wilcoxon exact p-value) is highly discrete with such small samples, resulting in many ties—e.g. many TCs with univariate AUC of 1.00 due to perfect separation—which the fold-change can be used to break, since perfect separation is less likely to be due to chance alone when the fold-change is larger. Log gene expression values were standardized to Z-scores with mean 0 and unit variance prior to forming the PC in step (2), so the PC was based on the correlation structure of the genes and could not be dominated by a small number of highly variable genes. Given that only one principal component (PC) was used in step (2), since (a) this is standard and (b) the sample size was too small to admit multiple derived predictors, the linear model used in step (3) was essentially only used to estimate the sign of the correlation between the PC and the outcome. The final classification score was thus a linear combination of the log gene expression values for the selected genes, with signed loadings given by the product of the PC loadings and the sign of the correlation of the PC with the outcome. Although not guaranteed by the method, the signed loadings always matched the direction of the fold-changes for the selected genes. Furthermore, the magnitudes of the loadings were nearly equal across genes, so the classification scores were effectively averages of the sign-corrected Z-transformed log expression for the selected genes.

Leave-one-pair-out (LOPO) cross-validation (CV) was used to choose the fold-change and univariate AUC thresholds that nearly maximized the AUC of the classification score based on our modified SPCA, with preference given to threshold combinations resulting in fewer selected genes in the case of nearly tied AUC. The fold-change threshold was selected from a grid of integers from 0 to 4 on the log 2 gene expression scale, corresponding to 1 (no filter), 2, 4, 8, and 16-fold change. The univariate AUC threshold was selected from a grid of 0.50 (no filter) to 1.00 (perfect separation) by 0.05. Fold change thresholds of 2-16 and univariate AUC thresholds of 0.90-1.00 were simultaneously selected, resulting in 1-77 genes per comparison (see Table 2).

To estimate the AUC of the adaptive LOPO-CV SPCA procedure, LOPO-CV was applied to the entire adaptive procedure, resulting in nested LOPO-CV with the inner loop used to select the tuning parameters and the outer loop used to quantify the performance of the adaptive procedure, free of any potential optimism due to overfitting. As expected, nested LOPO-CV AUC was generally a bit lower than single LOPO-CV AUC (not shown), which in turn was generally lower than the naïve AUC (not shown), which is generally highly optimistic.

In order to construct complete LOPO-CV ROC curves, the LOPO-CV data was pooled into a single expanded CV data set with multiple classification scores per subject, since each subject was paired with every subject in the other outcome group via LOPO-CV. The corresponding LOPO-CV AUC from these curves shown in FIG. 7 is generally a bit lower than that in Table 2 since construction of full ROC curves requires the implicit comparison of subjects trained on different CV training samples (unstratified AUC), unlike AUC which alternatively can be computed based on comparing only those pairs of subjects whose classification scores were built using the same training data (stratified AUC, which is preferable).

Biological Process Enrichment and Pathway Analysis

From the 28,476 TCs, we identified genes with differential mean microarray signal intensity in the three comparisons of virus-infected versus negative controls, with separate analyses for nasal and blood samples. To identify significantly enriched biological processes and pathways, we entered genes with significantly increased or decreased expression separately into the web gene set enrichment tool "Enrichr" (http://amp.pharm.mssm.edu/Enrichr/). This tool pre-computes background enrichment scores using Fisher's exact test for many random input gene lists for each term in the gene set library, and then tests whether a specific gene list has an enrichment score that is significantly different from the background enrichment score (51). Enrichr produces unadjusted p-values and uses the Benjamini-Hochberg (BH) procedure to derive q-values that are adjusted for multiple comparisons to determine the significance of enrichment scores. Enrichment results of Gene Ontology Biological Process (GO_BP) terms were exported into Excel spreadsheets for further interpretation. Enrichr was used to find up- and down-regulated processes for comparisons of nasal and blood samples from the three virus-infected groups (RSV and symptomatic nRSV and asymptomatic RV) each versus the asymptomatic virus-negative control group. For each comparison, we ranked the most important GO_BP terms by adjusted p-value after eliminating redundant terms (such as "regulation of" a GO_BP process) and terms with substantially overlapping gene content. Terms most representative of similar GO_BP terms were selected for display. (Supplementary Figure showing all terms and which ones were selected for display)

Confirmation by RT-PCR

Gene expression levels defined by the microarrays were validated for select genes using the Fluidigm Biomark HD system (a 48×48 dynamic array manufactured by the Fluidigm Corporation, San Francisco, California) according to the manufacturer's protocol. First, total RNA was reverse-transcribed (RT) to cDNAs using the SuperScript™ IV First-Strand Synthesis System (ThermoFisher Scientific/Invitrogen, Carlsbad, California). The starting RNA was 50 ng in a 10-μl RT reaction according to the manufacturer's standard protocol. 2.5 μl of the 10 μl post-RT reaction volume was distributed with the pool of primers/probe into individual wells for quantitative PCR (qPCR). qPCR assays were performed in triplicate. Pre-designed primers/probe reagents labeled with FAM reporter and MGB quencher were purchased from IDT (San Jose, California). Relative expression levels were normalized to the reference gene (ACTB) and a calibrator RNA (pool of multiple RNAs of the healthy controls in the study) using the $2\text{-}\Delta\Delta Ct$ method (52).

TABLE 1

Demographic characteristics of subjects

| Group | RSV | nRSVnRSV | asRVasRV | Negative controls |
|---|---|---|---|---|
| | Number (Percent) | | | |
| Number of subjects | 6 | 9 | 5 | 6 |
| Caucasian | 5 (83) | 6 (67) | 3 (60) | 5 (83) |
| Female | 4 (67) | 2 (22) | 3 (60) | 0 |
| Age in months (median) | 5 | 15 | 29 | 22 |
| Season of enrollment | | | | |
| Winter | 3 | 2 | 0 | 3 |
| Spring | 2 | 2 | 0 | 0 |
| Summer | 0 | 2 | 1 | 2 |
| Fall | 1 | 3 | 4 | 1 |

RSV, Respiratory Syncytial Virus (all were Symptomatic);
nRSV, Symptomatic Non-Respiratory Syncytial Virus;
asRV, Asymptomatic RV

TABLE 2

Performance of polygenic classification scores constructed via cross-validated modified supervised principal components, by sample type and comparison group.

| Sample type | Comparison | Nested CV AUC | Univariate AUC threshold | Fold-change threshold | # Genes |
|---|---|---|---|---|---|
| NP | nRSV vs Ctrl | 1.00 | 1.00 | 16 | 3 |
| NP | nRSV vs asRV | 0.78 | 1.00 | 2 | 3 |
| NP | RSV vs Ctrl | 1.00 | 1.00 | 16 | 6 |
| NP | nRSV vs RSV | 0.65 | 0.90 | 4 | 1 |
| NP | asRV vs Ctrl | 0.93 | 1.00 | 2 | 77 |
| NP | RSV + nRSV vs Ctrl | 1.00 | 1.00 | 16 | 3 |
| NP | RSV + nRSV vs asRV | 0.81 | 0.90 | 2 | 58 |
| Blood | nRSV vs Ctrl | 0.94 | 1.00 | 2 | 3 |
| Blood | nRSV vs asRV | 0.71 | 0.90 | 2 | 12 |
| Blood | RSV vs Ctrl | 0.92 | 1.00 | 8 | 1 |
| Blood | nRSV vs RSV | 0.79 | 1.00 | 2 | 14 |
| Blood | asRV vs Ctrl | 0.48 | 1.00 | 2 | 1 |
| Blood | RSV + nRSV vs Ctrl | 0.82 | 0.85 | 2 | 43 |
| Blood | RSV + nRSV vs asRV | 0.80 | 0.80 | 2 | 67 |

Genes were selected based on their univariate AUC and fold-change (estimated via Hodges-Lehmann median of all pairwise shifts in log expression), and then combined via their first principal component loadings. Thresholds for univariate AUC and fold-change were selected in the inner loop of nested CV, while the outer loop was used to estimate the AUC of the adaptive procedure.

Note that the nested CV AUC in this table is generally a bit higher than that reported in FIG. 7 since construction of full ROC curves requires the implicit comparison of subjects trained on different cross-validated training samples (un-stratified AUC), whereas the nested CV AUC here only compared pairs of subjects whose classification scores were built using the same training data (stratified AUC, which is preferable).

TABLE 3

| | | Number of genes with ≥1.5-fold change in mean signal intensity with P < 0.05 in the indicated comparison | | |
|---|---|---|---|---|
| Sample | Comparison | Up | Down | Total |
| Blood | RSV vs. Ctrl | 729 | 83 | 812 |
| Blood | nRSV vs. Ctrl | 517 | 6 | 523 |

TABLE 3-continued

| | | Number of genes with ≥1.5-fold change in mean signal intensity with P < 0.05 in the indicated comparison | | |
|---|---|---|---|---|
| Sample | Comparison | Up | Down | Total |
| Blood | asRV vs. Ctrl | 82 | 170 | 252 |
| Blood | RSV vs. nRSV | 268 | 166 | 434 |
| Blood | nRSV vs. asRV | 899 | 25 | 924 |
| Blood | RSV + nRSV vs. Ctrl | 455 | 9 | 464 |
| Blood | RSV + nRSV vs. asRV | 1179 | 40 | 1219 |
| Nasal | RSV vs. Ctrl | 610 | 3588 | 4198 |
| Nasal | nRSV vs. Ctrl | 630 | 1837 | 2467 |
| Nasal | asRV vs. Ctrl | 61 | 1075 | 1136 |
| Nasal | RSV vs. nRSV | 45 | 441 | 486 |
| Nasal | nRSV vs. asRV | 279 | 304 | 583 |
| Nasal | RSV + nRSV vs. Ctrl | 648 | 2564 | 3212 |
| Nasal | RSV + nRSV vs. asRV | 313 | 427 | 740 |

Number of genes with ≥1.5-fold-increased or -decreased mean signal intensity with uncorrected P value <0.05 in between-group comparisons examining nasal and blood samples. Genes were selected from 19,837 protein coding transcript clusters (19,655 genes). RSV, respiratory syncytial virus; nRSV; asRV; Ctrl, virus-negative asymptomatic controls.

TABLE 4

Gene classifiers from selected nasal samples using leave-one-our cross validation and the shrunken centroid and k-nearest-neighbor algorithms.

| Best models | sRV vs. Ctrl model (KNN7 var15) | sRV vs. Ctrl model (KNN5 var3) | asRV vs. Ctrl model (kNN3 var11) | asRV vs. Ctrl model (KNN5 var4) | RSV vs. Ctrl model (KNN9 var15) | RSV vs. Ctrl model (KNN5 var3) | RSV•sRV vs. Ctrl model (kNN7 var15) | RSV•sRV vs. Ctrl model (KNN5 var4) |
|---|---|---|---|---|---|---|---|---|
| 2-level CV correct % | 93.3 | 93.3 | 77.3 | 77.3 | 91.7 | 91.7 | 95.6 | 95.6 |
| 1-level CV correct % | 94.4 | 94.4 | 81.7 | 81.7 | 91.7 | 91.7 | 96.7 | 96.7 |
| # Genes | 15 genes | 3 genes | 11 genes | 4 genes | 15 genes | 3 genes | 15 genes | 4 genes |
| Classifier | AGBL2 | ANKFN1 | LEKR1 | LEKR1 | VWA3B | VWA3B | AGBL2 | AGBL2 |
| Classifier | ANKEN1 | MAATS1 | MAATS1 | MAATS1 | FAM216B | FAM216B | ANKEN1 | ANKFN1 |
| Classifier | ANKUB1 | VWA3B | IFT88 | IFT88 | CCDC81 | CCDC81 | ANKUB1 | DNAH10 |

TABLE 4-continued

Gene classifiers from selected from nasal samples using leave-one-our cross validation and the shrunken centroid and k-nearest-neighbor algorithms.

| Best models | sRV vs. Ctrl model (KNN7 var15) | sRV vs. Ctrl model (KNN5 var3) | asRV vs. Ctrl model (kNN3 var11) | asRV vs. Ctrl model (KNN5 var4) | RSV vs. Ctrl model (KNN9 var15) | RSV vs. Ctrl model (KNN5 var3) | RSV·sRV vs. Ctrl model (kNN7 var15) | RSV·sRV vs. Ctrl model (KNN5 var4) |
|---|---|---|---|---|---|---|---|---|
| Classifier | C1orf158 |  | DNAH6 | DNAH6 | STOML3 |  | CCDC81 | VWA3B |
| Classifier | CFAP206 |  | ANKUB1 |  | WFDC6 |  | CDKLI |  |
| Classifier | DNAH10 |  | AKAP14 |  | PIFO |  | CFAP206 |  |
| Classifier | DNAH6 |  | CCDC60 |  | DNAH10 |  | CFAP221 |  |
| Classifier | DYNC2H1 |  | DNAH10 |  | CDKLI |  | CFAP47 |  |
| Classifier | EFHB |  | CFAP126 |  | SPAG17 |  | DNAH10 |  |
| Classifier | EFHC2 |  | FAM216B |  | HHLA2 |  | FABP6 |  |
| Classifier | LMNTD1 |  | AGBL2 |  | CABCOCO1 |  | FBXO15 |  |
| Classifier | MAATS1 |  |  |  | ANKUB1 |  | LMNTD1 |  |
| Classifier | SPAG17 |  |  |  | AGBL2 |  | MAATS1 |  |
| Classifier | VWA3B |  |  |  | MORN5 |  | SPAG17 |  |
| Classifier | WDR78 |  |  |  | COLCA1 |  | VWA3B |  |

Columns B, D, F, and H show the 15 best classifiers for the indicated comparison; columns C, E, G, and I show the 3-4 best classifiers for each comparison.

REFERENCES

1. Ramilo O, Mejias A. Shifting the paradigm: host gene signatures for diagnosis of infectious diseases. Cell Host Microbe. 2009; 6 (3): 199-200.
2. Holcomb Z E, Tsalik E L, Woods C W, McClain M T. Host-Based Peripheral Blood Gene Expression Analysis for Diagnosis of Infectious Diseases. J Clin Microbiol. 2017; 55 (2): 360-8.
3. Ramilo O, Allman W, Chung W, Mejias A, Ardura M, Glaser C, et al. Gene expression patterns in blood leukocytes discriminate patients with acute infections. Blood. 2007; 109 (5): 2066-77.
4. Hu X, Yu J, Crosby S D, Storch G A. Gene expression profiles in febrile children with defined viral and bacterial infection. Proc Natl Acad Sci USA. 2013; 110 (31): 12792-7.
5. Sweeney T E, Wong H R, Khatri P. Robust classification of bacterial and viral infections via integrated host gene expression diagnostics. Sci Transl Med. 2016; 8 (346): 346ra91.
6. Fjaerli H O, Bukholm G, Krog A, Skjaeret C, Holden M, Nakstad B. Whole blood gene expression in infants with respiratory syncytial virus bronchiolitis. BMC Infect Dis. 2006; 6:175.
7. Zaas A K, Chen M, Varkey J, Veldman T, Hero A O, 3rd, Lucas J, et al. Gene expression signatures diagnose influenza and other symptomatic respiratory viral infections in humans. Cell Host Microbe. 2009; 6 (3): 207-17.
8. Parnell G P, McLean A S, Booth D R, Armstrong N J, Nalos M, Huang S J, et al. A distinct influenza infection signature in the blood transcriptome of patients with severe community-acquired pneumonia. Critical care. 2012; 16 (4): R157.
9. Zaas A K, Burke T, Chen M, McClain M, Nicholson B, Veldman T, et al. A host-based rt-PCR gene expression signature to identify acute respiratory viral infection. Sci Transl Med. 2013; 5 (203): 203ra126.
10. Woods C W, McClain M T, Chen M, Zaas A K, Nicholson B P, Varkey J, et al. A host transcriptional signature for presymptomatic detection of infection in humans exposed to influenza H1N1 or H3N2. PLoS One. 2013; 8 (1): e52198.
11. Mejias A, Dimo B, Suarez N M, Garcia C, Suarez-Arrabal M C, Jartti T, et al. Whole blood gene expression profiles to assess pathogenesis and disease severity in infants with respiratory syncytial virus infection. PLoS Med. 2013; 10 (11): e1001549.
12. Bucasas K L, Mian A I, Demmler-Harrison G J, Caviness A C, Piedra P A, Franco L M, et al. Global gene expression profiling in infants with acute respiratory syncytial virus bronchiolitis demonstrates systemic activation of interferon signaling networks. Pediatr Infect Dis J. 2013; 32 (2): e68-76.
13. Heinonen S, Jartti T, Garcia C, Oliva S, Smitherman C, Anguiano E, et al. Rhinovirus Detection in Symptomatic and Asymptomatic Children: Value of Host Transcriptome Analysis. Am J Respir Crit Care Med. 2015.
14. Zhai Y, Franco L M, Atmar R L, Quarles J M, Arden N, Bucasas K L, et al. Host Transcriptional Response to Influenza and Other Acute Respiratory Viral Infections—A Prospective Cohort Study. PLoS pathogens. 2015; 11 (6): e1004869.
15. Andres-Terre M, McGuire H M, Pouliot Y, Bongen E, Sweeney T E, Tato C M, et al. Integrated, Multi-cohort Analysis Identifies Conserved Transcriptional Signatures across Multiple Respiratory Viruses. Immunity. 2015; 43 (6): 1199-211.
16. Tsalik E L, Henao R, Nichols M, Burke T, Ko E R, McClain M T, et al. Host gene expression classifiers diagnose acute respiratory illness etiology. Sci Transl Med. 2016; 8 (322): 322ra11.
17. Suarez N M, Bunsow E, Falsey A R, Walsh E E, Mejias A, Ramilo O. Superiority of Transcriptional Profiling Over Procalcitonin for Distinguishing Bacterial From Viral Lower Respiratory Tract Infections in Hospitalized Adults. J Infect Dis. 2015.
18. Herberg J A, Kaforou M, Wright V J, Shailes H, Eleftherohorinou H, Hoggart C J, et al. Diagnostic Test Accuracy of a 2-Transcript Host RNA Signature for Discriminating Bacterial vs Viral Infection in Febrile Children. JAMA. 2016; 316 (8): 835-45.
19. Mahajan P, Kuppermann N, Mejias A, Suarez N, Chaussabel D, Casper T C, et al. Association of RNA Biosignatures With Bacterial Infections in Febrile Infants Aged 60 Days or Younger. JAMA. 2016; 316 (8): 846-57.

20. Simmons C P, Popper S, Dolocek C, Chau T N, Griffiths M, Dung N T, et al. Patterns of host genome-wide gene transcript abundance in the peripheral blood of patients with acute dengue hemorrhagic fever. J Infect Dis. 2007; 195 (8): 1097-107.
21. Caballero I S, Yen J Y, Hensley L E, Honko A N, Goff A J, Connor J H. Lassa and Marburg viruses elicit distinct host transcriptional responses early after infection. BMC Genomics. 2014; 15:960.
22. Eisfeld A J, Halfmann P J, Wendler J P, Kyle J E, Burnum-Johnson K E, Peralta Z, et al. Multi-platform 'Omics Analysis of Human Ebola Virus Disease Pathogenesis. Cell Host Microbe. 2017; 22 (6): 817-29 e8.
23. Anderson S T, Kaforou M, Brent A J, Wright V J, Banwell C M, Chagaluka G, et al. Diagnosis of childhood tuberculosis and host RNA expression in Africa. N Engl J Med. 2014; 370 (18): 1712-23.
24. Sweeney T E, Braviak L, Tato C M, Khatri P. Genome-wide expression for diagnosis of pulmonary tuberculosis: a multicohort analysis. Lancet Respir Med. 2016; 4 (3): 213-24.
25. Greninger A L, Chen E C, Sittler T, Scheinerman A, Roubinian N, Yu G, et al. A metagenomic analysis of pandemic influenza A (2009 H1N1) infection in patients from North America. PLoS One. 2010; 5 (10): e13381.
26. Proud D, Sanders S P, Wiehler S. Human rhinovirus infection induces airway epithelial cell production of human beta-defensin 2 both in vitro and in vivo. J Immunol. 2004; 172 (7): 4637-45.
27. Do L A H, Pellet J, van Doorn H R, Tran A T, Nguyen B H, Tran T T L, et al. Host Transcription Profile in Nasal Epithelium and Whole Blood of Hospitalized Children Under 2 Years of Age With Respiratory Syncytial Virus Infection. J Infect Dis. 2017; 217 (1): 134-46.
28. Zhong Y, Wan Y W, Pang K, Chow L M, Liu Z. Digital sorting of complex tissues for cell type-specific gene expression profiles. BMC Bioinformatics. 2013; 14:89.
29. Mejias A, Ramilo O. Transcriptional profiling in infectious diseases: ready for prime time? J Infect. 2014; 68 Suppl 1: S94-9.
30. Harkema J R, Carey S A, Wagner J G. The nose revisited: a brief review of the comparative structure, function, and toxicologic pathology of the nasal epithelium. Toxicol Pathol. 2006; 34 (3): 252-69.
31. Vareille M, Kieninger E, Edwards M R, Regamey N. The airway epithelium: soldier in the fight against respiratory viruses. Clinical microbiology reviews. 2011; 24 (1): 210-29.
32. Hariri B M, Cohen N A. New insights into upper airway innate immunity. Am J Rhinol Allergy. 2016; 30 (5): 319-23.
33. Troy N M, Bosco A. Respiratory viral infections and host responses; insights from genomics. Respir Res. 2016; 17 (1): 156.
34. Chu C Y, Qiu X, Wang L, Bhattacharya S, Lofthus G, Corbett A, et al. The Healthy Infant Nasal Transcriptome: A Benchmark Study. Sci Rep. 2016; 6:33994.
35. Poole A, Urbanek C, Eng C, Schageman J, Jacobson S, O'Connor B P, et al. Dissecting childhood asthma with nasal transcriptomics distinguishes subphenotypes of disease. J Allergy Clin Immunol. 2014.
36. Zhang X, Sebastiani P, Liu G, Schembri F, Dumas Y M, Langer E M, et al. Similarities and differences between smoking-related gene expression in nasal and bronchial epithelium. Physiological genomics. 2010; 41 (1): 1-8.
37. Westermann A J, Gorski S A, Vogel J. Dual RNA-seq of pathogen and host. Nat Rev Microbiol. 2012; 10 (9): 618-30.
38. Graf E H, Simmon K E, Tardif K D, Hymas W, Flygare S, Eilbeck K, et al. Unbiased Detection of Respiratory Viruses by Use of RNA Sequencing-Based Metagenomics: a Systematic Comparison to a Commercial PCR Panel. J Clin Microbiol. 2016; 54 (4): 1000-7.
39. Wolsk H M, Folsgaard N V, Birch S, Brix S, Hansel T T, Johnston S L, et al. Picornavirus-Induced Airway Mucosa Immune Profile in Asymptomatic Neonates. J Infect Dis. 2016; 213 (8): 1262-70.
40. Sarna M, Ware R S, Lambert S B, Sloots T P, Nissen M D, Grimwood K. Timing of first respiratory virus detection in infants: a community-based birth cohort study. Journal of Infectious Diseases. 2018.
41. van den Kieboom C H, Ahout I M, Zomer A, Brand K H, de Groot R, Ferwerda G, et al. Nasopharyngeal gene expression, a novel approach to study the course of respiratory syncytial virus infection. Eur Respir J. 2015; 45 (3): 718-25.
42. Proud D, Turner R B, Winther B, Wiehler S, Tiesman J P, Reichling T D, et al. Gene expression profiles during in vivo human rhinovirus infection: insights into the host response. Am J Respir Crit Care Med. 2008; 178 (9): 962-8.
43. Yahya M, Rulli M, Toivonen L, Waris M, Peltola V. Detection of Host Response to Viral Respiratory Infection by Measurement of Messenger RNA for MxA, TRIM21, and Viperin in Nasal Swabs. J Infect Dis. 2017; 216 (9): 1099-103.
44. Landry M L, Foxman E F. Antiviral Response in the Nasopharynx Identifies Patients With Respiratory Virus Infection. J Infect Dis. 2018; 217 (6): 897-905.
45. St John A, Price C P. Existing and Emerging Technologies for Point-of-Care Testing. Clin Biochem Rev. 2014; 35 (3): 155-67.
46. Kozel T R, Burnham-Marusich A R. Point-of-Care Testing for Infectious Diseases: Past, Present, and Future. J Clin Microbiol. 2017; 55 (8): 2313-20.
47. Fleming-Dutra K E, Hersh A L, Shapiro D J, Bartoces M, Enns E A, File T M, Jr., et al. Prevalence of Inappropriate Antibiotic Prescriptions Among US Ambulatory Care Visits, 2010-2011. JAMA. 2016; 315 (17): 1864-73.
48. Ritchie M E, Phipson B, Wu D, Hu Y, Law C W, Shi W, et al. limma powers differential expression analyses for RNA-sequencing and microarray studies. Nucleic acids research. 2015; 43 (7): e47.
49. Benjamini Y, Hochberg Y. Controlling the false discovery rate: a practical and powerful approach to multiple testing. J R Stat Soc Series B Stat Methodol. 1995; 57:289-300.
50. Tibshirani R, Hastie T, Narasimhan B, Chu G. Diagnosis of multiple cancer types by shrunken centroids of gene expression. Proc Natl Acad Sci USA. 2002; 99 (10): 6567-72.
51. Chen E Y, Tan C M, Kou Y, Duan Q, Wang Z, Meirelles G V, et al. Enrichr: interactive and collaborative HTML5 gene list enrichment analysis tool. BMC Bioinformatics. 2013; 14:128.
52. Livak K J, Schmittgen T D. Analysis of relative gene expression data using real-time quantitative PCR and the 2(-Delta Delta C(T)) Method. Methods. 2001; 25 (4): 402-8.
53. Bair E, Hastie T, Paul D, and Tibshirani R (2006). Prediction by supervised principal components. Journal of the American Statistical Association 101 (473): 119-137.

54. Airola A, Pahikkala T, Waegeman W, De Baets B, and Salakoski T (2010). A comparison of AUC estimators in small-sample studies. Journal of Machine Learning Research: Workshop and Conference Proceedings 8:3-13. Machine Learning in Systems Biology.

All cited references are herein expressly incorporated by reference in their entirety.

Whereas particular embodiments have been described above for purposes of illustration, it will be appreciated by those skilled in the art that numerous variations of the details may be made without departing from the disclosure as described in the appended claims.

Example 2

Figure 14:
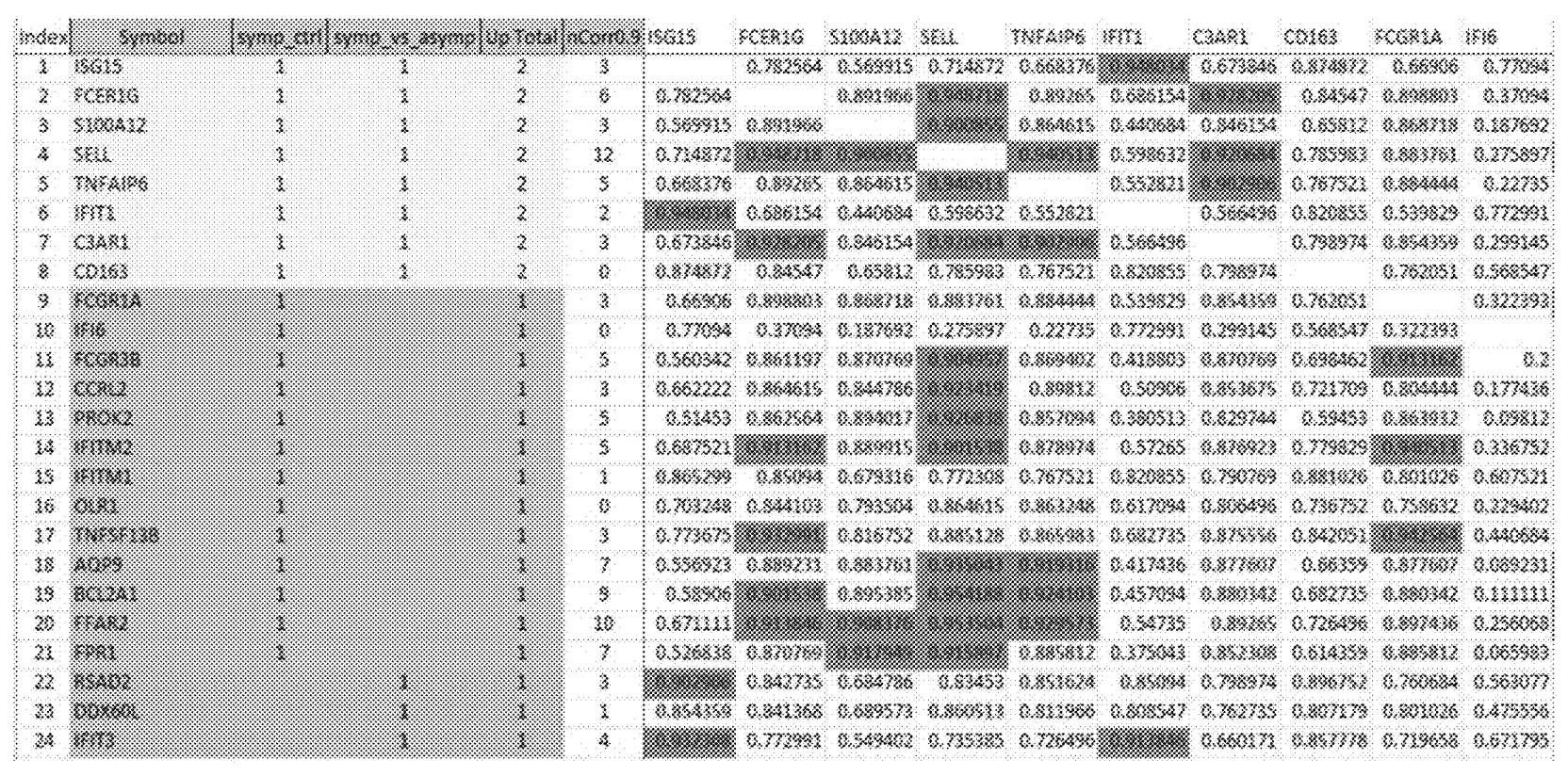
Figure 14:
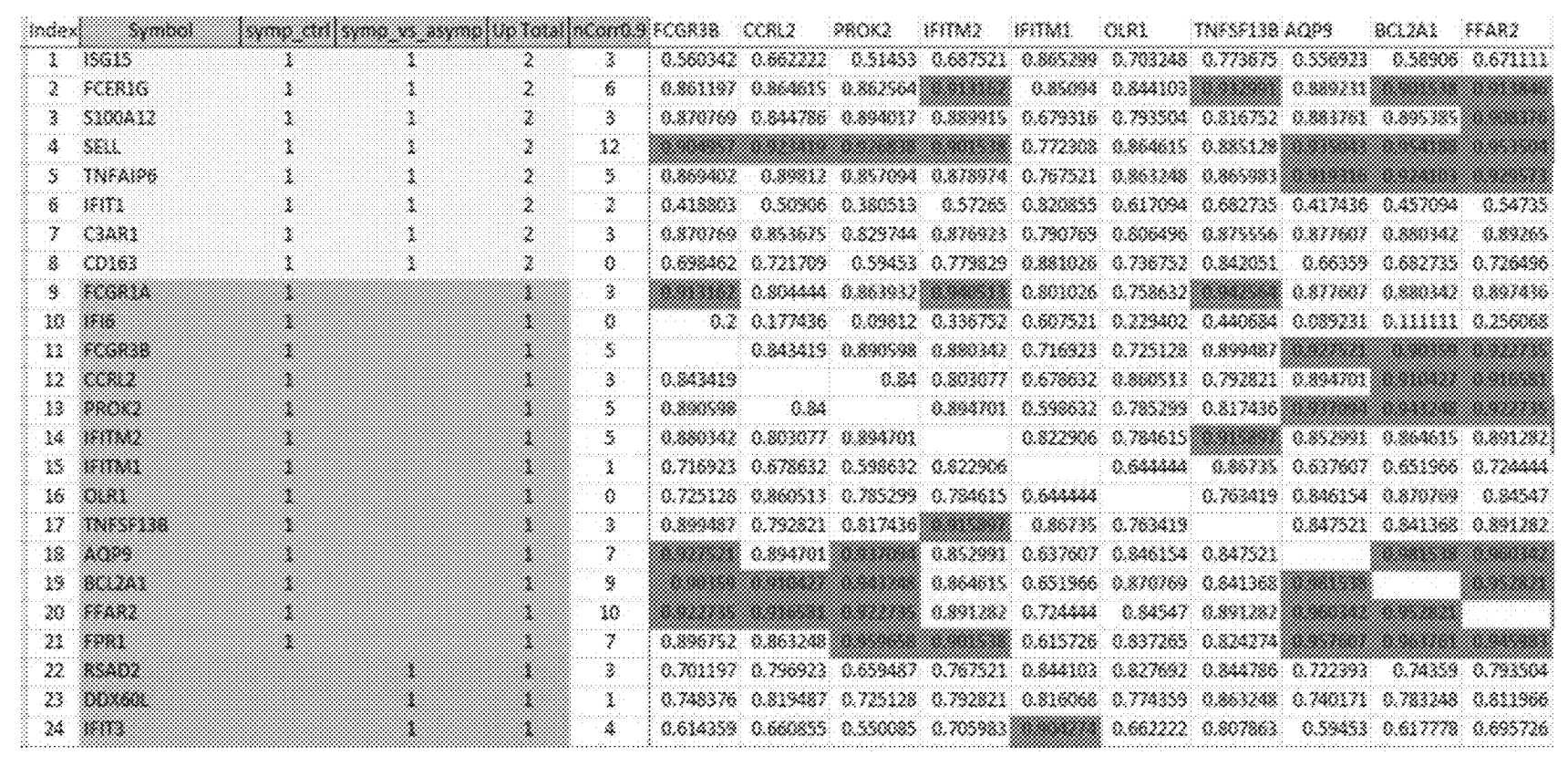
Figure 14:
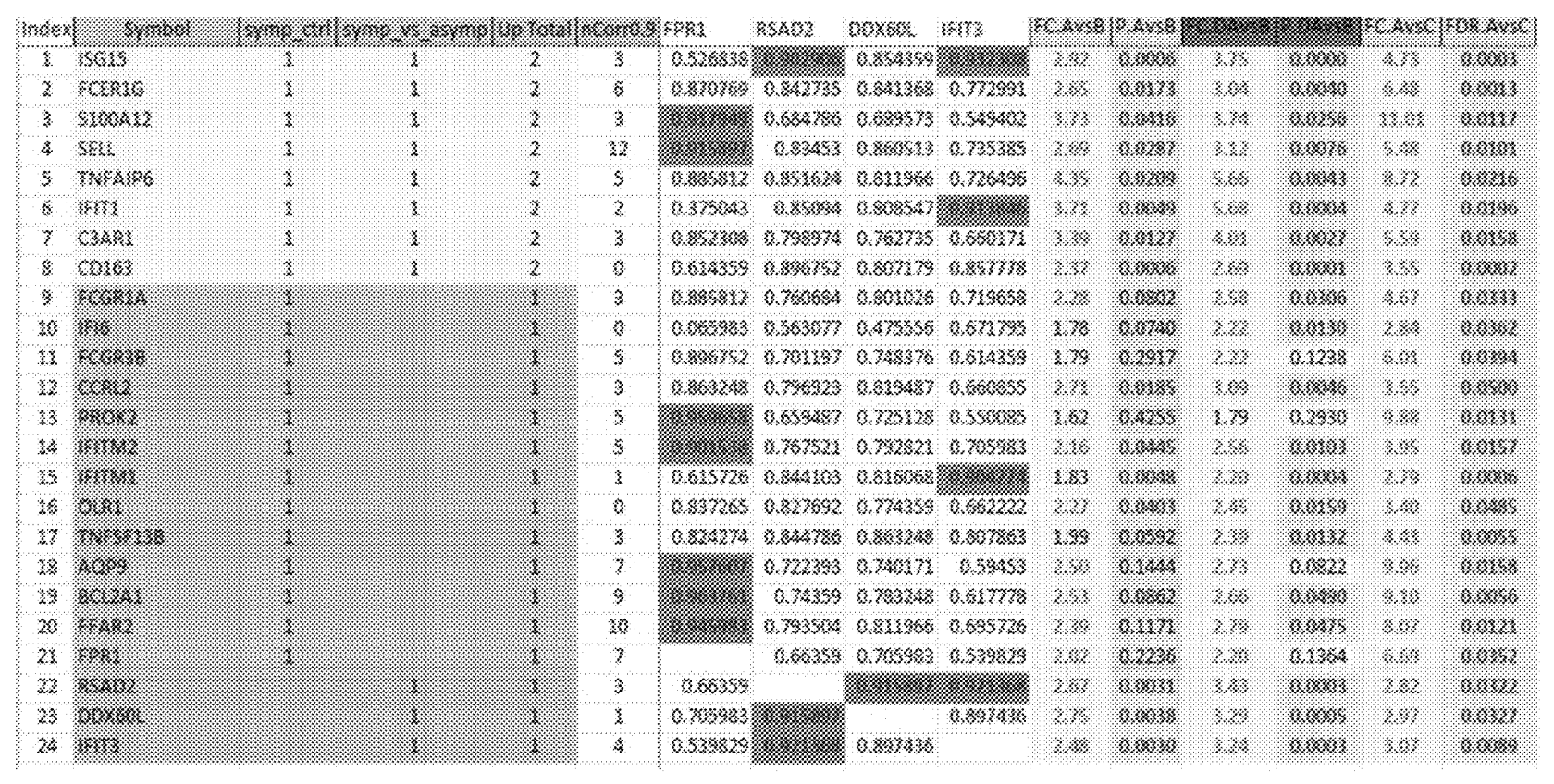
Figure 14:
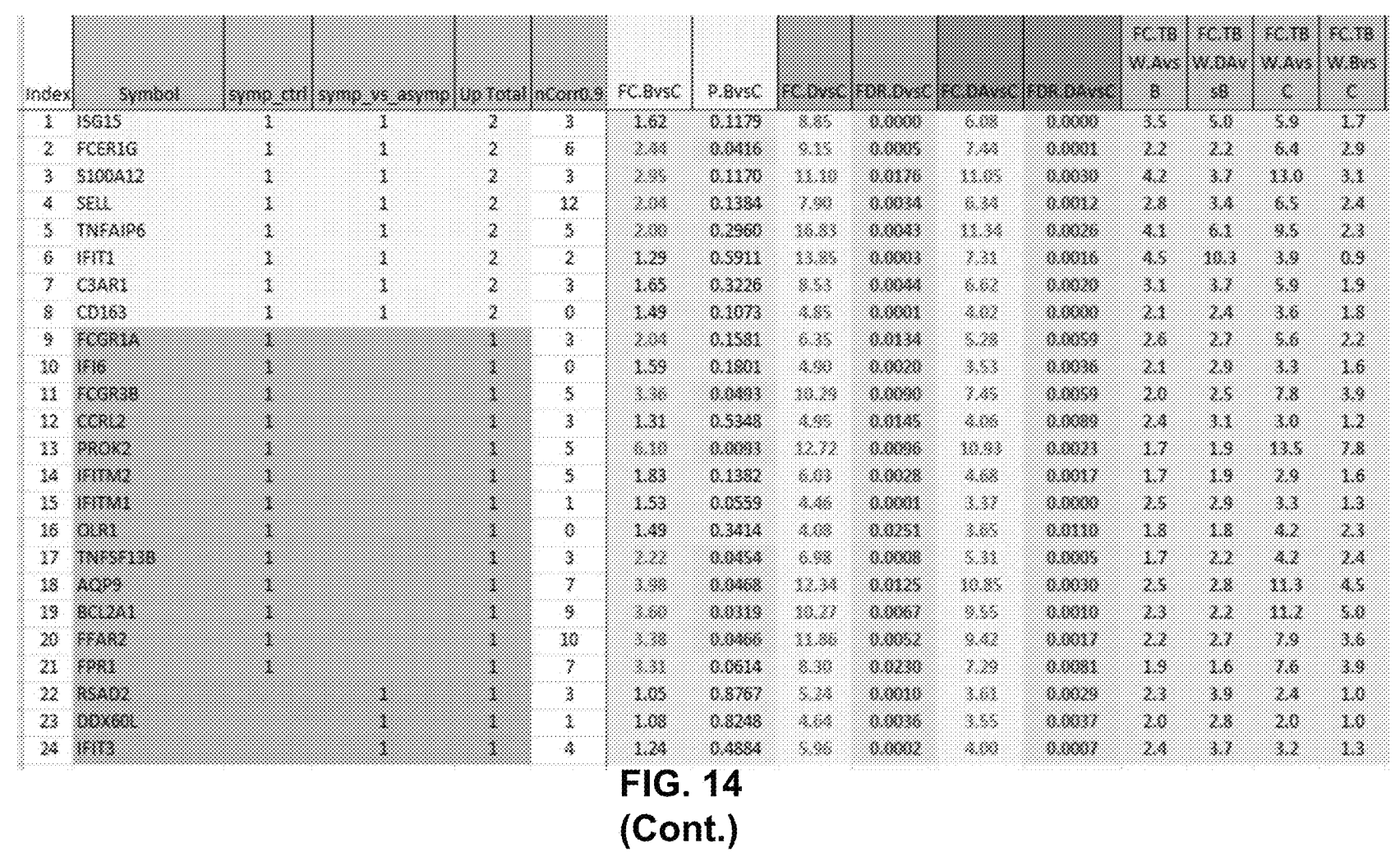

FIGS. 14-120 show various exemplary gene signatures, including 24 genes that are increased during symptomatic and symptomatic versus asymptomatic viral infections, 23 genes that are decreased during symptomatic and symptomatic versus asymptomatic viral infections, 79 genes with increased expression in symptomatic viral infections, 137 genes with decreased expression in symptomatic viral infections, 25 genes with increased expression in symptomatic versus asymptomatic viral infections and 67 gene with decreased expression in symptomatic versus asymptomatic viral infections.

What is claimed is:

1. A method for detecting a respiratory infection in a subject, the method comprising:
  a) measuring the level of expression of one or more host genes in a biological sample obtained from a subject, wherein the one or more host genes are selected from ANKFN1 (ankyrin-repeat and fibronectin type Ill domain containing 1), DNAH6 (dynein, axonemal, heavy chain 6), ECT2L (epithelial cell transforming 2 like), EFHB (EF-hand domain family, member B), FABP6 (fatty acid binding protein 6, ileal), LMNTD1 (lam in tail domain containing 1), LRRC6 (leucine rich repeat containing 6), MORN5 (MORN repeat containing 5), NEK5 (NIMA-related kinase 5), PIFO (primary cilia formation), TBC1 D8 (TBC1 domain family, member 8 (with GRAM domain)), and VWA3B (van Willebrand factor A domain containing 3B); and
  b) comparing the level of each of the one or more host genes with respective predetermined reference level, wherein a decrease relative to the predetermined reference level of one of ANKFN1, DNAH6, ECT2L, EFHB, FABP6, LMNTD1, LRRC6, MORN5, NEK5, PIFO, TBC1 D8, and VWA3B is indicative of the respiratory infection.

2. The method of claim 1, wherein the biological sample is a nasopharyngeal sample isolated from a nasal swab.

3. The method of claim 1, wherein said subject is suspected of having a bacterial infection or a viral infection.

4. The method of any one of claim 1, wherein the subject is suffering from acute respiratory illness symptoms.

5. The method of claim 1, wherein the one or more host genes further include IFT81 (Intraflagellar Transport 81), MUC16 (Mucin 16, Cell Surface Associated), MUC15 (Mucin 15, Cell Surface Associated), MUCL 1 (mucin like 1), BPIFB1 (BPI Fold Containing Family B Member 1), CDH1 (epithelial cadherin), CDHR3 (Cadherin Related Family Member 3), MS4A1 (Membrane Spanning 4-Domains A1), CD22 (cluster of differentiation-22), NCAM1 (Neural Cell Adhesion Molecule 1), KLRB1 (killer cell lectin like receptor B1), NCR1 (natural killer cell receptor NKp46), SIGLEC8 (Sialic acid-binding Ig-like lectin 8), CCR3 (C-C chemokine receptor type 3), CSF3R (Colony Stimulating Factor 3 Receptor), CXCR1 ((C-X-C Motif Chemokine Receptor 1)), CCR7 (C-C chemokine receptor type 7), CD83 (CD83 Molecule), SIRPA (Signal Regulatory Protein Alpha), CD14 (CD14 Molecule), CSF1 R (Colony Stimulating Factor 1 Receptor), CCR5 (C-C chemokine receptor type 5), FCAR (Fe fragment of IgA receptor), ITGAM (Integrin, Alpha M (Complement Component 3 Receptor 3 Subunit)), CR1 (Complement receptor type 1), OLR1 (oxidized low density lipoprotein (lectin-like) receptor 1), C3AR1 (complement component 3a receptor 1), CCRL2 (chemokine (C-C motif) receptor-like 2), AQP9 (aquaporin 9), PROK2 (prokineticin 2), BCL2A1 (BCL2-related protein A1), FFAR2 (free fatty acid receptor 2), FCGR3B (Fe fragment of IgG, low affinity IIIb, receptor (CD16b)), IFITM2 interferon induced transmembrane protein 2), IFI6 (interferon, alpha-inducible protein 6), ISG15 (ISG15 ubiquitin-like modifier), DDX60L (DEAD (Asp-Glu-Ala-Asp) box polypeptide 60-like), WFDC6 (WAP four-disulfide core domain 6), CCDC65 (coiled-coil domain containing 65), AGBL2 (ATP/GTP binding protein-like 2), KIAA2012, DNAL 1 (dynein, axonemal, light chain 1), OSBPL6 (oxysterol binding protein-like 6), CFAP126 (cilia and flagella associated protein 126), ECT2L (epithelial cell transforming 2 like), SPAG17 (sperm associated antigen 17), ANKUB1 (ankyrin repeat and ubiquitin domain containing 1), HHLA2 (HERV-H L TR-associating 2), LRRC7 4B (leucine rich repeat containing 7 4B), DTHD1 (death domain containing 1), TIMP1 (TIMP metallopeptidase inhibitor 1), LIRA1 (leukocyte immunoglobulin-like receptor, subfamily A (with TM domain), member 1), LILRB2 (leukocyte immunoglobulin-like receptor, subfamily B (with TM and ITIM domains), member 2), SLC7A5 (solute carrier family 7 (amino acid transporter light chain, L system), member 5), GPR183 (G protein-coupled receptor 183), LILRB1 (leukocyte immunoglobulin-like receptor, subfamily B (with TM and ITIM domains), member 1), MYO1 G (myosin IG), DOK2 (docking protein 2), EMP3 (epithelial membrane protein 3), CYBB (cytochrome b-245, beta polypeptide), SP140 (SP140 nuclear body protein), MLKL (mixed lineage kinase domain-like), DDX60L (DEAD (Asp-Glu-Ala-Asp) box polypeptide 60-like), FPR3 (formyl peptide receptor 3), MILR1 (mast cell immunoglobulin-like receptor 1), CD163 (CD163 molecule), CXorf21 (chromosome X open reading frame 21), TNFSF13B (tumor necrosis factor (ligand) superfamily, member 13b), CCR1 (chemokine (C-C motif) receptor 1), LGALS1 (lectin, galactoside-binding, soluble, 1), SLC15A3 (solute carrier family 15 (oligopeptide transporter), member 3), RELB (v-rel avian reticuloendotheliosis viral oncogene homolog B), FLNA (filamin A, alpha), FCER1 G (Fe fragment of IgE, high affinity I, receptor for; gamma polypeptide), L Y96 (lymphocyte antigen 96), SLAMF7 (SLAM family member 7), C3AR1 (complement component 3a receptor 1), CCRL2 (chemokine (C-C motif) receptor-like 2), TNFAIP6 (tumor necrosis factor, alpha-induced protein 6), SELL (selectin L) LILRB3 (leukocyte immunoglobulin-like receptor, subfamily B (with TM and ITIM domains), member 3), SIGLEC14 (sialic acid binding Ig-like lectin 14), DYSF (dysferlin), LAT2 (linker for activation of T-cells family member 2), CREB5 (CAMP responsive element binding protein 5), MNDA (myeloid cell nuclear differentiation antigen), SAMSN1 (SAM domain, SH3 domain and nuclear localization signals 1), PLEK (pleckstrin), CD53 (CD53 molecule), FCGR2A (Fe fragment of IgG, low affinity IIa, receptor (CD32) CSF2RB colony stimulating factor 2 receptor, beta, low-affinity (granulocyte-macrophage)), LINC01272 (long intergenic non-protein coding RNA 1272), PROK2 (prokineticin 2), SRGN (serglycin), AQP9 (aquaporin 9), BCL2A1 (BCL2-related protein A1 FFAR2 free fatty acid receptor 2), FPR1 (formyl peptide receptor 1), CSRNP1 (cysteine-serine-rich nuclear protein 1), IER2 (immediate early response 2), PLAUR (plasminogen activator, urokinase receptor), FCGR3B (Fe fragment of IgG, low affinity IIIb, receptor (CD16b)), FCGR3A (Fe fragment of IgG, low affinity IIIa, receptor (CD16a)), ARHGAP25 (Rho GTPase activating protein 25), EVI2A (ecotropic viral integration site 2A), IFITM2 (interferon induced transmembrane protein 2), CD48 (CD48 molecule), RAC2 (ras-related C3 botulinum toxin substrate 2 (rho family, small GTP binding protein Rac2)), WAS (Wiskott-Aldrich syndrome), COTL 1 (coactosin-like F-actin binding protein 1), FCGR1A (Fe fragment of IgG, high affinity 1a, receptor (CD64)), AIF1 (allograft inflammatory factor 1), GMFG (glia maturation factor, gamma), PTPRC (protein tyrosine phosphatase, receptor type, CCORO1A coronin, actin binding protein, 1A), MX2 (MX dynamin-like GTPase 2), IFIT1 (interferon-induced protein with tetratricopeptide repeats 1), ISG15 (ISG15 ubiquitin-like modifier), IFIT2 (interferon-induced protein with tetratricopeptide repeats 2), IFIT3 (interferon-induced protein with tetratricopeptide repeats 3), RSAD2 (radical S-adenosyl methionine domain containing 2), OASL (2-5-oligoadenylate synthetase-like IFI6 interferon, alpha-inducible protein 6), IFITM3 (interferon induced transmembrane protein 3), IFITM1 (interferon induced transmembrane protein 1), ISG20 (interferon stimulated exonuclease gene 20 kDa), C1orf158 (chromosome 1 open reading frame 158), CFAP57 (cilia and flagella associated protein 57), PALMO (palmdelphin), PPOX (protoporphyrinogen oxidase), FMO3 (flavin containing monooxygenase 3), SPATA17 (spermatogenesis associated 17), STPG1 (sperm-tail PG-rich repeat containing 1), BEST4 (bestrophin 4), CCDC17 (coiled-coil domain containing 17), C1 orf87 (Chromosome 1 open reading frame 87), WDR78 (WD repeat domain 78), APOBEC4 (apolipoprotein B mRNA editing enzyme, catalytic polypeptide-like 4 (putative)), CCDC30 (coiled-coil domain containing 30), CFAP45 (cilia and flagella associated protein 45), DRC1 (dynein regulatory complex subunit 1), FAM179A (family with sequence similarity 179, member A), CFAP221 (cilia and flagella associated protein 221), IGFBP2 (insulin like growth factor binding protein 2), IFT172 (intraflagellar transport 172), TSGA10 (testis specific 10), ALS2CR12 (amyotrophic lateral sclerosis 2 chromosome region candidate 12), MDH1 B (malate dehydrogenase 1 B), CFAP65 (cilia and flagella associated protein 65), MAP3K19 (mitogen-activated protein kinase kinase kinase 19), DLEC1 (deleted in lung and esophageal cancer 1), MAATS1 (MYCBP-associated, testis expressed 1), MLF1 (myeloid leukemia factor 1), NEK10 (NI MA-related kinase 10), ASB14 (ankyrin repeat and SOCS box containing 14), DNAH12 (dynein, axonemal, heavy chain 12), KIAA1257, NME9 (NME/NM23 family member 9), LRRC34 (leucine rich repeat containing 34), EFHB (EF-hand domain family, member B), PLCH1 (phospholipase C, eta 1), CC2D2A (coiled-coil and C2 domain containing 2A), DTHD1 (death domain containing 1), C4orf47 (chromosome 4 open reading frame 47), C4orf22 (chromosome 4 open reading frame 22), ROPN1 L (rhophilin associated tail protein 1-like), SPEF2 (sperm flagellar 2), FABP6 (fatty acid binding protein 6, ileal), DNAH5 (dynein, axonemal, heavy chain 5), LOC100505841 (zinc finger protein 474-like), TMEM232 (transmembrane protein 232), ANKRD66 (ankyrin repeat domain 66), EFHC1 (EF-hand domain (C-terminal) containing 1), ADGB (androglobin, CCDC170 coiled-coil domain containing 170), PPIL6 (peptidylprolyl isomerase (cyclophilin)-like 6), CFAP206 (cilia and flagella associated protein 206), DNAH11 (dynein, axonemal, heavy chain 11), RSPH10B2 (radial spoke head 10 homolog B2 (*Chlamydomonas*)), IQUB (IQ motif and ubiquitin domain containing), ZNF713 (zinc finger protein 713), CCDC146 (coiled-coil domain containing 146), RP1 (retinitis pigmentosa 1 (autosomal dominant)), TMEM67 (transmembrane protein 67), PPP1 R42 (protein phosphatase 1, regulatory subunit 42), DNAI1 (dynein, axonemal, intermediate chain 1), C9orf135 (chromosome 9 open reading frame 135), CCDC180 (coiled-coil domain containing 180), CFAP157 (cilia and flagella associated protein 157), FAM166B (family with sequence similarity 166, member B), CFAP47 (cilia and flagella associated protein 47), AKAP14 (A kinase (PRKA) anchor protein 14), EFHC2 (EF-hand domain (C-terminal) containing 2), CETN2 (centrin 2, ZNF487 zinc finger protein 487), SFXN3 (sideroflexin 3), ENKUR (enkurin, TRPC channel interacting protein, ARMC4 armadillo repeat containing 4), FRMPD2 (FERM and PDZ domain containing 2), CFAP70 (cilia and flagella associated protein 70), CFAP43 (cilia and flagella associated protein 43), CFAP46 (cilia and flagella associated protein 46), SPAG6 (sperm associated antigen 6), DNAJB13 (DnaJ (Hsp40) homolog, subfamily B, member 13), CCDC81 (coiled-coil domain containing 81), C11 orf88 (chromosome 11 open reading frame 88), STK33 (serine/threonine kinase 33), COLCA1 (colorectal cancer associated 1), BTG4 (B-cell translocation gene 4), PIH1 D2 (PIH1 domain containing 2), CCDC153 (coiled-coil domain containing 153), DCDC5 (doublecortin domain containing 5), DCDC1 (doublecortin domain containing 1), CFAP54 (cilia and flagella associated 54), CCDC60 (coiled-coil domain containing 60), LRRC43 (leucine rich repeat containing 43), DNAH10 (dynein, axonemal, heavy chain 10), CASC1 (cancer susceptibility candidate 1), TSPAN19 (tetraspanin 19), IQCD (IQ motif containing D), STX2 (syntaxin 2), WDR66 (WD repeat domain 66), TEX26 (testis expressed 26), STOML3 (stomatin (EPB72)-like 3), NEK5 (NIMA-related kinase 5), SAMD15 (sterile alpha motif domain containing 15), C14orf79 (chromosome 14 open reading frame 79), CDKL 1 (cyclin-dependent kinase-like 1 (CDC2-related kinase)), TEX9 (testis expressed 9), IQCH (IQ motif containing H), SAXO2 (stabilizer of axonemal microtubules 2), CCP110 (centriolar coiled coil protein 110 kDa), VWA3A (van Willebrand factor A domain containing 3A), DNAAF1 (dynein, axonemal, assembly factor 1), DNAH3 (dynein, axonemal, heavy chain 3), DRC3 (dynein regulatory complex subunit 3), FBXO15 (F-box protein 15), TTLL9 (tubulin tyrosine ligase-like family member 9), LCA5L (Leber congenital amaurosis 5-like), RSPH1 (radial spoke head 1 homolog (*Chlamydomonas*)), RSPH14 (radial spoke head 14 homolog (*Chlamydomonas*)), EFCAB6 (EF-hand calcium binding domain 6), ARHGAP25 (Rho GTPase activating protein 25), EVI2A (ecotropic viral integration site 2A), CCRL2 (chemokine (C-C motif) receptor-like 2), SIGLEC14 (sialic acid binding Ig-like lectin 14), EMP3 (epithelial membrane protein 3), CYBB (cytochrome b-245, beta polypeptide), L Y96 (lymphocyte antigen 96), SLAMF7 (SLAM family member 7), IFITM2 (interferon induced transmembrane protein 2), MX2 (MX dynamin-like GTPase 2), IFIT2 (interferon-induced protein with tetratricopeptide repeats 2), APOBEC3A (apolipoprotein B mRNA editing enzyme, catalytic polypeptide-like 3A), OLR1 (oxidized low density lipoprotein (lectin-like) receptor 1), or FPR3 (formyl peptide receptor 3).

6. The method of claim 5, wherein the subject is classified as having a symptomatic viral infection when one or more of TIMP1, APOBEC3A, LILRA1, LILRB2, S1 00A 12, SLC7 A5, OLR1, GPR183, LILRB1, MYO1 G, DOK2, EMP3, CYBB, SP140, MLKL, DDX60L, FPR3, MILR1, CD163, CXorf21, TNFSF13B, CCR1, LGALS1, SLC15A3, RELB, FLNA, FCER1 G, L Y96, SLAMF7, C3AR1, CCRL2, TNFAIP6, SELL, LILRB3, SIGLEC14, DYSF, LAT2, CREBS, MNDA, SAMSN1, PLEK, CD53, FCGR2A, CSF2RB, LINC01272, PROK2, SRGN, AQP9, BCL2A1, FFAR2, FPR1, CSRNP1, IER2, PLAUR, FCGR3B, FCGR3A, ARHGAP25, EVI2A, IFITM2, CD48, RAC2, WAS, COTL 1, FCGR1A, AIF1, GMFG, PTPRC, CORO1A, MX2, IFIT1, ISG15, IFIT2, IFIT3, RSAD2, OASL, IFI6, IFITM3, IFITM1, ISG20 are increased relative to the reference value and/or one or more of C1orf158, CFAP57, PALMO, PIFO, PPOX, FMO3, SPATA17, STPG1, BEST4, CCDC17, C1 orf87, WDR78, SPAG17, CFAP126, APOBEC4, CCDC30, CFAP45, DRC1, FAM179A, DNAH6, VWA3B, CFAP221, KIAA2012, IGFBP2, IFT172, TSGA 10, ALS2CR12, MDH1 B, CFAP65, OSBPL6, TBC1 D8, MAP3K19, DLEC1, HHLA2, MAATS1, MLF1, NEK10, ASB14, DNAH12, KIAA1257, NME9, LRRC34, EFHB, ANKUB1, PLCH1, CC2D2A, DTHD1, C4orf47, C4orf22, ROPN1L, SPEF2, FABP6, DNAH5, LOC100505841, TMEM232, ANKRD66, EFHC1, ECT2L, ADGB, CCDC170, PPIL6, CFAP206, RSPH10B2, DNAH11, RSPH10B2, IQUB, ZNF713 CCDC146, RP1, TMEM67, LRRC6, PPP1 R42, DNAI1, C9orf135, CCDC180, MORNS, CFAP157, FAM166B, CFAP47, AKAP14, EFHC2, CETN2, ZNF487, SFXN3, ENKUR, ARMC4, FRMPD2, CFAP70, CFAP43, CFAP46, SPAG6, DNAJB13, CCDC81, C11 orf88, STK33, AGBL2, COLCA 1, BTG4, PIH1 D2, CCDC153, DCDC5, DCDC1, CCDC65, CFAP54, CCDC60, LRRC43, DNAH10, CASC1, TSPAN19, IQCD, STX2, WDR66, LMNTD1, TEX26, STOML3, NEK5, DNAL 1, SAMD15, C14orf79, CDKL 1, TEX9, IQCH, SAXO2, CCP110, VWA3A, DNAAF1, DNAH3, DRC3, ANKFN1, FBXO15, TTLL9, WFDC6, LCA5L, RSPH1, LRRC74B, RSPH14, EFCAB6 are decreased relative to the reference value.

7. The method of claim 6, wherein the subject is classified as having a symptomatic viral infection when one or more of ISG15, FCER1G, S100A12, SELL, TNFAIP6, IFIT1, C3AR1, CD163, FCGR1A, IFI6, FCGR3B, CCRL2, PROK2, IFITM2, IFITM1, OLR1, TNFSF13B, AQP9, BCL2A1, FFAR2, FPR1 are increased relative to the reference value and/or one or more of SPAG17, LRRC74B, PIFO, CFAP126, DNAH6, VWA3B, KIAA2012, OSBPL6, TBC1 D8, HHLA2, ANKUB1, ECT2L, LRRC6, MORNS, AGBL2, CCDC65, LMNTD1, DNAL 1, ANKFN1, WFDC6 are decreased relative to the reference value.

8. The method of claim 1, wherein, the subject is classified as having a symptomatic viral infection versus an asymptomatic viral infection when one or more of ARHGAP25, EVI2A, C3AR1, CCRL2, TNFAIP6, SELL, S100A12, SIGLEC14, EMP3, FCER1 G, CYBB, L Y96, SLAMF7, IFITM2, MX2, IFIT1, ISG15, IFIT2, IFIT3, RSAD2, APOBEC3A, DDX60L, OLR1, FPR3, CD163 are increased relative to the reference value and/or one or more of DNAI1, DNAH6, SPAG6, NEK10, DTHD1, DNAH3, CFAP45, CFAP47, DNAJB13, LMNTD1, LRRC74B, CFAP157, AGBL2, KIAA2012, FBXO15, APOBEC4, TEX26, WDR78, DCDC5, NEK5, ADGB, CCDC81, CASC1, DNAH12, DNAH10, CFAP70, VWA3A, CFAP57, TTLL9, DNAH11, FABP6, RSPH1, EFHB, CDKL 1, ANKUB1, C9orf135, DNAAF1, CFAP221, PIFO, CFAP206, WDR66, IQUB, PPIL6, RSPH10B2, RSPH10B2, SPAG17, DRC3, C4orf22, EFHC2, STOML3, LRRC34, TSPAN19, CCDC65, HHLA2, DNAH5, MORNS, CCDC146, MAP3K19, VWA3B, LRRC43, TSGA 10, C11 orf88, DLEC1, IFT172, EFHC1, CFAP54, CETN2 are decreased relative to the reference value.

9. The method of claim 1, where in the subject is classified as having a symptomatic viral infection versus an asymptomatic viral infection when one or more of ISG15, FCER1G, S100A12, SELL, TNFAIP6, IFIT1, C3AR1, CD163 RSAD2, DDX60L, IFIT3 are increased relative to the reference value and/or one or more of SPAG17, LRRC7 4B, EFHB, DTHD1, FABP6 are decreased relative to the reference value.

10. The method of claim 1, wherein the level of one host gene is determined by measuring an amount of nucleic acid or protein in the biological sample.

11. A method of treating an acute respiratory illness (ARI) in a subject comprising:
a) measuring the level of expression of one or more host genes in a biological sample obtained from a subject, wherein the one or more host genes are selected from ANKFN1, DNAH6, ECT2L, EFHB, FABP6, LMNTD1, LRRC6, MORN5, NEK5, PIFO, TBC1 D8, and VWA3B;
b) comparing the level of each of the one or more host genes with a respective predetermined reference level, wherein a decrease relative to the predetermined reference level of one of ANKFN1, DNAH6, ECT2L, EFHB, FABP6, LMNTD1, LRRC6, MORN5, NEK5, PIFO, TBC1 D8, and VWA3B is indicative of a respiratory infection; and
c) administering to said subject a treatment regimen based on the comparison in (b).

12. The method of claim 11, wherein the biological sample is a nasopharyngeal sample isolated from a nasal swab.

13. The method of claim 11, wherein said subject is suspected of having a bacterial infection or a viral infection.

14. The method of claim 11, wherein the subject is suffering from acute respiratory illness symptoms.

15. The method of claim 11, wherein the one or more host genes further include IFT81 (Intraflagellar Transport 81), MUC16 (Mucin 16, Cell Surface Associated), MUC15 (Mucin 15, Cell Surface Associated), MUCL 1 (mucin like 1), BPIFB1 (BPI Fold Containing Family B Member 1), CDH1 (epithelial cadherin), CDHR3 (Cadherin Related Family Member 3), MS4A1 (Membrane Spanning 4-Domains A 1), CD22 (cluster of differentiation-22), NCAM1 (Neural Cell Adhesion Molecule 1), KLRB1 (killer cell lectin like receptor B1), NCR1 (natural killer cell receptor NKp46), SIGLEC8 (Sialic acid-binding Ig-like lectin 8), CCR3 (C-C chemokine receptor type 3), CSF3R (Colony Stimulating Factor 3 Receptor), CXCR1 ((C-X-C Motif Chemokine Receptor 1)), CCR7 (C-C chemokine receptor type 7), CD83 (CD83 Molecule), SIRPA (Signal Regulatory Protein Alpha), CD14 (CD14 Molecule), CSF1 R (Colony Stimulating Factor 1 Receptor), CCR5 (C-C chemokine receptor type 5), FCAR (Fe fragment of IgA receptor), ITGAM (Integrin, Alpha M (Complement Component 3 Receptor 3 Subunit)), CR1 (Complement receptor type 1), OLR1 (oxidized low density lipoprotein (lectin-like) receptor 1), TNFSF13B (tumor necrosis factor (ligand) superfamily, member 13b), C3AR1 (complement component 3a receptor 1), CCRL2 (chemokine (C-C motif) receptor-like 2), AQP9 (aquaporin 9), PROK2 (prokineticin 2), BCL2A1 (BCL2-related protein A1), FFAR2 (free fatty acid receptor 2), IFITM2 interferon induced transmembrane protein 2), IFI6 (interferon, alpha-inducible protein 6), IFITM1 (interferon induced transmembrane protein 1), ISG15 (ISG15 ubiquitin-like modifier), DDX60L (DEAD (Asp-Glu-Ala-Asp) box polypeptide 60-like), WFDC6 (WAP four-disulfide core domain 6), CCDC65 (coiled-coil domain containing 65), AGBL2 (ATP/GTP binding protein-like 2), KIAA2012, DNAL 1 (dynein, axonemal, light chain 1), OSBPL6 (oxysterol binding protein-like 6), CFAP126 (cilia and flagella associated protein 126), LRRC6 (leucine rich repeat containing 6), SPAG17 (sperm associated antigen 17), ANKUB1 (ankyrin repeat and ubiquitin domain containing 1), HHLA2 (HERV-H L TR-associating 2), LRRC7 4B (leucine rich repeat containing 7 4B), DTHD1 (death domain containing 1), TIMP1 (TIMP metallopeptidase inhibitor 1), LIRA1 (leukocyte immunoglobulin-like receptor, subfamily A (with TM domain), member 1), LILRB2 (leukocyte immunoglobulin-like receptor, subfamily B (with TM and ITIM domains), member 2), SLC7A5 (solute carrier family 7 (amino acid transporter light chain, L system), member 5), GPR183 (G protein-coupled receptor 183), LILRB1 (leukocyte immunoglobulin-like receptor, subfamily B (with TM and ITIM domains), member 1), MYO1 G (myosin IG), DOK2 (docking protein 2), EMP3 (epithelial membrane protein 3), CYBB (cytochrome b-245, beta polypeptide), SP140 (SP140 nuclear body protein), MLKL (mixed lineage kinase domain-like), DDX60L (DEAD (Asp-Glu-Ala-Asp) box polypeptide 60-like), FPR3 (formyl peptide receptor 3), MILR1 (mast cell immunoglobulin-like receptor 1), CD163 (CD163 molecule), CXorf21 (chromosome X open reading frame 21), TNFSF13B (tumor necrosis factor (ligand) superfamily, member 13b), CCR1 (chemokine (C-C motif) receptor 1), LGALS1 (lectin, galactoside-binding, soluble, 1), SLC15A3 (solute carrier family 15 (oligopeptide transporter), member 3), RELB (v-rel avian reticuloendotheliosis viral oncogene homolog B), FLNA (filamin A, alpha), FCER1 G (Fc fragment of IgE, high affinity I, receptor for; gamma polypeptide), L Y96 (lymphocyte antigen 96), SLAMF7 (SLAM family member 7), C3AR1 (complement component 3a receptor 1), CCRL2 (chemokine (C-C motif) receptor-like 2), TNFAIP6 (tumor necrosis factor, alpha-induced protein 6), SELL (selectin L) LILRB3 (leukocyte immunoglobulin-like receptor, subfamily B (with TM and ITIM domains), member 3), SIGLEC14 (sialic acid binding Ig-like lectin 14), DYSF (dysferlin), LAT2 (linker for activation of T-cells family member 2), CREBS (CAMP responsive element binding protein 5), MNDA (myeloid cell nuclear differentiation antigen), SAMSN1 (SAM domain, SH3 domain and nuclear localization signals 1), PLEK (pleckstrin), CD53 (CD53 molecule), FCGR2A (Fc fragment of IgG, low affinity IIa, receptor (CD32) CSF2RB colony stimulating factor 2 receptor, beta, low-affinity (granulocyte-macrophage)), LINC01272 (long intergenic non-protein coding RNA 1272), PROK2 (prokineticin 2), SRGN (serglycin), AQP9 (aquaporin 9), BCL2A1 (BCL2-related protein A1 FFAR2 free fatty acid receptor 2), FPR1 (formyl peptide receptor 1), CSRNP1 (cysteine-serine-rich nuclear protein 1), IER2 (immediate early response 2), PLAUR (plasminogen activator, urokinase receptor), FCGR3B (Fc fragment of IgG, low affinity IIIb, receptor (CD16b)), FCGR3A (Fc fragment of IgG, low affinity IIIa, receptor (CD16a)), ARHGAP25 (Rho GTPase activating protein 25), EVI2A (ecotropic viral integration site 2A), IFITM2 (interferon induced transmembrane protein 2), CD48 (CD48 molecule), RAC2 (ras-related C3 botulinum toxin substrate 2 (rho family, small GTP binding protein Rac2)), WAS (Wiskott-Aldrich syndrome), COTL 1 (coactosin-like F-actin binding protein 1), FCGR1A (Fc fragment of IgG, high affinity 1a, receptor (CD64)), AIF1 (allograft inflammatory factor 1), GMFG (glia maturation factor, gamma), PTPRC (protein tyrosine phosphatase, receptor type, CCORO1A coronin, actin binding protein, 1A), MX2 (MX dynamin-like GTPase 2), IFIT1 (interferon-induced protein with tetratricopeptide repeats 1), ISG15 (ISG15 ubiquitin-like modifier), IFIT2 (interferon-induced protein with tetratricopeptide repeats 2), IFIT3 (interferon-induced protein with tetratricopeptide repeats 3), RSAD2 (radical S-adenosyl methionine domain containing 2), OASL (2-5-oligoadenylate synthetase-like IF16 interferon, alpha-inducible protein 6), IFITM3 (interferon induced transmembrane protein 3), IFITM1 (interferon induced transmembrane protein 1), ISG20 (interferon stimulated exonuclease gene 20 kDa), C1orf158 (chromosome 1 open reading frame 158), CFAP57 (cilia and flagella associated protein 57), PALMO (palmdelphin), PPOX (protoporphyrinogen oxidase), FMO3 (flavin containing monooxygenase 3), SPATA17 (spermatogenesis associated 17), STPG1 (sperm-tail PG-rich repeat containing 1), BEST4 (bestrophin 4), CCDC17 (coiled-coil domain containing 17), C1 orf87 (Chromosome 1 open reading frame 87), WDR78 (WD repeat domain 78), APOBEC4 (apolipoprotein B mRNA editing enzyme, catalytic polypeptide-like 4 (putative)), CCDC30 (coiled-coil domain containing 30), CFAP45 (cilia and flagella associated protein 45), DRC1 (dynein regulatory complex subunit 1), FAM179A (family with sequence similarity 179, member A), CFAP221 (cilia and flagella associated protein 221), IGFBP2 (insulin like growth factor binding protein 2), IFT172 (intraflagellar transport 172), TSGA10 (testis specific 10), ALS2CR12 (amyotrophic lateral sclerosis 2 chromosome region candidate 12), MDH1 B (malate dehydrogenase 1 B), CFAP65 (cilia and flagella associated protein 65), MAP3K19 (mitogen-activated protein kinase kinase kinase 19), DLEC1 (deleted in lung and esophageal cancer 1), MAATS1 (MY-CBP-associated, testis expressed 1), MLF1 (myeloid leukemia factor 1), NEK10 (NI MA-related kinase 10), ASB14 (ankyrin repeat and SOCS box containing 14), DNAH12 (dynein, axonemal, heavy chain 12), KIAA1257, NME9 (NME/NM23 family member 9), LRRC34 (leucine rich repeat containing 34), EFHB (EF-hand domain family, member B), PLCH1 (phospholipase C, eta 1), CC2D2A (coiled-coil and C2 domain containing 2A), DTHD1 (death domain containing 1), C4orf47 (chromosome 4 open reading frame 47), C4orf22 (chromosome 4 open reading frame 22), ROPN1 L (rhophilin associated tail protein 1-like), SPEF2 (sperm flagellar 2), FABP6 (fatty acid binding protein 6, ileal), DNAH5 (dynein, axonemal, heavy chain 5), LOC100505841 (zinc finger protein 474-like), TMEM232 (transmembrane protein 232), ANKRD66 (ankyrin repeat domain 66), EFHC1 (EF-hand domain (C-terminal) containing 1), ADGB (androglobin, CCDC170 coiled-coil domain containing 170), PPIL6 (peptidylprolyl isomerase (cyclophilin)-like 6), CFAP206 (cilia and flagella associated protein 206), DNAH11 (dynein, axonemal, heavy chain 11), RSPH10B2 (radial spoke head 10 homolog B2 (*Chlamydomonas*)), IQUB (IQ motif and ubiquitin domain containing), ZNF713 (zinc finger protein 713), CCDC146 (coiled-coil domain containing 146), RP1 (retinitis pigmentosa 1 (autosomal dominant)), TMEM67 (transmembrane protein 67), PPP1 R42 (protein phosphatase 1, regulatory subunit 42), DNAI1 (dynein, axonemal, intermediate chain 1), C9orf135 (chromosome 9 open reading frame 135), CCDC180 (coiled-coil domain containing 180), CFAP157 (cilia and flagella associated protein 157), FAM166B (family with sequence similarity 166, member B), CFAP47 (cilia and flagella associated protein 47), AKAP14 (A kinase (PRKA) anchor protein 14), EFHC2 (EF-hand domain (C-terminal) containing 2), CETN2 (centrin 2, ZNF487 zinc finger protein 487), SFXN3 (sideroflexin 3), ENKUR (enkurin, TRPC channel interacting protein, ARMC4 armadillo repeat containing 4), FRMPD2 (FERM and PDZ domain containing 2), CFAP70 (cilia and flagella associated protein 70), CFAP43 (cilia and flagella associated protein 43), CFAP46 (cilia and flagella associated protein 46), SPAG6 (sperm associated antigen 6), DNAJB13 (DnaJ (Hsp40) homolog, subfamily B, member 13), CCDC81 (coiled-coil domain containing 81), C11 orf88 (chromosome 11 open reading frame 88), STK33 (serine/threonine kinase 33), COLCA1 (colorectal cancer associated 1), BTG4 (B-cell translocation gene 4), PIH1 D2 (PIH1 domain containing 2), CCDC153 (coiled-coil domain containing 153), DCDC5 (doublecortin domain containing 5), DCDC1 (doublecortin domain containing 1), CFAP54 (cilia and flagella associated 54), CCDC60 (coiled-coil domain containing 60), LRRC43 (leucine rich repeat containing 43), DNAH10 (dynein, axonemal, heavy chain 10), CASC1 (cancer susceptibility candidate 1), TSPAN19 (tetraspanin 19), IQCD (IQ motif containing D), STX2 (syntaxin 2), WDR66 (WD repeat domain 66), TEX26 (testis expressed 26), STOML3 (stomatin (EPB72)-like 3), SAMD15 (sterile alpha motif domain containing 15), C14orf79 (chromosome 14 open reading frame 79), CDKL 1 (cyclin-dependent kinase-like 1 (CDC2-related kinase)), TEX9 (testis expressed 9), IQCH (IQ motif containing H), SAXO2 (stabilizer of axonemal microtubules 2), CCP110 (centriolar coiled coil protein 110 kDa), VWA3A (van Willebrand factor A domain containing 3A), DNAAF1 (dynein, axonemal, assembly factor 1), DNAH3 (dynein, axonemal, heavy chain 3), DRC3 (dynein regulatory complex subunit 3), FBXO15 (F-box protein 15), TTLL9 (tubulin tyrosine ligase-like family member 9), LCA5L (Leber congenital amaurosis 5-like), RSPH1 (radial spoke head 1 homolog (*Chlamydomonas*)), RSPH14 (radial spoke head 14 homolog (*Chlamydomonas*)), EFCAB6 (EF-hand calcium binding domain 6), ARHGAP25 (Rho GTPase activating protein 25), EVI2A (ecotropic viral integration site 2A), CCRL2 (chemokine (C-C motif) receptor-like 2), SIGLEC14 (sialic acid binding Ig-like lectin 14), EMP3 (epithelial membrane protein 3), CYBB (cytochrome b-245, beta polypeptide), L Y96 (lymphocyte antigen 96), SLAMF7 (SLAM family member 7), IFITM2 (interferon induced transmembrane protein 2), MX2 (MX dynamin-like GTPase 2), IFIT2 (interferon-induced protein with tetratricopeptide repeats 2), APOBEC3A (apolipoprotein B mRNA editing enzyme, catalytic polypeptide-like 3A), OLR1 (oxidized low density lipoprotein (lectin-like) receptor 1), or FPR3 (formyl peptide receptor 3).

16. The method of claim 11, wherein the subject is classified as having a symptomatic viral infection when one or more of TIMP1, APOBEC3A, LILRA1, LILRB2, S1 00A 12, SLC7 A5, OLR1, GPR183, LILRB1, MYO1 G, DOK2, EMP3, CYBB, SP140, MLKL, DDX60L, FPR3, MILR1, CD163, CXorf21, TNFSF13B, CCR1, LGALS1, SLC15A3, RELB, FLNA, FCER1 G, L Y96, SLAMF7, C3AR1, CCRL2, TNFAIP6, SELL, LILRB3, SIGLEC14, DYSF, LAT2, CREBS, MNDA, SAMSN1, PLEK, CD53, FCGR2A, CSF2RB, LINC01272, PROK2, SRGN, AQP9, BCL2A1, FFAR2, FPR1, CSRNP1, IER2, PLAUR, FCGR3B, FCGR3A, ARHGAP25, EVI2A, IFITM2, CD48, RAC2, WAS, COTL 1, FCGR1A, AIF1, GMFG, PTPRC, CORO1A, MX2, IFIT1, ISG15, IFIT2, IFIT3, RSAD2, OASL, IFI6, IFITM3, IFITM1, ISG20 are increased relative to the reference value and/or one or more of C1orf158, CFAP57, PALMO, PIFO, PPOX, FMO3, SPATA17, STPG1, BEST4, CCDC17, C1 orf87, WDR78, SPAG17, CFAP126, APOBEC4, CCDC30, CFAP45, DRC1, FAM179A, DNAH6, VWA3B, CFAP221, KIAA2012, IGFBP2, IFT172, TSGA 10, ALS2CR12, MDH1 B, CFAP65, OSBPL6, TBC1 D8, MAP3K19, DLEC1, HHLA2, MAATS1, MLF1, NEK10, ASB14, DNAH12, KIAA1257, NME9, LRRC34, EFHB, ANKUB1, PLCH1, CC2D2A, DTHD1, C4orf47, C4orf22, ROPN1L, SPEF2 FABP6, DNAH5, LOC100505841, TMEM232, ANKRD66, EFHC1, ECT2L, ADGB, CCDC170, PPIL6, CFAP206, RSPH10B2, DNAH11, RSPH10B2, IQUB, ZNF713, CCDC146, RP1, TMEM67, LRRC6, PPP1 R42, DNAI1, C9orf135, CCDC180, MORNS, CFAP157, FAM166B, CFAP47, AKAP14, EFHC2, CETN2, ZNF487, SFXN3, ENKUR, ARMC4, FRMPD2, CFAP70, CFAP43, CFAP46, SPAG6, DNAJB13, CCDC81, C11 orf88, STK33, AGBL2, COLCA 1, BTG4, PIH1 D2, CCDC153, DCDC5, DCDC1, CCDC65, CFAP54, CCDC60, LRRC43, DNAH10, CASC1, TSPAN19, IQCD, STX2, WDR66, LMNTD1, TEX26, STOML3, NEK5, DNAL 1, SAMD15, C14orf79, CDKL 1, TEX9, IQCH, SAXO2, CCP110, VWA3A, DNAAF1, DNAH3, DRC3, ANKFN1, FBXO15, TTLL9, WFDC6, LCA5L, RSPH1, LRRC74B, RSPH14, EFCAB6 are decreased relative to the reference value.

17. The method of claim 11, wherein the subject is classified as having a symptomatic viral infection when one or more of ISG15, FCER1G, S100A12, SELL, TNFAIP6, IFIT1, C3AR1, CD163, FCGR1A, IFI6, FCGR3B, CCRL2, PROK2, IFITM2, IFITM1, OLR1, TNFSF13B, AQP9, BCL2A1, FFAR2, FPR1 are increased relative to the reference value and/or one or more of SPAG17, LRRC74B, PIFO, CFAP126, DNAH6, VWA3B, KIAA2012, OSBPL6, TBC1 D8, HHLA2, ANKUB1, ECT2L, LRRC6, MORNS, AGBL2, CCDC65, LMNTD1, DNAL 1, ANKFN1, WFDC6 are decreased relative to the reference value.

18. The method of claim 9, wherein, the subject is classified as having a symptomatic viral infection versus an asymptomatic viral infection when one or more of ARHGAP25, EVI2A, C3AR1, CCRL2, TNFAIP6, SELL, S100A12, SIGLEC14, EMP3, FCER1 G, CYBB, L Y96, SLAMF7, IFITM2, MX2, IFIT1, ISG15, IFIT2, IFIT3, RSAD2, APOBEC3A, DDX60L, OLR1, FPR3, CD163 are increased relative to the reference value and/or one or more of DNAI1, DNAH6, SPAG6, NEK10, DTHD1, DNAH3, CFAP45, CFAP47, DNAJB13, LMNTD1, LRRC74B, CFAP157, AGBL2, KIAA2012, FBXO15, APOBEC4, TEX26, WDR78, DCDC5, NEK5, ADGB, CCDC81, CASC1, DNAH12, DNAH10, CFAP70, VWA3A, CFAP57, TTLL9, DNAH11, FABP6, RSPH1, EFHB, CDKL 1, ANKUB1, C9orf135, DNAAF1, CFAP221, PIFO, CFAP206, WDR66, IQUB, PPIL6, RSPH10B2, RSPH10B2, SPAG17, DRC3, C4orf22, EFHC2, STOML3, LRRC34, TSPAN19, CCDC65, HHLA2, DNAH5, MORNS, CCDC146, MAP3K19, VWA3B, LRRC43, TSGA 10, C11 orf88, DLEC1, IFT172, EFHC1, CFAP54, CETN2 are decreased relative to the reference value.

19. The method of claim 9, where in the subject is classified as having a symptomatic viral infection versus an asymptomatic viral infection when one or more of ISG15, FCER1G, S100A12, SELL, TNFAIP6, IFIT1, C3AR1, CD163 RSAD2, DDX60L, IFIT3 are increased relative to the reference value and/or one or more of SPAG17, LRRC7 4B, EFHB, DTHD1, FABP6 are decreased relative to the reference value.

20. The method according to claim 9, wherein the appropriate treatment regimen comprises an antibacterial therapy when the etiology is determined to comprise a bacterial ARI, wherein the ARI is an infection of the upper or lower respiratory tract and characterized by rapid progression of symptoms over hours to days.

21. The method of claim 1, wherein:
a) the one or more host genes further comprise one or more of FCER1G (Fe fragment of IgE, high affinity I, receptor for; gamma polypeptide), FCER1A (Fe Fragment Of IgE, High Affinity I, Receptor For; Alpha Polypeptide), FCGR3B (Fe fragment of IgG, low affinity IIIb, receptor (CD16b)), FPR1 (formyl peptide receptor 1), IFIT1 (interferon-induced protein with tetratricopeptide repeats 1), IFIT3 (interferon-induced protein with tetratricopeptide repeats 3), IFITM1 (interferon induced transmembrane protein 1), RSAD2 (radical S-adenosyl methionine domain containing 2), S100A12 (S100 calcium binding protein A12), SELL (selectin L), TNFAIP6 (tumor necrosis factor, alpha-induced protein 6), and TNFSF13B (tumor necrosis factor (ligand) superfamily, member 13b); and
b) an increase relative to the reference level of one of FCER1G, FCER1A, FCGR3B, FPR1, IFIT1, IFIT3, IFITM1, RSAD2, S100A12, SELL, TNFAIP6, and TNFSF13B is indicative of the respiratory infection.

22. The method of claim 11, wherein:
a) the one or more host genes further comprise one or more of FCER1G (Fe fragment of IgE, high affinity I, receptor for; gamma polypeptide), FCER1A (Fe Fragment Of IgE, High Affinity I, Receptor For; Alpha Polypeptide), FCGR3B (Fe fragment of IgG, low affinity IIIb, receptor (CD16b)), FPR1 (formyl peptide receptor 1), IFIT1 (interferon-induced protein with tetratricopeptide repeats 1), IFIT3 (interferon-induced protein with tetratricopeptide repeats 3), IFITM1 (interferon induced transmembrane protein 1), RSAD2 (radical S-adenosyl methionine domain containing 2), S100A12 (S100 calcium binding protein A12), SELL (selectin L), TNFAIP6 (tumor necrosis factor, alpha-induced protein 6), and TNFSF13B (tumor necrosis factor (ligand) superfamily, member 13b); and
b) an increase relative to the reference level of one of FCER1G, FCER1A, FCGR3B, FPR1, IFIT1, IFIT3, IFITM1, RSAD2, S100A12, SELL, TNFAIP6, and TNFSF13B is indicative of the respiratory infection.

23. The method of claim 1, wherein
a) the one or more host genes comprise ANKFN1, DNAH6, ECT2L, EFHB, FABP6, LMNTD1, LRRC6, MORN5, NEK5, PIFO, TBC1 D8, VWA3B, FCER1G, FCER1A, FCGR3B, FPR1, IFIT1, IFIT3, IFITM1, RSAD2, S100A12, SELL, TNFAIP6, and TNFSF13B; and
b) decreases in the levels of ANKFN1, DNAH6, ECT2L, EFHB, FABP6, LMNTD1, LRRC6, MORN5, NEK5, PIFO, TBC1 D8, and VWA3B; and increases in the levels of FCER1G, FCER1A, FCGR3B, FPR1, IFIT1, IFIT3, IFITM1, RSAD2, S100A12, SELL, TNFAIP6, and TNFSF13B, relative to their respective predetermined reference levels is indicative of the respiratory infection.

24. The method of claim 11, wherein
a) the one or more host genes comprise ANKFN1, DNAH6, ECT2L, EFHB, FABP6, LMNTD1, LRRC6, MORN5, NEK5, PIFO, TBC1 D8, VWA3B, FCER1G, FCER1A, FCGR3B, FPR1, IFIT1, IFIT3, IFITM1, RSAD2, S100A12, SELL, TNFAIP6, and TNFSF13B; and
b) decreases in the levels of ANKFN1, DNAH6, ECT2L, EFHB, FABP6, LMNTD1, LRRC6, MORN5, NEK5, PIFO, TBC1 D8, and VWA3B; and increases in the levels of FCER1G, FCER1A, FCGR3B, FPR1, IFIT1, IFIT3, IFITM1, RSAD2, S100A12, SELL, TNFAIP6, and TNFSF13B, relative to their respective predetermined reference levels is indicative of the respiratory infection.

* * * * *